US011332739B2

(12) United States Patent
Gibert Pérez et al.

(10) Patent No.: US 11,332,739 B2
(45) Date of Patent: May 17, 2022

(54) PORCINE REPRODUCTIVE AND RESPIRATORY SYNDROME VIRUS CDNA CLONE AND USES THEREOF

(71) Applicants: HIPRA SCIENTIFIC, S.L.U., Amer (ES); CONSEJO SUPERIOR DE INVESTIGACIONES CIENTIFICAS (CSIC), Madrid (ES)

(72) Inventors: Xavier Gibert Pérez, Blanes (ES); Marta Sitjà Arnau, Girona (ES); Maria Mar Fenech Martínez, Barcelona (ES); Santiago Francisco Elena Fito, Valencia (ES); Susana Martín García, Valencia (ES)

(73) Assignees: HIPRA SCIENTIFIC, S.L.U., Amer (ES); CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 215 days.

(21) Appl. No.: 16/322,316

(22) PCT Filed: Jul. 31, 2017

(86) PCT No.: PCT/EP2017/069329
§ 371 (c)(1),
(2) Date: Jan. 31, 2019

(87) PCT Pub. No.: WO2018/024677
PCT Pub. Date: Feb. 8, 2018

(65) Prior Publication Data

US 2019/0177721 A1 Jun. 13, 2019

(30) Foreign Application Priority Data

Aug. 5, 2016 (EP) .................................... 16382391

(51) Int. Cl.
*C12N 15/10* (2006.01)
*C12N 7/00* (2006.01)
(Continued)

(52) U.S. Cl.
CPC .......... *C12N 15/1096* (2013.01); *A61K 39/12* (2013.01); *A61P 31/14* (2018.01); (Continued)

(58) Field of Classification Search
None
See application file for complete search history.

(56) References Cited

U.S. PATENT DOCUMENTS

2019/0177721 A1* 6/2019 Gibert Perez ............ C12N 7/00

FOREIGN PATENT DOCUMENTS

WO 2013173443 A1 11/2013

OTHER PUBLICATIONS

Amonsin et al. (Virology Journal 2009; 6: 143).*
Zhang et al. (Journal of Veterinary Diagnostic Investigation. 2017; 29 (1): 41-50).*
Vignuzzi et al. (Nature Medicine. 2008; 14 (2): 154-161).*
(Continued)

*Primary Examiner* — Shanon A. Foley
(74) *Attorney, Agent, or Firm* — Saul Ewing Arnstein & Lehr LLP; Kathryn Doyle

(57) ABSTRACT

The present invention relates to a method for preparing cDNA infectious clones based on the genome of an attenuated Porcine Reproductive and Respiratory Syndrome virus (PRRSV) and uses thereof for preparing efficacious and safety-enhanced vaccines against PRRSV. The invention further comprises an infectious cDNA clone obtainable by such method. The invention further provides an attenuated modified PRRSV, and immunogenic compositions and vaccines comprising that attenuated PRRSV. The present inven-
(Continued)

tion further provides the attenuated PRRSV for use in the prophylaxis and/or the treatment of PRRSV infections, and the attenuated PRRSV for use as vaccine or medicament in the prophylaxis and/or the treatment of PRRSV infections.

18 Claims, 16 Drawing Sheets

Specification includes a Sequence Listing.

(51) Int. Cl.

| | |
|---|---|
| ***A61K 39/12*** | (2006.01) |
| ***A61P 31/14*** | (2006.01) |
| ***C07K 14/005*** | (2006.01) |
| *A61K 39/00* | (2006.01) |

(52) U.S. Cl.

CPC .............. *C07K 14/005* (2013.01); *C12N 7/00* (2013.01); *A61K 2039/5254* (2013.01); *A61K 2039/552* (2013.01); *A61K 2039/58* (2013.01); *C12N 2770/10021* (2013.01); *C12N 2770/10022* (2013.01); *C12N 2770/10034* (2013.01)

(56) References Cited

OTHER PUBLICATIONS

Calzada-Nova et al. (Veterinary Immunology and Immunopathology. 2012; 148: 116-125).*

PCT/EP201 7/069329—International Search Report dated Oct. 27, 2017.

"Porcine reproductive and respiratory syndrome virus strain Amervac PRRS, complete genome", EBI Accession No. EM_STD:GU067771, published Nov. 9, 2009.

Brar, et al.,"Genomic Evolution of Porcine Reproductive and Respiratory Syndrome Virus (PRRSV) Isolates Revealed by Deep Sequencing.", 2014, PLOS ONE 9(4):e88807.

Hu, et al.,"Porcine Reproductive and Respiratory Syndrome Virus Vaccines: Current Status and Strategies to a Universal Vaccine.", 2013, Transboundary and Emerging Diseases 61(2):109-120.

McBurney, et al.,"Human immunodeficiency virus-like particles with consensus envelopes elicited broader cell-mediated peripheral and mucosal immune responses than polyvalent and monovalent Env vaccines.", 2009, Vaccine 27(32):4337-4349.

Renukaradhya, et al.,"Live porcine and respiratory syndrome virus vaccines: Current status and future direction.", 2015, Vaccine 33:4069-4080.

Vu, et al.,"A Synthetic Porcine Reproductive and Respiratory Syndrome Virus Strain Confers Unprecedented Levels of Heterologous Protection.", 2015, Journal of Virology 89(23):12070-12083.

* cited by examiner

SEQUENCE LISTING

```
<160> NUMBER OF SEQ ID NOS: 225

<210> SEQ ID NO 1
<211> LENGTH: 15132
<212> TYPE: DNA
<213> ORGANISM: Artificial Sequence
<220> FEATURE:
<223> OTHER INFORMATION: Consensus sequence of attenuated virus VP-046
      BIS

<400> SEQUENCE: 1

atgatgtgta gggtactccc cctacataca cgacacttct agtgtttgtg tgccttggag      60

gcgtgggtat agccccgccc cacccettgg cccctgttct agcccaacag gtatccttct     120

ctctcggggc gagcgcgccg cctgctgctc ccttgcagcg ggaaggacct cccgagtatt     180
```

-continued

```
tccggagagc acctgcttta cgggatctcc accctttaac catgtctggg acgttctccc    240
ggtgcatgtg caccccggct gcccgggtat tttggaacgc cggccaagtc ttttgcacac    300
ggtgtctcag tgcgcggtct cttctccctc cggagcttca ggaaactgac ctcgctgcaa    360
ttggcttgtt ttacaagcct aaagacaagc ttcactggaa agtccctatc ggcatccctc    420
aggtggagtg cactccatcc gggtgctgtt ggctctcagc catcttccca ttggcgcgca    480
tgacctccgg caatcacaac ttcctccaac gacttgtgag ggttgccgat gtgttgtacc    540
gtgatggttg cttggctcct cgacaccttc gtgaactcca agtttacgag cgcggctgca    600
actggtaccc gatcacgggg cccgtgcccg ggatgggttt gttcgcaaac tccatgcacg    660
tatccgacca gccgttccct ggtgccaccc atgtgttgac gaactcgccg ttgcctcaac    720
aggcttgtcg gcagccgttc tgtccatttg aggaggctca ttctagtgtg tacaggtgga    780
aaagatttgt ggttttcacg gattcctctc ccaacggtcg atctcgcatg atgtggacgc    840
cggaatccga tgattcagcc gccttggagg tattaccgcc tgaattagaa cgtcaggtcg    900
aaatcctcat tcggagtttt cctgctcatc accctgtcaa cctggccgac tgggagctca    960
ctgagtcccc tgagaacggt tttccttca acacgtctta ttcttgcggt caccttgtcc   1020
aaaaccccga cgtgtttgat ggcaagtgct ggctttcctg ctttttgggc cagtcggccg   1080
aagtgcgccg ccatgaggaa catttagctg acgccctcgg ttaccagacc aagtggggcg   1140
tgcctggcaa gtacctccag cgcaggcttc aggttcgcgg cattcgtgct gtagttgatc   1200
ctgatggccc cattcacgtc gaagcgctgt cttgcccccg gtcttggatc aggcacctga   1260
cttttgatga taatgtcacc ccaggatttg ttcgccttac gtcccttcgc attgtgccaa   1320
acaccgagcc tactgcttcc cggatcttcc ggtttggagc gcataagtgg tatggcgctg   1380
ccggcaaacg agctcgtgct aagcgtgccg ctaaaagtga gaaaatttcg gcccctaccc   1440
ccaaggttgc tcagccggtc cccacctgcg aaattaccac ctattctcca ccgacagacg   1500
ggtcttgtgg ttggcatgtt cttgccgcca taatgaaccg gatgatgaat ggtgacttca   1560
cgtcccctct gactcagtac aacagaccag aggatgactg ggcttctgat tatgaccttg   1620
ctcaggcgat ccaatgtctg caactgcccg ctaccgtagt tcggaatcgc gcctgtccta   1680
acgccaagta ccttataaaa cttaatggag ttcattggga ggtagaggtg aggcctggaa   1740
tggcccctcg ttccctttcc cgtgagtgtg tggttggcgt ctgttctgaa ggctgtatcg   1800
caccgcctta cccacaagac gggctgccta aacgtgcact tgaggccttg gcgtctgctt   1860
acagactacc ctccgactgt gttggttctg gtattgctga ctttcttgct aacccgcccc   1920
ctcaggagtt ttggaccctt gacaaaatgt tgacctcccc gtcaccagaa cggtccggct   1980
tctctagctt gtataaatta ctattggagg ttgttccgca gaaatgcggt gccacggaag   2040
gggctttcgt ctatgctgtt gagaggatgt tgaaggattg tccgagctcc aaacaggcca   2100
tggcccttct ggcaaaaatt aaagtcccat cctcaaaggc cccgtctgtg tctctggacg   2160
agtgcttccc tacggatgtt ccagcggact ccgagccagc gtttcaggaa aggccccaaa   2220
gttctggtgc tgctgttgtc ctgtgttcac cggacataaa agagttcgag gaagcagccc   2280
cagaagaagt tcaagagggt ggccacaagg ccgtccactc tgcactcctt gccgagggtc   2340
ttaacaatga gcaggtacag gtggttgccg gtgcgcaact aaagctcggc agttgtggct   2400
tggcagtcgg gaatactcat ggaggtgttc cggtttcagc tagtccaatt aacctggcag   2460
acgggaattt gccccccctcg gactccatga aaggaaacat gcccaatggc tgggaggacg   2520
aaccactgga tttgtcccaa tcagcactag caaccacaac gacccttgtg agagagcaaa   2580
```

-continued

```
cacccgacaa tctaggttct ggcgccggtg ccctccctgt caccattcga gaatttgtcc   2640
cgacaaggcc tataccccgt catgttgagc actgcggcac ggagtcgggc gacagcagtt   2700
cgcctctgga tctgtccgat gcgcaaaccc cggaccagcc tttaaatcta tccctggccg   2760
cttggccagt gagggccacc gcgtctgacc ccggctgggt ccacggtagg cgtgagcctg   2820
tttttgtaaa gcctcggggt gctttctctg atggcgattc agtccttcag ttcggggagc   2880
tttccgaatc cagctctatc atcgagattg accggacaaa agatgctcca gtggttgatg   2940
cccccgtcga cttgacggtt tcgaacgaag ctctctctgg gatcgatcct tttgaatttg   3000
ccgaactcaa gcgcccgcgt ttctccgctc aagccttaat tgaccgaggc ggcccactag   3060
ccgatgtcca tgcaaaaata aagaaccggg tatatgaaca gtgcctccag gcttgtgagc   3120
ctggcagtcg tgcaacccca gccaccaggg agtggctcga caaaatgtgg gatagggtgg   3180
acatgaagac ttggcgctgc acctcgcagt tccaagctgg tcacattctt gcgtccctca   3240
aattcctccc cgacatgatt caagacacac cgcctcctgt tcccaggaag agccgggcta   3300
gtgataatgc cggcctgaag caactggtgg cgcagtggga cagaaaattg agtgtaaccc   3360
ccccctaaa accggttggg ccggcgcttg gccaaaccgt ccctccgcct acggatattc   3420
agcaagaaga tgtcaccccc tccgataggc cacctcatgt gccggatctt cctagtcgag   3480
tgagcacggg tgggagttgg aaaggcctta tgctttccgg cacccgtctc gcggggtcta   3540
ttagtcagca cctcatgaca tgggtttttg aagttttctc ccatctccca gcttttatgc   3600
tcacactttt ctcgccacgg ggctctatgg ctccaggtga ttggctattt gcaggtgttg   3660
ttttacttgc tctcctgctc tgtcgttctt acccagtact cgggtgcctt cccttattgg   3720
gtgtcttttc tggttctttg cggcgtgttc gtctgggtgt tttggttct tggatggctt    3780
ttgctgtatt tttattctcg actccatccg acccagtcgg ttcttcttgt gaccacgatt   3840
cgccggagtg tcatgctgag cttttggctc ttgagcagcg ccaactttgg gaacctgtgc   3900
gsggccttgt ggtcggcccc tcgggyctct tatgtgtcat tcttggcaag ttactcggtg   3960
ggtcacgtta tctctggcat gttttcttac gtttatgcat gcttgcggat ttggcccttt   4020
ctcttgttta tgtggtgtcc caggggcgtt gtcacaagtg ttggggaaag tgtataagga   4080
cagctcctgc ggaggtggct ctcaatgtgt tccctttctt gcgcgctacc cgtgcctctc   4140
ttgtgtcctt gtgcgatcga ttccaagcgc caaaaggggt tgatcctgtg cacttggcaa   4200
caggttggcg cgggtgctgg cgcggtgaga gccccattca tcaaccgcac caaaagccca   4260
tagcttatgc caatttggat gaaaagaaaa tatctgccca aacggtggtt gctgtcccgt   4320
atgatcccag tcaggccatc aaatgcctga aagttctgca ggcgggaggg gctatcgtgg   4380
accagcccac acctgaggtc gtccgtgtgt ccgagatccc tttctcagcc ccattttttc   4440
caaaggttcc agtcaaccca gattgcaggg ttgtggtaga ttcggacact tttgtggctg   4500
cagttcgctg cggttactcg acggctcaac tggtcttagg ccggggcaac tttgccaagt   4560
taaatcagat cccctccagg aactctgtct ccaccaaaac gactggtggg gcctcttaca   4620
cccttgctgt ggctcaagtg tctgtgtgga ctcttgttca tttcatcctc ggtctttggt   4680
tcacgtcacc tcaagtgtgt ggccgaggaa cctctgaccc atggtgttca aatccttttt   4740
catatcctac ctatggcccc ggaatagtgt gctcctctcg actttgtgtg tctgccgacg   4800
gagtcactct gccattgttc tcagcagtgg cacaactctc cggtagagag gtggggattt   4860
tcattttggt gctcgtctcc ttgactgctc tggcccaccg tatggctctt aaggcagaca   4920
```

-continued

```
tgttagtggt cttttcggct ttttgtgctt acgcctggcc catgagctcc tggttaatct   4980
gcttctttcc tatattcttg aagtgggtca cccttcaccc tctcactatg ctttgggtgc   5040
actcattctt ggtgttttgt ctgccagcag ccggcgtcct ctcactaggg ataaccggcc   5100
ttctctgggc agttggccgc tttacccagg tcgccggaat tattacacct tatgacatcc   5160
accagtacac ctctgggcca cgtggtgcag ccgctgtggc cacggcccca gaaggcactt   5220
acatggccgc cgtccggaga gctgccttaa ctggacgaac cctcatcttc acaccatctg   5280
cggttggatc ccttcttgaa ggtgctttca ggacccataa accctgcctt aacaccgtga   5340
atgttgtagg ctcttccctt ggttccgggg gggttttcac cattgatggc agaagaactg   5400
ttgtcactgc tgcccatgtg ttgaacggcg acacagctag agtcaccggc gactcctaca   5460
accgcatgca cactttcaag accaatggtg attatgcctg gtcccatgct gatgactggc   5520
ggggcgttgc ccctgtggtc aaggtcgcga aggggtaccg cggtcgtgcc tactggcaaa   5580
catcaactgg tgtcgaaccc ggtattgttg ggaagggtt cgccttctgt tttaccaact   5640
gtggcgattc ggggtcacct gtcatctcag aatctggtga tcttgttgga atccacaccg   5700
gttcaaacaa actcggttct ggtcttgtga caacccctga aggggagacc tgctccatca   5760
aagaaaccaa gctctctgac ctttccaggt attttgcagg cccaagcgtc cctcttgggg   5820
atattaaatt gagtccggcc atcatccctg atgtaacatc cattccgagt gacttggcat   5880
cgctcctagc ctccgtccct gtaatggaag gcggcctctc gactgtccaa cttttgtgtg   5940
tctttttcct tctctggcgt atgatgggcc atgcctggac acccattgtt gccgtgggct   6000
tctttttgct gaatgaaatt cttccagcag ttttggtccg agccgtgttt tcttttgcgc   6060
tctttgtgct tgcatgggcc accccctggt ctgcacaggt gttgatgatc agactcctca   6120
cggcagctct caaccgcaac aggctttctc tggcgttcta cgcactcggg ggtgtcgtcg   6180
gtttggctgc tgaaattggg acctttgctg gtagattgtc tgaattgtct caagctcttt   6240
cgacatactg cttcttacct agggttcttg ctgtgactag ttatgttccc accatcatca   6300
ttggtggact ccataccctt ggtgtgatct tgtggctatt caaataccgg tgcctccaca   6360
acatgttagt tggtgatggg agtttttcaa gtgccttttt cctacggtat tttgcagagg   6420
gtaatctcag aaaaggtgtt tcacagtcct gtggcatgaa taacgagtcc ctgacagctg   6480
ctttagcttg caagttgtca caggctgacc ttgatttttt gtccagcttg acgaacttca   6540
agtgctttgt atctgcttca aacatgaaag atgctgctgg ccagtacatt gaggcagcgt   6600
atgccaaggc cctgcgccga gagttggcct ccctagtcca ggttgacaaa atgaaaggag   6660
ttttgtccaa gctcgaggcc tttgctgaaa cagccacccc gtcccttgac acaggtgacg   6720
tgattgtcct gcttgggcaa catcctcacg gatccatcct cgatattaat gtggggactg   6780
aaaggaaaac tgtgtctgtt caagagactc ggagcctagg cggctccaaa ttcagtgtct   6840
gcactgtcgt gtccaacaca cccgtggacg ccttggccgg cattccactt cagacaccaa   6900
ccccgctttt tgagaatggc ccgcgtcatc gcggtgagga agatgatctc aaagttgaga   6960
ggatgaagaa acattgtgtg tccctcggct tccacaacat caatggcaaa gtttactgta   7020
aagtttggga caagtccacc ggtgacacct tttacacgga tgattcccgg tacacccaag   7080
accatgcttt tcaggacagg tcagctgact atagagacag ggactatgag ggtgtgcaaa   7140
ccgcccccca acagggattt gatccaaaat ctgaaacccc tgttggcact gttgtaatcg   7200
gcggtattac gtataatarg tatctggtca aaggcaagga ggttctggtt cccaaacctg   7260
acaactgcct tgaagccgcc aagctgtccc tygagcaagc acttgctggg atgggccaaa   7320
```

-continued

```
cttgcgacct tacagttgcm gaggtggaaa agctaaagcg catcatcagt caactccaag   7380
gtttgaccac tgaacaggct ttaaactgct agccgccagc ggcttgaccc gctgtggccg   7440
cggcggcttg gttgtaactg aaacggcggt aaaaattata aaataccaca gcagaacttt   7500
cactttaggc cctttagacc taaaagtcac ttctgaggtr gaggtgaaga aatcaactga   7560
gcagggccac gccgttgtgg caaacctatg ttctggtgtc gtattgatga gacctcaccc   7620
accgtccctt gttgacgtcc ttctgaaacc cggacttgac acaacacccg acattcaacc   7680
ggggcatggg gccgggaata tggcgtgga cggttctatt tgggattttg aaaccgcacc    7740
cacaaaggca gaactcgagt tgtccaagca aataattcaa gcatgtgaag ttaggcgcgg   7800
agacgccccg aacctccaac tcccctacaa gctctatcct gtcagagggg atcctgagcg   7860
gcataaaggc cgccttatca acaccaggtt tggagacttg ccttacaaaa ctcctcaaga   7920
caccaagtcc gctatccatg cggcttgttg cctgcacccc aacggggccc ctgtgtctga   7980
tggtaaatcc acactaggca ccactcttca acatggtttc gagctttatg ttcccacagt   8040
gccctatagt gtcatggagt accttgattc acgccctgac acccctccca tgttcactaa   8100
acatggcact tccaaggctg ctgcagaaga cctccaaaaa tatgacctat ccacccaagg   8160
atttgtcctg cctggggtcc tacgcctagt gcgcagattc atctttggcc atgttggtaa   8220
ggcaccgcca ttgttcctcc catcaaccta tcccgccaag aactccatgg cagggattaa   8280
tggccagaga ttcccaacaa aggacgtcca gagcatacct gaaattgatg aaatgtgtgc   8340
ccgcgccgtc aaggagaatt ggcaaaccgt gacaccttgt actctcaaga aacagtactg   8400
ttccaagccc aaaaccagga ccatcctggg caccaacaac tttattgcct tggctcacag   8460
atcggcgctc agtggcgtca cccaggcatt catgaagaag gcttggaagt ccccaattgc   8520
cttggggaaa aacaagttca aggagctgca ttgtactgtc gccggcaggt gtcttgaggc   8580
tgacttggcc tcctgtgatc gcagcacccc cgccattgta agatggtttg ttgccaacct   8640
cctgtatgaa cttgcaggat gtgaagagta cttgcctagc tatgtgctta actgctgcca   8700
tgaccttgtg gcaacacagg atggtgcctt cacaaaacgc ggtggcctgt cgtccgggga   8760
ccccgtcacc agtgtgtcca ataccgtata ttcactggta atctatgccc agcacatggt   8820
attgtcagcc ttgaaaatgg gtcatgaaat tggtcttaag ttcctcgagg agcagctcaa   8880
attcgaggac ctccttgaaa ttcagcctat gttagtatac tctgacgacc ttgtcttgta   8940
cgctgaaaga cccacttttc ccaattacca ttggtgggtc gagcaccttg acctgatgct   9000
gggtttcaaa acggacccaa agaaaactgt cataactgat aaacccagct tcctcggctg   9060
caggattgag gcagggcgac agttagtccc caatcgcgac cgcatcctgg ctgcccttgc   9120
atatcacatg aaggcgcaga acgcctcaga atattatgcg tctgctgccg caatcctgat   9180
ggattcgtgt gcttgcattg accatgaccc tgagtggtat gaggacctca tctgtggtat   9240
tgcccggtgt gctcgccaag atggctatag tttcccgggc ccggcatttt tcatgtccat   9300
gtgggagaaa ctgaaaagtc ataatgaagg gaaaaaattc cgccactgcg gcatctgcga   9360
cgccaaggcc gaccatgcgt ccgcctgtgg actcgatttg tgcttgttcc actcgcattt   9420
tcatcagcac tgccctgtca ctctgagctg cggccatcat gccggttcta aggaatgtcc   9480
gcagtgtcag tcaccggttg gggctggtag atctcctctc gatgccgtgc taaaacaaat   9540
tccgtacaaa cctcctcgta ctgtcatcat gaaggtggat aataaaacaa cggcccttga   9600
tccggggagg tatcagtccc gtcgaggtct cgttgcagtc aagaggggta ttgcaggcaa   9660
```

-continued

```
tgaagttgac cttgctaatg gagactacca ggtggtgcct cttttgccga cttgcaaaga   9720
cataaacatg gtgaaggtgg cttgtaatgt gctactcagc aagttcatag tagggccacc   9780
aggttccgga aagaccacct ggttgctgag tcaagtccag gacgatgatg tcatttatac   9840
acccacccat cagactatgt ttgatatagt cagtgctctc aaagtttgca ggtattccat   9900
tccaggggct tcaggactcc ctttcccacc acctgccagg tccgggccgt gggtcaggct   9960
tgttgccagc gggcacgtcc ctggccgagt atcatacctc gatgaggctg gatattgtaa  10020
tcatctggac attctcagac tgctttccaa aacacccctt gtgtgtttag gtgaccttca  10080
gcaactccac cctgtcggct ttgattccta ctgttatgtg tttgatcaga tgcctcagaa  10140
gcagctgacc actatttaca gatttggctc caacatctgc gcagctatcc agccttgtta  10200
cagggagaaa cttgaatcca aggccaggaa caccaggata gtttttacca cccgacctgt  10260
agctttcggg caggtgctga caccatacca caaagatcgc atcggctcag cgataaccat  10320
agattcatct caggggggcca cctttgacat tgtgacattg catctaccat cgccaaagtc  10380
cctaaataaa tcccgagcac ttgtagccat cactcgggca agacacgggt tgttcatcta  10440
tgaccctcat aatcagctcc aggagttttt caacctaact cctgagcgca ctgattgtaa  10500
ccttgtgttt aaccgtgggg atgagctggt agttctggac gcggataatg cagtcacaac  10560
tgtggcgaag gccctagaga cgggtccatc tcgatttcga gtatcagacc caaggtgcga  10620
gtctctcttg gccgcttgct cggccagcct ggagggaagc tgcatgccac taccgcaagt  10680
ggcacataac ctggggtttt acttttcccc agatagtcca gcattcgcgc ctctgccaaa  10740
agaattggca ccacattggc cggtggttac ccatcagaat aaccgggcgt ggcctgaccg  10800
acttgttgct agtatgcgcc caattgatgc ccgttatagc aagccaatgg ttggtgcagg  10860
gtacgcggtc gggccgtcca cttttcttgg cactcctggt gtggtatcat actatctgac  10920
actgtacatc aggggtgagc cccaggcctt accagaaaca ctcgtgtcaa cagggcgcat  10980
agccacagat tgtcgggaat atctcgacgc cgctgaggaa gaggcagcaa aagaactccc  11040
tcacgcattc attggcgatg tcaaaggtac cacggttggg gggtgtcatc acatcacatc  11100
aaaataccta cctaggtccc tgcctaagga ctctgttgcc gtagttggag taagttcgcc  11160
cggcagggcc gctaaagccg tgtgcactct caccgatgtt tacctccccg agctccggcc  11220
atatctgcaa cctgagacgg catcaaaatg ctggaaactc aaattagact ttagagatgt  11280
ccgactaatg gtctggaaag gagccaccgc ctacttccag ctggaagggc ttacatggtc  11340
ggcgctgccc gactatgcca ggtttattca gctgcctaag gatgccgttg tgtacattga  11400
tccgtgcata ggaccggcaa cagccaaccg taaggtcgtg cggaccacag actggcgggc  11460
tgacctggca gtgacaccgt atgattacgg tgcccagaac attttgacaa cagcctggtt  11520
cgaggacctc gggccgcagt ggaagatttt ggggttgcag ccctttaggc gatcatttgg  11580
ctttgaaaac actgaggatt gggcaatcct tgcacgccgt atgaatgacg gcaaggacta  11640
cactgactat aactggaact gtgttcgaga acgcccacac gccatctacg ggcgcgctcg  11700
tgaccatacg tatcattttg cccccggcac agaattgcag gtagagctag gtaaaccccg  11760
gctgccgcct gagcaagtgc cgtgaatccg gagtgatgca atggggttac tgtggagtaa  11820
aattagccag ctgttcgtgg acgccttcac tgagttcctt gttagtgtgg ttgatattgt  11880
cattttcctt gccatactgt ttgggttcac cgtcgcagga tggttactgg tctttcttct  11940
cagagtggtt tgctccgcgc ttctccgttc gcgctctgcc attcactctc ccgaactatc  12000
gaaggtccta tgaaagcttg ctacccaatt gcagaccgga tgtcccacaa tttgcattca  12060
```

agcacccatt gggcatactt tggcacatgc gagtctccca cctaattgat gaaatggtct 12120
ctcgtcgcat ttaccggacc atggaacact caagtcaagc ggcctggaag caggtagtta 12180
gtgaggccac cctcacaaag ctgtcagggc ttgatatagt tactcatttc caacacctgg 12240
ccgcagtgga ggcggattct tgccgtttcc tcagctcacg acttgtgatg ctaaagaatc 12300
ttgccgttgg caatgtgagc ctacagtata acaccacgtt ggaccatgtt gagctcatct 12360
tccctacgcc aggtacgagg cccaagttga ccgatttcag acaatggctc atcagtgtgc 12420
acgcttccat tttttcctct gtggcttcat ctgttacctt gttcatagtg ttttggcttc 12480
gaattccagc cgtacgctat gtttttggtt tccattggcc cacggcaaca catcattcga 12540
gctaaccatc aactacacca tatgtatgcc ctgctctacc agccaagcgg ctagccaaag 12600
actcgagccc ggtcgtaaca tgtggtgcag aatagggcac gacaggtgtg aggaacgtga 12660
ccatgatgag ttgtcaatgt ccattccgtc agggtacgag aacctcaaac ttgagggtta 12720
ttatgcttgg ctggcctttt tgtccttttc ctacgcggcc caatttcatc cggagttgtt 12780
cggaatagga aacgtgtcgc gcgtctttgt ggacaagcga caccagttca tttgcgccga 12840
gcatgatgga caaaattcaa ccatatctac cggacacaac atctccgcat tatatgcggt 12900
gtattaccat caccaaatag acgggggcaa ttggttccat ttggaatggc tgcggccatt 12960
cttttcctcc tggctggtgc tcaatatctc atggtttctg aggcgttcgc ctgtaagccc 13020
tgtttctcga cgcatctatc agatattaag accaacacga ccgcggctgc cggtttcatg 13080
gtccttcagg acatcaattg tctccgacct cacggggtct caacagcgca agagamcatt 13140
yccttcggaa agccgtccca atgtcgcgag gccgtcggta ttccccagta cattacgata 13200
acggctaatg tgaccgatga atcgtatttg tacaacgcgg acttgctgat gctttctgcg 13260
tgccttttct acgcttcaga aatgagcgaa aagggcttca aagttatctt tgggaacgtc 13320
tctggcgttg tttctgcttg tgtcaatttt acagattatg tggctcatgt aatccaacat 13380
acccagcagc atcatctggt gattgatcac attcggttgc tgcatttcct gacaccatca 13440
acaatgaggt gggctacaac cattgcttgt ttgttcgcca ttctcttggc gatatgagat 13500
gttctcacaa attggagtgt ttcttgactc ctcactcttg cttctggtgg ctttttttgc 13560
tgtgtaccgg cttgtcttgg tcctttgtcg atggcaacga cagcagctcg acataccaat 13620
acatatataa tttgacgata tgcgagctga atgggaccga atcgttgtcc agccattttg 13680
actgggcagt cgagaccttt gtgctttacc cggttgccac tcatatcctt tcactgggtt 13740
ttctcacaac aagccatttt tttgatgcgc tcggtctcgg cgctgtgtcc actacaggat 13800
ttgttggcgg gcggtatgta ctcagcagcg tgtacggcgc ttgtgctttc gcagcgctcg 13860
tatgttttgt catccgcgct gctaaaaatt gcatggcttg ccgttatgcc cgtacccggt 13920
ttaccaactt cattgtggac gaccggggga ggatccatcg atggaagtct ccaatagtgg 13980
tagagaaatt gggcaaagct gaagtcggtg gcgacctcgt caccatcaaa catgtcgtcc 14040
tcgaaggggt taaagctcaa cccttgacga ggacttcggc tgagcaatgg gaagcctaga 14100
cgatttttgc aacgatccta ccgccgcaca aaagcttgtg ctagccttta gcatcacata 14160
tacacctata atgatatacg cccttaaggt gtcacgcggc cgcctcctgg ggctattgca 14220
catcttgata ttcctgaact gttcctttac attcggatac atgacatatg tgcattttca 14280
atccaccaac cgtgtcgcat ttactctggg ggccgttgtc gcccttctgt ggggtgttta 14340
cagcttcaca gagtcatgga agttcattac ttccagatgc agattgtgtt gcctaggccg 14400

-continued gcratacatt ctggcccctg cccatcacgt agaaagtgct gcaggtctcc attcaatccc 14460
agcgtctggt aaccgagcat acgctgtgag aaagcccgga ctaacatcag tgaacggcac 14520
tctagtacca ggacttcgga gcctcgtgct gggcggcaaa cgagctgtta aacgaggagt 14580
ggttaacctc gtcaagtatg gccggtaaaa atcagagcca gaagaaaaag aagaatacag 14640
ctccgatggg gaatggccag ccagtcaatc aactgtgcca gttgctgggt gcaatgataa 14700
agtcccagcg ccagcaacct aggggaggac aggcaaaaaa aagaaagcct gagaagccac 14760
attttcccct agctgctgaa gatgacattc ggcaccacct cacccagacc gaacgttccc 14820
tctgcttgca atcgatccag acggctttta aycaaggcgc aggaactgcg tcgctttcat 14880
ccagcgggaa ggtcagtttt caggttgagt tcatgctgcc ggttgctcat acagtgcgcc 14940
tgattcgcgt gacttctaca tccgccagtc agggtgcaaa ttaatttgac agtcaggtga 15000
atggccgcga ttgacgtgtg gcctctaagt cacctattca attagggcga tcacatgggg 15060
gtcaaactta atcaggcagg aaccatgtga ccgaaatyaa aaaaaaaaaa aaaaaaaaaa 15120
aaaaaaaaaa aa 15132

<210> SEQ ID NO 2
<211> LENGTH: 15145
<212> TYPE: DNA
<213> ORGANISM: Artificial Sequence
<220> FEATURE:
<223> OTHER INFORMATION: PRRSV genome in clone pVAC-T7-5

<400> SEQUENCE: 2
atgatgtgta gggtactccc cctacataca cgacacttct agtgtttgtg tgccttggag 60
gcgtgggtat agccccgccc caccccttgg cccctgttct agcccaacag gtatccttct 120
ctctcggggc gagcgcgccg cctgctgctc ccttgcagcg ggaaggacct cccgagtatt 180
tccggagagc acctgcttta cgggatctcc accctttaac catgtctggg acgttctccc 240
ggtgcatgtg caccccggct gcccgggtat tttggaacgc cggccaagtc ttttgcacac 300
ggtgtctcag tgcgcggtct cttctccctc cggagcttca ggaaactgac ctcgctgcaa 360
ttggcttgtt ttacaagcct aaagacaagc ttcactggaa agtccctatc ggcatccctc 420
aggtggagtg cactccatcc gggtgctgtt ggctctcagc catcttccca ttggcgcgca 480
tgacctccgg caatcacaac ttcctccaac gacttgtgag ggttgccgat gtgttgtacc 540
gtgatggttg cttggctcct cgacaccttc gtgaactcca agtttacgag cgcggctgca 600
actggtaccc gatcacgggg cccgtgcccg ggatgggttt gttcgcaaac tccatgcacg 660
tatccgacca gccgttccct ggtgccaccc atgtgttgac gaactcgccg ttgcctcaac 720
aggcttgtcg gcagccgttc tgtccatttg aggaggctca ttctagtgtg tacaggtgga 780
aaagatttgt ggttttcacg gattcctctc ccaacggtcg atctcgcatg atgtggacgc 840
cggaatccga tgattcagcc gccttggagg tattaccgcc tgaattagaa cgtcaggtcg 900
aaatcctcat tcggagtttt cctgctcatc accctgtcaa cctggccgac tgggagctca 960
ctgagtcccc tgagaacggt tttccttca acacgtctta ttcttgcggt caccttgtcc 1020
aaaaccccga cgtgtttgat ggcaagtgct ggctttcctg ctttttgggc cagtcggccg 1080
aagtgcgccg ccatgaggaa catttagctg acgccctcgg ttaccagacc aagtggggcg 1140
tgcctggcaa gtacctccag cgcaggcttc aggttcgcgg cattcgtgct gtagttgatc 1200
ctgatggccc cattcacgtc gaagcgctgt cttgcccccg gtcttggatc aggcacctga 1260
cttttgatga taatgtcacc ccaggatttg ttcgccttac gtcccttcgc attgtgccaa 1320

-continued

```
acaccgagcc tactgcttcc cggatcttcc ggtttggagc gcataagtgg tatggcgctg   1380
ccggcaaacg agctcgtgct aagcgtgccg ctaaaagtga gaaaatttcg gcccctaccc   1440
ccaaggttgc tcagccggtc cccacctgcg aaattaccac ctattctcca ccgacagacg   1500
ggtcttgtgg ttggcatgtt cttgccgcca taatgaaccg gatgatgaat ggtgacttca   1560
cgtcccctct gactcagtac aacagaccag aggatgactg ggcttctgat tatgaccttg   1620
ctcaggcgat ccaatgtctg caactgcccg ctaccgtagt tcggaatcgc gcctgtccta   1680
acgccaagta ccttataaaa cttaatggag ttcattggga ggtagaggtg aggcctggaa   1740
tggcccctcg ttccctttcc cgtgagtgtg tggttggcgt ctgttctgaa ggctgtatcg   1800
caccgcctta cccacaagac gggctgccta aacgtgcact tgaggccttg gcgtctgctt   1860
acagactacc ctccgactgt gttggttctg gtattgctga ctttcttgct aacccgcccc   1920
ctcaggagtt ttggaccctt gacaaaatgt tgacctcccc gtcaccagaa cggtccggct   1980
tctctagctt gtataaatta ctattggagg ttgttccgca gaaatgcggt gccacggaag   2040
gggctttcgt ctatgctgtt gagaggatgt tgaaggattg tccgagctcc aaacaggcca   2100
tggcccttct ggcaaaaatt aaagtcccat cctcaaaggc cccgtctgtg tctctggacg   2160
agtgcttccc tacggatgtt ccagcggact ccgagccagc gtttcaggaa aggccccaaa   2220
gttctggtgc tgctgttgtc ctgtgttcac cggacataaa agagttcgag gaagcagccc   2280
cagaagaagt tcaagagggt ggccacaagg ccgtccactc tgcactcctt gccgagggtc   2340
ttaacaatga gcaggtacag gtggttgccg gtgcgcaact aaagctcggc agttgtggct   2400
tggcagtcgg gaatactcat ggaggtgttc cggtttcagc tagtccaatt aacctggcag   2460
acgggaattt gcccccctcg gactccatga aaggaaacat gcccaatggc tgggaggacg   2520
aaccactgga tttgtcccaa tcagcactag caaccacaac gacccttgtg agagagcaaa   2580
cacccgacaa tctaggttct ggcgccggtg ccctccctgt caccattcga gaatttgtcc   2640
cgacaaggcc tataccccgt catgttgagc actgcggcac ggagtcgggc gacagcagtt   2700
cgcctctgga tctgtccgat gcgcaaaccc cggaccagcc tttaaatcta tccctggccg   2760
cttggccagt gagggccacc gcgtctgacc ccggctgggt ccacggtagg cgtgagcctg   2820
tttttgtaaa gcctcggggt gctttctctg atggcgattc agtccttcag ttcggggagc   2880
tttccgaatc cagctctatc atcgagattg accggacaaa agatgctcca gtggttgatg   2940
cccccgtcga cttgacggtt tcgaacgaag ctctctctgg gatcgatcct tttgaatttg   3000
ccgaactcaa gcgcccgcgt ttctccgctc aagccttaat tgaccgaggc ggcccactag   3060
ccgatgtcca tgcaaaaata aagaaccggg tatatgaaca gtgcctccag gcttgtgagc   3120
ctggcagtcg tgcaacccca gccaccaggg agtggctcga caaaatgtgg gatagggtgg   3180
acatgaagac ttggcgctgc acctcgcagt tccaagctgg tcacattctt gcgtccctca   3240
aattcctccc cgacatgatt caagacacac cgcctcctgt tcccaggaag agccgggcta   3300
gtgataatgc cggcctgaag caactggtgg cgcagtggga cagaaaattg agtgtaaccc   3360
ccccccctaaa accggttggg ccggcgcttg gccaaaccgt ccctccgcct acggatattc   3420
agcaagaaga tgtcaccccc tccgataggc cacctcatgt gccggatctt cctagtcgag   3480
tgagcacggg tgggagttgg aaaggcctta tgctttccgg cacccgtctc gcggggtcta   3540
ttagtcagca cctcatgaca tgggtttttg aagttttctc ccatctccca gcttttatgc   3600
tcacactttt ctcgccacgg ggctctatgg ctccaggtga ttggctattt gcaggtgttg   3660
```

-continued

```
ttttacttgc tctcctgctc tgtcgttctt acccagtact cgggtgcctt cccttattgg   3720
gtgtcttttc tggttctttg cggcgtgttc gtctgggtgt ttttggttct tggatggctt   3780
ttgctgtatt tttattctcg actccatccg acccagtcgg ttcttcttgt gaccacgatt   3840
cgccggagtg tcatgctgag cttttggctc ttgagcagcg ccaactttgg gaacctgtgc   3900
gcggccttgt ggtcggcccc tcgggtctct tatgtgtcat tcttggcaag ttactcggtg   3960
ggtcacgtta tctctggcat gtttttcttac gtttatgcat gcttgcggat ttggcccttt   4020
ctcttgttta tgtggtgtcc caggggcgtt gtcacaagtg ttggggaaag tgtataagga   4080
cagctcctgc ggaggtggct ctcaatgtgt tccctttctt gcgcgctacc cgtgcctctc   4140
ttgtgtcctt gtgcgatcga ttccaagcgc caaaaggggt tgatcctgtg cacttggcaa   4200
caggttggcg cgggtgctgg cgcggtgaga gccccattca tcaaccgcac caaaagccca   4260
tagcttatgc caatttggat gaaaagaaaa tatctgccca aacggtggtt gctgtcccgt   4320
atgatcccag tcaggccatc aaatgcctga aagttctgca ggcgggaggg gctatcgtgg   4380
accagcccac acctgaggtc gtccgtgtgt ccgagatccc tttctcagcc ccattttttc   4440
caaaggttcc agtcaaccca gattgcaggg ttgtggtaga ttcggacact tttgtggctg   4500
cagttcgctg cggttactcg acggctcaac tggtcttagg ccggggcaac tttgccaagt   4560
taaatcagat cccctccagg aactctgtct ccaccaaaac gactggtggg gcctcttaca   4620
cccttgctgt ggctcaagtg tctgtgtgga ctcttgttca tttcatcctc ggtctttggt   4680
tcacgtcacc tcaagtgtgt ggccgaggaa cctctgaccc atggtgttca aatccttttt   4740
catatcctac ctatggcccc ggaatagtgt gctcctctcg actttgtgtg tctgccgacg   4800
gagtcactct gccattgttc tcagcagtgg cacaactctc cggtagagag gtggggattt   4860
tcattttggt gctcgtctcc ttgactgctc tggcccaccg tatggctctt aaggcagaca   4920
tgttagtggt cttttcggct tttgtgcttt acgcctggcc catgagctcc tggttaatct   4980
gcttctttcc tatattcttg aagtgggtca cccttcaccc tctcactatg ctttgggtgc   5040
actcattctt ggtgttttgt ctgccagcag ccggcgtcct ctcactaggg ataaccggcc   5100
ttctctgggc agttggccgc tttacccagg tcgccggaat tattacacct tatgacatcc   5160
accagtacac ctctgggcca cgtggtgcag ccgctgtggc cacggcccca gaaggcactt   5220
acatggccgc cgtccggaga gctgccttaa ctggacgaac cctcatcttc acaccatctg   5280
cggttggatc ccttcttgaa ggtgctttca ggacccataa accctgcctt aacaccgtga   5340
atgttgtagg ctcttccctt ggttccgggg gggttttcac cattgatggc agaagaactg   5400
ttgtcactgc tgcccatgtg ttgaacggcg acacagctag agtcaccggc gactcctaca   5460
accgcatgca cactttcaag accaatggtg attatgcctg gtcccatgct gatgactggc   5520
ggggcgttgc ccctgtggtc aaggtcgcga aggggtaccg cggtcgtgcc tactggcaaa   5580
catcaactgg tgtcgaaccc ggtattgttg gggaagggtt cgccttctgt tttaccaact   5640
gtggcgattc ggggtcacct gtcatctcag aatctggtga tcttgttgga atccacaccg   5700
gttcaaacaa actcggttct ggtcttgtga caacccctga aggggagacc tgctccatca   5760
aagaaaccaa gctctctgac ctttccaggt attttgcagg cccaagcgtc cctcttgggg   5820
atattaaatt gagtccggcc atcatccctg atgtaacatc cattccgagt gacttggcat   5880
cgctcctagc ctccgtccct gtaatggaag gcggcctctc gactgtccaa cttttgtgtg   5940
tctttttcct tctctggcgt atgatgggcc atgcctggac acccattgtt gccgtgggct   6000
tctttttgct gaatgaaatt cttccagcag ttttggtccg agccgtgttt tcttttgcgc   6060
```

-continued

```
tctttgtgct tgcatgggcc acccccctggt ctgcacaggt gttgatgatc agactcctca   6120

cggcagctct caaccgcaac aggctttctc tggcgttcta cgcactcggg ggtgtcgtcg   6180

gtttggctgc tgaaattggg acctttgctg gtagattgtc tgaattgtct caagctcttt   6240

cgacatactg cttcttacct agggttcttg ctgtgactag ttatgttccc accatcatca   6300

ttggtggact ccataccctt ggtgtgatct tgtggctatt caaataccgg tgcctccaca   6360

acatgttagt tggtgatggg agtttttcaa gtgccttttt cctacggtat tttgcagagg   6420

gtaatctcag aaaaggtgtt tcacagtcct gtggcatgaa taacgagtcc ctgacagctg   6480

ctttagcttg caagttgtca caggctgacc ttgatttttt gtccagcttg acgaacttca   6540

agtgctttgt atctgcttca aacatgaaag atgctgctgg ccagtacatt gaggcagcgt   6600

atgccaaggc cctgcgccga gagttggcct ccctagtcca ggttgacaaa atgaaaggag   6660

ttttgtccaa gctcgaggcc tttgctgaaa cagccacccc gtcccttgac acaggtgacg   6720

tgattgtcct gcttgggcaa catcctcacg gatccatcct cgatattaat gtggggactg   6780

aaaggaaaac tgtgtctgtt caagagactc ggagcctagg cggctccaaa ttcagtgtct   6840

gcactgtcgt gtccaacaca cccgtggacg ccttggccgg cattccactt cagacaccaa   6900

ccccgctttt tgagaatggc ccgcgtcatc gcggtgagga agatgatctc aaagttgaga   6960

ggatgaagaa acattgtgtg tccctcggct tccacaacat caatggcaaa gtttactgta   7020

aagtttggga caagtccacc ggtgacacct tttacacgga tgattcccgg tacacccaag   7080

accatgcttt tcaggacagg tcagctgact atagagacag ggactatgag ggtgtgcaaa   7140

ccgcccccca acagggattt gatccaaaat ctgaaacccc tgttggcact gttgtaatcg   7200

gcggtattac gtataataag tatctggtca aaggcaagga ggttctggtt cccaaacctg   7260

acaactgcct tgaagccgcc aagctgtccc tcgagcaagc acttgctggg atgggccaaa   7320

cttgcgacct tacagttgcc gaggtggaaa agctaaagcg catcatcagt caactccaag   7380

gtttgaccac tgaacaggct ttaaactgct agccgccagc ggcttgaccc gctgtggccg   7440

cggcggcttg gttgtaactg aaacggcggt aaaaattata aaataccaca gcagaacttt   7500

cactttaggc cctttagacc taaaagtcac ttctgaggta gaggtgaaga aatcaactga   7560

gcagggccac gccgttgtgg caaacctatg ttctggtgtc gtattgatga gacctcaccc   7620

accgtccctt gttgacgtcc ttctgaaacc cggacttgac acaacacccg acattcaacc   7680

ggggcatggg gccgggaata tgggcgtgga cggttctatt tgggattttg aaaccgcacc   7740

cacaaaggca gaactcgagt tgtccaagca aataattcaa gcatgtgaag ttaggcgcgg   7800

agacgccccg aacctccaac tcccctacaa gctctatcct gtcagagggg atcctgagcg   7860

gcataaaggc cgccttatca acaccaggtt tggagacttg ccttacaaaa ctcctcaaga   7920

caccaagtcc gctatccatg cggcttgttg cctgcacccc aacggggccc ctgtgtctga   7980

tggtaaatcc acactaggca ccactcttca acatggtttc gagctttatg ttcccacagt   8040

gccctatagt gtcatggagt accttgattc acgccctgac acccctccca tgttcactaa   8100

acatggcact tccaaggctg ctgcagaaga cctccaaaaa tatgacctat ccacccaagg   8160

atttgtcctg cctggggtcc tacgcctagt gcgcagattc atctttggcc atgttggtaa   8220

ggcaccgcca ttgttcctcc catcaaccta tcccgccaag aactccatgg cagggattaa   8280

tggccagaga ttcccaacaa aggacgtcca gagcatacct gaaattgatg aaatgtgtgc   8340

ccgcgccgtc aaggagaatt ggcaaaccgt gacaccttgt actctcaaga aacagtactg   8400
```

-continued

```
ttccaagccc aaaaccagga ccatcctggg caccaacaac tttattgcct tggctcacag   8460
atcggcgctc agtggcgtca cccaggcatt catgaagaag gcttggaagt ccccaattgc   8520
cttggggaaa aacaagttca aggagctgca ttgtactgtc gccggcaggt gtcttgaggc   8580
tgacttggcc tcctgtgatc gcagcacccc cgccattgta agatggtttg ttgccaacct   8640
cctgtatgaa cttgcaggat gtgaagagta cttgcctagc tatgtgctta actgctgcca   8700
tgaccttgtg gcaacacagg atggtgcctt cacaaaacgc ggtggcctgt cgtccgggga   8760
ccccgtcacc agtgtgtcca ataccgtata ttcactggta atctatgccc agcacatggt   8820
attgtcagcc ttgaaaatgg gtcatgaaat tggtcttaag ttcctcgagg agcagctcaa   8880
attcgaggac ctccttgaaa ttcagcctat gttagtatac tctgacgacc ttgtcttgta   8940
cgctgaaaga cccacttttc ccaattacca ttggtgggtc gagcaccttg acctgatgct   9000
gggtttcaaa acggacccaa agaaaactgt cataactgat aaacccagct tcctcggctg   9060
caggattgag gcagggcgac agttagtccc caatcgcgac cgcatcctgg ctgcccttgc   9120
atatcacatg aaggcgcaga acgcctcaga atattatgcg tctgctgccg caatcctgat   9180
ggattcgtgt gcttgcattg accatgaccc tgagtggtat gaggacctca tctgtggtat   9240
tgcccggtgt gctcgccaag atggctatag tttcccgggc ccggcatttt tcatgtccat   9300
gtgggagaaa ctgaaaagtc ataatgaagg gaaaaaattc cgccactgcg gcatctgcga   9360
cgccaaggcc gaccatgcgt ccgcctgtgg actcgatttg tgcttgttcc actcgcattt   9420
tcatcagcac tgccctgtca ctctgagctg cggccatcat gccggttcta aggaatgtcc   9480
gcagtgtcag tcaccggttg ggctggtag atctcctctc gatgccgtgc taaaacaaat    9540
tccgtacaaa cctcctcgta ctgtcatcat gaaggtggat aataaaacaa cggcccttga   9600
tccggggagg tatcagtccc gtcgaggtct cgttgcagtc aagaggggta ttgcaggcaa   9660
tgaagttgac cttgctaatg gagactacca ggtggtgcct cttttgccga cttgcaaaga   9720
cataaacatg gtgaaggtgg cttgtaatgt gctactcagc aagttcatag tagggccacc   9780
aggttccgga aagaccacct ggttgctgag tcaagtccag gacgatgatg tcatttatac   9840
acccacccat cagactatgt ttgatatagt cagtgctctc aaagtttgca ggtattccat   9900
tccaggggct tcaggactcc ctttcccacc acctgccagg tccgggccgt gggtcaggct   9960
tgttgccagc gggcacgtcc ctggccgagt atcatacctc gatgaggctg gatattgtaa  10020
tcatctggac attctcagac tgctttccaa aacacccctt gtgtgtttag gtgaccttca  10080
gcaactccac cctgtcggct ttgattccta ctgttatgtg tttgatcaga tgcctcagaa  10140
gcagctgacc actatttaca gatttggctc caacatctgc gcagctatcc agccttgtta  10200
cagggagaaa cttgaatcca aggccaggaa caccaggata gtttttacca cccgacctgt  10260
agctttcggg caggtgctga caccatacca caaagatcgc atcggctcag cgataaccat  10320
agattcatct caggggggcca cctttgacat tgtgacattg catctaccat cgccaaagtc  10380
cctaaataaa tcccgagcac ttgtagccat cactcgggca agacacgggt tgttcatcta  10440
tgaccctcat aatcagctcc aggagttttt caacctaact cctgagcgca ctgattgtaa  10500
ccttgtgttt aaccgtgggg atgagctggt agttctggac gcggataatg cagtcacaac  10560
tgtggcgaag gccctagaga cgggtccatc tcgatttcga gtatcagacc caaggtgcga  10620
gtctctcttg gccgcttgct cggccagcct ggagggaagc tgcatgccac taccgcaagt  10680
ggcacataac ctggggtttt acttttcccc agatagtcca gcattcgcgc ctctgccaaa  10740
agaattggca ccacattggc cggtggttac ccatcagaat aaccgggcgt ggcctgaccg  10800
```

```
acttgttgct agtatgcgcc caattgatgc ccgttatagc aagccaatgg ttggtgcagg  10860
gtacgcggtc gggccgtcca cttttcttgg cactcctggt gtggtatcat actatctgac  10920
actgtacatc aggggtgagc cccaggcctt accagaaaca ctcgtgtcaa cagggcgcat  10980
agccacagat tgtcgggaat atctcgacgc cgctgaggaa gaggcagcaa aagaactccc  11040
tcacgcattc attggcgatg tcaaaggtac cacggttggg gggtgtcatc acatcacatc  11100
aaaataccta cctaggtccc tgcctaagga ctctgttgcc gtagttggag taagttcgcc  11160
cggcagggcc gctaaagccg tgtgcactct caccgatgtt tacctccccg agctccggcc  11220
atatctgcaa cctgagacgg catcaaaatg ctggaaactc aaattagact ttagagatgt  11280
ccgactaatg gtctggaaag gagccaccgc ctacttccag ctggaagggc ttacatggtc  11340
ggcgctgccc gactatgcca ggtttattca gctgcctaag gatgccgttg tgtacattga  11400
tccgtgcata ggaccggcaa cagccaaccg taaggtcgtg cggaccacag actggcgggc  11460
tgacctggca gtgacaccgt atgattacgg tgcccagaac attttgacaa cagcctggtt  11520
cgaggacctc gggccgcagt ggaagatttt ggggttgcag ccctttaggc gatcatttgg  11580
ctttgaaaac actgaggatt gggcaatcct tgcacgccgt atgaatgacg gcaaggacta  11640
cactgactat aactggaact gtgttcgaga acgcccacac gccatctacg ggcgcgctcg  11700
tgaccatacg tatcattttg cccccggcac agaattgcag gtagagctag gtaaaccccg  11760
gctgccgcct gagcaagtgc cgtgaatccg gagtgatgca atggggttac tgtggagtaa  11820
aattagccag ctgttcgtgg acgccttcac tgagttcctt gttagtgtgg ttgatattgt  11880
cattttcctt gccatactgt ttgggttcac cgtcgcagga tggttactgg tctttcttct  11940
cagagtggtt tgctccgcgc ttctccgttc gcgctctgcc attcactctc ccgaactatc  12000
gaaggtccta tgaaagcttg ctacccaatt gcagaccgga tgtcccacaa tttgcattca  12060
agcacccatt gggcatactt tggcacatgc gagtctccca cctaattgat gaaatggtct  12120
ctcgtcgcat ttaccggacc atggaacact caagtcaagc ggcctggaag caggtagtta  12180
gtgaggccac cctcacaaag ctgtcagggc ttgatatagt tactcatttc caacacctgg  12240
ccgcagtgga ggcggattct tgccgtttcc tcagctcacg acttgtgatg ctaaagaatc  12300
ttgccgttgg caatgtgagc ctacagtata acaccacgtt ggaccatgtt gagctcatct  12360
tccctacgcc aggtacgagg cccaagttga ccgatttcag acaatggctc atcagtgtgc  12420
acgcttccat tttttcctct gtggcttcat ctgttacctt gttcatagtg ttttggcttc  12480
gaattccagc cgtacgctat gtttttggtt tccattggcc cacggcaaca catcattcga  12540
gctaaccatc aactacacca tatgtatgcc ctgctctacc agccaagcgg ctagccaaag  12600
actcgagccc ggtcgtaaca tgtggtgcag aatagggcac gacaggtgtg aggaacgtga  12660
ccatgatgag ttgtcaatgt ccattccgtc agggtacgag aacctcaaac ttgagggtta  12720
ttatgcttgg ctggcctttt tgtccttttc ctacgcggcc caatttcatc cggagttgtt  12780
cggaatagga aacgtgtcgc gcgtctttgt ggacaagcga caccagttca tttgcgccga  12840
gcatgatgga caaaattcaa ccatatctac cggacacaac atctccgcat tatatgcggt  12900
gtattaccat caccaaatag acgggggcaa ttggttccat ttggaatggc tgcggccatt  12960
cttttcctcc tggctggtgc tcaatatctc atggtttctg aggcgttcgc ctgtaagccc  13020
tgtttctcga cgcatctatc agatattaag accaacacga ccgcggctgc cggtttcatg  13080
gtccttcagg acatcaattg tctccgacct cacggggtct caacagcgca agagaacatt  13140
```

-continued cccttcggaa agccgtccca atgtcgcgag gctgtcggta ttccccagta cattacgata 13200
acggctaatg tgaccgatga atcgtatttg tacaacgcgg acttgctgat gctttctgcg 13260
tgccttttct acgcttcaga aatgagcgaa aagggcttca aagttatctt tgggaacgtc 13320
tctggcgttg tttctgcttg tgtcaatttt acagattatg tggctcatgt aatccaacat 13380
acccagcagc atcatctggt gattgatcac attcggttgc tgcatttcct gacaccatca 13440
acaatgaggt gggctacaac cattgcttgt ttgttcgcca ttctcttggc gatatgagat 13500
gttctcacaa attggagtgt ttcttgactc ctcactcttg cttctggtgg cttttttttgc 13560 tgtgtaccgg cttgtcttgg tcctttgtcg atggcaacga cagcagctcg acataccaat 13620
acatatataa tttgacgata tgcgagctga atgggaccga atcgttgtcc agccattttg 13680
actgggcagt cgagaccttt gtgctttacc cggttgccac tcatatcctt tcactgggtt 13740
ttctcacaac aagccatttt tttgatgcgc tcggtctcgg cgctgtgtcc actacaggat 13800
ttgttggcgg gcggtatgta ctcagcagcg tgtacggcgc ttgtgctttc gcagcgctcg 13860
tatgttttgt catccgcgct gctaaaaatt gcatggcttg ccgttatgcc cgtacccggt 13920
tcaccaactt cattgtggac gaccggggga ggatccatcg atggaagtct ccaatagtgg 13980
tagagaaatt gggcaaagct gaagtcggtg gcgacctcgt caccatcaaa catgtcgtcc 14040
tcgaaggggt taaagctcaa cccttgacga ggacttcggc tgagcaatgg gaagcctaga 14100
cgatttttgc aacgatccta ccgccgcaca aaagcttgtg ctagccttta gcatcacata 14160
tacacctata atgatatacg cccttaaggt gtcacgcggc cgcctcctgg ggctattgca 14220
catcttgata ttcctgaact gttcctttac attcggatac atgacatatg tgcattttca 14280
atccaccaac cgtgtcgcat ttactctggg ggccgttgtc gcccttctgt ggggtgttta 14340
cagcttcaca gagtcatgga agttcattac ttccagatgc agattgtgtt gcctaggccg 14400
gcaatacatt ctggcccctg cccatcacgt agaaagtgct gcaggtctcc attcaatccc 14460
agcgtctggt aaccgagcat acgctgtgag aaagcccgga ctaacatcag tgaacggcac 14520
tctagtacca ggacttcgga gcctcgtgct gggcggcaaa cgagctgtta aacgaggagt 14580
ggttaacctc gtcaagtatg gccggtaaaa atcagagcca gaagaaaaag aagaatacag 14640
ctccgatggg gaatggccag ccagtcaatc aactgtgcca gttgctgggt gcaatgataa 14700
agtcccagcg ccagcaacct aggggaggac aggcaaaaaa aagaaagcct gagaagccac 14760
attttcccct agctgctgaa gatgacattc ggcaccacct cacccagacc gaacgttccc 14820
tctgcttgca atcgatccag acggctttta accaaggcgc aggaactgcg tcgctttcat 14880
ccagcgggaa ggtcagtttt caggttgagt tcatgctgcc ggttgctcat acagtgcgcc 14940
tgattcgcgt gacttctaca tccgccagtc agggtgcaaa ttaatttgac agtcaggtga 15000
atggccgcga ttgacgtgtg gcctctaagt cacctattca attagggcga tcacatgggg 15060
gtcaaactta atcaggcagg aaccatgtga ccgaaatcaa aaaaaaaaaa aaaaaaaaaa 15120
aaaaaaaaaa aaaaaaaaat ctaga 15145

<210> SEQ ID NO 3
<211> LENGTH: 15917
<212> TYPE: DNA
<213> ORGANISM: Artificial Sequence
<220> FEATURE:
<223> OTHER INFORMATION: Clone pVAC 5.0

<400> SEQUENCE: 3

```
ggctgtggca caggctgaac gccggaggat ccggcgcgcc atgcattagt tattaatagt      60
aatcaattac ggggtcatta gttcatagcc catatatgga gttccgcgtt acataactta     120
cggtaaatgg cccgcctggc tgaccgccca acgacccccg cccattgacg tcaataatga     180
cgtatgttcc catagtaacg ccaataggga ctttccattg acgtcaatgg gtggagtatt     240
tacggtaaac tgcccacttg gcagtacatc aagtgtatca tatgccaagt acgcccccta     300
ttgacgtcaa tgacggtaaa tggcccgcct ggcattatgc ccagtacatg accttatggg     360
actttcctac ttggcagtac atctacgtat tagtcatcgc tattaccatg gtgatgcggt     420
tttggcagta catcaatggg cgtggatagc ggtttgactc acggggattt ccaagtctcc     480
accccattga cgtcaatggg agtttgtttt ggcaccaaaa tcaacgggac tttccaaaat     540
gtcgtaacaa ctccgcccca ttgacgcaaa tgggcggtag gcgtgtacgg tgggaggtct     600
atataagcag agctggttta gtatttaaat atgatgtgta gggtactccc cctacataca     660
cgacacttct agtgtttgtg tgccttggag gcgtgggtat agccccgccc caccccttgg     720
cccctgttct agcccaacag gtatccttct ctctcggggc gagcgcgccg cctgctgctc     780
ccttgcagcg ggaaggacct cccgagtatt tccggagagc acctgcttta cgggatctcc     840
accctttaac catgtctggg acgttctccc ggtgcatgtg caccccggct gcccgggtat     900
tttggaacgc cggccaagtc ttttgcacac ggtgtctcag tgcgcggtct cttctccctc     960
cggagcttca ggaaactgac ctcgctgcaa ttggcttgtt ttacaagcct aaagacaagc    1020
ttcactggaa agtccctatc ggcatccctc aggtggagtg cactccatcc gggtgctgtt    1080
ggctctcagc catcttccca ttggcgcgca tgacctccgg caatcacaac ttcctccaac    1140
gacttgtgag ggttgccgat gtgttgtacc gtgatggttg cttggctcct cgacaccttc    1200
gtgaactcca agtttacgag cgcggctgca actggtaccc gatcacgggg cccgtgcccg    1260
ggatgggttt gttcgcaaac tccatgcacg tatccgacca gccgttccct ggtgccaccc    1320
atgtgttgac gaactcgccg ttgcctcaac aggcttgtcg gcagccgttc tgtccatttg    1380
aggaggctca ttctagtgtg tacaggtgga aaagatttgt ggttttcacg gattcctctc    1440
ccaacggtcg atctcgcatg atgtggacgc cggaatccga tgattcagcc gccttggagg    1500
tattaccgcc tgaattagaa cgtcaggtcg aaatcctcat tcggagtttt cctgctcatc    1560
accctgtcaa cctggccgac tgggagctca ctgagtcccc tgagaacggt tttccttca     1620
acacgtctta ttcttgcggt caccttgtcc aaaaccccga cgtgtttgat ggcaagtgct    1680
ggctttcctg ctttttgggc cagtcggccg aagtgcgccg ccatgaggaa catttagctg    1740
acgccctcgg ttaccagacc aagtggggcg tgcctggcaa gtacctccag cgcaggcttc    1800
aggttcgcgg cattcgtgct gtagttgatc ctgatggccc cattcacgtc gaagcgctgt    1860
cttgcccccg gtcttggatc aggcacctga cttttgatga taatgtcacc ccaggatttg    1920
ttcgccttac gtcccttcgc attgtgccaa acaccgagcc tactgcttcc cggatcttcc    1980
ggtttggagc gcataagtgg tatggcgctg ccggcaaacg agctcgtgct aagcgtgccg    2040
ctaaaagtga gaaaatttcg gcccctaccc ccaaggttgc tcagccggtc cccacctgcg    2100
aaattaccac ctattctcca ccgacagacg ggtcttgtgg ttggcatgtt cttgccgcca    2160
taatgaaccg gatgatgaat ggtgacttca cgtcccctct gactcagtac aacagaccag    2220
aggatgactg ggcttctgat tatgaccttg ctcaggcgat ccaatgtctg caactgcccg    2280
```

```
ctaccgtagt tcggaatcgc gcctgtccta acgccaagta ccttataaaa cttaatggag   2340
ttcattggga ggtagaggtg aggcctggaa tggcccctcg ttccctttcc cgtgagtgtg   2400
tggttggcgt ctgttctgaa ggctgtatcg caccgcctta cccacaagac gggctgccta   2460
aacgtgcact tgaggccttg gcgtctgctt acagactacc ctccgactgt gttggttctg   2520
gtattgctga ctttcttgct aacccgcccc ctcaggagtt ttggaccctt gacaaaatgt   2580
tgacctcccc gtcaccagaa cggtccggct tctctagctt gtataaatta ctattggagg   2640
ttgttccgca gaaatgcggt gccacggaag ggctttcgt  ctatgctgtt gagaggatgt   2700
tgaaggattg tccgagctcc aaacaggcca tggcccttct ggcaaaaatt aaagtcccat   2760
cctcaaaggc cccgtctgtg tctctggacg agtgcttccc tacggatgtt ccagcggact   2820
ccgagccagc gtttcaggaa aggccccaaa gttctggtgc tgctgttgtc ctgtgttcac   2880
cggacataaa agagttcgag gaagcagccc cagaagaagt tcaagagggt ggccacaagg   2940
ccgtccactc tgcactcctt gccgagggtc ttaacaatga gcaggtacag gtggttgccg   3000
gtgcgcaact aaagctcggc agttgtggct tggcagtcgg gaatactcat ggaggtgttc   3060
cggtttcagc tagtccaatt aacctggcag acgggaattt gcccccctcg gactccatga   3120
aaggaaacat gcccaatggc tgggaggacg aaccactgga tttgtcccaa tcagcactag   3180
caaccacaac gacccttgtg agagagcaaa cacccgacaa tctaggttct ggcgccggtg   3240
ccctccctgt caccattcga gaatttgtcc cgacaaggcc tataccccgt catgttgagc   3300
actgcggcac ggagtcgggc gacagcagtt cgcctctgga tctgtccgat gcgcaaaccc   3360
cggaccagcc tttaaatcta tccctggccg cttggccagt gagggccacc gcgtctgacc   3420
ccggctgggt ccacggtagg cgtgagcctg tttttgtaaa gcctcggggt gctttctctg   3480
atggcgattc agtccttcag ttcggggagc tttccgaatc cagctctatc atcgagattg   3540
accggacaaa agatgctcca gtggttgatg cccccgtcga cttgacggtt tcgaacgaag   3600
ctctctctgg gatcgatcct tttgaatttg ccgaactcaa gcgcccgcgt ttctccgctc   3660
aagccttaat tgaccgaggc ggcccactag ccgatgtcca tgcaaaaata aagaaccggg   3720
tatatgaaca gtgcctccag gcttgtgagc ctggcagtcg tgcaacccca gccaccaggg   3780
agtggctcga caaaatgtgg gatagggtgg acatgaagac ttggcgctgc acctcgcagt   3840
tccaagctgg tcacattctt gcgtccctca aattcctccc cgacatgatt caagacacac   3900
cgcctcctgt tcccaggaag agccgggcta gtgataatgc cggcctgaag caactggtgg   3960
cgcagtggga cagaaaattg agtgtaaccc ccccctaaa  accggttggg ccggcgcttg   4020
gccaaaccgt ccctccgcct acggatattc agcaagaaga tgtcaccccc tccgataggc   4080
cacctcatgt gccggatctt cctagtcgag tgagcacggg tgggagttgg aaaggcctta   4140
tgctttccgg cacccgtctc gcggggtcta ttagtcagca cctcatgaca tgggtttttg   4200
aagttttctc ccatctccca gcttttatgc tcacactttt ctcgccacgg ggctctatgg   4260
ctccaggtga ttggctattt gcaggtgttg ttttacttgc tctcctgctc tgtcgttctt   4320
acccagtact cgggtgcctt cccttattgg gtgtcttttc tggttctttg cggcgtgttc   4380
gtctgggtgt ttttggttct tggatggctt ttgctgtatt tttattctcg actccatccg   4440
acccagtcgg ttcttcttgt gaccacgatt cgccggagtg tcatgctgag cttttggctc   4500
ttgagcagcg ccaactttgg gaacctgtgc gcggccttgt ggtcggcccc tcgggtctct   4560
tatgtgtcat tcttggcaag ttactcggtg ggtcacgtta tctctggcat gttttcttac   4620
gtttatgcat gcttgcggat ttggcccttt ctcttgttta tgtggtgtcc caggggcgtt   4680
```

-continued

```
gtcacaagtg ttggggaaag tgtataagga cagctcctgc ggaggtggct ctcaatgtgt   4740
tccctttctt gcgcgctacc cgtgcctctc ttgtgtcctt gtgcgatcga ttccaagcgc   4800
caaaaggggt tgatcctgtg cacttggcaa caggttggcg cgggtgctgg cgcggtgaga   4860
gccccattca tcaaccgcac caaaagccca tagcttatgc caatttggat gaaaagaaaa   4920
tatctgccca aacggtggtt gctgtcccgt atgatcccag tcaggccatc aaatgcctga   4980
aagttctgca ggcgggaggg gctatcgtgg accagcccac acctgaggtc gtccgtgtgt   5040
ccgagatccc tttctcagcc ccattttttc caaaggttcc agtcaaccca gattgcaggg   5100
ttgtggtaga ttcggacact tttgtggctg cagttcgctg cggttactcg acggctcaac   5160
tggtcttagg ccggggcaac tttgccaagt taaatcagat cccctccagg aactctgtct   5220
ccaccaaaac gactggtggg gcctcttaca cccttgctgt ggctcaagtg tctgtgtgga   5280
ctcttgttca tttcatcctc ggtctttggt tcacgtcacc tcaagtgtgt ggccgaggaa   5340
cctctgaccc atggtgttca aatccttttt catatcctac ctatggcccc ggaatagtgt   5400
gctcctctcg actttgtgtg tctgccgacg gagtcactct gccattgttc tcagcagtgg   5460
cacaactctc cggtagagag gtggggattt tcattttggt gctcgtctcc ttgactgctc   5520
tggcccaccg tatggctctt aaggcagaca tgttagtggt cttttcggct tttgtgcttt   5580
acgcctggcc catgagctcc tggttaatct gcttctttcc tatattcttg aagtgggtca   5640
cccttcaccc tctcactatg ctttgggtgc actcattctt ggtgttttgt ctgccagcag   5700
ccggcgtcct ctcactaggg ataaccggcc ttctctgggc agttggccgc tttacccagg   5760
tcgccggaat tattacacct tatgacatcc accagtacac ctctgggcca cgtggtgcag   5820
ccgctgtggc cacggcccca gaaggcactt acatggccgc cgtccggaga gctgccttaa   5880
ctggacgaac cctcatcttc acaccatctg cggttggatc ccttcttgaa ggtgctttca   5940
ggacccataa accctgcctt aacaccgtga atgttgtagg ctcttccctt ggttccgggg   6000
gggttttcac cattgatggc agaagaactg ttgtcactgc tgcccatgtg ttgaacggcg   6060
acacagctag agtcaccggc gactcctaca accgcatgca cactttcaag accaatggtg   6120
attatgcctg gtcccatgct gatgactggc ggggcgttgc ccctgtggtc aaggtcgcga   6180
aggggtaccg cggtcgtgcc tactggcaaa catcaactgg tgtcgaaccc ggtattgttg   6240
gggaagggtt cgccttctgt tttaccaact gtggcgattc ggggtcacct gtcatctcag   6300
aatctggtga tcttgttgga atccacaccg gttcaaacaa actcggttct ggtcttgtga   6360
caacccctga aggggagacc tgctccatca aagaaaccaa gctctctgac ctttccaggt   6420
attttgcagg cccaagcgtc cctcttgggg atattaaatt gagtccggcc atcatccctg   6480
atgtaacatc cattccgagt gacttggcat cgctcctagc ctccgtccct gtaatggaag   6540
gcggcctctc gactgtccaa cttttgtgtg tctttttcct tctctggcgt atgatgggcc   6600
atgcctggac acccattgtt gccgtgggct tctttttgct gaatgaaatt cttccagcag   6660
ttttggtccg agccgtgttt tcttttgcgc tctttgtgct tgcatgggcc accccctggt   6720
ctgcacaggt gttgatgatc agactcctca cggcagctct caaccgcaac aggctttctc   6780
tggcgttcta cgcactcggg ggtgtcgtcg gtttggctgc tgaaattggg acctttgctg   6840
gtagattgtc tgaattgtct caagctcttt cgacatactg cttcttacct agggttcttg   6900
ctgtgactag ttatgttccc accatcatca ttggtggact ccataccctt ggtgtgatct   6960
tgtggctatt caaataccgg tgcctccaca acatgttagt tggtgatggg agtttttcaa   7020
```

-continued

```
gtgccttttt cctacggtat tttgcagagg gtaatctcag aaaaggtgtt tcacagtcct   7080
gtggcatgaa taacgagtcc ctgacagctg ctttagcttg caagttgtca caggctgacc   7140
ttgatttttt gtccagcttg acgaacttca agtgctttgt atctgcttca aacatgaaag   7200
atgctgctgg ccagtacatt gaggcagcgt atgccaaggc cctgcgccga gagttggcct   7260
ccctagtcca ggttgacaaa atgaaaggag ttttgtccaa gctcgaggcc tttgctgaaa   7320
cagccacccc gtcccttgac acaggtgacg tgattgtcct gcttgggcaa catcctcacg   7380
gatccatcct cgatattaat gtggggactg aaaggaaaac tgtgtctgtt caagagactc   7440
ggagcctagg cggctccaaa ttcagtgtct gcactgtcgt gtccaacaca cccgtggacg   7500
ccttggccgg cattccactt cagacaccaa ccccgctttt tgagaatggc ccgcgtcatc   7560
gcggtgagga agatgatctc aaagttgaga ggatgaagaa acattgtgtg tccctcggct   7620
tccacaacat caatggcaaa gtttactgta aagtttggga caagtccacc ggtgacacct   7680
tttacacgga tgattcccgg tacacccaag accatgcttt tcaggacagg tcagctgact   7740
atagagacag ggactatgag ggtgtgcaaa ccgcccccca acagggattt gatccaaaat   7800
ctgaaacccc tgttggcact gttgtaatcg gcggtattac gtataataag tatctggtca   7860
aaggcaagga ggttctggtt cccaaacctg acaactgcct tgaagccgcc aagctgtccc   7920
tcgagcaagc acttgctggg atgggccaaa cttgcgacct tacagttgcc gaggtggaaa   7980
agctaaagcg catcatcagt caactccaag gtttgaccac tgaacaggct ttaaactgct   8040
agccgccagc ggcttgaccc gctgtggccg cggcggcttg gttgtaactg aaacggcggt   8100
aaaaattata aaataccaca gcagaacttt cactttaggc cctttagacc taaaagtcac   8160
ttctgaggta gaggtgaaga aatcaactga gcagggccac gccgttgtgg caaacctatg   8220
ttctggtgtc gtattgatga gacctcaccc accgtccctt gttgacgtcc ttctgaaacc   8280
cggacttgac acaacacccg acattcaacc ggggcatggg gccgggaata tgggcgtgga   8340
cggttctatt tgggattttg aaaccgcacc cacaaaggca gaactcgagt tgtccaagca   8400
aataattcaa gcatgtgaag ttaggcgcgg agacgccccg aacctccaac tcccctacaa   8460
gctctatcct gtcagagggg atcctgagcg gcataaaggc cgccttatca acaccaggtt   8520
tggagacttg ccttacaaaa ctcctcaaga caccaagtcc gctatccatg cggcttgttg   8580
cctgcacccc aacggggccc ctgtgtctga tggtaaatcc acactaggca ccactcttca   8640
acatggtttc gagctttatg ttcccacagt gccctatagt gtcatggagt accttgattc   8700
acgccctgac acccctccca tgttcactaa acatggcact tccaaggctg ctgcagaaga   8760
cctccaaaaa tatgacctat ccacccaagg atttgtcctg cctggggtcc tacgcctagt   8820
gcgcagattc atctttggcc atgttggtaa ggcaccgcca ttgttcctcc catcaaccta   8880
tcccgccaag aactccatgg cagggattaa tggccagaga ttcccaacaa aggacgtcca   8940
gagcatacct gaaattgatg aaatgtgtgc ccgcgccgtc aaggagaatt ggcaaaccgt   9000
gacaccttgt actctcaaga aacagtactg ttccaagccc aaaaccagga ccatcctggg   9060
caccaacaac tttattgcct tggctcacag atcggcgctc agtggcgtca cccaggcatt   9120
catgaagaag gcttggaagt ccccaattgc cttggggaaa aacaagttca aggagctgca   9180
ttgtactgtc gccggcaggt gtcttgaggc tgacttggcc tcctgtgatc gcagcacccc   9240
cgccattgta agatggtttg ttgccaacct cctgtatgaa cttgcaggat gtgaagagta   9300
cttgcctagc tatgtgctta actgctgcca tgaccttgtg gcaacacagg atggtgcctt   9360
cacaaaacgc ggtggcctgt cgtccgggga ccccgtcacc agtgtgtcca ataccgtata   9420
```

-continued ttcactggta atctatgccc agcacatggt attgtcagcc ttgaaaatgg gtcatgaaat 9480
tggtcttaag ttcctcgagg agcagctcaa attcgaggac ctccttgaaa ttcagcctat 9540
gttagtatac tctgacgacc ttgtcttgta cgctgaaaga cccacttttc ccaattacca 9600
ttggtgggtc gagcaccttg acctgatgct gggtttcaaa acggacccaa agaaaactgt 9660
cataactgat aaacccagct tcctcggctg caggattgag gcagggcgac agttagtccc 9720
caatcgcgac cgcatcctgg ctgcccttgc atatcacatg aaggcgcaga acgcctcaga 9780
atattatgcg tctgctgccg caatcctgat ggattcgtgt gcttgcattg accatgaccc 9840
tgagtggtat gaggacctca tctgtggtat tgcccggtgt gctcgccaag atggctatag 9900
tttcccgggc ccggcatttt tcatgtccat gtgggagaaa ctgaaaagtc ataatgaagg 9960
gaaaaaattc cgccactgcg gcatctgcga cgccaaggcc gaccatgcgt ccgcctgtgg 10020
actcgatttg tgcttgttcc actcgcattt tcatcagcac tgccctgtca ctctgagctg 10080
cggccatcat gccggttcta aggaatgtcc gcagtgtcag tcaccggttg gggctggtag 10140
atctcctctc gatgccgtgc taaaacaaat tccgtacaaa cctcctcgta ctgtcatcat 10200
gaaggtggat aataaaacaa cggcccttga tccggggagg tatcagtccc gtcgaggtct 10260
cgttgcagtc aagaggggta ttgcaggcaa tgaagttgac cttgctaatg gagactacca 10320
ggtggtgcct cttttgccga cttgcaaaga cataaacatg gtgaaggtgg cttgtaatgt 10380
gctactcagc aagttcatag tagggccacc aggttccgga aagaccacct ggttgctgag 10440
tcaagtccag gacgatgatg tcatttatac acccacccat cagactatgt ttgatatagt 10500
cagtgctctc aaagtttgca ggtattccat tccaggggct tcaggactcc ctttcccacc 10560
acctgccagg tccgggccgt gggtcaggct tgttgccagc gggcacgtcc ctggccgagt 10620
atcatacctc gatgaggctg gatattgtaa tcatctggac attctcagac tgctttccaa 10680
aacacccctt gtgtgtttag gtgaccttca gcaactccac cctgtcggct ttgattccta 10740
ctgttatgtg tttgatcaga tgcctcagaa gcagctgacc actatttaca gatttggctc 10800
caacatctgc gcagctatcc agccttgtta cagggagaaa cttgaatcca aggccaggaa 10860
caccaggata gtttttacca cccgacctgt agctttcggg caggtgctga caccatacca 10920
caaagatcgc atcggctcag cgataaccat agattcatct caggggggcca cctttgacat 10980
tgtgacattg catctaccat cgccaaagtc cctaaataaa tcccgagcac ttgtagccat 11040
cactcgggca agacacgggt tgttcatcta tgaccctcat aatcagctcc aggagttttt 11100
caacctaact cctgagcgca ctgattgtaa ccttgtgttt aaccgtgggg atgagctggt 11160
agttctggac gcggataatg cagtcacaac tgtggcgaag gccctagaga cgggtccatc 11220
tcgatttcga gtatcagacc caaggtgcga gtctctcttg gccgcttgct cggccagcct 11280
ggagggaagc tgcatgccac taccgcaagt ggcacataac ctggggtttt acttttcccc 11340
agatagtcca gcattcgcgc ctctgccaaa agaattggca ccacattggc cggtggttac 11400
ccatcagaat aaccgggcgt ggcctgaccg acttgttgct agtatgcgcc caattgatgc 11460
ccgttatagc aagccaatgg ttggtgcagg gtacgcggtc gggccgtcca cttttcttgg 11520
cactcctggt gtggtatcat actatctgac actgtacatc aggggtgagc cccaggcctt 11580
accagaaaca ctcgtgtcaa cagggcgcat agccacagat tgtcgggaat atctcgacgc 11640
cgctgaggaa gaggcagcaa aagaactccc tcacgcattc attggcgatg tcaaaggtac 11700
cacggttggg ggtgtcatc acatcacatc aaaataccta cctaggtccc tgcctaagga 11760

-continued ctctgttgcc gtagttggag taagttcgcc cggcagggcc gctaaagccg tgtgcactct 11820
caccgatgtt tacctccccg agctccggcc atatctgcaa cctgagacgg catcaaaatg 11880
ctggaaactc aaattagact ttagagatgt ccgactaatg gtctggaaag gagccaccgc 11940
ctacttccag ctggaagggc ttacatggtc ggcgctgccc gactatgcca ggtttattca 12000
gctgcctaag gatgccgttg tgtacattga tccgtgcata ggaccggcaa cagccaaccg 12060
taaggtcgtg cggaccacag actggcgggc tgacctggca gtgacaccgt atgattacgg 12120
tgcccagaac attttgacaa cagcctggtt cgaggacctc gggccgcagt ggaagatttt 12180
ggggttgcag ccctttaggc gatcatttgg ctttgaaaac actgaggatt gggcaatcct 12240
tgcacgccgt atgaatgacg gcaaggacta cactgactat aactggaact gtgttcgaga 12300
acgcccacac gccatctacg ggcgcgctcg tgaccatacg tatcattttg cccccggcac 12360
agaattgcag gtagagctag gtaaaccccg gctgccgcct gagcaagtgc cgtgaatccg 12420
gagtgatgca atggggttac tgtggagtaa aattagccag ctgttcgtgg acgccttcac 12480
tgagttcctt gttagtgtgg ttgatattgt cattttcctt gccatactgt ttgggttcac 12540
cgtcgcagga tggttactgg tctttcttct cagagtggtt tgctccgcgc ttctccgttc 12600
gcgctctgcc attcactctc ccgaactatc gaaggtccta tgaaagcttg ctacccaatt 12660
gcagaccgga tgtcccacaa tttgcattca agcacccatt gggcatactt tggcacatgc 12720
gagtctccca cctaattgat gaaatggtct ctcgtcgcat ttaccggacc atggaacact 12780
caagtcaagc ggcctggaag caggtagtta gtgaggccac cctcacaaag ctgtcagggc 12840
ttgatatagt tactcatttc caacacctgg ccgcagtgga ggcggattct tgccgtttcc 12900
tcagctcacg acttgtgatg ctaaagaatc ttgccgttgg caatgtgagc ctacagtata 12960
acaccacgtt ggaccatgtt gagctcatct tccctacgcc aggtacgagg cccaagttga 13020
ccgatttcag acaatggctc atcagtgtgc acgcttccat tttttcctct gtggcttcat 13080
ctgttacctt gttcatagtg ttttggcttc gaattccagc cgtacgctat gtttttggtt 13140
tccattggcc cacggcaaca catcattcga gctaaccatc aactacacca tatgtatgcc 13200
ctgctctacc agccaagcgg ctagccaaag actcgagccc ggtcgtaaca tgtggtgcag 13260
aatagggcac gacaggtgtg aggaacgtga ccatgatgag ttgtcaatgt ccattccgtc 13320
agggtacgag aacctcaaac ttgagggtta ttatgcttgg ctggcctttt tgtccttttc 13380
ctacgcggcc caatttcatc cggagttgtt cggaatagga aacgtgtcgc gcgtctttgt 13440
ggacaagcga caccagttca tttgcgccga gcatgatgga caaaattcaa ccatatctac 13500
cggacacaac atctccgcat tatatgcggt gtattaccat caccaaatag acgggggcaa 13560
ttggttccat ttggaatggc tgcggccatt cttttcctcc tggctggtgc tcaatatctc 13620
atggtttctg aggcgttcgc ctgtaagccc tgtttctcga cgcatctatc agatattaag 13680
accaacacga ccgcggctgc cggtttcatg gtccttcagg acatcaattg tctccgacct 13740
cacggggtct caacagcgca agagaacatt cccttcggaa agccgtccca atgtcgcgag 13800
gctgtcggta ttccccagta cattacgata acggctaatg tgaccgatga atcgtatttg 13860
tacaacgcgg acttgctgat gctttctgcg tgccttttct acgcttcaga aatgagcgaa 13920
aagggcttca aagttatctt tgggaacgtc tctggcgttg tttctgcttg tgtcaatttt 13980
acagattatg tggctcatgt aatccaacat acccagcagc atcatctggt gattgatcac 14040
attcggttgc tgcatttcct gacaccatca acaatgaggt gggctacaac cattgcttgt 14100
ttgttcgcca ttctcttggc gatatgagat gttctcacaa attggagtgt ttcttgactc 14160

-continued

```
ctcactcttg cttctggtgg cttttttgc tgtgtaccgg cttgtcttgg tcctttgtcg  14220

atggcaacga cagcagctcg acataccaat acatatataa tttgacgata tgcgagctga  14280

atgggaccga atcgttgtcc agccatttg actgggcagt cgagaccttt gtgctttacc  14340

cggttgccac tcatatcctt tcactgggtt ttctcacaac aagccatttt tttgatgcgc  14400

tcggtctcgg cgctgtgtcc actacaggat ttgttggcgg gcggtatgta ctcagcagcg  14460

tgtacggcgc ttgtgctttc gcagcgctcg tatgttttgt catccgcgct gctaaaaatt  14520

gcatggcttg ccgttatgcc cgtacccggt tcaccaactt cattgtggac gaccggggga  14580

ggatccatcg atggaagtct ccaatagtgg tagagaaatt gggcaaagct gaagtcggtg  14640

gcgacctcgt caccatcaaa catgtcgtcc tcgaaggggt taaagctcaa cccttgacga  14700

ggacttcggc tgagcaatgg gaagcctaga cgatttttgc aacgatccta ccgccgcaca  14760

aaagcttgtg ctagccttta gcatcacata tacacctata atgatatacg cccttaaggt  14820

gtcacgcggc cgcctcctgg ggctattgca catcttgata ttcctgaact gttcctttac  14880

attcggatac atgacatatg tgcattttca atccaccaac cgtgtcgcat ttactctggg  14940

ggccgttgtc gcccttctgt ggggtgttta cagcttcaca gagtcatgga agttcattac  15000

ttccagatgc agattgtgtt gcctaggccg gcaatacatt ctggcccctg cccatcacgt  15060

agaaagtgct gcaggtctcc attcaatccc agcgtctggt aaccgagcat acgctgtgag  15120

aaagcccgga ctaacatcag tgaacggcac tctagtacca ggacttcgga gcctcgtgct  15180

gggcggcaaa cgagctgtta aacgaggagt ggttaacctc gtcaagtatg gccggtaaaa  15240

atcagagcca gaagaaaaag aagaatacag ctccgatggg gaatggccag ccagtcaatc  15300

aactgtgcca gttgctgggt gcaatgataa agtcccagcg ccagcaacct aggggaggac  15360

aggcaaaaaa aagaaagcct gagaagccac attttcccct agctgctgaa gatgacattc  15420

ggcaccacct cacccagacc gaacgttccc tctgcttgca atcgatccag acggctttta  15480

accaaggcgc aggaactgcg tcgctttcat ccagcgggaa ggtcagtttt caggttgagt  15540

tcatgctgcc ggttgctcat acagtgcgcc tgattcgcgt gacttctaca tccgccagtc  15600

agggtgcaaa ttaatttgac agtcaggtga atggccgcga ttgacgtgtg gcctctaagt  15660

cacctattca attagggcga tcacatgggg gtcaaactta atcaggcagg aaccatgtga  15720

ccgaaattaa aaaaaaaaaa aaaaaaaaaa aaaggccggc atggtcccag cctcctcgct  15780

ggcgccggct gggcaacatt ccgaggggac cgtcccctcg gtaatggcga atgggactct  15840

agagcccttc cggctggctg gtttattgct gataaatctg gagccggtga gcgtgggtct  15900

cgcggtatca ttgcagc                                                15917
```

<210> SEQ ID NO 4
<211> LENGTH: 15917
<212> TYPE: DNA
<213> ORGANISM: Artificial Sequence
<220> FEATURE:
<223> OTHER INFORMATION: Clone pVAC 5.2

<400> SEQUENCE: 4

```
ggctgtggca caggctgaac gccggaggat ccggcgcgcc atgcattagt tattaatagt     60

aatcaattac ggggtcatta gttcatagcc catatatgga gttccgcgtt acataactta    120

cggtaaatgg cccgcctggc tgaccgccca acgacccccg cccattgacg tcaataatga    180

cgtatgttcc catagtaacg ccaataggga ctttccattg acgtcaatgg gtggagtatt    240
```

-continued

```
tacggtaaac tgcccacttg gcagtacatc aagtgtatca tatgccaagt acgcccccta    300
ttgacgtcaa tgacggtaaa tggcccgcct ggcattatgc ccagtacatg accttatggg    360
actttcctac ttggcagtac atctacgtat tagtcatcgc tattaccatg gtgatgcggt    420
tttggcagta catcaatggg cgtggatagc ggtttgactc acggggattt ccaagtctcc    480
accccattga cgtcaatggg agtttgtttt ggcaccaaaa tcaacgggac tttccaaaat    540
gtcgtaacaa ctccgcccca ttgacgcaaa tgggcggtag gcgtgtacgg tgggaggtct    600
atataagcag agctggttta gtatttaaat atgatgtgta gggtactccc cctacataca    660
cgacacttct agtgtttgtg tgccttggag gcgtgggtat agccccgccc caccccttgg    720
cccctgttct agcccaacag gtatccttct ctctcggggc gagcgcgccg cctgctgctc    780
ccttgcagcg ggaaggacct cccgagtatt tccggagagc acctgcttta cgggatctcc    840
accctttaac catgtctggg acgttctccc ggtgcatgtg caccccggct gcccgggtat    900
tttggaacgc cggccaagtc ttttgcacac ggtgtctcag tgcgcggtct cttctccctc    960
cggagcttca ggaaactgac ctcgctgcaa ttggcttgtt ttacaagcct aaagacaagc   1020
ttcactggaa agtccctatc ggcatccctc aggtggagtg cactccatcc gggtgctgtt   1080
ggctctcagc catcttccca ttggcgcgca tgacctccgg caatcacaac ttcctccaac   1140
gacttgtgag ggttgccgat gtgttgtacc gtgatggttg cttggctcct cgacaccttc   1200
gtgaactcca agtttacgag cgcggctgca actggtaccc gatcacgggg cccgtgcccg   1260
ggatgggttt gttcgcaaac tccatgcacg tatccgacca gccgttccct ggtgccaccc   1320
atgtgttgac gaactcgccg ttgcctcaac aggcttgtcg gcagccgttc tgtccatttg   1380
aggaggctca ttctagtgtg tacaggtgga aaagatttgt ggttttcacg gattcctctc   1440
ccaacggtcg atctcgcatg atgtggacgc cggaatccga tgattcagcc gccttggagg   1500
tattaccgcc tgaattagaa cgtcaggtcg aaatcctcat tcggagtttt cctgctcatc   1560
accctgtcaa cctggccgac tgggagctca ctgagtcccc tgagaacggt tttttccttca   1620
acacgtctta ttcttgcggt caccttgtcc aaaaccccga cgtgtttgat ggcaagtgct   1680
ggctttcctg ctttttgggc cagtcggccg aagtgcgccg ccatgaggaa catttagctg   1740
acgccctcgg ttaccagacc aagtggggcg tgcctggcaa gtacctccag cgcaggcttc   1800
aggttcgcgg cattcgtgct gtagttgatc ctgatggccc cattcacgtc gaagcgctgt   1860
cttgcccccg gtcttggatc aggcacctga cttttgatga taatgtcacc ccaggatttg   1920
ttcgccttac gtcccttcgc attgtgccaa acaccgagcc tactgcttcc cggatcttcc   1980
ggtttggagc gcataagtgg tatggcgctg ccggcaaacg agctcgtgct aagcgtgccg   2040
ctaaaagtga gaaaatttcg gcccctaccc ccaaggttgc tcagccggtc cccacctgcg   2100
aaattaccac ctattctcca ccgacagacg ggtcttgtgg ttggcatgtt cttgccgcca   2160
taatgaaccg gatgatgaat ggtgacttca cgtcccctct gactcagtac aacagaccag   2220
aggatgactg ggcttctgat tatgaccttg ctcaggcgat ccaatgtctg caactgcccg   2280
ctaccgtagt tcggaatcgc gcctgtccta acgccaagta ccttataaaa cttaatggag   2340
ttcattggga ggtagaggtg aggcctggaa tggcccctcg ttccctttcc cgtgagtgtg   2400
tggttggcgt ctgttctgaa ggctgtatcg caccgcctta cccacaagac gggctgccta   2460
aacgtgcact tgaggccttg gcgtctgctt acagactacc ctccgactgt gttggttctg   2520
gtattgctga ctttcttgct aacccgcccc ctcaggagtt ttggaccctt gacaaaatgt   2580
tgacctcccc gtcaccagaa cggtccggct tctctagctt gtataaatta ctattggagg   2640
```

-continued

```
ttgttccgca gaaatgcggt gccacggaag gggctttcgt ctatgctgtt gagaggatgt   2700
tgaaggattg tccgagctcc aaacaggcca tggcccttct ggcaaaaatt aaagtcccat   2760
cctcaaaggc cccgtctgtg tctctggacg agtgcttccc tacggatgtt ccagcggact   2820
ccgagccagc gtttcaggaa aggccccaaa gttctggtgc tgctgttgtc ctgtgttcac   2880
cggacataaa agagttcgag gaagcagccc cagaagaagt tcaagagggt ggccacaagg   2940
ccgtccactc tgcactcctt gccgagggtc ttaacaatga gcaggtacag gtggttgccg   3000
gtgcgcaact aaagctcggc agttgtggct tggcagtcgg gaatactcat ggaggtgttc   3060
cggtttcagc tagtccaatt aacctggcag acgggaattt gcccccctcg gactccatga   3120
aaggaaacat gcccaatggc tgggaggacg aaccactgga tttgtcccaa tcagcactag   3180
caaccacaac gacccttgtg agagagcaaa cacccgacaa tctaggttct ggcgccggtg   3240
ccctccctgt caccattcga gaatttgtcc cgacaaggcc tataccccgt catgttgagc   3300
actgcggcac ggagtcgggc gacagcagtt cgcctctgga tctgtccgat gcgcaaaccc   3360
cggaccagcc tttaaatcta tccctggccg cttggccagt gagggccacc gcgtctgacc   3420
ccggctgggt ccacggtagg cgtgagcctg tttttgtaaa gcctcggggt gctttctctg   3480
atggcgattc agtccttcag ttcggggagc tttccgaatc cagctctatc atcgagattg   3540
accggacaaa agatgctcca gtggttgatg cccccgtcga cttgacggtt tcgaacgaag   3600
ctctctctgg gatcgatcct tttgaatttg ccgaactcaa gcgcccgcgt ttctccgctc   3660
aagccttaat tgaccgaggc ggcccactag ccgatgtcca tgcaaaaata aagaaccggg   3720
tatatgaaca gtgcctccag gcttgtgagc ctggcagtcg tgcaacccca gccaccaggg   3780
agtggctcga caaaatgtgg gatagggtgg acatgaagac ttggcgctgc acctcgcagt   3840
tccaagctgg tcacattctt gcgtccctca aattcctccc cgacatgatt caagacacac   3900
cgcctcctgt tcccaggaag agccgggcta gtgataatgc cggcctgaag caactggtgg   3960
cgcagtggga cagaaaattg agtgtaaccc ccccccctaaa accggttggg ccggcgcttg  4020
gccaaaccgt ccctccgcct acggatattc agcaagaaga tgtcaccccc tccgataggc   4080
cacctcatgt gccggatctt cctagtcgag tgagcacggg tgggagttgg aaaggcctta   4140
tgctttccgg cacccgtctc gcggggtcta ttagtcagca cctcatgaca tgggtttttg   4200
aagttttctc ccatctccca gcttttatgc tcacactttt ctcgccacgg ggctctatgg   4260
ctccaggtga ttggctattt gcaggtgttg ttttacttgc tctcctgctc tgtcgttctt   4320
acccagtact cgggtgcctt cccttattgg gtgtcttttc tggttctttg cggcgtgttc   4380
gtctgggtgt ttttggttct tggatggctt ttgctgtatt tttattctcg actccatccg   4440
acccagtcgg ttcttcttgt gaccacgatt cgcccggagtg tcatgctgag cttttggctc  4500
ttgagcagcg ccaactttgg gaacctgtgc gcggccttgt ggtcggcccc tcgggtctct   4560
tatgtgtcat tcttggcaag ttactcggtg ggtcacgtta tctctggcat gttttcttac   4620
gtttatgcat gcttgcggat ttggcccttt ctcttgttta tgtggtgtcc caggggcgtt   4680
gtcacaagtg ttggggaaag tgtataagga cagctcctgc ggaggtggct ctcaatgtgt   4740
tccctttctt gcgcgctacc cgtgcctctc ttgtgtcctt gtgcgatcga ttccaagcgc   4800
caaaaggggt tgatcctgtg cacttggcaa caggttggcg cgggtgctgg cgcggtgaga   4860
gccccattca tcaaccgcac caaaagccca tagcttatgc caatttggat gaaaagaaaa   4920
tatctgccca aacggtggtt gctgtcccgt atgatcccag tcaggccatc aaatgcctga   4980
```

-continued

```
aagttctgca ggcgggaggg gctatcgtgg accagcccac acctgaggtc gtccgtgtgt   5040
ccgagatccc tttctcagcc ccattttttc caaaggttcc agtcaaccca gattgcaggg   5100
ttgtggtaga ttcggacact tttgtggctg cagttcgctg cggttactcg acggctcaac   5160
tggtcttagg ccggggcaac tttgccaagt taaatcagat cccctccagg aactctgtct   5220
ccaccaaaac gactggtggg gcctcttaca cccttgctgt ggctcaagtg tctgtgtgga   5280
ctcttgttca tttcatcctc ggtctttggt tcacgtcacc tcaagtgtgt ggccgaggaa   5340
cctctgaccc atggtgttca aatccttttt catatcctac ctatggcccc ggaatagtgt   5400
gctcctctcg actttgtgtg tctgccgacg gagtcactct gccattgttc tcagcagtgg   5460
cacaactctc cggtagagag gtggggattt tcattttggt gctcgtctcc ttgactgctc   5520
tggcccaccg tatggctctt aaggcagaca tgttagtggt cttttcggct tttgtgcttt   5580
acgcctggcc catgagctcc tggttaatct gcttctttcc tatattcttg aagtgggtca   5640
cccttcaccc tctcactatg ctttgggtgc actcattctt ggtgttttgt ctgccagcag   5700
ccggcgtcct ctcactaggg ataaccggcc ttctctgggc agttggccgc tttacccagg   5760
tcgccggaat tattacacct tatgacatcc accagtacac ctctgggcca cgtggtgcag   5820
ccgctgtggc cacggcccca gaaggcactt acatggccgc cgtccggaga gctgccttaa   5880
ctggacgaac cctcatcttc acaccatctg cggttggatc ccttcttgaa ggtgctttca   5940
ggacccataa accctgcctt aacaccgtga atgttgtagg ctcttccctt ggttccgggg   6000
gggttttcac cattgatggc agaagaactg ttgtcactgc tgcccatgtg ttgaacggcg   6060
acacagctag agtcaccggc gactcctaca accgcatgca cactttcaag accaatggtg   6120
attatgcctg gtcccatgct gatgactggc ggggcgttgc ccctgtggtc aaggtcgcga   6180
aggggtaccg cggtcgtgcc tactggcaaa catcaactgg tgtcgaaccc ggtattgttg   6240
gggaagggtt cgccttctgt tttaccaact gtggcgattc ggggtcacct gtcatctcag   6300
aatctggtga tcttgttgga atccacaccg gttcaaacaa actcggttct ggtcttgtga   6360
caacccctga aggggagacc tgctccatca aagaaaccaa gctctctgac ctttccaggt   6420
attttgcagg cccaagcgtc cctcttgggg atattaaatt gagtccggcc atcatccctg   6480
atgtaacatc cattccgagt gacttggcat cgctcctagc ctccgtccct gtaatggaag   6540
gcggcctctc gactgtccaa cttttgtgtg tcttttttcct tctctggcgt atgatgggcc   6600
atgcctggac acccattgtt gccgtgggct tctttttgct gaatgaaatt cttccagcag   6660
ttttggtccg agccgtgttt tcttttgcgc tctttgtgct tgcatgggcc accccctggt   6720
ctgcacaggt gttgatgatc agactcctca cggcagctct caaccgcaac aggctttctc   6780
tggcgttcta cgcactcggg ggtgtcgtcg gtttggctgc tgaaattggg acctttgctg   6840
gtagattgtc tgaattgtct caagctcttt cgacatactg cttcttacct agggttcttg   6900
ctgtgactag ttatgttccc accatcatca ttggtggact ccatacccctt ggtgtgatct   6960
tgtggctatt caaataccgg tgcctccaca acatgttagt tggtgatggg agtttttcaa   7020
gtgccttttt cctacggtat tttgcagagg gtaatctcag aaaaggtgtt tcacagtcct   7080
gtggcatgaa taacgagtcc ctgacagctg ctttagcttg caagttgtca caggctgacc   7140
ttgatttttt gtccagcttg acgaacttca agtgctttgt atctgcttca aacatgaaag   7200
atgctgctgg ccagtacatt gaggcagcgt atgccaaggc cctgcgccga gagttggcct   7260
ccctagtcca ggttgacaaa atgaaaggag ttttgtccaa gctcgaggcc tttgctgaaa   7320
cagccacccc gtcccttgac acaggtgacg tgattgtcct gcttgggcaa catcctcacg   7380
```

gatccatcct cgatattaat gtggggactg aaaggaaaac tgtgtctgtt caagagactc 7440
ggagcctagg cggctccaaa ttcagtgtct gcactgtcgt gtccaacaca cccgtggacg 7500
ccttggccgg cattccactt cagacaccaa ccccgctttt tgagaatggc ccgcgtcatc 7560
gcggtgagga agatgatctc aaagttgaga ggatgaagaa acattgtgtg tccctcggct 7620
tccacaacat caatggcaaa gtttactgta aagtttggga caagtccacc ggtgacacct 7680
tttacacgga tgattcccgg tacacccaag accatgcttt tcaggacagg tcagctgact 7740
atagagacag ggactatgag ggtgtgcaaa ccgcccccca acagggattt gatccaaaat 7800
ctgaaacccc tgttggcact gttgtaatcg gcggtattac gtataataag tatctggtca 7860
aaggcaagga ggttctggtt cccaaacctg acaactgcct tgaagccgcc aagctgtccc 7920
tcgagcaagc acttgctggg atgggccaaa cttgcgacct tacagttgcc gaggtggaaa 7980
agctaaagcg catcatcagt caactccaag gtttgaccac tgaacaggct ttaaactgct 8040
agccgccagc ggcttgaccc gctgtggccg cggcggcttg gttgtaactg aaacggcggt 8100
aaaaattata aaataccaca gcagaacttt cactttaggc cctttagacc taaaagtcac 8160
ttctgaggta gaggtgaaga aatcaactga gcagggccac gccgttgtgg caaacctatg 8220
ttctggtgtc gtattgatga gacctcaccc accgtccctt gttgacgtcc ttctgaaacc 8280
cggacttgac acaacacccg acattcaacc ggggcatggg gccgggaata tgggcgtgga 8340
cggttctatt tgggattttg aaaccgcacc cacaaaggca gaactcgagt tgtccaagca 8400
aataattcaa gcatgtgaag ttaggcgcgg agacgccccg aacctccaac tcccctacaa 8460
gctctatcct gtcagagggg atcctgagcg gcataaaggc cgccttatca acaccaggtt 8520
tggagacttg ccttacaaaa ctcctcaaga caccaagtcc gctatccatg cggcttgttg 8580
cctgcacccc aacggggccc ctgtgtctga tggtaaatcc acactaggca ccactcttca 8640
acatggtttc gagctttatg ttcccacagt gccctatagt gtcatggagt accttgattc 8700
acgccctgac acccctccca tgttcactaa acatggcact tccaaggctg ctgcagaaga 8760
cctccaaaaa tatgacctat ccacccaagg atttgtcctg cctggggtcc tacgcctagt 8820
gcgcagattc atctttggcc atgttggtaa ggcaccgcca ttgttcctcc catcaaccta 8880
tcccgccaag aactccatgg cagggattaa tggccagaga ttcccaacaa aggacgtcca 8940
gagcatacct gaaattgatg aaatgtgtgc ccgcgccgtc aaggagaatt ggcaaaccgt 9000
gacaccttgt actctcaaga aacagtactg ttccaagccc aaaaccagga ccatcctggg 9060
caccaacaac tttattgcct tggctcacag atcggcgctc agtggcgtca cccaggcatt 9120
catgaagaag gcttggaagt ccccaattgc cttggggaaa aacaagttca aggagctgca 9180
ttgtactgtc gccggcaggt gtcttgaggc tgacttggcc tcctgtgatc gcagcacccc 9240
cgccattgta agatggtttg ttgccaacct cctgtatgaa cttgcaggat gtgaagagta 9300
cttgcctagc tatgtgctta actgctgcca tgaccttgtg gcaacacagg atggtgcctt 9360
cacaaaacgc ggtggcctgt cgtccgggga ccccgtcacc agtgtgtcca ataccgtata 9420
ttcactggta atctatgccc agcacatggt attgtcagcc ttgaaaatgg gtcatgaaat 9480
tggtcttaag ttcctcgagg agcagctcaa attcgaggac ctccttgaaa ttcagcctat 9540
gttagtatac tctgacgacc ttgtcttgta cgctgaaaga ccccactttc ccaattacca 9600
ttggtgggtc gagcaccttg acctgatgct gggtttcaaa acggacccaa agaaaactgt 9660
cataactgat aaacccagct tcctcggctg caggattgag gcagggcgac agttagtccc 9720

-continued

```
caatcgcgac cgcatcctgg ctgcccttgc atatcacatg aaggcgcaga acgcctcaga   9780
atattatgcg tctgctgccg caatcctgat ggattcgtgt gcttgcattg accatgaccc   9840
tgagtggtat gaggacctca tctgtggtat tgcccggtgt gctcgccaag atggctatag   9900
tttcccgggc ccggcatttt tcatgtccat gtgggagaaa ctgaaaagtc ataatgaagg   9960
gaaaaaattc cgccactgcg gcatctgcga cgccaaggcc gaccatgcgt ccgcctgtgg  10020
actcgatttg tgcttgttcc actcgcattt tcatcagcac tgccctgtca ctctgagctg  10080
cggccatcat gccggttcta aggaatgtcc gcagtgtcag tcaccggttg gggctggtag  10140
atctcctctc gatgccgtgc taaaacaaat tccgtacaaa cctcctcgta ctgtcatcat  10200
gaaggtggat aataaaacaa cggcccttga tccggggagg tatcagtccc gtcgaggtct  10260
cgttgcagtc aagaggggta ttgcaggcaa tgaagttgac cttgctaatg gagactacca  10320
ggtggtgcct cttttgccga cttgcaaaga cataaacatg gtgaaggtgg cttgtaatgt  10380
gctactcagc aagttcatag tagggccacc aggttccgga aagaccacct ggttgctgag  10440
tcaagtccag gacgatgatg tcatttatac acccacccat cagactatgt ttgatatagt  10500
cagtgctctc aaagtttgca ggtattccat tccaggggct tcaggactcc ctttcccacc  10560
acctgccagg tccgggccgt gggtcaggct tgttgccagc gggcacgtcc ctggccgagt  10620
atcatacctc gatgaggctg gatattgtaa tcatctggac attctcagac tgctttccaa  10680
aacacccctt gtgtgtttag gtgaccttca gcaactccac cctgtcggct ttgattccta  10740
ctgttatgtg tttgatcaga tgcctcagaa gcagctgacc actatttaca gatttggctc  10800
caacatctgc gcagctatcc agccttgtta cagggagaaa cttgaatcca aggccaggaa  10860
caccaggata gtttttacca cccgacctgt agctttcggg caggtgctga caccatacca  10920
caaagatcgc atcggctcag cgataaccat agattcatct caggggggcca cctttgacat  10980
tgtgacattg catctaccat cgccaaagtc cctaaataaa tcccgagcac ttgtagccat  11040
cactcgggca agacacgggt tgttcatcta tgaccctcat aatcagctcc aggagttttt  11100
caacctaact cctgagcgca ctgattgtaa ccttgtgttt aaccgtgggg atgagctggt  11160
agttctggac gcggataatg cagtcacaac tgtggcgaag gccctagaga cgggtccatc  11220
tcgatttcga gtatcagacc caaggtgcga gtctctcttg gccgcttgct cggccagcct  11280
ggagggaagc tgcatgccac taccgcaagt ggcacataac ctggggtttt acttttcccc  11340
agatagtcca gcattcgcgc ctctgccaaa agaattggca ccacattggc cggtggttac  11400
ccatcagaat aaccgggcgt ggcctgaccg acttgttgct agtatgcgcc caattgatgc  11460
ccgttatagc aagccaatgg ttggtgcagg gtacgcggtc gggccgtcca cttttcttgg  11520
cactcctggt gtggtatcat actatctgac actgtacatc aggggtgagc cccaggcctt  11580
accagaaaca ctcgtgtcaa cagggcgcat agccacagat tgtcgggaat atctcgacgc  11640
cgctgaggaa gaggcagcaa aagaactccc tcacgcattc attggcgatg tcaaaggtac  11700
cacggttggg gggtgtcatc acatcacatc aaaataccta cctaggtccc tgcctaagga  11760
ctctgttgcc gtagttggag taagttcgcc cggcagggcc gctaaagccg tgtgcactct  11820
caccgatgtt tacctccccg agctccggcc atatctgcaa cctgagacgg catcaaaatg  11880
ctggaaactc aaattagact ttagagatgt ccgactaatg gtctggaaag gagccaccgc  11940
ctacttccag ctggaagggc ttacatggtc ggcgctgccc gactatgcca ggtttattca  12000
gctgcctaag gatgccgttg tgtacattga tccgtgcata ggaccggcaa cagccaaccg  12060
taaggtcgtg cggaccacag actggcgggc tgacctggca gtgacaccgt atgattacgg  12120
```

-continued

```
tgcccagaac attttgacaa cagcctggtt cgaggacctc gggccgcagt ggaagatttt  12180
ggggttgcag ccctttaggc gatcatttgg ctttgaaaac actgaggatt gggcaatcct  12240
tgcacgccgt atgaatgacg gcaaggacta cactgactat aactggaact gtgttcgaga  12300
acgcccacac gccatctacg ggcgcgctcg tgaccatacg tatcattttg cccccggcac  12360
agaattgcag gtagagctag gtaaaccccg gctgccgcct gagcaagtgc cgtgaatccg  12420
gagtgatgca atggggttac tgtggagtaa aattagccag ctgttcgtgg acgccttcac  12480
tgagttcctt gttagtgtgg ttgatattgt cattttcctt gccatactgt ttgggttcac  12540
cgtcgcagga tggttactgg tctttcttct cagagtggtt tgctccgcgc ttctccgttc  12600
gcgctctgcc attcactctc ccgaactatc gaaggtccta tgaaagcttg ctacccaatt  12660
gcagaccgga tgtcccacaa tttgcattca agcacccatt gggcatactt tggcacatgc  12720
gagtctccca cctaattgat gaaatggtct ctcgtcgcat ttaccggacc atggaacact  12780
caagtcaagc ggcctggaag caggtagtta gtgaggccac cctcacaaag ctgtcagggc  12840
ttgatatagt tactcatttc caacacctgg ccgcagtgga ggcggattct tgccgtttcc  12900
tcagctcacg acttgtgatg ctaaagaatc ttgccgttgg caatgtgagc ctacagtata  12960
acaccacgtt ggaccatgtt gagctcatct tccctacgcc aggtacgagg cccaagttga  13020
ccgatttcag acaatggctc atcagtgtgc acgcttccat tttttcctct gtggcttcat  13080
ctgttacctt gttcatagtg ttttggcttc gaattccagc cgtacgctat gtttttggtt  13140
tccattggcc cacggcaaca catcattcga gctaaccatc aactacacca tatgtatgcc  13200
ctgctctacc agccaagcgg ctagccaaag actcgagccc ggtcgtaaca tgtggtgcag  13260
aatagggcac gacaggtgtg aggaacgtga ccatgatgag ttgtcaatgt ccattccgtc  13320
agggtacgag aacctcaaac ttgagggtta ttatgcttgg ctggcctttt tgtccttttc  13380
ctacgcggcc caatttcatc cggagttgtt cggaatagga aacgtgtcgc gcgtctttgt  13440
ggacaagcga caccagttca tttgcgccga gcatgatgga caaaattcaa ccatatctac  13500
cggacacaac atctccgcat tatatgcggt gtattaccat caccaaatag acgggggcaa  13560
ttggttccac ttggaatggc tgcggccatt cttttcctcc tggctggtgc tcaatatctc  13620
atggtttctg aggcgttcgc ctgtaagccc tgtttctcga cgcatctatc agatattaag  13680
accaacacga ccgcggctgc cggtttcatg gtccttcagg acatcaattg tctccgacct  13740
cacggggtct caacagcgca agagaccatt tccttcggaa agccgtccca atgtcgcgag  13800
gccgtcggta ttccccagta cattacgata acggctaatg tgaccgatga atcgtatttg  13860
tacaacgcgg acttgctgat gctttctgcg tgccttttct acgcttcaga aatgagcgaa  13920
aagggcttca aagttatctt tgggaacgtt tctggcgttg tttctgcttg tgtcaatttt  13980
acagattatg tggctcatgt aatccaacat acccagcagc atcatctggt gattgatcac  14040
attcggttgc tgcatttcct gacaccatca acaatgaggt gggctacaac cattgcttgt  14100
ttgttcgcca ttctcttggc gatatgagat gttctcacaa attggagcgt ttcttgactc  14160
ctcactcttg cttctggtgg ctttttttgc tttgtaccgg cttgtcttgg tcctttgtcg  14220
atggcaacga cagcagctcg acataccaat acatatataa tttgacgata tgcgagctga  14280
atgggaccga atggttgccc agccattttg actgggcagt cgagaccttt gtgctttacc  14340
cggttgccac tcatatcctt tcactgggtt ttctcacaac aagccatttt tttgatgcgc  14400
tcggtctcgg cgctgtgtcc actacaggat ttgttggcgg gcggtatgta ctcagcagcg  14460
```

-continued

```
tgtacggcgc ttgtgctttc gcagcgctcg tatgttttgt catccgcgct gctaaaaatt  14520

gcatggcttg ccgttatgcc cgcacccggt ttaccaactt cattgtggac gaccggggga  14580

ggatccatcg atggaagtct ccaatagtgg tagagaaatt gggcaaagct gaagtcggtg  14640

gcgacctcgt caccatcaaa catgtcgtcc tcgaaggggt taaagctcaa cccttgacga  14700

ggacttcggc tgagcaatgg gaagcctaga cgatttttgc aacgatccta ccgccgcaca  14760

aaagcttgtg ctagccttta gcatcacata tacacctata atgatatacg cccttaaggt  14820

gtcacgcggc cgcctcctgg ggctattgca catcttgata ttcctgaact gttcctttac  14880

attcggatac atgacatatg tgcattttca atccaccaac cgtgtcgcat ttactctggg  14940

ggccgttgtc gcccttctgt ggggtgttta cagcttcaca gagtcatgga agttcattac  15000

ttccagatgc agattgtgtt gcctaggccg gcaatacatt ctggcccctg cccatcacgt  15060

agaaagtgct gcaggtctcc attcaatccc agcgtctggt aaccgagcat acgctgtgag  15120

aaagcccgga ctaacatcag tgaacggcac tctagtacca ggacttcgga gcctcgtgct  15180

gggcggcaaa cgagctgtta aacgaggagt ggttaacctc gtcaagtatg gccggtaaaa  15240

atcagagcca gaagaaaaag aagaatacag ctccgatggg gaatggccag ccagtcaatc  15300

aactgtgcca gttgctgggt gcaatgataa agtcccagcg ccagcaacct aggggaggac  15360

aggcaaaaaa aagaaagcct gagaagccac attttcccct agctgctgaa gatgacattc  15420

ggcaccacct cacccagacc gaacgttccc tctgcttgca atcgatccag acggctttta  15480

accaaggcgc aggaactgcg tcgctttcat ccagcgggaa ggtcagtttt caggttgagt  15540

tcatgctgcc ggttgctcat acagtgcgcc tgattcgcgt gacttctaca tccgccagtc  15600

agggtgcaaa ttaatttgac agtcaggtga atggccgcga ttgacgtgtg gcctctaagt  15660

cacctattca attagggcga tcacatgggg gtcaaactta atcaggcagg aaccatgtga  15720

ccgaaattaa aaaaaaaaaa aaaaaaaaaa aaaggccggc atggtcccag cctcctcgct  15780

ggcgccggct gggcaacatt ccgaggggac cgtcccctcg gtaatggcga atgggactct  15840

agagcccttc cggctggctg gtttattgct gataaatctg gagccggtga gcgtgggtct  15900

cgcggtatca ttgcagc                                                 15917
```

<210> SEQ ID NO 5
<211> LENGTH: 15917
<212> TYPE: DNA
<213> ORGANISM: Artificial Sequence
<220> FEATURE:
<223> OTHER INFORMATION: Clone pVAC 5.1

<400> SEQUENCE: 5

```
ggctgtggca caggctgaac gccggaggat ccggcgcgcc atgcattagt tattaatagt     60

aatcaattac ggggtcatta gttcatagcc catatatgga gttccgcgtt acataactta    120

cggtaaatgg cccgcctggc tgaccgccca acgacccccg cccattgacg tcaataatga    180

cgtatgttcc catagtaacg ccaataggga ctttccattg acgtcaatgg gtggagtatt    240

tacggtaaac tgcccacttg gcagtacatc aagtgtatca tatgccaagt acgcccccta    300

ttgacgtcaa tgacggtaaa tggcccgcct ggcattatgc ccagtacatg accttatggg    360

actttcctac ttggcagtac atctacgtat tagtcatcgc tattaccatg gtgatgcggt    420

tttggcagta catcaatggg cgtggatagc ggtttgactc acggggattt ccaagtctcc    480

accccattga cgtcaatggg agtttgtttt ggcaccaaaa tcaacgggac tttccaaaat    540

gtcgtaacaa ctccgcccca ttgacgcaaa tgggcggtag gcgtgtacgg tgggaggtct    600
```

-continued

```
atataagcag agctggttta gtatttaaat atgatgtgta gggtactccc cctacataca    660
cgacacttct agtgtttgtg tgccttggag gcgtgggtat agccccgccc cacccccttgg   720
cccctgttct agcccaacag gtatccttct ctctcggggc gagcgcgccg cctgctgctc    780
ccttgcagcg ggaaggacct cccgagtatt tccggagagc acctgcttta cgggatctcc    840
accctttaac catgtctggg acgttctccc ggtgcatgtg caccccggct gcccgggtat    900
tttggaacgc cggccaagtc ttttgcacac ggtgtctcag tgcgcggtct cttctccctc    960
cggagcttca ggaaactgac ctcgctgcaa ttggcttgtt ttacaagcct aaagacaagc   1020
ttcactggaa agtccctatc ggcatccctc aggtggagtg cactccatcc gggtgctgtt   1080
ggctctcagc catcttccca ttggcgcgca tgacctccgg caatcacaac ttcctccaac   1140
gacttgtgag ggttgccgat gtgttgtacc gtgatggttg cttggctcct cgacaccttc   1200
gtgaactcca agtttacgag cgcggctgca actggtaccc gatcacgggg cccgtgcccg   1260
ggatgggttt gttcgcaaac tccatgcacg tatccgacca gccgttccct ggtgccaccc   1320
atgtgttgac gaactcgccg ttgcctcaac aggcttgtcg gcagccgttc tgtccatttg   1380
aggaggctca ttctagtgtg tacaggtgga aaagatttgt ggttttcacg gattcctctc   1440
ccaacggtcg atctcgcatg atgtggacgc cggaatccga tgattcagcc gccttggagg   1500
tattaccgcc tgaattagaa cgtcaggtcg aaatcctcat tcggagtttt cctgctcatc   1560
accctgtcaa cctggccgac tgggagctca ctgagtcccc tgagaacggt tttttccttca  1620
acacgtctta ttcttgcggt caccttgtcc aaaaccccga cgtgtttgat ggcaagtgct   1680
ggctttcctg ctttttgggc cagtcggccg aagtgcgccg ccatgaggaa catttagctg   1740
acgccctcgg ttaccagacc aagtggggcg tgcctggcaa gtacctccag cgcaggcttc   1800
aggttcgcgg cattcgtgct gtagttgatc ctgatggccc cattcacgtc gaagcgctgt   1860
cttgcccccg gtcttggatc aggcacctga cttttgatga taatgtcacc ccaggatttg   1920
ttcgccttac gtcccttcgc attgtgccaa acaccgagcc tactgcttcc cggatcttcc   1980
ggtttggagc gcataagtgg tatggcgctg ccggcaaacg agctcgtgct aagcgtgccg   2040
ctaaaagtga gaaaatttcg gcccctaccc ccaaggttgc tcagccggtc cccacctgcg   2100
aaattaccac ctattctcca ccgacagacg ggtcttgtgg ttggcatgtt cttgccgcca   2160
taatgaaccg gatgatgaat ggtgacttca cgtcccctct gactcagtac aacagaccag   2220
aggatgactg ggcttctgat tatgaccttg ctcaggcgat ccaatgtctg caactgcccg   2280
ctaccgtagt tcggaatcgc gcctgtccta acgccaagta ccttataaaa cttaatggag   2340
ttcattggga ggtagaggtg aggcctggaa tggcccctcg ttccctttcc cgtgagtgtg   2400
tggttggcgt ctgttctgaa ggctgtatcg caccgcctta cccacaagac gggctgccta   2460
aacgtgcact tgaggccttg gcgtctgctt acagactacc ctccgactgt gttggttctg   2520
gtattgctga ctttcttgct aacccgcccc ctcaggagtt ttggaccctt gacaaaatgt   2580
tgacctcccc gtcaccagaa cggtccggct tctctagctt gtataaatta ctattggagg   2640
ttgttccgca gaaatgcggt gccacggaag ggcctttcgt ctatgctgtt gagaggatgt   2700
tgaaggattg tccgagctcc aaacaggcca tggcccttct ggcaaaaatt aaagtcccat   2760
cctcaaaggc cccgtctgtg tctctggacg agtgcttccc tacggatgtt ccagcggact   2820
ccgagccagc gtttcaggaa aggccccaaa gttctggtgc tgctgttgtc ctgtgttcac   2880
cggacataaa agagttcgag gaagcagccc cagaagaagt tcaagagggt ggccacaagg   2940
```

-continued

```
ccgtccactc tgcactcctt gccgagggtc ttaacaatga gcaggtacag gtggttgccg   3000
gtgcgcaact aaagctcggc agttgtggct tggcagtcgg gaatactcat ggaggtgttc   3060
cggtttcagc tagtccaatt aacctggcag acgggaattt gcccccctcg gactccatga   3120
aaggaaacat gcccaatggc tgggaggacg aaccactgga tttgtcccaa tcagcactag   3180
caaccacaac gacccttgtg agagagcaaa cacccgacaa tctaggttct ggcgccggtg   3240
ccctccctgt caccattcga gaatttgtcc cgacaaggcc tataccccgt catgttgagc   3300
actgcggcac ggagtcgggc gacagcagtt cgcctctgga tctgtccgat gcgcaaaccc   3360
cggaccagcc tttaaatcta tccctggccg cttggccagt gagggccacc gcgtctgacc   3420
ccggctgggt ccacggtagg cgtgagcctg tttttgtaaa gcctcggggt gctttctctg   3480
atggcgattc agtccttcag ttcggggagc tttccgaatc cagctctatc atcgagattg   3540
accggacaaa agatgctcca gtggttgatg cccccgtcga cttgacggtt tcgaacgaag   3600
ctctctctgg gatcgatcct tttgaattta ccgaactcaa gcgcccgcgt ttctccgctc   3660
aagccttaat tgaccgaggc ggcccactag ccgatgtcca tgcaaaaata aagaaccggg   3720
tatatgaaca gtgcctccag gcttgtgagc ctggcagtcg tgcaaccccc gccaccaggg   3780
agtggctcga caaaatgtgg gatagggtgg acatgaagac ttggcgctgc acctcgcagt   3840
tccaagctgg tcacattctt gcgtccctca aattcctccc cgacatgatt caagacacac   3900
cgcctcctgt tcccaggaag agccgggcta gtgataatgc cggcctgaag caactggtgg   3960
cgcagtggga cagaaaattg agtgtaaccc ccccccctaaa accggttggg ccggcgcttg   4020
gccaaaccgt ccctccgcct acggatattc agcaagaaga tgtcaccccc tccgataggc   4080
cacctcatgt gccggatctt cctagtcgag tgagcacggg tgggagttgg aaaggcctta   4140
tgctttccgg cacccgtctc gcggggtcta ttagtcagca cctcatgaca tgggtttttg   4200
aagttttctc ccatctccca gcttttatgc tcacactttt ctcgccacgg ggctctatgg   4260
ctccaggtga ttggctattt gcaggtgttg ttttacttgc tctcctgctc tgtcgttctt   4320
acccagtact cgggtgcctt cccttattgg gtgtcttttc tggttctttg cggcgtgttc   4380
gtctgggtgt ttttggttct tggatggctt ttgctgtatt tttattctcg actccatccg   4440
acccagtcgg ttcttcttgt gaccacgatt cgccggagtg tcatgctgag cttttggctc   4500
ttgagcagcg ccaactttgg gaacctgtgc ggggccttgt ggtcggcccc tcgggcctct   4560
tatgtgtcat tcttggcaag ttactcggtg ggtcacgtta tctctggcat gttttcttac   4620
gtttatgcat gcttgcggat ttggcccttt ctcttgttta tgtggtgtcc caggggcgtt   4680
gtcacaagtg ttggggaaag tgtataagga cagctcctgc ggaggtggct ctcaatgtgt   4740
tccctttctt gcgcgctacc cgtgcctctc ttgtgtcctt gtgcgatcga ttccaagcgc   4800
caaaaggggt tgatcctgtg cacttggcaa caggttggcg cgggtgctgg cgcggtgaga   4860
gccccattca tcaaccgcac caaaagccca tagcttatgc caatttggat gaaaagaaaa   4920
tatctgccca aacggtggtt gctgtcccgt atgatcccag tcaggccatc aaatgcctga   4980
aagttctgca ggcgggaggg gctatcgtgg accagcccac acctgaggtc gtccgtgtgt   5040
ccgagatccc tttctcagcc ccatttttc caaaggttcc agtcaaccca gattgcaggg   5100
ttgtggtaga ttcggacact tttgtggctg cagttcgctg cggttactcg acggctcaac   5160
tggtcttagg ccggggcaac tttgccaagt taaatcagat cccctccagg aactctgtct   5220
ccaccaaaac gactggtggg gcctcttaca cccttgctgt ggctcaagtg tctgtgtgga   5280
ctcttgttca tttcatcctc ggtctttggt tcacgtcacc tcaagtgtgt ggccgaggaa   5340
```

cctctgaccc atggtgttca aatccttttt catatcctac ctatggcccc ggaatagtgt 5400
gctcctctcg actttgtgtg tctgccgacg gagtcactct gccattgttc tcagcagtgg 5460
cacaactctc cggtagagag gtggggattt tcattttggt gctcgtctcc ttgactgctc 5520
tggcccaccg tatggctctt aaggcagaca tgttagtggt cttttcggct ttttgtgcct 5580
acgcctggcc catgagctcc tggttaatct gcttctttcc tatattcttg aagtgggtca 5640
cccttcaccc tctcactatg ctttgggtgc actcattctt ggtgttttgt ctgccagcag 5700
ccggcgtcct ctcactaggg ataaccggcc ttctctgggc agttggccgc tttacccagg 5760
tcgccggaat tattacacct tatgacatcc accagtacac ctctgggcca cgtggtgcag 5820
ccgctgtggc cacggcccca gaaggcactt acatggccgc cgtccggaga gctgccttaa 5880
ctggacgaac cctcatcttc acaccatctg cggttggatc ccttcttgaa ggtgctttca 5940
ggacccataa accctgcctt aacaccgtga atgttgtagg ctcttccctt ggttccgggg 6000
gggttttcac cattgatggc agaagaactg ttgtcactgc tgcccatgtg ttgaacggcg 6060
acacagctag agtcaccggc gactcctaca accgcatgca cactttcaag accaatggtg 6120
attatgcctg gtcccatgct gatgactggc ggggcgttgc ccctgtggtc aaggtcgcga 6180
aggggtaccg cggtcgtgcc tactggcaaa catcaactgg tgtcgaaccc ggtattgttg 6240
gggaagggtt cgccttctgt tttaccaact gtggcgattc ggggtcacct gtcatctcag 6300
aatctggtga tcttgttgga atccacaccg gttcaaacaa actcggttct ggtcttgtga 6360
caacccctga aggggagacc tgctccatca aagaaaccaa gctctctgac ctttccaggt 6420
attttgcagg cccaagcgtc cctcttgggg atattaaatt gagtccggcc atcatccctg 6480
atgtaacatc cattccgagt gacttggcat cgctcctagc ctccgtccct gtaatggaag 6540
gcggcctctc gactgtccaa cttttgtgtg tcttttttcct tctctggcgt atgatgggcc 6600
atgcctggac acccattgtt gccgtgggct tctttttgct gaatgaaatt cttccagcag 6660
ttttggtccg agccgtgttt tcttttgcgc tctttgtgct tgcatgggcc accccctggt 6720
ctgcacaggt gttgatgatc agactcctca cggcagctct caaccgcaac aggctttctc 6780
tggcgttcta cgcactcggg ggtgtcgtcg gtttggctgc tgaaattggg acctttgctg 6840
gtagattgtc tgaattgtct caagctcttt cgacatactg cttcttacct agggttcttg 6900
ctgtgactag ttatgttccc accatcatca ttggtggact ccataccctt ggtgtgatct 6960
tgtggctatt caaataccgg tgcctccaca acatgttagt tggtgatggg agtttttcaa 7020
gtgccttttt cctacggtat tttgcagagg gtaatctcag aaaaggtgtt tcacagtcct 7080
gtggcatgaa taacgagtcc ctgacagctg ctttagcttg caagttgtca caggctgacc 7140
ttgatttttt gtccagcttg acgaacttca agtgctttgt atctgcttca aacatgaaag 7200
atgctgctgg ccagtacatt gaggcagcgt atgccaaggc cctgcgccga gagttggcct 7260
ccctagtcca ggttgacaaa atgaaaggag ttttgtccaa gctcgaggcc tttgctgaaa 7320
cagccacccc gtcccttgac acaggtgacg tgattgtcct gcttgggcaa catcctcacg 7380
gatccatcct cgatattaat gtggggactg aaaggaaaac tgtgtctgtt caagagactc 7440
ggagcctagg cggctccaaa ttcagtgtct gcactgtcgt gtccaacaca cccgtggacg 7500
ccttggccgg cattccactt cagacaccaa ccccgctttt tgagaatggc ccgcgtcatc 7560
gcggtgagga agatgatctc aaagttgaga ggatgaagaa acattgtgtg tccctcggct 7620
tccacaacat caatggcaaa gtttactgta aagtttggga caagtccacc ggtgacacct 7680

-continued

```
tttacacgga tgattcccgg tacacccaag accatgcttt tcaggacagg tcagctgact   7740
atagagacag ggactatgag ggtgtgcaaa ccgcccccca acagggattt gatccaaaat   7800
ctgaaacccc tgttggcact gttgtaatcg gcggtattac gtataatagg tatctggtca   7860
aaggcaagga ggttctggtt cccaaacctg acaactgcct tgaagccgcc aagctgtccc   7920
ttgagcaagc acttgctggg atgggccaaa cttgcgacct tacagttgca gaggtggaaa   7980
agctaaagcg catcatcagt caactccaag gtttgaccac tgaacaggct ttaaactgct   8040
agccgccagc ggcttgaccc gctgtggccg cggcggcttg gttgtaactg aaacggcggt   8100
aaaaattata aaataccaca gcagaacttt cactttaggc cctttagacc taaaagtcac   8160
ttctgaggta gaggtgaaga aatcaactga gcagggccac gccgttgtgg caaacctatg   8220
ttctggtgtc gtattgatga gacctcaccc accgtccctt gttgacgtcc ttctgaaacc   8280
cggacttgac acaacacccg acattcaacc ggggcatggg gccgggaata tgggcgtgga   8340
cggttctatt tgggatttg aaaccgcacc cacaaaggca gaactcgagt tgtccaagca   8400
aataattcaa gcatgtgaag ttaggcgcgg agacgccccg aacctccaac tcccctacaa   8460
gctctatcct gtcagagggg atcctgagcg gcataaaggc cgccttatca acaccaggtt   8520
tggagacttg ccttacaaaa ctcctcaaga caccaagtcc gctatccatg cggcttgttg   8580
cctgcacccc aacggggccc ctgtgtctga tggtaaatcc acactaggca ccactcttca   8640
acatggtttc gagctttatg ttcccacagt gccctatagt gtcatggagt accttgattc   8700
acgccctgac acccctccca tgttcactaa acatggcact tccaaggctg ctgcagaaga   8760
cctccaaaaa tatgacctat ccacccaagg atttgtcctg cctggggtcc tacgcctagt   8820
gcgcagattc atctttggcc atgttggtaa ggcaccgcca ttgttcctcc catcaaccta   8880
tcccgccaag aactccatgg cagggattaa tggccagaga ttcccaacaa aggacgtcca   8940
gagcatacct gaaattgatg aaatgtgtgc ccgcgccgtc aaggagaatt ggcaaaccgt   9000
gacaccttgt actctcaaga aacagtactg ttccaagccc aaaaccagga ccatcctggg   9060
caccaacaac tttattgcct tggctcacag atcggcgctc agtggcgtca cccaggcatt   9120
catgaagaag gcttggaagt ccccaattgc cttggggaaa aacaagttca aggagctgca   9180
ttgtactgtc gccggcaggt gtcttgaggc tgacttggcc tcctgtgatc gcagcacccc   9240
cgccattgta agatggtttg ttgccaacct cctgtatgaa cttgcaggat gtgaagagta   9300
cttgcctagc tatgtgctta actgctgcca tgaccttgtg gcaacacagg atggtgcctt   9360
cacaaaacgc ggtggcctgt cgtccgggga ccccgtcacc agtgtgtcca ataccgtata   9420
ttcactggta atctatgccc agcacatggt attgtcagcc ttgaaaatgg gtcatgaaat   9480
tggtcttaag ttcctcgagg agcagctcaa attcgaggac ctccttgaaa ttcagcctat   9540
gttagtatac tctgacgacc ttgtcttgta cgctgaaaga cccacttttc ccaattacca   9600
ttggtgggtc gagcaccttg acctgatgct gggtttcaaa acggacccaa agaaaactgt   9660
cataactgat aaacccagct tcctcggctg caggattgag gcagggcgac agttagtccc   9720
caatcgcgac cgcatcctgg ctgcccttgc atatcacatg aaggcgcaga acgcctcaga   9780
atattatgcg tctgctgccg caatcctgat ggattcgtgt gcttgcattg accatgaccc   9840
tgagtggtat gaggacctca tctgtggtat tgcccggtgt gctcgccaag atggctatag   9900
tttcccgggc ccggcatttt tcatgtccat gtgggagaaa ctgaaaagtc ataatgaagg   9960
gaaaaaattc cgccactgcg gcatctgcga cgccaaggcc gaccatgcgt ccgcctgtgg  10020
actcgatttg tgcttgttcc actcgcattt tcatcagcac tgccctgtca ctctgagctg  10080
```

-continued cggccatcat gccggttcta aggaatgtcc gcagtgtcag tcaccggttg gggctggtag 10140
atctcctctc gatgccgtgc taaaacaaat tccgtacaaa cctcctcgta ctgtcatcat 10200
gaaggtggat aataaaacaa cggcccttga tccggggagg tatcagtccc gtcgaggtct 10260
cgttgcagtc aagaggggta ttgcaggcaa tgaagttgac cttgctaatg gagactacca 10320
ggtggtgcct cttttgccga cttgcaaaga cataaacatg gtgaaggtgg cttgtaatgt 10380
gctactcagc aagttcatag tagggccacc aggttccgga aagaccacct ggttgctgag 10440
tcaagtccag gacgatgatg tcatttatac acccacccat cagactatgt ttgatatagt 10500
cagtgctctc aaagtttgca ggtattccat tccaggggct tcaggactcc ctttcccacc 10560
acctgccagg tccgggccgt gggtcaggct tgttgccagc gggcacgtcc ctggccgagt 10620
atcatacctc gatgaggctg gatattgtaa tcatctggac attctcagac tgctttccaa 10680
aacacccctt gtgtgtttag gtgaccttca gcaactccac cctgtcggct ttgattccta 10740
ctgttatgtg tttgatcaga tgcctcagaa gcagctgacc actatttaca gatttggctc 10800
caacatctgc gcagctatcc agccttgtta cagggagaaa cttgaatcca aggccaggaa 10860
caccaggata gtttttacca cccgacctgt agctttcggg caggtgctga caccatacca 10920
caaagatcgc atcggctcag cgataaccat agattcatct caggggggcca cctttgacat 10980
tgtgacattg catctaccat cgccaaagtc cctaaataaa tcccgagcac ttgtagccat 11040
cactcgggca agacacgggt tgttcatcta tgaccctcat aatcagctcc aggagttttt 11100
caacctaact cctgagcgca ctgattgtaa ccttgtgttt aaccgtgggg atgagctggt 11160
agttctggac gcggataatg cagtcacaac tgtggcgaag gccctagaga cgggtccatc 11220
tcgatttcga gtatcagacc caaggtgcga gtctctcttg gccgcttgct cggccagcct 11280
ggagggaagc tgcatgccac taccgcaagt ggcacataac ctggggtttt acttttcccc 11340
agatagtcca gcattcgcgc ctctgccaaa agaattggca ccacattggc cggtggttac 11400
ccatcagaat aaccgggcgt ggcctgaccg acttgttgct agtatgcgcc caattgatgc 11460
ccgttatagc aagccaatgg ttggtgcagg gtacgcggtc gggccgtcca cttttcttgg 11520
cactcctggt gtggtatcat actatctgac actgtacatc aggggtgagc cccaggcctt 11580
accagaaaca ctcgtgtcaa cagggcgcat agccacagat tgtcgggaat atctcgacgc 11640
cgctgaggaa gaggcagcaa aagaactccc tcacgcattc attggcgatg tcaaaggtac 11700
cacggttggg gggtgtcatc acatcacatc aaaataccta cctaggtccc tgcctaagga 11760
ctctgttgcc gtagttggag taagttcgcc cggcagggcc gctaaagccg tgtgcactct 11820
caccgatgtt tacctccccg agctccggcc atatctgcaa cctgagacgg catcaaaatg 11880
ctggaaactc aaattagact ttagagatgt ccgactaatg gtctggaaag gagccaccgc 11940
ctacttccag ctggaagggc ttacatggtc ggcgctgccc gactatgcca ggtttattca 12000
gctgcctaag gatgccgttg tgtacattga tccgtgcata ggaccggcaa cagccaaccg 12060
taaggtcgtg cggaccacag actggcgggc tgacctggca gtgacaccgt atgattacgg 12120
tgcccagaac attttgacaa cagcctggtt cgaggacctc gggccgcagt ggaagatttt 12180
ggggttgcag ccctttaggc gatcatttgg ctttgaaaac actgaggatt gggcaatcct 12240
tgcacgccgt atgaatgacg gcaaggacta cactgactat aactggaact gtgttcgaga 12300
acgcccacac gccatctacg ggcgcgctcg tgaccatacg tatcattttg cccccggcac 12360
agaattgcag gtagagctag gtaaaccccg gctgccgcct gagcaagtgc cgtgaatccg 12420

-continued

```
gagtgatgca atggggttac tgtggagtaa aattagccag ctgttcgtgg acgccttcac  12480
tgagttcctt gttagtgtgg ttgatattgt cattttcctt gccatactgt ttgggttcac  12540
cgtcgcagga tggttactgg tctttcttct cagagtggtt tgctccgcgc ttctccgttc  12600
gcgctctgcc attcactctc ccgaactatc gaaggtccta tgaaagcttg ctacccaatt  12660
gcagaccgga tgtcccacaa tttgcattca agcacccatt gggcatactt tggcacatgc  12720
gagtctccca cctaattgat gaaatggtct ctcgtcgcat ttaccggacc atggaacact  12780
caagtcaagc ggcctggaag caggtagtta gtgaggccac cctcacaaag ctgtcagggc  12840
ttgatatagt tactcatttc caacacctgg ccgcagtgga ggcggattct tgccgtttcc  12900
tcagctcacg acttgtgatg ctaaagaatc ttgccgttgg caatgtgagc ctacagtata  12960
acaccacgtt ggaccatgtt gagctcatct tccctacgcc aggtacgagg cccaagttga  13020
ccgatttcag acaatggctc atcagtgtgc acgcttccat tttttcctct gtggcttcat  13080
ctgttacctt gttcatagtg ttttggcttc gaattccagc cgtacgctat gtttttggtt  13140
tccattggcc cacggcaaca catcattcga gctaaccatc aactacacca tatgtatgcc  13200
ctgctctacc agccaagcgg ctagccaaag actcgagccc ggtcgtaaca tgtggtgcag  13260
aatagggcac gacaggtgtg aggaacgtga ccatgatgag ttgtcaatgt ccattccgtc  13320
agggtacgag aacctcaaac ttgagggtta ttatgcttgg ctggcctttt tgtccttttc  13380
ctacgcggcc caatttcatc cggagttgtt cggaatagga aacgtgtcgc gcgtctttgt  13440
ggacaagcga caccagttca tttgcgccga gcatgatgga caaaattcaa ccatatctac  13500
cggacacaac atctccgcat tatatgcggt gtattaccat caccaaatag acgggggcaa  13560
ttggttccac ttggaatggc tgcggccatt cttttcctcc tggctggtgc tcaatatctc  13620
atggtttctg aggcgttcgc ctgtaagccc tgtttctcga cgcatctatc agatattaag  13680
accaacacga ccgcggctgc cggtttcatg gtccttcagg acatcaattg tctccgacct  13740
cacggggtct caacagcgca agagaccatt tccttcggaa agccgtccca atgtcgcgag  13800
gccgtcggta ttccccagta cattacgata acggctaatg tgaccgatga atcgtatttg  13860
tacaacgcgg acttgctgat gctttctgcg tgccttttct acgcttcaga aatgagcgaa  13920
aagggcttca aagttatctt tgggaacgtt tctggcgttg tttctgcttg tgtcaatttt  13980
acagattatg tggctcatgt aatccaacat acccagcagc atcatctggt gattgatcac  14040
attcggttgc tgcatttcct gacaccatca acaatgaggt gggctacaac cattgcttgt  14100
ttgttcgcca ttctcttggc gatatgagat gttctcacaa attggagcgt ttcttgactc  14160
ctcactcttg cttctggtgg cttttttttgc tttgtaccgg cttgtcttgg tcctttgtcg  14220
atggcaacga cagcagctcg acataccaat acatatataa tttgacgata tgcgagctga  14280
atgggaccga atggttgccc agccattttg actgggcagt cgagaccttt gtgctttacc  14340
cggttgccac tcatatcctt tcactgggtt ttctcacaac aagccatttt tttgatgcgc  14400
tcggtctcgg cgctgtgtcc actacaggat ttgttggcgg gcggtatgta ctcagcagcg  14460
tgtacggcgc ttgtgctttc gcagcgctcg tatgttttgt catccgcgct gctaaaaatt  14520
gcatggcttg ccgttatgcc cgcacccggt ttaccaactt cattgtggac gaccggggga  14580
ggatccatcg atggaagtct ccaatagtgg tagagaaatt gggcaaagct gaagtcggtg  14640
gcgacctcgt caccatcaaa catgtcgtcc tcgaaggggt taaagctcaa cccttgacga  14700
ggacttcggc tgagcaatgg gaagcctaga cgatttttgc aacgatccta ccgccgcaca  14760
aaagcttgtg ctagccttta gcatcacata tacacctata atgatatacg cccttaaggt  14820
```

gtcacgcggc cgcctcctgg ggctattgca catcttgata ttcctgaact gttcctttac 14880
attcggatac atgacatatg tgcattttca atccaccaac cgtgtcgcat ttactctggg 14940
ggccgttgtc gcccttctgt ggggtgttta cagcttcaca gagtcatgga agttcattac 15000
ttccagatgc agattgtgtt gcctaggccg gcaatacatt ctggcccctg cccatcacgt 15060
agaaagtgct gcaggtctcc attcaatccc agcgtctggt aaccgagcat acgctgtgag 15120
aaagcccgga ctaacatcag tgaacggcac tctagtacca ggacttcgga gcctcgtgct 15180
gggcggcaaa cgagctgtta aacgaggagt ggttaacctc gtcaagtatg gccggtaaaa 15240
atcagagcca gaagaaaaag aagaatacag ctccgatggg gaatggccag ccagtcaatc 15300
aactgtgcca gttgctgggt gcaatgataa agtcccagcg ccagcaacct aggggaggac 15360
aggcaaaaaa aagaaagcct gagaagccac attttcccct agctgctgaa gatgacattc 15420
ggcaccacct cacccagacc gaacgttccc tctgcttgca atcgatccag acggctttta 15480
accaaggcgc aggaactgcg tcgctttcat ccagcgggaa ggtcagtttt caggttgagt 15540
tcatgctgcc ggttgctcat acagtgcgcc tgattcgcgt gacttctaca tccgccagtc 15600
agggtgcaaa ttaatttgac agtcaggtga atggccgcga ttgacgtgtg gcctctaagt 15660
cacctattca attagggcga tcacatgggg gtcaaactta atcaggcagg aaccatgtga 15720
ccgaaattaa aaaaaaaaaa aaaaaaaaaa aaaggccggc atggtcccag cctcctcgct 15780
ggcgccggct gggcaacatt ccgaggggac cgtcccctcg gtaatggcga atgggactct 15840
agagcccttc cggctggctg gtttattgct gataaatctg gagccggtga gcgtgggtct 15900
cgcggtatca ttgcagc 15917

<210> SEQ ID NO 6
<211> LENGTH: 1214
<212> TYPE: DNA
<213> ORGANISM: Artificial Sequence
<220> FEATURE:
<223> OTHER INFORMATION: SMART_VAC8_consensus_sequence_(reversed).
Positions 12937 to 14170 of the virus genome

<400> SEQUENCE: 6
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatacatata taatttgacg atatgcgagc tgaatgggac 720
cgaatggttg cccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900

```
cgcttgtgct ttcgcagcgc tcgtatgttt tgtcatccgc gctgctaaaa attgcatggc    960

ttgccgttat gcccgcaccc ggtttaccaa cttcattgtg gacgaccggg ggaggatcca   1020

tcgatggaag tctccaatag tggtagagaa attgggcaaa gctgaagtcg gtggcgacct   1080

cgtcaccatc aaacatgtcg tcctcgaagg ggttaaagct caacccttga cgaggacttc   1140

ggctgagcaa tgggaagcct agacgatttt tgcaacgatc ctaccgccgc acaaaagctt   1200

gtgctagcct ttag                                                     1214
```

<210> SEQ ID NO 7
<211> LENGTH: 1214
<212> TYPE: DNA
<213> ORGANISM: Artificial Sequence
<220> FEATURE:
<223> OTHER INFORMATION: SMART_VAC23_consensus_sequence_(reversed). Positions 12937 to 14170 of the virus genome

<400> SEQUENCE: 7

```
cacttggaat ggctgcggcc attcttttcc tcctggctgg tgctcaatat ctcatggttt     60

ctgaggcgtt cgcctgtaag ccctgtttct cgacgcatct atcagatatt aagaccaaca    120

cgaccgcggc tgccggtttc atggtccttc aggacatcaa ttgtctccga cctcacgggg    180

tctcaacagc gcaagagacc atttccttcg gaaagccgtc ccaatgtcgc gaggccgtcg    240

gtattcccca gtacattacg ataacggcta atgtgaccga tgaatcgtat ttgtacaacg    300

cggacttgct gatgctttct gcgtgccttt tctacgcttc agaaatgagc gaaaagggct    360

tcaaagttat ctttgggaac gtttctggcg ttgtttctgc ttgtgtcaat tttacagatt    420

atgtggctca tgtaatccaa catacccagc agcatcatct ggtgattgat cacattcggt    480

tgctgcattt cctgacacca tcaacaatga ggtgggctac aaccattgct tgtttgttcg    540

ccattctctt ggcgatatga gatgttctca caaattggag cgtttcttga ctcctcactc    600

ttgcttctgg tggctttttt tgctttgtac cggcttgtct tggtcctttg tcgatggcaa    660

cgacagcagc tcgacatacc aatacatata taatttgacg atatgcgagc tgaatgggac    720

cgaatggttg cccagccatt ttgactgggc agtcgagacc tttgtgcttt acccggttgc    780

cactcatatc ctttcactgg gttttctcac aacaagccat ttttttgatg cgctcggtct    840

cggcgctgtg tccactacag gatttgttgg cgggcggtat gtactcagca gcgtgtacgg    900

cgcttgtgct ttcgcagcgc tcgtatgttt tgtcatccgc gctgctaaaa attgcatggc    960

ttgccgttat gcccgcaccc ggtttaccaa cttcattgtg gacgaccggg ggaggatcca   1020

tcgatggaag tctccaatag tggtagagaa attgggcaaa gctgaagtcg gtggcgacct   1080

cgtcaccatc aaacatgtcg tcctcgaagg ggttaaagct caacccttga cgaggacttc   1140

ggctgagcaa tgggaagcct agacgatttt tgcaacgatc ctaccgccgc acaaaagctt   1200

gtgctagcct ttag                                                     1214
```

<210> SEQ ID NO 8
<211> LENGTH: 1214
<212> TYPE: DNA
<213> ORGANISM: Artificial Sequence
<220> FEATURE:
<223> OTHER INFORMATION: SMART_VAC16_consensus_sequence 2 reads from SMART mapped to 5xVAC8 consensus sequence (reversed). Positions 12937 to 14170 of the virus genome

<400> SEQUENCE: 8
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatacatata taatttgacg atatgcgagc tgaatgggac 720
cgaatggttg cccagccatt ttgactgggc agtcgagacc tttgtgcttt acccggttgc 780
cactcatatc ctttcactgg gtttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgcaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 9
<211> LENGTH: 1214
<212> TYPE: DNA
<213> ORGANISM: Artificial Sequence
<220> FEATURE:
<223> OTHER INFORMATION: SMART_VAC13_consensus_sequence_(reversed).
Positions 12937 to 14170 of the virus genome

<400> SEQUENCE: 9
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatacatata taatttgacg atatgcgagc tgaatgggac 720
cgaatggttg cccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgcaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 10
<211> LENGTH: 1214
<212> TYPE: DNA
<213> ORGANISM: Artificial Sequence
<220> FEATURE:
<223> OTHER INFORMATION: SMART_VAC11_consensus_sequence_(reversed). Positions 12937 to 14170 of the virus genome

<400> SEQUENCE: 10
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatacatata taatttgacg atatgcgagc tgaatgggac 720
cgaatggttg cccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgcaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 11
<211> LENGTH: 1214
<212> TYPE: DNA
<213> ORGANISM: Artificial Sequence
<220> FEATURE:

<223> OTHER INFORMATION: SMART_VAC2_consensus_sequence. Positions 12937
to 14170 of the virus genome

<400> SEQUENCE: 11
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaacg 300
cggacttgct gatgcttttct gcgtgccttt tctacgcttc agagatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatatatata taatttgacg atatgcgagc tgaatgggac 720
cgaatggttg cccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgtaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 12
<211> LENGTH: 1214
<212> TYPE: DNA
<213> ORGANISM: Artificial Sequence
<220> FEATURE:
<223> OTHER INFORMATION: SMART_VAC20_consensus_sequence. Positions 12937
to 14170 of the virus genome

<400> SEQUENCE: 12
catttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatacatata taatttgacg atatgcgagc tgaatgggac 720
cgaatggttg cccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgtaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 13
<211> LENGTH: 1214
<212> TYPE: DNA
<213> ORGANISM: Artificial Sequence
<220> FEATURE:
<223> OTHER INFORMATION: SMART_VAC4_consensus_sequence_(reversed). Positions 12937 to 14170 of the virus genome

<400> SEQUENCE: 13
catttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagaac attcccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatacatata taatttgacg atatgcgagc tgaatgggac 720
cgaatggttg cccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgtaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 14
<211> LENGTH: 1214
<212> TYPE: DNA
<213> ORGANISM: Artificial Sequence -continued
<220> FEATURE:
<223> OTHER INFORMATION: SMART_VAC6_consensus_sequence_(reversed). Positions 12937 to 14170 of the virus genome

<400> SEQUENCE: 14

```
catttggaat ggctgcggcc attcttttcc tcctggctgg tgctcaatat ctcatggttt     60

ctgaggcgtt cgcctgtaag ccctgtttct cgacgcatct atcagatatt aagaccaaca    120

cgaccgcggc tgccggtttc atggtccttc aggacatcaa ttgtctccga cctcacgggg    180

tctcaacagc gcaagagaac attcccttcg gaaagccgtc ccaatgtcgc gaggccgtcg    240

gtattcccca gtacattacg ataacggcta atgtgaccga tgaatcgtat ttgtacaacg    300

cggacttgct gatgctttct gcgtgccttt tctacgcttc agaaatgagc gaaaagggct    360

tcaaagttat ctttgggaac gtctctggcg ttgtttctgc ttgtgtcaat tttacagatt    420

atgtggctca tgtaacccaa catacccagc agcatcatct ggtgattgat cacattcggt    480

tgctgcattt cctgacacca tcaacaatga ggtgggctac aaccattgct tgtttgttcg    540

ccattctctt ggcgatatga gatgttctca caaattggag tgtttcttga ctcctcactc    600

ttgcttctgg tggctttttt tgctgtgtac cggcttgtct tggtcctttg tcgatggcaa    660

cgacagcagc tcgacatacc aatacatata taatttgacg atatgcgagc tgaatgggac    720

cgaattgttg tccagccatt ttgactgggc agtcgagacc tttgtgcttt acccggttgc    780

cactcatatc ctttcactgg gttttctcac aacaagccat ttttttgatg cgctcggtct    840

cggcgctgtg tccactacag gatttgttgg cgggcggtat gtactcagca gcgtgtacgg    900

cgcttgtgct ttcgcagcgc tcgtatgttt tgtcatccgc gctgctaaaa attgcatggc    960

ttgccgttat gcccgtaccc ggtttaccaa cttcattgtg gacgaccggg ggaggatcca   1020

tcgatggaag tctccaatag tggtagagaa attgggcaaa gctgaagtcg gtggcgacct   1080

cgtcaccatc aaacatgtcg tcctcgaagg ggttaaagct caacccttga cgaggacttc   1140

ggctgagcaa tgggaagcct agacgatttt tgcaacgatc ctaccgccgc acaaaagctt   1200

gtgctagcct ttag                                                     1214
```

<210> SEQ ID NO 15
<211> LENGTH: 1214
<212> TYPE: DNA
<213> ORGANISM: Artificial Sequence
<220> FEATURE:
<223> OTHER INFORMATION: SMART_VAC21_consensus_sequence. Positions 12937 to 14170 of the virus genome

<400> SEQUENCE: 15

```
catttggaat ggctgcggcc attcttttcc tcctggctgg tgctcaatat ctcatggttt     60

ctgaggcgtt cgcctgtaag ccctgtttct cgacgcatct atcagatatt aagaccaaca    120

cgaccgcggc tgccggtttc atggtccttc aggacatcaa ttgtctccga cctcacgggg    180

tctcaacagc gcaagagaac atttccttca gaaagccgtc ccaatgtcgc gaggccgtcg    240

gtattcccca gtacattacg ataacggcta atgtgaccga tgaatcgtat ttgtacaacg    300

cggacttgct gatgctttct gcgtgccttt tctacgcttc agaaatgagc gaaaagggct    360

tcaaagttat ctttgggaac gtctctggcg ttgtttctgc ttgtgtcaat tttacagatt    420

atgtggctca tgtaatccaa catacccagc agcatcatct ggtgattgat cacattcggt    480

tgctgcattt cctgacacca tcaacaatga ggtgggctac aaccattgct tgtttgttcg    540

ccattctctt ggcgatatga gatgttctca caaattggag cgtttcttga ctcctcactc    600
```

-continued

```
ttgcttctgg tggctttttt tgctttgtac cggcttgtct tggtcctttg tcgatggcaa    660

cgacagcagc tcgacatacc aatacatata taatttgacg atatgcgagc tgaatgggac    720

cgaatggttg cccagccatt ttgactgggc agtcgagacc tttgtgcttt acccggttgc    780

cactcatatc ctttcactgg gttttctcac aacaagccat ttttttgatg cgctcggtct    840

cggcgctgtg tccactacag gatttgttgg cgggcggtat gtactcagca gcgtgtacgg    900

cgcttgtgct ttcgcagcgc tcgtatgttt tgtcatccgc gctgctaaaa attgcatggc    960

ttgccgttat gcccgtaccc ggtttaccaa cttcattgtg gacgaccggg ggaggatcca   1020

tcgatggaag tctccaatag tggtagagaa attgggcaaa gctgaagtcg gtggcgacct   1080

cgtcaccatc aaacatgtcg tcctcgaagg ggttaaagct caacccttga cgaggacttc   1140

ggctgagcaa tgggaagcct agacgatttt tgcaacgatc ctaccgccgc acaaaagctt   1200

gtgctagcct ttag                                                     1214
```

<210> SEQ ID NO 16
<211> LENGTH: 1214
<212> TYPE: DNA
<213> ORGANISM: Artificial Sequence
<220> FEATURE:
<223> OTHER INFORMATION: SMART_VAC10_consensus_sequence. Positions 12937 to 14170 of the virus genome

<400> SEQUENCE: 16

```
catttggaat ggctgcggcc attcttttcc tcctggctgg tgctcaatat ctcatggttt     60

ctgaggcgtt cgcctgtaag ccctgtttct cgacacatct atcagatatt aagaccaaca    120

cgaccgcggc tgccggtttc atggtccttc aggacatcaa ttgtctccga cctcacgggg    180

tctcaacagc gcaagagaac attcccttcg gaaagccgtc ccaatgtcgc gaggccgtcg    240

gtattcccca gtacattacg ataacggcta atgtgaccga tgaatcgtat ttgtacaacg    300

cggacttgct gatgctttct gcgtgccttt tctacgcttc agaaatgagc gaaaagggct    360

tcaaagttat ctttgggaac gtttctggcg ttgtttctgc ttgtgtcaat tttacagatt    420

atgtggctca tgtaatccaa catacccagc agcatcatct ggtgattgat cacattcggt    480

tgctgcattt cctgacacca tcaacaatga ggtgggctac aaccattgct tgtttgttcg    540

ccattctctt ggcgatatga gatgttctca caaattggag cgtttcttga ctcctcactc    600

ttgcttctgg tggctttttt tgctttgtac cggcttgtct tggtcctttg tcgatggcaa    660

cgacagcagc tcgacatacc aatacatata taatttgacg atatgcgagc tgaatgggac    720

cgaatggttg cccagccatt ttgactgggc agtcgagacc tttgtgcttt acccggttgc    780

cactcatatc ctttcactgg gttttctcac aacaagccat ttttttgatg cgctcggtct    840

cggcgctgtg tccactacag gatttgttgg cgggcggtat gtactcagca gcgtgtacgg    900

cgcttgtgct ttcgcagcgc tcgtatgttt tgtcatccgc gctgctaaaa attgcatggc    960

ttgccgttat gcccgtaccc ggtttaccaa cttcattgtg gacgaccggg ggaggatcca   1020

tcgatggaag tctccaatag tggtagagaa attgggcaaa gctgaagtcg gtggcgacct   1080

cgtcaccatc aaacatgtcg tcctcgaagg ggttaaagct caacccttga cgaggacttc   1140

ggctgagcaa tgggaagcct agacgatttt tgcaacgatc ctaccgccgc acaaaagctt   1200

gtgctagcct ttag                                                     1214
```

<210> SEQ ID NO 17
<211> LENGTH: 1214
<212> TYPE: DNA

<213> ORGANISM: Artificial Sequence
<220> FEATURE:
<223> OTHER INFORMATION: SMART_VAC19_consensus_sequence_(reversed).
Positions 12937 to 14170 of the virus genome

<400> SEQUENCE: 17
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaatg 300
cggacttgct gatgctttct gcgtgccttt tctacgcttc agaaatgagc gaaaagggct 360
tcaaagttat ctttgggaac gtctctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag tgtttcttga ctcctcactc 600
ttgcttctgg tggctttttt tgctgtgtac cggcttgtct tggtcctttg tcgatggcaa 660
cgacagcagc tcgacatacc aatacatata taatttgacg atatgcgagc tgaatgggac 720
cgaatcgttg tccagccatt ttgactgggc agtcgagacc tttgtgcttt acccggttgc 780
cactcatatc ctttcactgg gtttctcac aacaagccat tttttgatg cgctcggtct 840 cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgcaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 18
<211> LENGTH: 1214
<212> TYPE: DNA
<213> ORGANISM: Artificial Sequence
<220> FEATURE:
<223> OTHER INFORMATION: SMART_VAC12_consensus_sequence_(reversed).
Positions 12937 to 14170 of the virus genome

<400> SEQUENCE: 18
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatacatata taatttgacg atatgcgagc tgaatgggac 720
cgaatggttg cccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgcaccc ggtttaccaa cttcattgta gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 19
<211> LENGTH: 1214
<212> TYPE: DNA
<213> ORGANISM: Artificial Sequence
<220> FEATURE:
<223> OTHER INFORMATION: SMART_VAC14_consensus_sequence_(reversed). Positions 12937 to 14170 of the virus genome

<400> SEQUENCE: 19
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatacatata taatttgacg atatgcgagc tgaatgggac 720
cgaatggttg cccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgtaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 20
<211> LENGTH: 1214

<212> TYPE: DNA
<213> ORGANISM: Artificial Sequence
<220> FEATURE:
<223> OTHER INFORMATION: SMART_VAC9_consensus_sequence_(reversed).
      Positions 12937 to 14170 of the virus genome

<400> SEQUENCE: 20
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagaac attccctttg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag tgtttcttga ctcctcactc 600
ttgcttctgg tggctttttt tgctgtgtac cggcttgtct tggtcctttg tcgatggcaa 660
cgacagcagc tcgacatacc aatacatata taatttgacg atatgcgagc tgaatgggac 720
cgaatcgttg tccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgtaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 21
<211> LENGTH: 1214
<212> TYPE: DNA
<213> ORGANISM: Artificial Sequence
<220> FEATURE:
<223> OTHER INFORMATION: SMART_VAC17_consensus_sequence_(reversed).
      Positions 12937 to 14170 of the virus genome

<400> SEQUENCE: 21
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagaac attcccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtctctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540

```
ccattctctt ggcgatatga gatgttctca caaattggag tgtttcttga ctcctcactc    600

ttgcttctgg tggctttttt tgctgtgtac cggcttgtct tggtcctttg tcgatggcaa    660

cgacagcagc tcgacatacc aatacatata taatttgacg atatgcgagc tgaatgggac    720

cgaatcgttg tccagccatt ttgactgggc agtcgagacc tttgtgcttt acccggttgc    780

cactcatatc ctttcactgg gttttctcac aacaagccat ttttttgatg cgctcggtct    840

cggcgctgtg tccactacag gatttgttgg cgggcggtat gtactcagca gcgtgtacgg    900

cgcttgtgct ttcgcagcgc tcgtatgttt tgtcatccgc gctgctaaaa attgcatggc    960

ttgccgttat gcccgtaccc ggtttaccaa cttcattgtg gacgaccggg ggaggatcca   1020

tcgatggaag tctccaatag tggtagagaa attgggcaaa gctgaagtcg gtggcgacct   1080

cgtcaccatc aaacatgtcg tcctcgaagg ggttaaagct caacccttga cgaggacttc   1140

ggctgagcaa tgggaagcct agacgatttt tgcaacgatc ctaccgccgc acaaaagctt   1200

gtgctagcct ttag                                                     1214
```

<210> SEQ ID NO 22
<211> LENGTH: 1214
<212> TYPE: DNA
<213> ORGANISM: Artificial Sequence
<220> FEATURE:
<223> OTHER INFORMATION: SMART_VAC22_consensus_sequence_(reversed). Positions 12937 to 14170 of the virus genome

<400> SEQUENCE: 22

```
cacttggaat ggctgcggcc attcttttcc tcctggctgg tgctcaatat ctcatggttt     60

ctgaggcgtt cgcctgtaag ccctgtttct cgacgcatct atcagatatt aagaccaaca    120

cgaccgcggc tgccggtttc atggtccttc aggacatcaa ttgtctccga cctcacgggg    180

tctcaacagc gcaagagacc atttccttcg gaaagccgtc ccaatgtcgc gaggccgtcg    240

gtattcccca gtacattacg ataacggcta atgtgaccga tgaatcgtat ttgtacaacg    300

cggacttgct gatgctttct gcgtgccttt tctacgcttc agaaatgagc gaaaagggct    360

tcaaagttat ctttgggaac gtttctggcg ttgtttctgc ttgtgtcaat tttacagatt    420

atgtggctca tgtaatccaa catacccagc agcatcatct ggtgattgat cacattcggt    480

tgctgcattt cctgacacca tcaacaatga ggtgggctac aaccattgct tgtttgttcg    540

ccattctctt ggcgatatga gatgttctca caaattggag cgtttcttga ctcctcactc    600

ttgcttctgg tggctttttt tgctgtgtac cggcttgtct tggtcctttg tcgatggcaa    660

cgacagcagc tcgacatacc aatacatata taatttgacg atatgcgagc tgaatgggac    720

cgaatggttg cccagccatt ttgactgggc agtcgagacc tttgtgcttt acccggttgc    780

cactcatatc ctttcactgg gttttctcac aacaagccat ttttttgatg cgctcggtct    840

cggcgctgtg tccactacag gatttgttgg cgggcggtat gtactcagca gcgtgtacgg    900

cgcttgtgct ttcgcagcgc tcgtatgttt tgtcatccgc gctgctaaaa attgcatggc    960

ttgccgttat gcccgtaccc ggtttaccaa cttcattgtg gacgaccggg ggaggatcca   1020

tcgatggaag tctccaatag tggtagagaa attgggcaaa gctgaagtcg gtggcgacct   1080

cgtcaccatc aaacatgtcg tcctcgaagg ggttaaagct caacccttga cgaggacttc   1140

ggctgagcaa tgggaagcct agacgatttt tgcaacgatc ctaccgccgc acaaaagctt   1200

gtgctagcct ttag                                                     1214
```

<210> SEQ ID NO 23

<211> LENGTH: 1214
<212> TYPE: DNA
<213> ORGANISM: Artificial Sequence
<220> FEATURE:
<223> OTHER INFORMATION: SMART_VAC18_consensus_sequence. Positions 12937 to 14170 of the virus genome

<400> SEQUENCE: 23
cacttggaat ggctgcggcc attcttttcc tcctggctgg tgctcaacat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatacatata taatttgacg atatgcgagc tgaatgggac 720
cgaatggttg cccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttac gcccgtaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 24
<211> LENGTH: 1214
<212> TYPE: DNA
<213> ORGANISM: Artificial Sequence
<220> FEATURE:
<223> OTHER INFORMATION: SMART_VAC15_consensus_sequence_(reversed). Positions 12937 to 14170 of the virus genome

<400> SEQUENCE: 24
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttca gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540

```
ccattctctt ggcgatatga gatgttctca caaattggag cgtttcttga ctcctcactc    600

ttgcttctgg tggctttttt tgctttgtac cggcttgtct tggtcctttg tcgatggcaa    660

cgacagcagc tcgacatacc aatacatata taatttgacg atatgcgagc tgaatgggac    720

cgaatggttg cccagccatt ttgactgggc agtcgagacc tttgtgcttt acccggttgc    780

cactcatatc ctttcactgg gttttctcac aacaagccat ttttttgatg cgctcggtct    840

cggcgctgtg tccactacag gatttgttgg cgggcggtat gtactcagca gcgtgtacgg    900

cgcttgtgct ttcgcagcgc tcgtatgttt tgtcatccgc gctgctaaaa attgcatggc    960

ttgccgttat gcccgtaccc ggtttaccaa cttcattgtg gacgaccggg ggaggatcca   1020

tcgatggaag tctccaatag tggtagagaa attgggcaaa gctgaagtcg gtggcgacct   1080

cgtcaccatc aaacatgtcg tcctcgaagg ggttaaagct caacccttga cgaggacttc   1140

ggctgagcaa tgggaagcct agacgatttt tgcaacgatc ctaccgccgc acaaaagctt   1200

gtgctagcct ttag                                                     1214
```

<210> SEQ ID NO 25
<211> LENGTH: 1214
<212> TYPE: DNA
<213> ORGANISM: Artificial Sequence
<220> FEATURE:
<223> OTHER INFORMATION: SMART_VAC3_consensus_sequence. Positions 12937 to 14170 of the virus genome

<400> SEQUENCE: 25

```
cacttggaat ggctgcggcc attcttttcc tcctggctgg tgctcaatat ctcatggttt     60

ctgaggcgtt cgcctgtaag ccctgtttct cgacgcatct atcagatatt aagaccaaca    120

cgaccgcggc tgccggtttc atggtccttc aggacatcaa ttgtctccga cctcacgggg    180

tctcaacagc gcaagagacc atttccctcg gaaagccgtc ccaatgtcgc gaggccgtcg    240

gtattcccca gtacattacg ataacggcta atgtgaccga tgaatcgtat ttgtacaacg    300

cggacttgct gatgctttct gcgtgccttt tctacgcttc agaaatgagc gaaaagggct    360

tcaaagttat ctttgggaac gtttctggcg ttgtttctgc ttgtgtcaat tttacagatt    420

atgtggctca tgtaatccaa catacccagc agcatcatct ggtgattgat cacattcggt    480

tgctgcattt cctgacacca tcaacaatga ggtgggctac aaccattgct tgtttgttcg    540

ccattctctt ggcgatatga gatgttctca caaattggag cgtttcttga ctcctcactc    600

ttgcttctgg tggctttttt tgctttgtac cggcttgtct tggtcctttg tcgatggcaa    660

cgacagcagc tcgacatacc aatacatata taatttgacg atatgcgagc tgaatgggac    720

cgaatggttg cccagccatt ttgactgggc agtcgagacc tttgtgcttt acccggttgc    780

cactcatatc ctttcactgg gttttctcac aacaagccat ttttttgatg cgctcggtct    840

cggcgctgtg tccactacag gatttgttgg cgggcggtat gtactcagca gcgtgtacgg    900

cgcttgtgct ttcgcagcgc tcgtatgttt tgtcatccgc gctgctaaaa attgcatggc    960

ttgccgttat gcccgcaccc ggtttaccaa cttcattgtg gacgaccggg ggaggatcca   1020

tcgatggaag tctccaatag tggtagagaa attgggcaaa gctgaagtcg gtggcgacct   1080

cgtcaccatc aaacatgtcg tcctcgaagg ggttaaagct caacccttga cgaggacttc   1140

ggctgagcaa tgggaagcct agacgatttt tgcaacgatc ctaccgccgc acaaaagctt   1200

gtgctagcct ttag                                                     1214
```

<210> SEQ ID NO 26
<211> LENGTH: 1214
<212> TYPE: DNA
<213> ORGANISM: Artificial Sequence
<220> FEATURE:
<223> OTHER INFORMATION: SMART_VAC7_consensus_sequence. Positions 12937 to 14170 of the virus genome

<400> SEQUENCE: 26
cacttggaat ggctgcggcc attcttttcc tcctggctgg tgctcaatat ctcatggttt 60
ctgaggcgtt cgcctgtaag ccctgtttct cgacgcatct atcagatatt aagaccaaca 120
cgaccgcggc tgccggtttc atggtccttc aggacatcaa ttgtctccga cctcacgggg 180
tctcaacagc gcaagagacc atttccttcg gaaagccgtc ccaatgtcgc gaggccgtcg 240
gtattcccca gtacattacg ataacggcta atgtgaccga tgaatcgtat ttgtacaacg 300
cggacttgct gatgctttct gcgtgccttt tctacgcttc agaaatgagc gaaaagggct 360
tcaaagttat ctttgggaac gtttctggcg ttgtttctgc ttgtgtcaat tttacagatt 420
atgtggctca tgtaatccaa catacccagc agcatcatct ggtgattgat cacattcggt 480
tgctgcattt cctgacacca tcaacaatga ggtgggctac aaccattgct tgtttgttcg 540
ccattctctt ggcgatatga gatgttctca caaattggag cgtttcttga ctcctcactc 600
ttgcttctgg tggctttttt tgctttgtac cggcttgtct tggtcctttg tcgatggcaa 660
cgacagcagc tcgacatacc aatacatata taatttgacg atatgcgagc tgaatgggac 720
cgaatcgttg tccagccatt ttgactgggc agtcgagacc tttgtgcttt acccggttgc 780
cactcatatc ctttcactgg gttttctcac aacaagccat ttttttgatg cgctcggtct 840
cggcgctgtg tccactacag gatttgttgg cgggcggtat gtactcagca gcgtgtacgg 900
cgcttgtgct ttcgcagcgc tcgtatgttt tgtcatccgc gctgctaaaa attgcatggc 960
ttgccgttat gcccgtaccc ggtttaccaa cttcattgtg gacgaccggg ggaggatcca 1020
tcgatggaag tctccaatag tggtagagaa attgggcaaa gctgaagtcg gtggcgacct 1080
cgtcaccatc aaacatgtcg tcctcgaagg ggttaaagct caacccttga cgaggacttc 1140
ggctgagcaa tgggaagcct agacgatttt tgcaacgatc ctaccgccgc acaaaagctt 1200
gtgctagcct ttag 1214

<210> SEQ ID NO 27
<211> LENGTH: 2093
<212> TYPE: DNA
<213> ORGANISM: Artificial Sequence
<220> FEATURE:
<223> OTHER INFORMATION: Sequence of viral cDNA in clone GPsM-clon 1 (Positions 12492 to 14584). BsiWI cuts between 12491 and 12492. HpaI cuts between 14584 and 14585

<400> SEQUENCE: 27
gtacgctatg tttttggttt ccattggccc acggcaacac atcattcgag ctaaccatca 60
actacaccat atgtatgccc tgctctacca gccaagcggc tagccaaaga ctcgagcccg 120
gtcgtaacat gtggtgcaga atagggcacg acaggtgtga ggaacgtgac catgatgagt 180
tgtcaatgtc cattccgtca gggtacgaga acctcaaact tgagggttat tatgcttggc 240
tggccttttt gtcctttccc tacgcggccc aatttcatcc ggagttgttc ggaataggaa 300
acgtgtcgcg cgtctttgtg gacaagcgac accagttcat ttgcgccgag catgatggac 360
aaaattcaac catatctacc ggacacaaca tctccgcatt atatgcggtg tattaccatc 420
accaaataga cgggggcaat tggttccact tggaatggct gcggccattc ttttcctcct 480

```
ggctggtgct caatatctca tggtttctga ggcgttcgcc tgtaagccct gtttctcgac    540

gcatctatca gatattaaga ccaacacgac cgcggctgcc ggtttcatgg tccttcagga    600

catcaattgt ctccgacctc acggggtctc aacagcgcaa gagaccattt ccttcggaaa    660

gccgtcccaa tgtcgcgagg ccgtcggtat tccccagtac attacgataa cggctaatgt    720

gaccgatgaa tcgtatttgt acaacgcgga cttgctgatg ctttctgcgt gccttttcta    780

cgcttcagaa atgagcgaaa agggcttcaa agttatcttt gggaacgttt ctggcgttgt    840

ttctgcttgt gtcaatttta cagattatgt ggctcatgta atccaacata cccagcagca    900

tcatctggtg attgatcaca ttcggttgct gcatttcctg acaccatcaa caatgaggtg    960

ggctacaacc attgcttgtt tgttcgccat tctcttggcg atatgagatg ttctcacaaa   1020

ttggagcgtt tcttgactcc tcactcttgc ttctggtggc ttttttgct ttgtaccggc    1080

ttgtcttggt cctttgtcga tggcaacgac agcagctcga cataccaata catatataat   1140

ttgacgatat gcgagctgaa tgggaccgaa tggttgccca gccattttga ctgggcagtc   1200

gagacctttg tgctttaccc ggttgccact catatccttt cactgggttt tctcacaaca   1260

agccattttt ttgatgcgct cggtctcggc gctgtgtcca ctacaggatt tgttggcggg   1320

cggtatgtac tcagcagcgt gtacggcgct tgtgctttcg cagcgctcgt atgttttgtc   1380

atccgcgctg ctaaaaattg catggcttgc cgttatgccc gcacccggtt taccaacttc   1440

attgtggacg accgggggag gatccatcga tggaagtctc caatagtggt agagaaattg   1500

ggcaaagctg aagtcggtgg cgacctcgtc accatcaaac atgtcgtcct cgaaggggtt   1560

aaagctcaac ccttgacgag gacttcggct gagcaatggg aagcctagac gatttttgca   1620

acgatcctac cgccgcacaa aagcttgtgc tagcctttag catcacatat acacctataa   1680

tgatatacgc ccttaaggtg tcacgcggcc gcctcctggg gctattgcac atcttgatat   1740

tcctgaactg ttcctttaca ttcggataca tgacatatgt gcattttcaa tccaccaacc   1800

gtgtcgcatt tactctgggg gccgttgtcg cccttctgtg ggtgtttac agcttcacag    1860

agtcatggaa gttcattact tccagatgca gattgtgttg cctaggccgg caatacattc   1920

tggcccctgc ccatcacgta gaaagtgctg caggtctcca ttcaatccca gcgtctggta   1980

accgagcata cgctgtgaga aagcccggac taacatcagt gaacggcact ctagtaccag   2040

gacttcggag cctcgtgctg ggcggcaaac gagctgttaa acgaggagtg gtt          2093
```

```
<210> SEQ ID NO 28
<211> LENGTH: 881
<212> TYPE: DNA
<213> ORGANISM: Artificial Sequence
<220> FEATURE:
<223> OTHER INFORMATION: Sequence of clone SM_32-97-5 of the attenuated
      virus VP-046 BIS. Positions 6792 to 7672 of the virus genome

<400> SEQUENCE: 28
```

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420
```

tataatagggt atctggtcaa aggcaaggag gttctggttc ccaaacctga caactgcctt 480
gaagccgcca agctgtccct tgagcaagca cttgctggga tgggccaaac ttgcgacctt 540
acagttgcag aggtggaaaa gctaaagcgc atcatcagtc aactccaagg tttgaccact 600
gaacaggctt taaactgcta gccgccagcg gcttgacccg ctgtggccgc ggcggcttgg 660
ttgtaactga aacggcggta aaaattataa aataccacag cagaactttc actttaggcc 720
ctttagacct aaaagtcact tctgaggtag aggtgaagaa atcaactgag cagggccacg 780
ccgttgtggc aaacctatgt tctggtgtcg tattgatgag acctcaccca ccgtcccttg 840
ttgacgtcct tctgaaaccc ggacttgaca caacacccga c 881

<210> SEQ ID NO 29
<211> LENGTH: 881
<212> TYPE: DNA
<213> ORGANISM: Artificial Sequence
<220> FEATURE:
<223> OTHER INFORMATION: Sequence of clone SM_32-97-24 of the attenuated virus VP-046 BIS. Positions 6792 to 7672 of the virus genome

<400> SEQUENCE: 29
gtgtctgttc aagagactcg gagcctaggc ggctccaaat tcagtgtctg cactgtcgtg 60
tccaacacac ccgtggacgc cttggccggc attccacttc agacaccaac cccgcttttt 120
gagaatggcc cgcgtcatcg cggtgaggaa gatgatctca aagttgagag gatgaagaaa 180
cattgtgtgt ccctcggctt ccacaacatc aatggcaaag tttactgtaa agtttgggac 240
aagtccaccg gtgacacctt ttacacggat gattcccggt acacccaaga ccatgctttt 300
caggacaggt cagctgacta tagagacagg gactatgagg gtgtgcaaac cgccccccaa 360
cagggatttg atccaaaatc tgaaacccct gttggcactg ttgtaatcgg cggtattacg 420 tataatagggt atctggtcaa aggcaaggag gttctggttc ccaaacctga caactgcctt 480
gaagccgcca agctgtccct tgagcaagca cttgctggga tgggccaaac ttgcgacctt 540
acagttgcag aggtggaaaa gctaaagcgc atcatcagtc aactccaagg tttgaccact 600
gaacaggctt taaactgcta gccgccagcg gcttgacccg ctgtggccgc ggcggcttgg 660
ttgtaactga aacggcggta aaaattataa aataccacag cagaactttc actttaggcc 720
ctttagacct aaaagtcact tctgaggtag aggtgaagaa atcaactgag cagggccacg 780
ccgttgtggc aaacctatgt tctggtgtcg tattgatgag acctcaccca ccgtcccttg 840
ttgacgtcct tctgaaaccc ggacttgaca caacacccga c 881

<210> SEQ ID NO 30
<211> LENGTH: 881
<212> TYPE: DNA
<213> ORGANISM: Artificial Sequence
<220> FEATURE:
<223> OTHER INFORMATION: Sequence of clone SM 32-97-23 of the attenuated virus VP-046 BIS. Positions 6792 to 7672 of the virus genome

<400> SEQUENCE: 30
gtgtctgttc aagagactcg gagcctaggc ggctccaaat tcagtgtctg cactgtcgtg 60
tccaacacac ccgtggacgc cttggccggc attccacttc agacaccaac cccgcttttt 120
gagaatggcc cgcgtcatcg cggtgaggaa gatgatctca aagttgagag gatgaagaaa 180
cattgtgtgt ccctcggctt ccacaacatc aatggcaaag tttactgtaa agtttgggac 240

-continued

```
aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

<210> SEQ ID NO 31
<211> LENGTH: 881
<212> TYPE: DNA
<213> ORGANISM: Artificial Sequence
<220> FEATURE:
<223> OTHER INFORMATION: Sequence of clone SM 32-97-19 of the attenuated virus VP-046 BIS. Positions 6792 to 7672 of the virus genome

<400> SEQUENCE: 31

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

<210> SEQ ID NO 32
<211> LENGTH: 881
<212> TYPE: DNA
<213> ORGANISM: Artificial Sequence
<220> FEATURE:
<223> OTHER INFORMATION: Sequence of clone SM_32-97-17 of the attenuated virus VP-046 BIS. Positions 6792 to 7672 of the virus genome

<400> SEQUENCE: 32

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120
```

```
gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

<210> SEQ ID NO 33
<211> LENGTH: 881
<212> TYPE: DNA
<213> ORGANISM: Artificial Sequence
<220> FEATURE:
<223> OTHER INFORMATION: Sequence of clone SM_32-97-15 of the attenuated virus VP-046 BIS. Positions 6792 to 7672 of the virus genome

<400> SEQUENCE: 33

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

<210> SEQ ID NO 34
<211> LENGTH: 881
<212> TYPE: DNA
<213> ORGANISM: Artificial Sequence
<220> FEATURE:
<223> OTHER INFORMATION: Sequence of clone SM_32-97-14 of the attenuated virus VP-046 BIS. Positions 6792 to 7672 of the virus genome

<400> SEQUENCE: 34

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

<210> SEQ ID NO 35
<211> LENGTH: 881
<212> TYPE: DNA
<213> ORGANISM: Artificial Sequence
<220> FEATURE:
<223> OTHER INFORMATION: Sequence of clone SM_32-97-13 of the attenuated virus VP-046 BIS. Positions 6792 to 7672 of the virus genome

<400> SEQUENCE: 35

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

<210> SEQ ID NO 36
<211> LENGTH: 881
<212> TYPE: DNA
<213> ORGANISM: Artificial Sequence
<220> FEATURE:
<223> OTHER INFORMATION: Sequence of clone SM_32-97-12 of the attenuated virus VP-046 BIS. Positions 6792 to 7672 of the virus genome

<400> SEQUENCE: 36

```
gtgtctgttc aagagactcg gagcctaggc ggctccaaat tcagtgtctg cactgtcgtg     60
tccaacacac ccgtggacgc cttggccggc attccacttc agacaccaac cccgcttttt    120
gagaatggcc cgcgtcatcg cggtgaggaa gatgatctca aagttgagag gatgaagaaa    180
cattgtgtgt ccctcggctt ccacaacatc aatggcaaag tttactgtaa agtttgggac    240
aagtccaccg gtgacacctt ttacacggat gattcccggt acacccaaga ccatgctttt    300
caggacaggt cagctgacta tagagacagg gactatgagg gtgtgcaaac cgcccccccaa    360
cagggatttg atccaaaatc tgaaacccct gttggcactg ttgtaatcgg cggtattacg    420
tataataggt atctggtcaa aggcaaggag gttctggttc ccaaacctga caactgcctt    480
gaagccgcca agctgtccct tgagcaagca cttgctggga tgggccaaac ttgcgacctt    540
acagttgcag aggtggaaaa gctaaagcgc atcatcagtc aactccaagg tttgaccact    600
gaacaggctt taaactgcta gccgccagcg gcttgacccg ctgtggccgc ggcggcttgg    660
ttgtaactga aacggcggta aaaattataa aataccacag cagaactttc actttaggcc    720
ctttagacct aaaagtcact tctgaggtag aggtgaagaa atcaactgag cagggccacg    780
ccgttgtggc aaacctatgt tctggtgtcg tattgatgag acctcaccca ccgtcccttg    840
ttgacgtcct tctgaaaccc ggacttgaca caacacccga c                        881
```

<210> SEQ ID NO 37
<211> LENGTH: 881
<212> TYPE: DNA
<213> ORGANISM: Artificial Sequence
<220> FEATURE:
<223> OTHER INFORMATION: Sequence of clone SM_32-97-10 of the attenuated virus VP-046 BIS. Positions 6792 to 7672 of the virus genome

<400> SEQUENCE: 37

```
gtgtctgttc aagagactcg gagcctaggc ggctccaaat tcagtgtctg cactgtcgtg     60
tccaacacac ccgtggacgc cttggccggc attccacttc agacaccaac cccgcttttt    120
gagaatggcc cgcgtcatcg cggtgaggaa gatgatctca aagttgagag gatgaagaaa    180
cattgtgtgt ccctcggctt ccacaacatc aatggcaaag tttactgtaa agtttgggac    240
aagtccaccg gtgacacctt ttacacggat gattcccggt acacccaaga ccatgctttt    300
caggacaggt cagctgacta tagagacagg gactatgagg gtgtgcaaac cgcccccccaa    360
cagggatttg atccaaaatc tgaaacccct gttggcactg ttgtaatcgg cggtattacg    420
tataataggt atctggtcaa aggcaaggag gttctggttc ccaaacctga caactgcctt    480
gaagccgcca agctgtccct tgagcaagca cttgctggga tgggccaaac ttgcgacctt    540
acagttgcag aggtggaaaa gctaaagcgc atcatcagtc aactccaagg tttgaccact    600
gaacaggctt taaactgcta gccgccagcg gcttgacccg ctgtggccgc ggcggcttgg    660
ttgtaactga aacggcggta aaaattataa aataccacag cagaactttc actttaggcc    720
ctttagacct aaaagtcact tctgaggtag aggtgaagaa atcaactgag cagggccacg    780
ccgttgtggc aaacctatgt tctggtgtcg tattgatgag acctcaccca ccgtcccttg    840
ttgacgtcct tctgaaaccc ggacttgaca caacacccga c                        881
```

<210> SEQ ID NO 38
<211> LENGTH: 881
<212> TYPE: DNA
<213> ORGANISM: Artificial Sequence
<220> FEATURE:
<223> OTHER INFORMATION: Sequence of clone SM_32-97-7 of the attenuated virus VP-046 BIS. Positions 6792 to 7672 of the virus genome

<400> SEQUENCE: 38

```
gtgtctgttc aagagactcg gagcctaggc ggctccaaat tcagtgtctg cactgtcgtg     60
tccaacacac ccgtggacgc cttggccggc attccacttc agacaccaac cccgcttttt    120
gagaatggcc cgcgtcatcg cggtgaggaa gatgatctca aagttgagag gatgaagaaa    180
cattgtgtgt ccctcggctt ccacaacatc aatggcaaag tttactgtaa agtttgggac    240
aagtccaccg gtgacacctt ttacacggat gattcccggt acacccaaga ccatgctttt    300
caggacaggt cagctgacta tagagacagg gactatgagg gtgtgcaaac cgccccccaa    360
cagggatttg atccaaaatc tgaaacccct gttggcactg ttgtaatcgg cggtattacg    420
tataataggt atctggtcaa aggcaaggag gttctggttc ccaaacctga caactgcctt    480
gaagccgcca agctgtccct tgagcaagca cttgctggga tgggccaaac ttgcgacctt    540
acagttgcag aggtggaaaa gctaaagcgc atcatcagtc aactccaagg tttgaccact    600
gaacaggctt taaactgcta gccgccagcg gcttgacccg ctgtggccgc ggcggcttgg    660
ttgtaactga aacggcggta aaaattataa aataccacag cagaactttc actttaggcc    720
ctttagacct aaaagtcact tctgaggtag aggtgaagaa atcaactgag cagggccacg    780
ccgttgtggc aaacctatgt tctggtgtcg tattgatgag acctcaccca ccgtcccttg    840
ttgacgtcct tctgaaaccc ggacttgaca caacacccga c                        881
```

<210> SEQ ID NO 39
<211> LENGTH: 881
<212> TYPE: DNA
<213> ORGANISM: Artificial Sequence
<220> FEATURE:
<223> OTHER INFORMATION: Sequence of clone SM_32-97-5 of the attenuated virus VP-046 BIS. Positions 6792 to 7672 of the virus genome

<400> SEQUENCE: 39

```
gtgtctgttc aagagactcg gagcctaggc ggctccaaat tcagtgtctg cactgtcgtg     60
tccaacacac ccgtggacgc cttggccggc attccacttc agacaccaac cccgcttttt    120
gagaatggcc cgcgtcatcg cggtgaggaa gatgatctca aagttgagag gatgaagaaa    180
cattgtgtgt ccctcggctt ccacaacatc aatggcaaag tttactgtaa agtttgggac    240
aagtccaccg gtgacacctt ttacacggat gattcccggt acacccaaga ccatgctttt    300
caggacaggt cagctgacta tagagacagg gactatgagg gtgtgcaaac cgccccccaa    360
cagggatttg atccaaaatc tgaaacccct gttggcactg ttgtaatcgg cggtattacg    420
tataataggt atctggtcaa aggcaaggag gttctggttc ccaaacctga caactgcctt    480
gaagccgcca agctgtccct tgagcaagca cttgctggga tgggccaaac ttgcgacctt    540
acagttgcag aggtggaaaa gctaaagcgc atcatcagtc aactccaagg tttgaccact    600
gaacaggctt taaactgcta gccgccagcg gcttgacccg ctgtggccgc ggcggcttgg    660
ttgtaactga aacggcggta aaaattataa aataccacag cagaactttc actttaggcc    720
ctttagacct aaaagtcact tctgaggtag aggtgaagaa atcaactgag cagggccacg    780
```

-continued

```
ccgttgtggc aaacctatgt tctggtgtcg tattgatgag acctcaccca ccgtcccttg    840

ttgacgtcct tctgaaaccc ggacttgaca caacacccga c                       881
```

```
<210> SEQ ID NO 40
<211> LENGTH: 881
<212> TYPE: DNA
<213> ORGANISM: Artificial Sequence
<220> FEATURE:
<223> OTHER INFORMATION: Sequence of clone SM_INT-13  of the attenuated
      virus VP-046 BIS. Positions 6792 to 7672 of the virus genome

<400> SEQUENCE: 40

gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                       881
```

```
<210> SEQ ID NO 41
<211> LENGTH: 881
<212> TYPE: DNA
<213> ORGANISM: Artificial Sequence
<220> FEATURE:
<223> OTHER INFORMATION: Sequence of clone SM_INT-8 of the attenuated
      virus VP-046 BIS. Positions 6792 to 7672 of the virus genome

<400> SEQUENCE: 41

gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660
```

-continued

```
ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

```
<210> SEQ ID NO 42
<211> LENGTH: 881
<212> TYPE: DNA
<213> ORGANISM: Artificial Sequence
<220> FEATURE:
<223> OTHER INFORMATION: Sequence of clone SM_INT-3 of the attenuated
      virus VP-046 BIS. Positions 6792 to 7672 of the virus genome

<400> SEQUENCE: 42

gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

```
<210> SEQ ID NO 43
<211> LENGTH: 881
<212> TYPE: DNA
<213> ORGANISM: Artificial Sequence
<220> FEATURE:
<223> OTHER INFORMATION: Sequence of clone SM_INT of the attenuated
      virus VP-046 BIS. Positions 6792 to 7672 of the virus genome

<400> SEQUENCE: 43

gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600
```

-continued gaacaggctt taaactgcta gccgccagcg gcttgacccg ctgtggccgc ggcggcttgg 660
ttgtaactga aacggcggta aaaattataa aataccacag cagaactttc actttaggcc 720
ctttagacct aaaagtcact tctgaggtag aggtgaagaa atcaactgag cagggccacg 780
ccgttgtggc aaacctatgt tctggtgtcg tattgatgag acctcaccca ccgtcccttg 840
ttgacgtcct tctgaaaccc ggacttgaca caacacccga c 881

<210> SEQ ID NO 44
<211> LENGTH: 881
<212> TYPE: DNA
<213> ORGANISM: Artificial Sequence
<220> FEATURE:
<223> OTHER INFORMATION: Sequence of clone SM_INT-1 of the attenuated virus VP-046 BIS. Positions 6792 to 7672 of the virus genome

<400> SEQUENCE: 44
gtgtctgttc aagagactcg gagcctaggc ggctccaaat tcagtgtctg cactgtcgtg 60
tccaacacac ccgtggacgc cttggccggc attccacttc agacaccaac cccgcttttt 120
gagaatggcc cgcgtcatcg cggtgaggaa gatgatctca aagttgagag gatgaagaaa 180
cattgtgtgt ccctcggctt ccacaacatc aatggcaaag tttactgtaa agtttgggac 240
aagtccaccg gtgacacctt ttacacggat gattcccggt acacccaaga ccatgctttt 300
caggacaggt cagctgacta tagagacagg gactatgagg gtgtgcaaac cgccccccaa 360
cagggatttg atccaaaatc tgaaacccct gttggcactg ttgtaatcgg cggtattacg 420
tataataggt atctggtcaa aggcaaggag gttctggttc ccaaacctga caactgcctt 480
gaagccgcca agctgtccct tgagcaagca cttgctggga tgggccaaac ttgcgacctt 540
acagttgcag aggtggaaaa gctaaagcgc atcatcagtc aactccaagg tttgaccact 600
gaacaggctt taaactgcta gccgccagcg gcttgacccg ctgtggccgc ggcggcttgg 660
ttgtaactga aacggcggta aaaattataa aataccacag cagaactttc actttaggcc 720
ctttagacct aaaagtcact tctgaggtag aggtgaagaa atcaactgag cagggccacg 780
ccgttgtggc aaacctatgt tctggtgtcg tattgatgag acctcatcca ccgtcccttg 840
ttgacgtcct tctgaaaccc ggacttgaca caacacccga c 881

<210> SEQ ID NO 45
<211> LENGTH: 881
<212> TYPE: DNA
<213> ORGANISM: Artificial Sequence
<220> FEATURE:
<223> OTHER INFORMATION: Sequence of clone SM_32-97-8 of the attenuated virus VP-046 BIS. Positions 6792 to 7672 of the virus genome

<400> SEQUENCE: 45
gtgtctgttc aagagactcg gagcctaggc ggctccaaat tcagtgtctg cactgtcgtg 60
tccaacacac ccgtggacgc cttggccggc attccacttc agacaccaac cccgcttttt 120
gagaatggcc cgcgtcatcg cggtgaggaa gatgatctca aagttgagag gatgaagaaa 180
cattgtgtgt ccctcggctt ccacaacatc aatggcaaag tttactgtaa agtttgggac 240
aagtccaccg gtgacacctt ttacacggat gattcccggt acacccaaga ccatgctttt 300
caggacaggt cagctgacta tagagacagg gactatgagg gtgtgcaaac cgccccccaa 360
cagggatttg atccaaaatc tgaaacccct gttggcactg ttgtaatcgg cggtattacg 420
tataataggt atctggtcaa aggcaaggag gttctggttc ccaaacctga caactgcctt 480

-continued

```
gaagccgcca agctgtccct cgagcaagca cttgctggga tgggccaaac ttgcgacctt    540

acagttgccg aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

<210> SEQ ID NO 46
<211> LENGTH: 881
<212> TYPE: DNA
<213> ORGANISM: Artificial Sequence
<220> FEATURE:
<223> OTHER INFORMATION: Sequence of clone SM_32-97-2 of the attenuated virus VP-046 BIS. Positions 6792 to 7672 of the virus genome

<400> SEQUENCE: 46

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct cgagcaagca cttgctggga tgggccaaac ttgcgacctt    540

acagttgccg aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

<210> SEQ ID NO 47
<211> LENGTH: 881
<212> TYPE: DNA
<213> ORGANISM: Artificial Sequence
<220> FEATURE:
<223> OTHER INFORMATION: Sequence of clone SM_INT-14 of the attenuated virus VP-046 BIS. Positions 6792 to 7672 of the virus genome

<400> SEQUENCE: 47

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420
```

tataataggt atctggtcaa aggcaaggag gttctggttc ccaaacctga caactgcctt 480
gaagccgcca agctgtccct cgagcaagca cttgctggga tgggccaaac ttgcgacctt 540
acagttgccg aggtggaaaa gctaaagcgc atcatcagtc aactccaagg tttgaccact 600
gaacaggctt taaactgcta gccgccagcg gcttgacccg ctgtggccgc ggcggcttgg 660
ttgtaactga aacggcggta aaaattataa aataccacag cagaactttc actttaggcc 720
ctttagacct aaaagtcact tctgaggtag aggtgaagaa atcaactgag cagggccacg 780
ccgttgtggc aaacctatgt tctggtgtcg tattgatgag acctcaccca ccgtcccttg 840
ttgacgtcct tctgaaaccc ggacttgaca caacacccga c 881

<210> SEQ ID NO 48
<211> LENGTH: 881
<212> TYPE: DNA
<213> ORGANISM: Artificial Sequence
<220> FEATURE:
<223> OTHER INFORMATION: Sequence of clone SM_32-97-20 of the attenuated
virus VP-046 BIS. Positions 6792 to 7672 of the virus genome

<400> SEQUENCE: 48
gtgtctgttc aagagactcg gagcctaggc ggctccaaat tcagtgtctg cactgtcgtg 60
tccaacacac ccgtggacgc cttggccggc attccacttc agacaccaac cccgcttttt 120
gagaatggcc cgcgtcatcg cggtgaggaa gatgatctca aagttgagag gatgaagaaa 180
cattgtgtgt ccctcggctt ccacaacatc aatggcaaag tttactgtaa agtttgggac 240
aagtccaccg gtgacacctt ttacacggat gattcccggt acacccaaga ccatgctttt 300
caggacaggt cagctgacta tagagacagg gactatgagg gtgtgcaaac cgcccccccaa 360 cagggatttg atccaaaatc tgaaacccct gttggcactg ttgtaatcgg cggtattacg 420
tataataagt atctggtcaa aggcaaggag gttctggttc ccaaacctga caactgcctt 480
gaagccgcca agctgtccct cgagcaagca cttgctggga tgggccaaac ttgcgacctt 540
acagttgccg aggtggaaaa gctaaagcgc atcatcagtc aactccaagg tttgaccact 600
gaacaggctt taaactgcta gccgccagcg gcttgacccg ctgtggccgc ggcggcttgg 660
ttgtaactga aacggcggta aaaattataa aataccacag cagaactttc actttaggcc 720
ctttagacct aaaagtcact tctgaggtag aggtgaagaa atcaactgag cagggccacg 780
ccgttgtggc aaacctatgt tctggtgtcg tattgatgag acctcaccca ccgtcccttg 840
ttgacgtcct tctgaaaccc ggacttgaca caacacccga c 881

<210> SEQ ID NO 49
<211> LENGTH: 881
<212> TYPE: DNA
<213> ORGANISM: Artificial Sequence
<220> FEATURE:
<223> OTHER INFORMATION: Sequence of clone SM_32-97-6 of the attenuated
virus VP-046 BIS. Positions 6792 to 7672 of the virus genome

<400> SEQUENCE: 49
gtgtctgttc aagagactcg gagcctaggc ggctccaaat tcagtgtctg cactgtcgtg 60
tccaacacac ccgtggacgc cttggccggc attccacttc agacaccaac cccgcttttt 120
gagaatggcc cgcgtcatcg cggtgaggaa gatgatctca aagttgagag gatgaagaaa 180
cattgtgtgt ccctcggctt ccacaacatc aatggcaaag tttactgtaa agtttgggac 240
aagtccaccg gtgacacctt ttacacggat gattcccggt acacccaaga ccatgctttt 300

-continued

```
caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataagt atctggtcaa aggcaaggag gttctggttc ccaaacctga caactgcctt    480

gaagccgcca agctgtccct cgagcaagca cttgctggga tgggccaaac ttgcgacctt    540

acagttgccg aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

```
<210> SEQ ID NO 50
<211> LENGTH: 881
<212> TYPE: DNA
<213> ORGANISM: Artificial Sequence
<220> FEATURE:
<223> OTHER INFORMATION: Sequence of clone SM_32-97-4 of the attenuated
      virus VP-046 BIS. Positions 6792 to 7672 of the virus genome

<400> SEQUENCE: 50

gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataagt atctggtcaa aggcaaggag gttctggttc ccaaacctga caactgcctt    480

gaagccgcca agctgtccct cgagcaagca cttgctggga tgggccaaac ttgcgacctt    540

acagttgccg aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

```
<210> SEQ ID NO 51
<211> LENGTH: 881
<212> TYPE: DNA
<213> ORGANISM: Artificial Sequence
<220> FEATURE:
<223> OTHER INFORMATION: Sequence of clone SM_32-97-1 of the attenuated
      virus VP-046 BIS. Positions 6792 to 7672 of the virus genome

<400> SEQUENCE: 51

gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240
```

-continued

```
aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataagt atctggtcaa aggcaaggag gttctggttc ccaaacctga caactgcctt    480

gaagccgcca agctgtccct cgagcaagca cttgctggga tgggccaaac ttgcgacctt    540

acagttgccg aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

<210> SEQ ID NO 52
<211> LENGTH: 881
<212> TYPE: DNA
<213> ORGANISM: Artificial Sequence
<220> FEATURE:
<223> OTHER INFORMATION: Sequence of clone SM_INT-9 of the attenuated
      virus VP-046 BIS. Positions 6792 to 7672 of the virus genome

<400> SEQUENCE: 52

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataagt atctggtcaa aggcaaggag gttctggttc ccaaacctga caactgcctt    480

gaagccgcca agctgtccct cgagcaagca cttgctggga tgggccaaac ttgcgacctt    540

acagttgccg aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

<210> SEQ ID NO 53
<211> LENGTH: 881
<212> TYPE: DNA
<213> ORGANISM: Artificial Sequence
<220> FEATURE:
<223> OTHER INFORMATION: Sequence of clone SM_32-97-11 of the attenuated
      virus VP-046 BIS. Positions 6792 to 7672 of the virus genome

<400> SEQUENCE: 53

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120
```

```
gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataagt atctggtcaa aggcaaggag gttctggttc ccaaacctga caactgcctt    480

gaagccgcca agctgtccct cgagcaagca cttgctggga tgggccaaac ttgcgacctt    540

acagttgccg aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggtg aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881
```

```
<210> SEQ ID NO 54
<211> LENGTH: 881
<212> TYPE: DNA
<213> ORGANISM: Artificial Sequence
<220> FEATURE:
<223> OTHER INFORMATION: Sequence of clone SM_32-97-21 of the attenuated
      virus VP-046 BIS. Positions 6792 to 7672 of the virus genome

<400> SEQUENCE: 54

gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccctccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaagttataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca caacacccga c                        881

<210> SEQ ID NO 55
<211> LENGTH: 881
<212> TYPE: DNA
<213> ORGANISM: Artificial Sequence
<220> FEATURE:
<223> OTHER INFORMATION: Sequence of clone SM_32-97-16 of the attenuated
      virus VP-046 BIS. Positions 6792 to 7672 of the virus genome
```

<400> SEQUENCE: 55

```
gtgtctgttc aagagactcg gagcctaggc ggctccaaat tcagtgtctg cactgtcgtg     60
tccaacacac ccgtggacgc cttggccggc attccacttc agacaccaac cccgtttttt    120
gagaatggcc cgcgtcatcg cggtgaggaa gatgatctca aagttgagag gatgaagaaa    180
cattgtgtgt ccctcggctt ccacaacatc aatggcaaag tttactgtaa agtttgggac    240
aagtccaccg gtgacacctt ttacacggat gattcccggt acacccaaga ccatgctttt    300
caggacaggt cagctgacta tagagacagg gactatgagg gtgtgcaaac cgccccccaa    360
cagggatttg atccaaaatc tgaaacccct gttggcactg ttgtaatcgg cggtattacg    420
tataataggt atctggtcaa aggcaaggag gttctggttc ccaaacctga caactgcctt    480
gaagccgcca agctgtccct tgagcaagca cttgctggga tgggccaaac ttgcgacctt    540
acagttgcag aggtggaaaa gctaaagcgc atcatcagtc aactccaagg tttgaccact    600
gaacaggctt taaactgcta gccgccagcg gcttgacccg ctgtggccgc ggcggcttgg    660
ttgtaactga aacggcggta aaaattataa aataccacag cagaactttc actttaggcc    720
ctttagacct aaaagtcact tctgaggtag aggtgaagaa atcaactgag cagggccacg    780
ccgttgtggc aaacctatgt tctggtgtcg tattgatgag acctcaccca ccgtcccttg    840
ttgacgtcct tctgaaaccc ggacttgaca caacacccga c                        881
```

<210> SEQ ID NO 56
<211> LENGTH: 881
<212> TYPE: DNA
<213> ORGANISM: Artificial Sequence
<220> FEATURE:
<223> OTHER INFORMATION: Sequence of clone SM_32-97-9 of the attenuated virus VP-046 BIS. Positions 6792 to 7672 of the virus genome

<400> SEQUENCE: 56

```
gtgtctgttc aagagactcg gagcctaggc ggctccaaat tcagtgtctg cactgtcgtg     60
tccaacacac ccgtggacgc cttggccggc attccacttc agacaccaac cccgcttttt    120
gagaatggcc cgcgtcatcg cggtgaggaa gatgatctca aagttgagag gatgaagaaa    180
cattgtgtgt ccctcggctt ccacaacatc aatggcaaag tttactgtaa attttgggac    240
aagtccaccg gtgacacctt ttacacggat gattcccggt acacccaaga ccatgctttt    300
caggacaggt cagctgacta tagagacagg gactatgagg gtgtgcaaac cgccccccaa    360
cagggatttg atccaaaatc tgaaacccct gttggcactg ttgtaatcgg cggtattacg    420
tataataggt atctggtcaa aggcaaggag gttctggttc ccaaacctga caactgcctt    480
gaagccgcca agctgtccct tgagcaagca cttgctggga tgggccaaac ttgcgacctt    540
acagttgcag aggtggaaaa gctaaagcgc atcatcagtc aactccaagg tttgaccact    600
gaacaggctt taaactgcta gccgccagcg gcttgacccg ctgtggccgc ggcggcttgg    660
ttgtaactga aacggcggta aaaattataa aataccacag cagaactttc actttaggcc    720
ctttagacct aaaagtcact tctgaggtag aggtgaagaa atcaactgag cagggccacg    780
ccgttgtggc aaacctatgt tctggtgtcg tattgatgag acctcaccca ccgtcccttg    840
ttgacgtcct tctgaaaccc ggacttgaca caacacccga c                        881
```

<210> SEQ ID NO 57
<211> LENGTH: 881
<212> TYPE: DNA
<213> ORGANISM: Artificial Sequence
<220> FEATURE:
<223> OTHER INFORMATION: Sequence of clone SM_INT-12 of the attenuated
virus VP-046 BIS. Positions 6792 to 7672 of the virus genome

<400> SEQUENCE: 57

```
gtgtctgttc aagagactcg gagcctaggc ggctccaaat tcagtgtctg cactgtcgtg     60

tccaacacac ccgtggacgc cttggccggc attccacttc agacaccaac cccgcttttt    120

gagaatggcc cgcgtcatcg cggtgaggaa gatgatctca aagttgagag gatgaagaaa    180

cattgtgtgt ccctcggctt ccacaacatc aatggcaaag tttactgtaa agtttgggac    240

aagtccaccg gtgacacctt ttacacggat gattcccggt acacccaaga ccatgctttt    300

caggacaggt cagctgacta tagagacagg gactatgagg gtgtgcaaac cgccccccaa    360

cagggatttg atccaaaatc tgaaacccct gttggcactg ttgtaatcgg cggtattacg    420

tataataggt atctggtcaa aggcaaggag gttctggttc ccaaacctga caactgcctt    480

gaagccgcca agctgtccct tgagcaagca cttgctggga tgggccaaac ttgcgacctt    540

acagttgcag aggtggaaaa gctaaagcgc atcatcagtc aactccaagg tttgaccact    600

gaacaggctt taaactgcta gccgccagcg gcttgacccg ctgtggccgc ggcggcttgg    660

ttgtaactga aacggcggta aaaattataa aataccacag cagaactttc actttaggcc    720

ctttagacct aaaagtcact tctgaggtag aggtgaagaa atcaactgag cagggccacg    780

ccgttgtggc aaacctatgt tctggtgtcg tattgatgag acctcaccca ccgtcccttg    840

ttgacgtcct tctgaaaccc ggacttgaca cgacacccga c                        881
```

<210> SEQ ID NO 58
<211> LENGTH: 3232
<212> TYPE: DNA
<213> ORGANISM: Artificial Sequence
<220> FEATURE:
<223> OTHER INFORMATION: Sequence of viral cDNA in clone pUC19-INT-4
(partial) (Positions 6277 to 9509). SpeI cuts between 6266 and
6277, BglII cuts between 9509 and 9510.
<220> FEATURE:
<221> NAME/KEY: misc_feature
<222> LOCATION: (1953)..(1953)
<223> OTHER INFORMATION: n is a, c, g, or t
<220> FEATURE:
<221> NAME/KEY: misc_feature
<222> LOCATION: (1981)..(1982)
<223> OTHER INFORMATION: n is a, c, g, or t
<220> FEATURE:
<221> NAME/KEY: misc_feature
<222> LOCATION: (1985)..(1990)
<223> OTHER INFORMATION: n is a, c, g, or t
<220> FEATURE:
<221> NAME/KEY: misc_feature
<222> LOCATION: (1994)..(1995)
<223> OTHER INFORMATION: n is a, c, g, or t
<220> FEATURE:
<221> NAME/KEY: misc_feature
<222> LOCATION: (1999)..(1999)
<223> OTHER INFORMATION: n is a, c, g, or t
<220> FEATURE:
<221> NAME/KEY: misc_feature
<222> LOCATION: (2001)..(2001)
<223> OTHER INFORMATION: n is a, c, g, or t
<220> FEATURE:
<221> NAME/KEY: misc_feature
<222> LOCATION: (2004)..(2005)
<223> OTHER INFORMATION: n is a, c, g, or t

<400> SEQUENCE: 58

```
ctagttatgt tcccaccatc atcattggtg gactccatac ccttggtgtg atcttgtggc     60

tattcaaata ccggtgcctc cacaacatgt tagttggtga tgggagtttt tcaagtgcct    120
```

-continued

```
ttttcctacg gtattttgca gagggtaatc tcagaaaagg tgtttcacag tcctgtggca    180
tgaataacga gtccctgaca gctgctttag cttgcaagtt gtcacaggct gaccttgatt    240
ttttgtccag cttgacgaac ttcaagtgct ttgtatctgc ttcaaacatg aaagatgctg    300
ctggccagta cattgaggca gcgtatgcca aggccctgcg ccgagagttg gcctccctag    360
tccaggttga caaaatgaaa ggagttttgt ccaagctcga ggcctttgct gaaacagcca    420
ccccgtccct tgacacaggt gacgtgattg tcctgcttgg gcaacatcct cacggatcca    480
tcctcgatat taatgtgggg actgaaagga aaactgtgtc tgttcaagag actcggagcc    540
taggcggctc caaattcagt gtctgcactg tcgtgtccaa cacacccgtg gacgccttgg    600
ccggcattcc acttcagaca ccaaccccgc tttttgagaa tggcccgcgt catcgcggtg    660
aggaagatga tctcaaagtt gagaggatga agaaacattg tgtgtccctc ggcttccaca    720
acatcaatgg caaagtttac tgtaaagttt gggacaagtc caccggtgac accttttaca    780
cggatgattc ccggtacacc caagaccatg cttttcagga caggtcagct gactatagag    840
acagggacta tgagggtgtg caaaccgccc cccaacaggg atttgatcca aaatctgaaa    900
cccctgttgg cactgttgta atcggcggta ttacgtataa taggtatctg gtcaaaggca    960
aggaggttct ggttcccaaa cctgacaact gccttgaagc cgccaagctg tcccttgagc   1020
aagcacttgc tgggatgggc caaacttgcg accttacagt tgcagaggtg gaaaagctaa   1080
agcgcatcat cagtcaactc caaggtttga ccactgaaca ggctttaaac tgctagccgc   1140
cagcggcttg acccgctgtg gccgcggcgg cttggttgta actgaaacgg cggtaaaaat   1200
tataaaatac cacagcagaa ctttcacttt aggcccttta gacctaaaag tcacttctga   1260
ggtagaggtg aagaaatcaa ctgagcaggg ccacgccgtt gtggcaaacc tatgttctgg   1320
tgtcgtattg atgagacctc acccaccgtc ccttgttgac gtccttctga aacccggact   1380
tgacacaaca cccgacattc aaccggggca tggggccggg aatatgggcg tggacggttc   1440
tatttgggat tttgaaaccg cacccacaaa ggcagaactc gagttgtcca agcaaataat   1500
tcaagcatgt gaagttaggc gcggagacgc cccgaacctc caactcccct acaagctcta   1560
tcctgtcaga ggggatcctg agcggcataa aggccgcctt atcaacacca ggtttggaga   1620
cttgccttac aaaactcctc aagacaccaa gtccgctatc catgcggctt gttgcctgca   1680
ccccaacggg gcccctgtgt ctgatggtaa atccacacta ggcaccactc ttcaacatgg   1740
tttcgagctt tatgttccca cagtgcccta tagtgtcatg gagtacctta ttcacgccct   1800
gacacccctc ccatgttcac taaacatggc acttccaagg ctgctgcaga agacctccaa   1860
aaatatgacc tatccaccca aggatttgtc ctgcctgggg tcctacgcct agtgcgcaga   1920
ttcatctttg gccatgttgg taaggcaccg ccnttgttcc tcccatcaac ctatcccgcc   1980
nnganannnn tggnngggna ntannggcag agattcccaa caaaggacgt ccagagcata   2040
cctgaaattg atgaaatgtg tgcccgcgcc gtcaaggaga attggcaaac cgtgacacct   2100
tgtactctca agaaacagta ctgttccaag cccaaaacca ggaccatcct gggcaccaac   2160
aactttattg ccttggctca cagatcggcg ctcagtggcg tcacccaggc attcatgaag   2220
aaggcttgga agtccccaat tgccttgggg aaaaacaagt tcaaggagct gcattgtact   2280
gtcgccggca ggtgtcttga ggctgacttg gcctcctgtg atcgcagcac ccccgccatt   2340
gtaagatggt ttgttgccaa cctcctgtat gaacttgcag gatgtgaaga gtacttgcct   2400
agctatgtgc ttaactgctg ccatgacctt gtggcaacac aggatggtgc cttcacaaaa   2460
```

cgcggtggcc tgtcgtccgg ggaccccgtc accagtgtgt ccaataccgt atattcactg 2520
gtaatctatg cccagcacat ggtattgtca gccttgaaaa tgggtcatga aattggtctt 2580
aagttcctcg aggagcagct caaattcgag gacctccttg aaattcagcc tatgttagta 2640
tactctgacg accttgtctt gtacgctgaa agacccactt ttcccaatta ccattggtgg 2700
gtcgagcacc ttgacctgat gctgggtttc aaaacggacc caaagaaaac tgtcataact 2760
gataaaccca gcttcctcgg ctgcaggatt gaggcagggc gacagttagt ccccaatcgc 2820
gaccgcatcc tggctgccct tgcatatcac atgaaggcgc agaacgcctc agaatattat 2880
gcgtctgctg ccgcaatcct gatggattcg tgtgcttgca ttgaccatga ccctgagtgg 2940
tatgaggacc tcatctgtgg tattgcccgg tgtgctcgcc aagatggcta tagtttcccg 3000
ggcccggcat ttttcatgtc catgtgggag aaactgaaaa gtcataatga agggaaaaaa 3060
ttccgccact gcggcatctg cgacgccaag gccgaccatg cgtccgcctg tggactcgat 3120
ttgtgcttgt tccactcgca ttttcatcag cactgccctg tcactctgag ctgcggccat 3180
catgccggtt ctaaggaatg tccgcagtgt cagtcaccgg ttggggctgg ta 3232

<210> SEQ ID NO 59
<211> LENGTH: 58
<212> TYPE: DNA
<213> ORGANISM: Artificial Sequence
<220> FEATURE:
<223> OTHER INFORMATION: Sequence of clone SM_DEG-16-93F_ of the attenuated virus VP-046 BIS. Positions 3902 to 3926 of the virus genome

<400> SEQUENCE: 59
cggccttgtg gtcggcccct cgggtctctt atgtgtcatt cttggcaagt tactcggt 58

<210> SEQ ID NO 60
<211> LENGTH: 58
<212> TYPE: DNA
<213> ORGANISM: Artificial Sequence
<220> FEATURE:
<223> OTHER INFORMATION: Sequence of clone SM_DEG-17-93F_ of the attenuated virus VP-046 BIS. Positions 3902 to 3926 of the virus genome

<400> SEQUENCE: 60
cggccttgtg gtcggcccct cgggtctctt atgtgtcatt cttggcaagt tactcggt 58

<210> SEQ ID NO 61
<211> LENGTH: 58
<212> TYPE: DNA
<213> ORGANISM: Artificial Sequence
<220> FEATURE:
<223> OTHER INFORMATION: Sequence of clone SM_DEG-18-93F_ of the attenuated virus VP-046 BIS. Positions 3902 to 3926 of the virus genome

<400> SEQUENCE: 61
cggccttgtg gtcggcccct cgggtctctt atgtgtcatt cttggcaagt tactcggt 58

<210> SEQ ID NO 62
<211> LENGTH: 58
<212> TYPE: DNA
<213> ORGANISM: Artificial Sequence
<220> FEATURE:
<223> OTHER INFORMATION: Sequence of clone SM_91-67-1-67R of the attenuated virus VP-046 BIS. Positions 3902 to 3926 of the virus genome

<400> SEQUENCE: 62
cggccttgtg gtcggcccct cgggtctctt atgtgtcatt cttggcaagt tactcggt 58

<210> SEQ ID NO 63
<211> LENGTH: 58
<212> TYPE: DNA
<213> ORGANISM: Artificial Sequence
<220> FEATURE:
<223> OTHER INFORMATION: Sequence of clone SM_91-67-24-67R of the attenuated virus VP-046 BIS. Positions 3902 to 3926 of the virus genome

<400> SEQUENCE: 63
cggccttgtg gtcggcccct cgggtctctt atgtgtcatt cttggcaagt tactcggt 58

<210> SEQ ID NO 64
<211> LENGTH: 58
<212> TYPE: DNA
<213> ORGANISM: Artificial Sequence
<220> FEATURE:
<223> OTHER INFORMATION: Sequence of clone SM_91-67-11-67R of the attenuated virus VP-046 BIS. Positions 3902 to 3926 of the virus genome

<400> SEQUENCE: 64
cggccttgtg gtcggcccct cgggtctctt atgtgtcatt cttggcaagt tactcggt 58

<210> SEQ ID NO 65
<211> LENGTH: 58
<212> TYPE: DNA
<213> ORGANISM: Artificial Sequence
<220> FEATURE:
<223> OTHER INFORMATION: Sequence of clone SM_DEG-13-93F of the attenuated virus VP-046 BIS. Positions 3902 to 3926 of the virus genome

<400> SEQUENCE: 65
cggccttgtg gtcggcccct cgggtctctt atgtgtcatt cttggcaagt tactcggt 58

<210> SEQ ID NO 66
<211> LENGTH: 58
<212> TYPE: DNA
<213> ORGANISM: Artificial Sequence
<220> FEATURE:
<223> OTHER INFORMATION: Sequence of clone SM_DEG-14-93F of the attenuated virus VP-046 BIS. Positions 3902 to 3926 of the virus genome

<400> SEQUENCE: 66
cggccttgtg gtcggcccct cgggtctctt atgtgtcatt cttggcaagt tactcggt 58

<210> SEQ ID NO 67
<211> LENGTH: 58
<212> TYPE: DNA
<213> ORGANISM: Artificial Sequence
<220> FEATURE:
<223> OTHER INFORMATION: Sequence of clone SM_DEG-8-93F of the attenuated virus VP-046 BIS. Positions 3902 to 3926 of the virus genome

<400> SEQUENCE: 67
cggccttgtg gtcggcccct cgggtctctt atgtgtcatt cttggcaagt tactcggt 58

<210> SEQ ID NO 68
<211> LENGTH: 58
<212> TYPE: DNA

<213> ORGANISM: Artificial Sequence
<220> FEATURE:
<223> OTHER INFORMATION: Sequence of clone SM_DEG-6-93F of the attenuated virus VP-046 BIS. Positions 3902 to 3926 of the virus genome

<400> SEQUENCE: 68
cggccttgtg gtcggcccct cgggtctctt atgtgtcatt cttggcaagt tactcggt 58

<210> SEQ ID NO 69
<211> LENGTH: 58
<212> TYPE: DNA
<213> ORGANISM: Artificial Sequence
<220> FEATURE:
<223> OTHER INFORMATION: Sequence of clone SM_DEG-11-93F of the attenuated virus VP-046 BIS. Positions 3902 to 3926 of the virus genome

<400> SEQUENCE: 69
cggccttgtg gtcggcccct cgggcctctt atgtgtcatt cttggcaagt tactcggt 58

<210> SEQ ID NO 70
<211> LENGTH: 58
<212> TYPE: DNA
<213> ORGANISM: Artificial Sequence
<220> FEATURE:
<223> OTHER INFORMATION: Sequence of clone SM_DEG-1-93F of the attenuated virus VP-046 BIS. Positions 3902 to 3926 of the virus genome

<400> SEQUENCE: 70
cggccttgcg gtcggcccct cgggtctctt atgtgtcatt cttggcaagt tactcggt 58

<210> SEQ ID NO 71
<211> LENGTH: 58
<212> TYPE: DNA
<213> ORGANISM: Artificial Sequence
<220> FEATURE:
<223> OTHER INFORMATION: Sequence of clone SM_DEG-3-93F of the attenuated virus VP-046 BIS. Positions 3902 to 3926 of the virus genome

<400> SEQUENCE: 71
gggccttgtg gtcggcccct cgggtctctt atgtgtcatt cttggcaagt tactcggt 58

<210> SEQ ID NO 72
<211> LENGTH: 58
<212> TYPE: DNA
<213> ORGANISM: Artificial Sequence
<220> FEATURE:
<223> OTHER INFORMATION: Sequence of clone SM_91-67-22-67R of the attenuated virus VP-046 BIS. Positions 3902 to 3926 of the virus genome

<400> SEQUENCE: 72
gggccttgtg gttggcccct cgggcctctt atgtgtcatt cttggcaagt tactcggt 58

<210> SEQ ID NO 73
<211> LENGTH: 58
<212> TYPE: DNA
<213> ORGANISM: Artificial Sequence
<220> FEATURE:
<223> OTHER INFORMATION: Sequence of clone SM_DEG-4-93F of the attenuated virus VP-046 BIS. Positions 3902 to 3926 of the virus genome

<400> SEQUENCE: 73
gggccttgtg gtcggcccct cgggcctctt atgtgtcatt cttggcaagt tactcggt 58

<210> SEQ ID NO 74
<211> LENGTH: 58
<212> TYPE: DNA
<213> ORGANISM: Artificial Sequence
<220> FEATURE:
<223> OTHER INFORMATION: Sequence of clone SM_DEG-7-93F of the attenuated virus VP-046 BIS. Positions 3902 to 3926 of the virus genome

<400> SEQUENCE: 74
gggccttgtg gtcggcccct cgggcctctt atgtgtcatt cttggcaagt tactcggt 58

<210> SEQ ID NO 75
<211> LENGTH: 58
<212> TYPE: DNA
<213> ORGANISM: Artificial Sequence
<220> FEATURE:
<223> OTHER INFORMATION: Sequence of clone SM_DEG-5-93F of the attenuated virus VP-046 BIS. Positions 3902 to 3926 of the virus genome

<400> SEQUENCE: 75
gggccttgtg gtcggcccct cgggcctctt atgtgtcatt cttggcaagt tactcggt 58

<210> SEQ ID NO 76
<211> LENGTH: 58
<212> TYPE: DNA
<213> ORGANISM: Artificial Sequence
<220> FEATURE:
<223> OTHER INFORMATION: Sequence of clone SM_DEG-10-93F of the attenuated virus VP-046 BIS. Positions 3902 to 3926 of the virus genome

<400> SEQUENCE: 76
gggccttgtg gtcggcccct cgggcctctt atgtgtcatt cttggcaagt tactcggt 58

<210> SEQ ID NO 77
<211> LENGTH: 58
<212> TYPE: DNA
<213> ORGANISM: Artificial Sequence
<220> FEATURE:
<223> OTHER INFORMATION: Sequence of clone SM_DEG-9-93F of the attenuated virus VP-046 BIS. Positions 3902 to 3926 of the virus genome

<400> SEQUENCE: 77
gggccttgtg gtcggcccct cgggcctctt atgtgtcatt cttggcaagt tactcggt 58

<210> SEQ ID NO 78
<211> LENGTH: 58
<212> TYPE: DNA
<213> ORGANISM: Artificial Sequence
<220> FEATURE:
<223> OTHER INFORMATION: Sequence of clone SM_DEG-15-93F of the attenuated virus VP-046 BIS. Positions 3902 to 3926 of the virus genome

<400> SEQUENCE: 78
gggccttgtg gtcggcccct cgggcctctt atgtgtcatt cttggcaagt tactcggt 58

<210> SEQ ID NO 79
<211> LENGTH: 58
<212> TYPE: DNA
<213> ORGANISM: Artificial Sequence
<220> FEATURE:

<223> OTHER INFORMATION: Sequence of clone SM_DEG-12-93F of the attenuated virus VP-046 BIS. Positions 3902 to 3926 of the virus genome

<400> SEQUENCE: 79
gggccttgtg gtcggcccct cgggcctctt atgtgtcatt cttggcaagt tactcggt 58

<210> SEQ ID NO 80
<211> LENGTH: 58
<212> TYPE: DNA
<213> ORGANISM: Artificial Sequence
<220> FEATURE:
<223> OTHER INFORMATION: Sequence of clone SM_91-67-3-67R of the attenuated virus VP-046 BIS. Positions 3902 to 3926 of the virus genome

<400> SEQUENCE: 80
gggccttgtg gtcggcccct cgggcctctt atgtgtcatt cttggcaagt tactcggt 58

<210> SEQ ID NO 81
<211> LENGTH: 58
<212> TYPE: DNA
<213> ORGANISM: Artificial Sequence
<220> FEATURE:
<223> OTHER INFORMATION: Sequence of clone SM_91-67-10-67R of the attenuated virus VP-046 BIS. Positions 3902 to 3926 of the virus genome

<400> SEQUENCE: 81
gggccttgtg gtcggcccct cgggcctctt atgtgtcatt cttggcaagt tactcggt 58

<210> SEQ ID NO 82
<211> LENGTH: 58
<212> TYPE: DNA
<213> ORGANISM: Artificial Sequence
<220> FEATURE:
<223> OTHER INFORMATION: Sequence of clone SM_91-67-19-67R of the attenuated virus VP-046 BIS. Positions 3902 to 3926 of the virus genome

<400> SEQUENCE: 82
gggccttgtg gtcggcccct cgggcctctt atgtgtcatt cttggcaagt tactcggt 58

<210> SEQ ID NO 83
<211> LENGTH: 58
<212> TYPE: DNA
<213> ORGANISM: Artificial Sequence
<220> FEATURE:
<223> OTHER INFORMATION: Sequence of clone SM_91-67-16-67R of the attenuated virus VP-046 BIS. Positions 3902 to 3926 of the virus genome

<400> SEQUENCE: 83
gggccttgtg gtcggcccct cgggcctctt atgtgtcatt cttggcaagt tactcggt 58

<210> SEQ ID NO 84
<211> LENGTH: 4304
<212> TYPE: DNA
<213> ORGANISM: Artificial Sequence
<220> FEATURE:
<223> OTHER INFORMATION: Sequence of viral cDNA in clone pUC19-DEG3 (Positions 1973 to 6276). RsrII cuts between 1973-1973, SpeI cuts between 6276 and 6277

<400> SEQUENCE: 84
gtccggcttc tctagcttgt ataaattact attggaggtt gttccgcaga aatgcggtgc 60
cacggaaggg gctttcgtct atgctgttga gaggatgttg aaggattgtc cgagctccaa 120

-continued

```
acaggccatg gcccttctgg caaaaattaa agtcccatcc tcaaaggccc cgtctgtgtc    180
tctggacgag tgcttcccta cggatgttcc agcggactcc gagccagcgt ttcaggaaag    240
gccccaaagt tctggtgctg ctgttgtcct gtgttcaccg gacataaaag agttcgagga    300
agcagcccca gaagaagttc aagagggtgg ccacaaggcc gtccactctg cactccttgc    360
cgagggtctt aacaatgagc aggtacaggt ggttgccggt gcgcaactaa agctcggcag    420
ttgtggcttg gcagtcggga atactcatgg aggtgttccg gtttcagcta gtccaattaa    480
cctggcagac gggaatttgc ccccctcgga ctccatgaaa ggaaacatgc ccaatggctg    540
ggaggacgaa ccactggatt tgtcccaatc agcactagca accacaacga cccttgtgag    600
agagcaaaca cccgacaatc taggttctgg cgccggtgcc ctccctgtca ccattcgaga    660
atttgtcccg acaaggccta taccccgtca tgttgagcac tgcggcacgg agtcgggcga    720
cagcagttcg cctctggatc tgtccgatgc gcaaaccccg gaccagcctt taaatctatc    780
cctggccgct tggccagtga gggccaccgc gtctgacccc ggctgggtcc acggtaggcg    840
tgagcctgtt tttgtaaagc ctcggggtgc tttctctgat ggcgattcag tccttcagtt    900
cggggagctt tccgaatcca gctctatcat cgagattgac cggacaaaag atgctccagt    960
ggttgatgcc cccgtcgact tgacggtttc gaacgaagct ctctctggga tcgatccttt   1020
tgaatttacc gaactcaagc gcccgcgttt ctccgctcaa gccttaattg accgaggcgg   1080
cccactagcc gatgtccatg caaaaataaa gaaccgggta tatgaacagt gcctccaggc   1140
ttgtgagcct ggcagtcgtg caaccccagc caccagggag tggctcgaca aaatgtggga   1200
tagggtggac atgaagactt ggcgctgcac ctcgcagttc caagctggtc acattcttgc   1260
gtccctcaaa ttcctccccg acatgattca agacacaccg cctcctgttc ccaggaagag   1320
ccgggctagt gataatgccg gcctgaagca actggtggcg cagtgggaca gaaaattgag   1380
tgtaaccccc cccctaaaac cggttgggcc ggcgcttggc caaaccgtcc ctccgcctac   1440
ggatattcag caagaagatg tcaccccctc cgataggcca cctcatgtgc cggatcttcc   1500
tagtcgagtg agcacgggtg ggagttggaa aggccttatg ctttccggca cccgtctcgc   1560
ggggtctatt agtcagcacc tcatgacatg ggtttttgaa gttttctccc atctcccagc   1620
ttttatgctc acacttttct cgccacgggg ctctatggct ccaggtgatt ggctatttgc   1680
aggtgttgtt ttacttgctc tcctgctctg tcgttcttac ccagtactcg ggtgccttcc   1740
cttattgggt gtcttttctg gttctttgcg gcgtgttcgt ctgggtgttt ttggttcttg   1800
gatggctttt gctgtatttt tattctcgac tccatccgac ccagtcggtt cttcttgtga   1860
ccacgattcg ccggagtgtc atgctgagct tttggctctt gagcagcgcc aactttggga   1920
acctgtgcgg ggccttgtgg tcggcccctc gggcctctta tgtgtcattc ttggcaagtt   1980
actcggtggg tcacgttatc tctggcatgt tttcttacgt ttatgcatgc ttgcggattt   2040
ggccctttct cttgtttatg tggtgtccca ggggcgttgt cacaagtgtt ggggaaagtg   2100
tataaggaca gctcctgcgg aggtggctct caatgtgttc cctttcttgc gcgctacccg   2160
tgcctctctt gtgtccttgt gcgatcgatt ccaagcgcca aaaggggttg atcctgtgca   2220
cttggcaaca ggttggcgcg ggtgctggcg cggtgagagc cccattcatc aaccgcacca   2280
aaagcccata gcttatgcca atttggatga aaagaaaata tctgcccaaa cggtggttgc   2340
tgtcccgtat gatcccagtc aggccatcaa atgcctgaaa gttctgcagg cgggaggggc   2400
tatcgtggac cagcccacac ctgaggtcgt ccgtgtgtcc gagatccctt tctcagcccc   2460
```

-continued

```
atttttttcca aaggttccag tcaacccaga ttgcagggtt gtggtagatt cggacacttt   2520

tgtggctgca gttcgctgcg gttactcgac ggctcaactg gtcttaggcc ggggcaactt   2580

tgccaagtta aatcagatcc cctccaggaa ctctgtctcc accaaaacga ctggtggggc   2640

ctcttacacc cttgctgtgg ctcaagtgtc tgtgtggact cttgttcatt tcatcctcgg   2700

tctttggttc acgtcacctc aagtgtgtgg ccgaggaacc tctgacccat ggtgttcaaa   2760

tcctttttca tatcctacct atggccccgg aatagtgtgc tcctctcgac tttgtgtgtc   2820

tgccgacgga gtcactctgc cattgttctc agcagtggca caactctccg gtagagaggt   2880

ggggatttc atttggtgc tcgtctcctt gactgctctg gcccaccgta tggctcttaa   2940

ggcagacatg ttagtggtct tttcggcttt ttgtgcctac gcctggccca tgagctcctg   3000

gttaatctgc ttctttccta tattcttgaa gtgggtcacc cttcaccctc tcactatgct   3060

ttgggtgcac tcattcttgg tgttttgtct gccagcagcc ggcgtcctct cactagggat   3120

aaccggcctt ctctgggcag ttggccgctt tacccaggtc gccggaatta ttacacctta   3180

tgacatccac cagtacacct ctgggccacg tggtgcagcc gctgtggcca cggccccaga   3240

aggcacttac atggccgccg tccggagagc tgccttaact ggacgaaccc tcatcttcac   3300

accatctgcg gttggatccc ttcttgaagg tgctttcagg acccataaac cctgccttaa   3360

caccgtgaat gttgtaggct cttcccttgg ttccgggggg gttttcacca ttgatggcag   3420

aagaactgtt gtcactgctg cccatgtgtt gaacggcgac acagctagag tcaccggcga   3480

ctcctacaac cgcatgcaca ctttcaagac caatggtgat tatgcctggt cccatgctga   3540

tgactggcgg ggcgttgccc ctgtggtcaa ggtcgcgaag ggtaccgcg gtcgtgccta   3600

ctggcaaaca tcaactggtg tcgaacccgg tattgttggg gaagggttcg ccttctgttt   3660

taccaactgt ggcgattcgg ggtcacctgt catctcagaa tctggtgatc ttgttggaat   3720

ccacaccggt tcaaacaaac tcggttctgg tcttgtgaca acccctgaag ggagacctg   3780

ctccatcaaa gaaaccaagc tctctgacct ttccaggtat tttgcaggcc caagcgtccc   3840

tcttggggat attaaattga gtccggccat catccctgat gtaacatcca ttccgagtga   3900

cttggcatcg ctcctagcct ccgtccctgt aatggaaggc ggcctctcga ctgtccaact   3960

tttgtgtgtc tttttccttc tctggcgtat gatgggccat gcctggacac ccattgttgc   4020

cgtgggcttc tttttgctga atgaaattct tccagcagtt ttggtccgag ccgtgttttc   4080

ttttgcgctc tttgtgcttg catgggccac cccctggtct gcacaggtgt tgatgatcag   4140

actcctcacg gcagctctca accgcaacag gctttctctg gcgttctacg cactcggggg   4200

tgtcgtcggt ttggctgctg aaattgggac ctttgctggt agattgtctg aattgtctca   4260

agctctttcg acatactgct tcttacctag ggttcttgct gtga                   4304
```

<210> SEQ ID NO 85
<211> LENGTH: 20
<212> TYPE: DNA
<213> ORGANISM: Artificial Sequence
<220> FEATURE:
<223> OTHER INFORMATION: primer

<400> SEQUENCE: 85

```
aagtcgttgg aggaagttgt                                                20
```

<210> SEQ ID NO 86
<211> LENGTH: 20
<212> TYPE: DNA
<213> ORGANISM: Artificial Sequence
<220> FEATURE:
<223> OTHER INFORMATION: primer

<400> SEQUENCE: 86
cctagattgt cgggtgtttg 20

<210> SEQ ID NO 87
<211> LENGTH: 21
<212> TYPE: DNA
<213> ORGANISM: Artificial Sequence
<220> FEATURE:
<223> OTHER INFORMATION: primer

<400> SEQUENCE: 87
ccsagtaacy tgccaagaat g 21

<210> SEQ ID NO 88
<211> LENGTH: 34
<212> TYPE: DNA
<213> ORGANISM: Artificial Sequence
<220> FEATURE:
<223> OTHER INFORMATION: primer

<400> SEQUENCE: 88
ccaaatcctc tagaatgcat aaacgtaaga aaac 34

<210> SEQ ID NO 89
<211> LENGTH: 23
<212> TYPE: DNA
<213> ORGANISM: Artificial Sequence
<220> FEATURE:
<223> OTHER INFORMATION: primer

<400> SEQUENCE: 89
ttkgaagcag awacaaagca ctt 23

<210> SEQ ID NO 90
<211> LENGTH: 22
<212> TYPE: DNA
<213> ORGANISM: Artificial Sequence
<220> FEATURE:
<223> OTHER INFORMATION: primer

<400> SEQUENCE: 90
ggacttccar gccttyttca tg 22

<210> SEQ ID NO 91
<211> LENGTH: 23
<212> TYPE: DNA
<213> ORGANISM: Artificial Sequence
<220> FEATURE:
<223> OTHER INFORMATION: primer

<400> SEQUENCE: 91
tcraagccra cagggtgaag ttg 23

<210> SEQ ID NO 92
<211> LENGTH: 23
<212> TYPE: DNA
<213> ORGANISM: Artificial Sequence
<220> FEATURE:
<223> OTHER INFORMATION: primer

<400> SEQUENCE: 92
tcraagccra cagggtgaag ttg 23

<210> SEQ ID NO 93
<211> LENGTH: 22
<212> TYPE: DNA
<213> ORGANISM: Artificial Sequence
<220> FEATURE:
<223> OTHER INFORMATION: primer

<400> SEQUENCE: 93
caaccacact aacaagraac tc 22

<210> SEQ ID NO 94
<211> LENGTH: 20
<212> TYPE: DNA
<213> ORGANISM: Artificial Sequence
<220> FEATURE:
<223> OTHER INFORMATION: primer

<400> SEQUENCE: 94
taaaaaagrc acgcrgarag 20

<210> SEQ ID NO 95
<211> LENGTH: 22
<212> TYPE: DNA
<213> ORGANISM: Artificial Sequence
<220> FEATURE:
<223> OTHER INFORMATION: primer

<400> SEQUENCE: 95
crcgaatyar gcgcacygtr tg 22

<210> SEQ ID NO 96
<211> LENGTH: 69
<212> TYPE: DNA
<213> ORGANISM: Artificial Sequence
<220> FEATURE:
<223> OTHER INFORMATION: primer

<400> SEQUENCE: 96
ggcgatcggg cgtctaggaa ttctagattt tttttttttt tttttttttt tttttttttt 60 ttttttttv 69

<210> SEQ ID NO 97
<211> LENGTH: 20
<212> TYPE: DNA
<213> ORGANISM: Artificial Sequence
<220> FEATURE:
<223> OTHER INFORMATION: primer

<400> SEQUENCE: 97
cccacatttt rtcragccac 20

<210> SEQ ID NO 98
<211> LENGTH: 41
<212> TYPE: DNA
<213> ORGANISM: Artificial Sequence
<220> FEATURE:
<223> OTHER INFORMATION: primer

<400> SEQUENCE: 98
ggcgcgccta atacgactca ctatagatga tgtgtagggt a 41

<210> SEQ ID NO 99
<211> LENGTH: 33
<212> TYPE: DNA
<213> ORGANISM: Artificial Sequence
<220> FEATURE:
<223> OTHER INFORMATION: primer

<400> SEQUENCE: 99
cagtgaagct ttctagaagg cttgtaaaac aag 33

<210> SEQ ID NO 100
<211> LENGTH: 22
<212> TYPE: DNA
<213> ORGANISM: Artificial Sequence
<220> FEATURE:
<223> OTHER INFORMATION: primer

<400> SEQUENCE: 100
ttycggagmg sacctgcttt ac 22

<210> SEQ ID NO 101
<211> LENGTH: 20
<212> TYPE: DNA
<213> ORGANISM: Artificial Sequence
<220> FEATURE:
<223> OTHER INFORMATION: primer

<400> SEQUENCE: 101
cctagattgt cgggtgtttg 20

<210> SEQ ID NO 102
<211> LENGTH: 21
<212> TYPE: DNA
<213> ORGANISM: Artificial Sequence
<220> FEATURE:
<223> OTHER INFORMATION: primer

<400> SEQUENCE: 102
ttytggacyc tygacaaaat g 21

<210> SEQ ID NO 103
<211> LENGTH: 21
<212> TYPE: DNA
<213> ORGANISM: Artificial Sequence
<220> FEATURE:
<223> OTHER INFORMATION: primer

<400> SEQUENCE: 103
ccsagtaacy tgccaagaat g 21

<210> SEQ ID NO 104
<211> LENGTH: 30
<212> TYPE: DNA
<213> ORGANISM: Artificial Sequence
<220> FEATURE:
<223> OTHER INFORMATION: primer

<400> SEQUENCE: 104
actgtgttgg ttctggtatt gctgactttc 30

<210> SEQ ID NO 105
<211> LENGTH: 34
<212> TYPE: DNA
<213> ORGANISM: Artificial Sequence
<220> FEATURE:
<223> OTHER INFORMATION: primer

<400> SEQUENCE: 105
ccaaatcctc tagaatgcat aaacgtaaga aaac 34

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
tyaarttcct cccygacatg 20

<210> SEQ ID NO 107
<211> LENGTH: 23
<212> TYPE: DNA
<213> ORGANISM: Artificial Sequence
<220> FEATURE:
<223> OTHER INFORMATION: primer

<400> SEQUENCE: 107
ttkgaagcag awacaaagca ctt 23

<210> SEQ ID NO 108
<211> LENGTH: 20
<212> TYPE: DNA
<213> ORGANISM: Artificial Sequence
<220> FEATURE:
<223> OTHER INFORMATION: primer

<400> SEQUENCE: 108
atgatggrcc atgcctggac 20

<210> SEQ ID NO 109
<211> LENGTH: 22
<212> TYPE: DNA
<213> ORGANISM: Artificial Sequence
<220> FEATURE:
<223> OTHER INFORMATION: primer

<400> SEQUENCE: 109
ggacttccar gccttyttca tg 22

<210> SEQ ID NO 110
<211> LENGTH: 22
<212> TYPE: DNA
<213> ORGANISM: Artificial Sequence
<220> FEATURE:
<223> OTHER INFORMATION: primer

<400> SEQUENCE: 110
raccacygar cargctttaa ac 22

<210> SEQ ID NO 111
<211> LENGTH: 23
<212> TYPE: DNA
<213> ORGANISM: Artificial Sequence
<220> FEATURE:
<223> OTHER INFORMATION: primer

<400> SEQUENCE: 111
tcraagccra cagggtgaag ttg 23

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
atgatggrcc atgcctggac 20

<210> SEQ ID NO 113
<211> LENGTH: 21
<212> TYPE: DNA
<213> ORGANISM: Artificial Sequence
<220> FEATURE:
<223> OTHER INFORMATION: primer

<400> SEQUENCE: 113
gactgcatct agacctcgac g 21

<210> SEQ ID NO 114
<211> LENGTH: 19
<212> TYPE: DNA
<213> ORGANISM: Artificial Sequence
<220> FEATURE:
<223> OTHER INFORMATION: primer

<400> SEQUENCE: 114
ctygcatayc acatgaarg 19

<210> SEQ ID NO 115
<211> LENGTH: 22
<212> TYPE: DNA
<213> ORGANISM: Artificial Sequence
<220> FEATURE:
<223> OTHER INFORMATION: primer

<400> SEQUENCE: 115
caaccacact aacaagraac tc 22

<210> SEQ ID NO 116
<211> LENGTH: 22
<212> TYPE: DNA
<213> ORGANISM: Artificial Sequence
<220> FEATURE:
<223> OTHER INFORMATION: primer

<400> SEQUENCE: 116
ayaacytrgg gttytacttt tc 22

<210> SEQ ID NO 117
<211> LENGTH: 20
<212> TYPE: DNA
<213> ORGANISM: Artificial Sequence
<220> FEATURE:
<223> OTHER INFORMATION: primer

<400> SEQUENCE: 117
taaaaaagrc acgcrgarag 20

<210> SEQ ID NO 118
<211> LENGTH: 26
<212> TYPE: DNA
<213> ORGANISM: Artificial Sequence
<220> FEATURE:
<223> OTHER INFORMATION: primer

<400> SEQUENCE: 118
tacgytmtgt ttttggtttc caytgg 26

<210> SEQ ID NO 119

<211> LENGTH: 22
<212> TYPE: DNA
<213> ORGANISM: Artificial Sequence
<220> FEATURE:
<223> OTHER INFORMATION: primer

<400> SEQUENCE: 119
crcgaatyar gcgcacygtr tg 22

<210> SEQ ID NO 120
<211> LENGTH: 27
<212> TYPE: DNA
<213> ORGANISM: Artificial Sequence
<220> FEATURE:
<223> OTHER INFORMATION: primer

<400> SEQUENCE: 120
ttccagatgc agattgtgtt gcctagg 27

<210> SEQ ID NO 121
<211> LENGTH: 69
<212> TYPE: DNA
<213> ORGANISM: Artificial Sequence
<220> FEATURE:
<223> OTHER INFORMATION: primer

<400> SEQUENCE: 121
ggcgatcggg cgtctaggaa ttctagattt tttttttttt tttttttttt tttttttttt 60 tttttttttv 69

<210> SEQ ID NO 122
<211> LENGTH: 30
<212> TYPE: DNA
<213> ORGANISM: Artificial Sequence
<220> FEATURE:
<223> OTHER INFORMATION: primer

<400> SEQUENCE: 122
actgtgttgg ttctggtatt gctgactttc 30

<210> SEQ ID NO 123
<211> LENGTH: 34
<212> TYPE: DNA
<213> ORGANISM: Artificial Sequence
<220> FEATURE:
<223> OTHER INFORMATION: primer

<400> SEQUENCE: 123
ccaaatcctc tagaatgcat aaacgtaaga aaac 34

<210> SEQ ID NO 124
<211> LENGTH: 70
<212> TYPE: DNA
<213> ORGANISM: Artificial Sequence
<220> FEATURE:
<223> OTHER INFORMATION: polynucleotide fragment

<400> SEQUENCE: 124
gaacgccgga ggatccggcg cgccgatatc ttaattaaac gcgttctaga gcccttccgg 60
ctggctggtt 70

<210> SEQ ID NO 125
<211> LENGTH: 20
<212> TYPE: DNA
<213> ORGANISM: Artificial Sequence
<220> FEATURE:
<223> OTHER INFORMATION: primer

<400> SEQUENCE: 125
aagtcgttgg aggaagttgt 20

<210> SEQ ID NO 126
<211> LENGTH: 20
<212> TYPE: DNA
<213> ORGANISM: Artificial Sequence
<220> FEATURE:
<223> OTHER INFORMATION: primer

<400> SEQUENCE: 126
aatgggaaga tggctgagag 20

<210> SEQ ID NO 127
<211> LENGTH: 33
<212> TYPE: DNA
<213> ORGANISM: Artificial Sequence
<220> FEATURE:
<223> OTHER INFORMATION: primer

<400> SEQUENCE: 127
cagtgaagct ttctagaagg cttgtaaaac aag 33

<210> SEQ ID NO 128
<211> LENGTH: 17
<212> TYPE: DNA
<213> ORGANISM: Artificial Sequence
<220> FEATURE:
<223> OTHER INFORMATION: primer

<400> SEQUENCE: 128
gtaaaacgac ggccagt 17

<210> SEQ ID NO 129
<211> LENGTH: 17
<212> TYPE: DNA
<213> ORGANISM: Artificial Sequence
<220> FEATURE:
<223> OTHER INFORMATION: primer

<400> SEQUENCE: 129
caggaaacag ctatgac 17

<210> SEQ ID NO 130
<211> LENGTH: 20
<212> TYPE: DNA
<213> ORGANISM: Artificial Sequence
<220> FEATURE:
<223> OTHER INFORMATION: primer

<400> SEQUENCE: 130
aaccatgtct gggacgttct 20

<210> SEQ ID NO 131
<211> LENGTH: 31
<212> TYPE: DNA
<213> ORGANISM: Artificial Sequence
<220> FEATURE:
<223> OTHER INFORMATION: primer

<400> SEQUENCE: 131
ccaatagtaa tttatacaat ctagagaagc c 31

<210> SEQ ID NO 132
<211> LENGTH: 30
<212> TYPE: DNA
<213> ORGANISM: Artificial Sequence
<220> FEATURE:
<223> OTHER INFORMATION: primer

<400> SEQUENCE: 132
actgtgttgg ttctggtatt gctgactttc 30

<210> SEQ ID NO 133
<211> LENGTH: 34
<212> TYPE: DNA
<213> ORGANISM: Artificial Sequence
<220> FEATURE:
<223> OTHER INFORMATION: primer

<400> SEQUENCE: 133
ccaaatcctc tagaatgcat aaacgtaaga aaac 34

<210> SEQ ID NO 134
<211> LENGTH: 28
<212> TYPE: DNA
<213> ORGANISM: Artificial Sequence
<220> FEATURE:
<223> OTHER INFORMATION: primer

<400> SEQUENCE: 134
tccagccgta cgctatgttt ttggtttc 28

<210> SEQ ID NO 135
<211> LENGTH: 28
<212> TYPE: DNA
<213> ORGANISM: Artificial Sequence
<220> FEATURE:
<223> OTHER INFORMATION: primer

<400> SEQUENCE: 135
ttcttctggc tctagatttt taccggcc 28

<210> SEQ ID NO 136
<211> LENGTH: 18
<212> TYPE: DNA
<213> ORGANISM: Artificial Sequence
<220> FEATURE:
<223> OTHER INFORMATION: primer

<400> SEQUENCE: 136
cagtaccgac ggtgatat 18

<210> SEQ ID NO 137
<211> LENGTH: 20
<212> TYPE: DNA
<213> ORGANISM: Artificial Sequence
<220> FEATURE:
<223> OTHER INFORMATION: primer

<400> SEQUENCE: 137
ccgtcgtgta gataactacg 20

<210> SEQ ID NO 138
<211> LENGTH: 17
<212> TYPE: DNA
<213> ORGANISM: Artificial Sequence
<220> FEATURE:
<223> OTHER INFORMATION: primer

<400> SEQUENCE: 138
gtaaaacgac ggccagt 17

<210> SEQ ID NO 139
<211> LENGTH: 17
<212> TYPE: DNA
<213> ORGANISM: Artificial Sequence
<220> FEATURE:
<223> OTHER INFORMATION: primer

<400> SEQUENCE: 139
caggaaacag ctatgac 17

<210> SEQ ID NO 140
<211> LENGTH: 28
<212> TYPE: DNA
<213> ORGANISM: Artificial Sequence
<220> FEATURE:
<223> OTHER INFORMATION: primer

<400> SEQUENCE: 140
ggcgcgccat ttaaatatga tgtgtagg 28

<210> SEQ ID NO 141
<211> LENGTH: 29
<212> TYPE: DNA
<213> ORGANISM: Artificial Sequence
<220> FEATURE:
<223> OTHER INFORMATION: primer

<400> SEQUENCE: 141
ttatacaagc tagagaagcc ggaccgttc 29

<210> SEQ ID NO 142
<211> LENGTH: 22
<212> TYPE: DNA
<213> ORGANISM: Artificial Sequence
<220> FEATURE:
<223> OTHER INFORMATION: primer

<400> SEQUENCE: 142
tgttaaacga ggagtggtta ac 22

<210> SEQ ID NO 143
<211> LENGTH: 79
<212> TYPE: DNA
<213> ORGANISM: Artificial Sequence
<220> FEATURE:
<223> OTHER INFORMATION: primer

<400> SEQUENCE: 143
atgttgccca gccggcgcca gcgaggaggc tgggaccatg ccggcctttt tttttttttt 60
tttttttttt taatttcgg 79

<210> SEQ ID NO 144
<211> LENGTH: 58
<212> TYPE: DNA
<213> ORGANISM: Artificial Sequence
<220> FEATURE:
<223> OTHER INFORMATION: primer

<400> SEQUENCE: 144
ggtctagagt cccattcgcc attaccgagg ggacggtccc ctcggaatgt tgcccagc 58

-continued

<210> SEQ ID NO 145
<211> LENGTH: 28
<212> TYPE: DNA
<213> ORGANISM: Artificial Sequence
<220> FEATURE:
<223> OTHER INFORMATION: primer

<400> SEQUENCE: 145
ggcgcgccat gcattagtta ttaatagt 28

<210> SEQ ID NO 146
<211> LENGTH: 35
<212> TYPE: DNA
<213> ORGANISM: Artificial Sequence
<220> FEATURE:
<223> OTHER INFORMATION: primer

<400> SEQUENCE: 146
catatttaaa tactaaacca gctctgctta tatag 35

<210> SEQ ID NO 147
<211> LENGTH: 19
<212> TYPE: DNA
<213> ORGANISM: Artificial Sequence
<220> FEATURE:
<223> OTHER INFORMATION: primer

<400> SEQUENCE: 147
tcagtaccga cggtgatat 19

<210> SEQ ID NO 148
<211> LENGTH: 20
<212> TYPE: DNA
<213> ORGANISM: Artificial Sequence
<220> FEATURE:
<223> OTHER INFORMATION: primer

<400> SEQUENCE: 148
ccgtcgtgta gataactacg 20

<210> SEQ ID NO 149
<211> LENGTH: 44
<212> TYPE: DNA
<213> ORGANISM: Artificial Sequence
<220> FEATURE:
<223> OTHER INFORMATION: primer

<400> SEQUENCE: 149
cgatagggac tttccagtga agtctagatt taggcttgta aaac 44

<210> SEQ ID NO 150
<211> LENGTH: 19
<212> TYPE: DNA
<213> ORGANISM: Artificial Sequence
<220> FEATURE:
<223> OTHER INFORMATION: primer

<400> SEQUENCE: 150
tagacggggg yaaytggtt 19

<210> SEQ ID NO 151
<211> LENGTH: 23
<212> TYPE: DNA
<213> ORGANISM: Artificial Sequence
<220> FEATURE:
<223> OTHER INFORMATION: primer

<400> SEQUENCE: 151
gacaccttaa grgcrtatat cat 23

<210> SEQ ID NO 152
<211> LENGTH: 21
<212> TYPE: DNA
<213> ORGANISM: Artificial Sequence
<220> FEATURE:
<223> OTHER INFORMATION: primer

<400> SEQUENCE: 152
gaattccagc cgtacgctat g 21

<210> SEQ ID NO 153
<211> LENGTH: 25
<212> TYPE: DNA
<213> ORGANISM: Artificial Sequence
<220> FEATURE:
<223> OTHER INFORMATION: primer

<400> SEQUENCE: 153
tacttgacga ggttaaccac tcctc 25

<210> SEQ ID NO 154
<211> LENGTH: 23
<212> TYPE: DNA
<213> ORGANISM: Artificial Sequence
<220> FEATURE:
<223> OTHER INFORMATION: primer

<400> SEQUENCE: 154
gtgactagtt atgttcccac cat 23

<210> SEQ ID NO 155
<211> LENGTH: 20
<212> TYPE: DNA
<213> ORGANISM: Artificial Sequence
<220> FEATURE:
<223> OTHER INFORMATION: primer

<400> SEQUENCE: 155
agaggagatc taccagcccc 20

<210> SEQ ID NO 156
<211> LENGTH: 25
<212> TYPE: DNA
<213> ORGANISM: Artificial Sequence
<220> FEATURE:
<223> OTHER INFORMATION: primer

<400> SEQUENCE: 156
cggatccatc ctcgatatta atgtg 25

<210> SEQ ID NO 157
<211> LENGTH: 20
<212> TYPE: DNA
<213> ORGANISM: Artificial Sequence
<220> FEATURE:
<223> OTHER INFORMATION: primer

<400> SEQUENCE: 157
tgcagtttca aaatcccaaa 20

<210> SEQ ID NO 158

<211> LENGTH: 22
<212> TYPE: DNA
<213> ORGANISM: Artificial Sequence
<220> FEATURE:
<223> OTHER INFORMATION: primer

<400> SEQUENCE: 158
catgctgagc ttttggctct tg 22

<210> SEQ ID NO 159
<211> LENGTH: 34
<212> TYPE: DNA
<213> ORGANISM: Artificial Sequence
<220> FEATURE:
<223> OTHER INFORMATION: primer

<400> SEQUENCE: 159
ccaaatcctc tagaatgcat aaacgtaaga aaac 34

<210> SEQ ID NO 160
<211> LENGTH: 18
<212> TYPE: DNA
<213> ORGANISM: Artificial Sequence
<220> FEATURE:
<223> OTHER INFORMATION: primer

<400> SEQUENCE: 160
cagaacggtc cggcttct 18

<210> SEQ ID NO 161
<211> LENGTH: 25
<212> TYPE: DNA
<213> ORGANISM: Artificial Sequence
<220> FEATURE:
<223> OTHER INFORMATION: primer

<400> SEQUENCE: 161
acataactag tcacagcaag aaccc 25

<210> SEQ ID NO 162
<211> LENGTH: 18745
<212> TYPE: DNA
<213> ORGANISM: Artificial Sequence
<220> FEATURE:
<223> OTHER INFORMATION: Clone pVAC 6.1

<400> SEQUENCE: 162
atgatgtgtg ggtattccc cctacataca caacactccc agtgtttgtg tgccttggag 60
gcgcgggtat agccccgccc cacccccttgg cccctgttct agcccaacag gtatccttct 120
ctctcggggc gagcgcgcca cctgctgctc ccttgcagcg ggaaggacct cccgagtatt 180
tccggagagc acctgcttta cgggatctcc accctttaac catgtctggg acgttctccc 240
ggtgcatgtg caccccggct gcccgggtat tttggaacgc cggccaagtc ttttgcacac 300
ggtgtctcag cgcacggtct cttctccctc cggagcttca ggaaactgac cttgctgcaa 360
ttggcttgtt ttacaagcct aaagacaagc ttcactggaa ggtccctatc ggcatccctc 420
aggtggagtg cactccatcc gggtgctgtt ggctctcagc catcttccct ttggcgcgca 480
tgacctccgg caatcacaac ttcctccaac gacttgtgag ggttgccgat gtgttgtacc 540
gtgacggttg cctggctcct cgacaccttc gtgaactcca agtttacgaa cgcggctgca 600
actggtaccc aatcacgggg cccgtgcctg ggatgggttt gttcgcaaac tccatgcacg 660
tatccgacca gccgttccct ggtgccaccc atgtgttgac gaactcgccg ttgcctcaac 720

-continued

```
aagcctgtcg gcagctgttt tgtccatttg aggaagctca ttctagcatg tacaggtgga    780
aaagatttgt ggttttcgcg gattcctctc ctaacggtcg acctcgtatg atgtggatgc    840
cggagtccga tggttcagcc gtcttggagg tattaccgcc tgaattagaa catcaggtcg    900
aaatcctcat tcggaatttt cctgctcatc accctgtcaa cctggccgac tgggagctca    960
ctgagtcccc tgagaacggt tttttccttca acacgtccta ttcttgcggt cacctcgtcc   1020
agaaccccga cgtgtttgat ggtaagtgct ggctttcctg ctttttgggc cagccggccg   1080
aggtgcgacg ccatgaggaa catttagctg acgcattcgg ttaccagacc aagtggggcg   1140
tgcctggcaa gtacctccag cgcaggcttc aggttcgcgg cattcgtgct gtaattgatc   1200
ctgacggccc cattcatgtc gaagcgctgt cttgccccgg gtcttggatc aggcacctga   1260
cctttgatga taatgtcacc ccgggatttg ttcgccttac gtcccttcgc attgtgccaa   1320
acaccgagtc tactggtctc cgaatcttcc ggtttggagc gcataagtgg tatggcgctg   1380
caggcagacg tgctcgtgct aagcgtgccg ctagaagtga gggaatttcg gcccctatcc   1440
ccgaggttgt tcagccggtc tccacctgcg aaattaccac ctattctccg ccgacagacg   1500
ggtcttgtgg ttggcatgtt cttgccgcca taataaaccg gatgatgaat ggtgacttca   1560
cgtctcctct gactcagtac aacaggccag aggatgactg ggcttctgat tatgaccttg   1620
ctcaggcaat ccaatgtttg caactgcccg ctaccgtagt tcggaatcgt gcctgcccta   1680
acgccaagta cctcataaaa cttaatggag ttcattggga ggtagaggtg aggtctggaa   1740
tggccccccg ctccctttcc cgcgagtgtg tggttggcgt ttgttctgaa gactgtatcg   1800
caccgcctta cccacaagac gggctgcctg aacgtgcact tgaggccttg gcgtctgctt   1860
acagactacc ctccgattgt gtttgttctg gtattactga ttttcttgcc aacccgcccc   1920
ctaaggagtt ttggaccctt gacaaaatgt tgacctcccc gtcaccggaa cggtccggct   1980
tctctagctt gtataaatta ctattggagg ttgtcccgca gaaatgcggt gccacggagg   2040
gggccttcgt ctatgctgtt gagaggatgt tgaaggattg tccgagctcc aaacaagcca   2100
tggccctcct ggcaaaaatc aaagttccat cctccaaggc cccgtctgtg tctctggatg   2160
agtgtttccc cacggatgtt ccggcggact ccgagtcagc gtttcaggaa aggccccgag   2220
cttctggtgc tgctgttgtc ctgtgttcgc caggcatgaa agagttcgag gaagcagtcc   2280
cagaagaagt tcaagagggt ggccgtaagg ccgtccactc tgcactcctc gccgagggtc   2340
ttaacaatga gcgggcgcag gtggttgcca gtgcgcaacc aaagcccgga agttgcggtt   2400
tggcatctgg gaatactcat ggaggtgttc cggttctagc tagcccaatc aacctagcag   2460
acgggaattt gccctcctcg gaatccatga aaggaaacat gcccaatggt cgggaggacg   2520
aaccactgga tttgtcccaa tcagcaccgg caatcacaac gacccttatg agagagcaag   2580
caccggacag tctgagtttt ggcgccggtg ctccccctgt cacgattcga gaatttgccc   2640
cgacaaggcc cgtaccccgt cttgttgagc tctgcggcac agagtcagac gacagcagtt   2700
cgcctctgga tctgtccaat gcacaaaccc cggaccagcc tttggatcta tctttggctg   2760
cttggccagt gagggccacc gcgtctgacc ccggctgggt ccacggtagg cgtgagcctg   2820
tttttgtaaa gcctcggggt gctttctctg atggcgattc agtccttcag ttcggggagt   2880
tttccgaatc cggttctatc accgagatcg accggacaaa acatgctcca gtggttaatg   2940
cccccgtcga cttgacggtt tcaaatgaag ctctctctgg ggtcgatcct tttgaatttg   3000
ccgaacccaa gcgcccgcgt ttctccgctc aagccctaat tgaccgaggc ggcccactag   3060
```

-continued ccgatgtcca tgcaaaaata aagaatcggg tatacgaaca gtgcctccag gcttgtgagc 3120
ctggcagtcg tgcaacccca gccactaagg agtggcttga caaaatgtgg gacagggtgg 3180
acatgaagac ctggcgctgc acctcgcagt tccaagctgg tcgcattctt gcgtccctca 3240
aatttctccc cgacatgatt caagacacac cgcctcctgt tcccaggaag agccgagcta 3300
gtgataatgc cggcctgaag cgactggtgg cgcagcggga cagaaaattg ggtgcaaccc 3360 ccccccctaaa atcggttggg tcggcacttg accaaaccgc ccctccgcct gcggatattc 3420
agcaagaaga tgtcaccccc tccgataggc cacctcatat gccggatctt cctagtcaag 3480
tgagcacggg tgggagttgg aaaggccttg tgctttccgg cactcgtctc gcggggtcta 3540
ctagtcaaca cctcatgaca tgggtttttg aagttttctc ccatctcccg gctttcatgc 3600
tcacactttt ctcgccacgg ggctctatgg ctccaggtga ttggctgttt gcaggtgttg 3660
ttttacttgc tctcctgctc tgtcgttctt acccggtatt cgggtgcctt cccttattgg 3720
gtgtcttttc tggttctttg cggcgtgttc gtctgggtgt ttttggttct tggatggctt 3780
ttgctgtatt tttattctcg actccatccg acccagtcgg ttcttcttgt gaccacgatt 3840
cgccggagtg tcatgctgag cttttggctc ttgagcagcg ccaactttgg gaacctgtgc 3900
ggggccttgt ggtcggtccc tcgggtctct tatgcgtcat tcttggtaag ttactcggtg 3960
ggtcacgtta tctctggcat attctcttac gtttatgcat gcttgcggat ttggcccttt 4020
ctcttgttta tgtggtgtcc caggggcgtt gtcacaagtg ttggggaaag tgtataagaa 4080
cagctcctac ggaggtggca ctcaacgtgt tccctttctt gcgcgctacc cgcacctcgc 4140
ttgtgtcctt atgtgatcga ttccaagcgc cgaaaggggt tgatcctgtg cacttggcaa 4200
caggttggcg cgggtgctgg cgcggtgaga gtcccattca tcaaccgcac caaaagccca 4260
tagcttatgc caacttggat gaaaagaaaa tatctgccca aacggtggtt gctgtcccgt 4320
atgatcccag tcaggccatc aaatgcctga aagttctgca ggcgggaggg gctattgtgg 4380
accaacccac acctgaggtc gtccgtgtgt ccgaaatccc tttctcagcc ccatttttc 4440 caaaggttcc agttaaccca gattgcaggg ttgtggtaga ttcggacact tttgtggctg 4500
cagttcgctg tggttactcg acggctcaac tggtcttagg ccgtggcaac tttgccaagt 4560
taaatcagac tccccccagg aactctgtct ccaccaagac gactggtggg gcttcttaca 4620
cccttgctgt ggctcaggtg tctgtgtgga cccttgttca tttcatcctc ggtctttggt 4680
ttacatcacc tcaagtgtgt ggtcgaggaa cctctgaccc atggtgttca aatcctttt 4740 cataccctac ctatggcccc ggaatagtgt gctcctcccg actttgcgtg tctgccgacg 4800
gagtcactct gccattgttt tcagcagtag cacaactctc cggtagagag gtggggattt 4860
ttattttggt gctcgtctcc ttgactgctc tggcccaccg tatggctctt aaggcagaca 4920
tgttagtggt cttttcggct tttgtgctt acgcctggcc aatgagctcc tggttaatct 4980
gtttctttcc tgtatccctg aagtgggtca cccttcaccc tcttaccatg ctttgggtgc 5040
actcattctt ggtgttttgt ctgccagcag ccggcgtcct ctcactaggg ataaccggcc 5100
ttctctgggc agttggccgc tttacccagg tcgccgggat tattacacct tatgacatcc 5160
accagtacac ctctggacca cgtggtgcag ccgctgtggc cacggccccg gaaggcactt 5220
acatggccgc cgtccggaga gctgccttaa ccggacgaac cctcattttc acaccatctg 5280
cagttggatc ccttcttgaa ggtgctttca ggacccacaa accctgcctt aacactgtga 5340
acgttgtggg ctcttccctt ggttccgggg gggttttcac cattgatggc aggagaactg 5400
ttgttactgc tgcccatgtg ttgaacggcg acacagctag agtcaccggc gactcctaca 5460

-continued

```
accgcatgca cactttcaag accaatggtg attatgcctg gtcccatgct gatgactggc   5520
ggggcgttgc ccctgtggtc aaggtcgcga aggggtaccg cggtcgtgcc tactggcaaa   5580
catcaactgg tgtcgaaccc ggtattgttg ggaagggtt cgccttttgt tttaccaact    5640
gtggcgattc gggatcacct gtcatctcgg aatccggtga tcttgtcggg atccacaccg   5700
gttcaaacaa actcggttct ggtcttgtga caacccctga aggggagacc tgctccatca   5760
aagaaaccaa gctctctgac ctttccaggt attttgcagg cccaagcgtc cctctcgggg   5820
atattaaatt gagtccggcc attatccctg atgtaacaac cattccgagt gacttggcat   5880
cgcttctagc ctctgtccct gtaatggaag gcggcctctc gactgttcaa cttttgtgtg   5940
tctttttcct tctctggcgt atgatgggcc atgcctggac acccattgtt gccgtgggct   6000
tctttttgct gaatgaaatc cttccagcag tcttggtcag agccgtgttt tcttttgcac   6060
tctttgtgct cgcatgggcc accccttggt ctgcacaggt gttgatgatc agactcctca   6120
cagcagctct caaccgcaac aggctttctc tggcgttcta cgcactcggg ggtgtcgtcg   6180
gtttggctgc tgaaattggg acctttgctg gtagattttc cgaattatct caagctcttt   6240
cgacatactg cttcttacct agggttctcg ctgtgactag ttatgttccc accattatta   6300
ttggcggact ccatgccctt ggtgtgatct tgtggctatt caaataccgg tgcctccaca   6360
acatgttagt tggtgatggg agtttttcaa gtgctttttt cttacggtac tttgcagaag   6420
gcaatctcag aaaaggtgta tcgcaatcct gcggcatgaa taacgagtcc ctgacagctg   6480
ctttggctta taagttgtca caggccgacc ttgacttttt gtccagcttg acgaacttta   6540
agtgctttgt gtctgcttca aacatgaagg atgccgctgg acagtacatt gaggcagcgt   6600
atgccaaggc cctgcgccga gagttggcct ccctagtcca ggttgacaaa atgaaaggag   6660
ttttgtccaa gctcgaggcc tttgctgaaa cagccacccc gtcccttgac acaggtgacg   6720
tgattgtcct gcttgggcaa catcctcatg gatccatcct cgatatcaat gtggggactg   6780
aaaggaaaac tgtgtccgtt caagagactc ggagcctagg cggctccaaa ttcagtgtct   6840
gcactgtcgt gtccaacaca cccgtggacg ccttgaccgg cattccactc cagacaccaa   6900
ccccgctttt tgagaatggc ccgcgccatc gcggtgagga agatgatctt aaagttgaga   6960
ggatgaagaa acattgtgtg tctctcggct tccacaacat caatggcaaa gtttactgta   7020
aagtttggga caagtccacc ggtgacacct tttacacgga tgattctcgg tacacccaag   7080
actatgcttt tcaggacagg tcagctgact atagagacag ggactatgag ggcgtgcaaa   7140
tcgcccccca acagggattt gacccaaaat ctgaaacccc tgttggcact gttgtaattg   7200
gcggtatcac gtataataag tatttggtca aaggcaagga ggttctggtt cccaaacccg   7260
acaactgcct tgaagccgcc aggctgtccc ttgagcaagc acttgctggg atgggccaaa   7320
cctgtgacct tacagctgca gaggtggaaa agctaaagcg catcatcagt caacttcaag   7380
gtttgaccac tgaacaggct ttaaactgct agccgccagc ggcttgaccc gctgtggccg   7440
cggcggtttg gttgtaactg aaacggcggt aaaaattgta aaataccaca gcagaacttt   7500
cactttgggc cctttagacc taaaagtcac ttctgaggta gaggtgaaga agtcaactga   7560
gcagggccac gccgttgtgg caaatctatg ttctggtgtt gttttgatga gacctcaccc   7620
accgtccctt gttgacgtcc ttctgaaacc cggacttgac acaacacccg gtattcaacc   7680
cgggcatggg gccgggaata tgggcgtgga cggttccatt tgggattttg aaaccacacc   7740
cacaaaagca gaacttgagt tgtccaagca aataattcaa gcatgtgaag tcaggcgcgg   7800
```

-continued

```
ggatgccccg aacctccaac tcccctacaa gctctatcct gtcagagggg atcctgagcg   7860
gcataaaggc cgccttatca acaccaggtt tggagattta ccttacaaaa ctcctcaaga   7920
caccaagtcc gctatccatg cggcttgttg cctgcatccc aacggtgccc ctgtgtctga   7980
tggtaaatcc acactaggca ccactcttca acatggtttc gagctttacg ttcccacagt   8040
gccttatagt gtcatggaat accttgattc acgccccgac acccctccca tgttcactaa   8100
acatggcact tccaaggccg ctgcagaaga cctccaaaaa tatgacctat ccacccaagg   8160
atttgtcctg cctggggtcc tgcgcctagt acgcagattc atctttggcc atattggcaa   8220
ggcaccacca ttgttcctcc cgtcaactta ccccgccagg aactccatgg cagggattaa   8280
tggccagaga ttcccaacaa aggacgtcca gagcatacct gaaattgatg aaatgtgtgc   8340
ccgcgctgtc aaggcgaatt ggcaaaccgt gacaccttgt actctcaaga aacagtactg   8400
ttccaagccc aaaaccagga ctatcctagg taccaataac tttattgcct tggctcacag   8460
atcggcgctc agtggcgtca ctcaggcatt catgaagaaa gcttggaagt ccccaattgc   8520
cttgggggaaa aacaagttca aggaactgca ttgtaccgtc gccggcagat gtcttgaggc   8580
tgacctggcc tcctgtgatc gcagcacccc cgccattgta aggtggtttg ttgccaacct   8640
cctgtatgaa cttgcagggt gtgaagagta cttgcctagc tatgtgctta actgctgcca   8700
tgaccttgtg gcaacacagg atggtgcctt cacaaaacgc ggtggcctgt cgtccgggga   8760
ccccgttacc agtgtgtcca ataccgtgta ttcactggta atatacgccc agcacatggt   8820
attgtcagcc ttgaagatgg gtcatgaaat tggtcttaag ttcctcgagg agcagctcaa   8880
attcgaggat ctccttgaaa ttcagcctat gttagtatac tctgacgacc ttgtcttgta   8940
cgctgaaaga cccgcttttc ccaattacca ctggtgggtc gagcaccttg acctgatgct   9000
gggtttcaaa acggacccaa agaagactgt cataactgat aaacccagct tcctcggctg   9060
taggattgag gcagggcgac agctagtccc caatcgcgac cgcatcctag cagcccttgc   9120
atatcacatg aaggcgcaga acgcctcaga atattatgcg tctgccgccg caatcctaat   9180
ggattcgtgc gcttgcattg accatgatcc tgagtggtat gaggacctca tctgtggtat   9240
cgcccggtgt gctcgccaag atggctatag tttcccgggc ccggcatttt tcatgtccat   9300
gtgggagaaa ctgaaaagtc ataacgaagg aaaaaaattc cgccactgcg gcatctgcga   9360
cgccaaggcc gaccatgcgt ccgcctgtgg gctcgatttg tgcttgttcc actcgcattt   9420
tcatcaacac tgccctgtca ctctgggctg tggccatcat gccggttcta aggaatgtcc   9480
gcagtgtcag tcaccggttg gggctggtag aactcctctt gacgccgtgc taaaacaaat   9540
tccatacaaa cccccctcgca ctgtcattat gaaggtggat aataaaacaa cggccctcga   9600
tccggggagg tatcagtccc gtcgaggtct cgttgcagtc aagaggggta ttgcaggcaa   9660
tgaggttgat cttgcagatg gagactacca ggtggtgcct cttttgccga cctgcaaaga   9720
tataaacatg gtgaaggtag cttgtaatgt gctactcagc aagttcatag tagggccacc   9780
aggttccgga aagaccacct ggttgctgag tcaagtccag gacgatgatg tcatctacac   9840
acccacccat cagactatgt ttgatatagt cagtgctctc aaagtttgca ggtattccat   9900
tccgggggcc tcaggactcc ctttcccacc acctgccaga tccgggccgt gggtcaggct   9960
tgttgccagy gggcacgccc ctggccgagt gtcatacctt gatgaggctg gatattgtaa  10020
tcatctggac attcttagac tgctttccaa aacacccctt gtgtgtttag gcgaccttca  10080
gcaactccac cctgtcggct ttgattccta ctgttatgtg tttgaccaaa tgcctcagaa  10140
gcagctgact actatttaca ggtttggccc caacatctgc gcagccattc agccttgtta  10200
```

caaggagaaa cttgaatcca aggctaggaa caccaggata gttttcacca tccgacctgt 10260
ggcattcggg caggtgctga caccatacca caaagatcgc accggctcag cgataaccat 10320
agattcgtct cagggggcca ccttcgacat tgtgacattg catctaccat cgccaaagtc 10380
cctaaataaa tcccgagcac tagtagccat cactcgggca agacacgggt tgttcatcta 10440
tgatcctcat aatcagcttc aggagttttt caacctgact cctgaacgca ctgattgtaa 10500
ccttgtgttt aaccgtgggg atgagctgat agttctggac gcagctaatg cagtcacaac 10560
tgttgcgaag gccctagaaa cggtccatc tcggtttcga gtatcagacc caaggtgcaa 10620
gtctcttttg gccgcttgtt cggtcagcct ggagggaagc tgcatgccac taccacaagt 10680
ggcacataac ctagggtttt acttttcccc agatagttca gcattcgcgc ccttgccaaa 10740
agaattggcg ccacactggc cggtggtcac tcatcaggac aaccgggcgt ggcctgaccg 10800
acttgtcgct agtatgcgcc caattgatgc ccgttacagc aagccaatgg ttggtgcagg 10860
gtatgtggtc ggtccgtcca cttttcttgg cactcctggt gtggtatcat attacttgac 10920
actgtacatc aggggtgagc cccaggcctt accagaaaca cttgtgtcaa cagggcgcat 10980
agccacagat tgtcgggagt atctcgacgc cgctgaggaa gaggcggcaa aagaactccc 11040
ccacgcattc attggcgatg tcaaaggcac cacggttggg gggtgtcatc acatcacatc 11100
aaaataccta cctaggtccc tgcctaagga ctctgttgcc gtagttggag taagttcgcc 11160
cggccgggcc gccaaagccg tgtgcactct caccgatgtt taccttcccg agctccggcc 11220
gtatctgcat cctgagacgg catcaaaatg ctggaaactc aaattagact tcagagatgt 11280
tcgactaatg gtctggaaag gagccaccgc ctacttccag ctggaagggc ttacatggtc 11340
ggcgctgcct gactacgcca ggtttattca gctgcctaag gatgccgtcg tgtacattga 11400
tccgtgcata ggaccggcaa cagccaaccg taaggtcgtg cggaccacgg actggcgggc 11460
tgacctggca gtaacaccgt atgattacgg tgcccagaac attttgacaa cagcctggtt 11520
cgaggacctc gggccgcagt ggaagattct ggggttgcag ccctttagac gatcatttgg 11580
ccttgaaaac actgaggatt gggcaatcct tgcacgccgt atgaatgacg gcaaggacta 11640
cactgactac aactggaact gtgttcgagt acgcccacac gccatttacg ggcgtgctcg 11700
tgaccatacg tatcattttg ccctcggcac ggaattgcag gtagagctgg gtaaaccccg 11760
gctgacgcct gagcaagtgc cgtgaatccg gagtgatgca atggggtcac tgtggagtaa 11820
aattagccag ctgttcgtgg acgccttcac tgagttcctt gtcagtgtgg ttgatattgt 11880
cattttcctt gccatactgt ttgggttcac cgtcgcagga tggttactgg tctttcttct 11940
cagggtggtt tgctccgcgc ttctccgttc gcgctctgcc attcaccctc ccgaactatc 12000
gaaggtccta tgaaagctta ctacccaatt gcagaccgga cgtcccacaa tttgcattta 12060
agcacccatt gggcatgtta tggcacatgc gagtctccca cctaatcgat gaaatggtct 12120
ctcgtcgcat ttaccggact atggaacact cgggtcaagc ggcctggaag caggtggtta 12180
gtgaagccac cctcacaaag ttgtcagggc ttgatatagt tactcatttc caacacctgg 12240
ccgcagtgga ggcagattct tgccgtttcc tcagctcacg acttgcgatg ctaaagaatc 12300
ttgccgttgg caatgtgagc ctgcagtata ataccacgtt ggatcatgtt gagctcatct 12360
ttcctacgcc aggtacgagg cccaagttga ccgatttcag acaatggctc atcagtgtgc 12420
acgcctccat cttttcctct gtggcttcat ctgttacctt gttcatagtg ttttggcttc 12480
gaattccagc cgtacgctat gtttttggtt tccattggcc cacggcaata catcattcga 12540

-continued

```
gctaaccatc aattacacca tatgtatgcc ctgctctacc agccaagcgg ctagtcaaag  12600
actcgagccc ggtcgtaaca tgtggtgcag aatagggcat gacaggtgtg aggaacgcga  12660
ccatgatgag ttgtcaatgt ccatcccgtc agggtacgag aacctcaaac ttgagggtta  12720
ttatgcttgg ctggcttttt tgtccttttc ctatgcggca caatttcacc cggagttgtt  12780
cggaatagga aatgtgtcgc gcgtcttcgt ggacaagcga caccagttca tttgtgccga  12840
gcatgatgga caaaattcaa ccgtatctgc cggacacgac atctccgcat tatacgcggt  12900
gtattaccat caccaaatag acgggggcaa ttggttccat ttggaatggc tgcggccatt  12960
cttttcctcc tggctggtgc tcaacatctc atggtttctg aggcgttcgc ctgtaagccc  13020
tgtttctcga cgcatttatc agatattaag accaacacga ccgcggctgc cggtttcatg  13080
gtccttcagg acatcaattg tctccaaccc cacggggtct cgacagcgca agagggacct  13140
cccttcagaa agtcgtccca atgtcgcgag gccatcggta ctccccagta cattacgata  13200
acggctaatg tgaccgatga atcgtatttg tacaacgcgg acctgctgat gctctctgcg  13260
tgcctttttt acgcctcgga aatgagtgaa aagggcttca aagtcatctt tgggaacgtt  13320
tctggcgttg tttctgcttg tgtcaatttt acggattatg tggctcatgt aacccaacat  13380
actcagcagc atcatctggt gattgatcat gttcggttgc tgcatttcct gacaccatca  13440
acaatgaggt gggctacaac cattgcttgt ttgttcgcca ttctcttggc gatatgaaat  13500
gttctcacag attggagcgt ttcttgactc ctcacttttg cttctggtgg tttttttgc  13560
tttgtaccgg cttgtcttgg tcctttgtcg atggcaacga caacagctcg acataccaat  13620
acatatataa tttgacgata tgtgagctga atgggaccgc atggttgtcc agccattttg  13680
actgggcagt cgagaccttt gtgctttacc cggttgccac tcatatcctt tcactgggtt  13740
ttctcacaac aagccatttt tttgatgcgc tcggtctcgg cgctgtgtcc actacaggat  13800
ttgttggcgg gcggtatgta ctcagcagcg tgtatggcgc ttgtgctttc gcagcgctcg  13860
tatgttttgt catccgcgct gcaaaaaatt gcatggcttg ccgttatgcc cgtacccggt  13920
ttaccaactt cattgtggac gaccggggga ggatccatcg atggaagtca ccaatagtgg  13980
tagagaagtt gggcaaagcc gaagtcggtg gcaacctcgt caccatcaaa catgtcgtcc  14040
tcgaaggggt taaagctcaa cccttgacga ggacttcggc tgagcaatgg gaagcctaga  14100
cggtttttgc aatgattcta ccgccgcaca aaagcttgtg ttagctttca gcatcacata  14160
cacacctata atgatatacg ccctcaaggt gtcacgcggt cgcctcctag ggctattgca  14220
catcctgata ttcctgaact gttcctttac gttcggatac atgacgtatg tgcattttca  14280
atccaccaac cgtgtcgcac ttactctggg ggccgttgtc gcccttctat ggggtgttta  14340
cagcttcaca gagtcatgga agtttattac ttccagatgc agattgtgtt gcctaggccg  14400
gcgatacatt ctggcccctg cccatcacgt agaaagtgct gcaggtctcc attcaatccc  14460
agcgtctggt aaccgagcat acgctgtgag aaagcccgga ctaacatcag tgaacggcac  14520
tctagtacca ggacttcgga gcctcgtgct gggcggcaaa cgagctgtta aacgaggagt  14580
ggttaacctc gtcaagtatg gccggtaaaa atcagagcca gaagaaaaag aagaatacag  14640
ctccgatggg gaatggccag ccagtcaatc aactgtgcca gctgctgggt gcaatgataa  14700
agtcccagcg ccagcaatct aggagaggac aggcaaaaaa aggaaagcct gagaagccac  14760
attttcccct agctgctgaa gatgacattc ggcaccacct cacccaaact gaacgttccc  14820
tctgcttgca atcgatccag acggctttta atcaaggcgc aggaactgcg tcgctttcat  14880
ccagcgggaa ggtcggtttt caggttgagt tcatgctgcc ggttgctcat acagtgcgcc  14940
```

-continued

```
tgattcgcgt gacttccaca tccgccagtc agggtgcaaa ttaatttgat agtcaggtga  15000
atggccacga ttgacgtgtg gcctttaagt cacctattca attagggcga tcacatgggg  15060
gtcagactta atcaggcagg aaccatgtga ccgaaattaa aaaaaaaaaa aaaaaaaaaa  15120
aaaggccggc atggtcccag cctcctcgct ggcgccggct gggcaacatt ccgaggggac  15180
cgtcccctcg gtaatggcga atgggactct agagcccttc cggctggctg gtttattgct  15240
gataaatctg gagccggtga gcgtgggtct cgcggtatca ttgcagcact ggggccagat  15300
ggtaagccct cccgtatcgt agttatctac acgacgggga gtcaggcaac tatggatgaa  15360
cgaaatagac agatcgctga gataggtgcc tcactgatta agcattggta actgtcagac  15420
caagtttact catatatact ttagattgat ttaaaacttc atttttaatt taaaaggatc  15480
taggtgaaga tcctttttga taatctcatg accaaaatcc cttaacgtga gttttcgttc  15540
cactgagcgt cagacccctt aataagatga tcttcttgag atcgttttgg tctgcgcgta  15600
atctcttgct ctgaaaacga aaaaaccgcc ttgcagggcg gtttttcgaa ggttctctga  15660
gctaccaact ctttgaaccg aggtaactgg cttggaggag cgcagtcacc aaaacttgtc  15720
ctttcagttt agccttaacc ggcgcatgac ttcaagacta actcctctaa atcaattacc  15780
agtggctgct gccagtggtg cttttgcatg tctttccggg ttggactcaa gacgatagtt  15840
accggataag gcgcagcggt cggactgaac ggggggttcg tgcatacagt ccagcttgga  15900
gcgaactgcc tacccggaac tgagtgtcag gcgtggaatg agacaaacgc ggccataaca  15960
gcggaatgac accggtaaac cgaaaggcag gaacaggaga gcgcacgagg gagccgccag  16020
ggggaaacgc ctggtatctt tatagtcctg tcgggtttcg ccaccactga tttgagcgtc  16080
agatttcgtg atgcttgtca ggggggcgga gcctatggaa aaacggcttt gccgcggccc  16140
tctcacttcc ctgttaagta tcttcctggc atcttccagg aaatctccgc cccgttcgta  16200
agccatttcc gctcgccgca gtcgaacgac cgagcgtagc gagtcagtga gcgaggaagc  16260
ggaatatatc ctgtatcaca tattctgctg acgcaccggt gcagcctttt ttctcctgcc  16320
acatgaagca cttcactgac accctcatca gtgccaacat agtaagccag tatacactcc  16380
gctagcgctg aggtctgcct cgtgaagaag gtgttgctga ctcataccag gcctgaatcg  16440
ccccatcatc cagccagaaa gtgagggagc cacggttgat gagagctttg ttgtaggtgg  16500
accagttggt gattttgaac ttttgctttg ccacggaacg gtctgcgttg tcgggaagat  16560
gcgtgatctg atccttcaac tcagcaaaag ttcgatttat tcaacaaagc cacgttgtgt  16620
ctcaaaatct ctgatgttac attgcacaag ataaaaatat atcatcatga acaataaaac  16680
tgtctgctta cataaacagt aatacaaggg gtgttatgag ccatattcaa cgggaaacgt  16740
cttgctcgag gccgcgatta aattccaaca tggatgctga tttatatggg tataaatggg  16800
ctcgcgataa tgtcgggcaa tcaggtgcga caatctatcg attgtatggg aagcccgatg  16860
cgccagagtt gtttctgaaa catggcaaag gtagcgttgc caatgatgtt acagatgaga  16920
tggtcagact aaactggctg acggaattta tgcctcttcc gaccatcaag cattttatcc  16980
gtactcctga tgatgcatgg ttactcacca ctgcgatccc cgggaaaaca gcattccagg  17040
tattagaaga atatcctgat tcaggtgaaa atattgttga tgcgctggca gtgttcctgc  17100
gccggttgca ttcgattcct gtttgtaatt gtccttttaa cagcgatcgc gtatttcgtc  17160
tcgctcaggc gcaatcacga atgaataacg gtttggttga tgcgagtgat tttgatgacg  17220
agcgtaatgg ctggcctgtt gaacaagtct ggaaagaaat gcataagctt ttgccattct  17280
```

-continued

```
caccggattc agtcgtcact catggtgatt tctcacttga taaccttatt tttgacgagg  17340
ggaaattaat aggttgtatt gatgttggac gagtcggaat cgcagaccga taccaggatc  17400
ttgccatcct atggaactgc ctcggtgagt tttctccttc attacagaaa cggctttttc  17460
aaaaatatgg tattgataat cctgatatga ataaattgca gtttcatttg atgctcgatg  17520
agtttttcta atcagaattg gttaattggt tgtaacactg gcagagcatt acgctgactt  17580
gacgggacgg cggctttgtt gaataaatcg aacttttgct gagttgaagg atcagatcac  17640
gcatcttccc gacaacgcag accgttccgt ggcaaagcaa aagttcaaaa tcaccaactg  17700
gtccacctac aacaaagctc tcatcaaccg tggctccctc actttctggc tggatgatgg  17760
ggcgattcag gcctggtatg agtcagcaac accttcttca cgaggcagac ctcagcgctc  17820
aaagatgcag ggtaaaagc taaccgcatc tttaccgaca aggcatccgg cagttcaaca  17880
gatcgggaag ggctggattt gctgaggatg aaggtggagg aaggtgatgt cattctggtg  17940
aagaagctcg accgtcttgg ccgcgacacc gccgacatga tccaactgat aaaagagttt  18000
gatgctcagg gtgtagcggt tcggtttatt gacgacggga tcagtaccga cggtgatatg  18060
gggcaaatgg tggtcaccat cctgtcggct gtggcacagg ctgaacgccg gagtcggctg  18120
tggcacaggc tgaacgccgg aggatccggc gcgccatgca ttagttatta atagtaatca  18180
attacggggt cattagttca tagcccatat atggagttcc gcgttacata acttacggta  18240
aatggcccgc ctggctgacc gcccaacgac ccccgcccat tgacgtcaat aatgacgtat  18300
gttcccatag taacgccaat agggactttc cattgacgtc aatgggtgga gtatttacgg  18360
taaactgccc acttggcagt acatcaagtg tatcatatgc caagtacgcc ccctattgac  18420
gtcaatgacg gtaaatggcc cgcctggcat tatgcccagt acatgacctt atgggacttt  18480
cctacttggc agtacatcta cgtattagtc atcgctatta ccatggtgat gcggttttgg  18540
cagtacatca atgggcgtgg atagcggttt gactcacggg gatttccaag tctccacccc  18600
attgacgtca atgggagttt gttttggcac caaaatcaac gggactttcc aaaatgtcgt  18660
aacaactccg ccccattgac gcaaatgggc ggtaggcgtg tacggtggga ggtctatata  18720
agcagagctg gtttagtatt taaat                                        18745
```

<210> SEQ ID NO 163
<211> LENGTH: 15146
<212> TYPE: DNA
<213> ORGANISM: Artificial Sequence
<220> FEATURE:
<223> OTHER INFORMATION: Consensus sequence of attenuated virus
      V1042-P62

<400> SEQUENCE: 163

```
atgatgtgtg gggtattccc cctacataca caacactccc agtgtttgtg tgccttggag     60
gcgcgggtat agccccgccc cacccccttgg cccctgttct agcccaacag gtatccttct    120
ctctcggggc gagcgcgcca cctgctgctc ccttgcagcg ggaaggacct cccgagtatt    180
tccggagagc acctgcttta cgggatctcc accctttaac catgtctggg acgttctccc    240
ggtgcatgtg caccccggct gcccgggtat tttggaacgc cggccaagtc ttttgcacac    300
ggtgtctcag cgcacggtct cttctccctc cggagcttca ggaaactgac cttgctgcaa    360
ttggcttgtt ttacaagcct aaagacaagc ttcactggaa ggtccctatc ggcatccctc    420
aggtggagtg cactccatcc gggtgctgtt ggctctcagc catcttccct ttggcgcgca    480
tgacctccgg caatcacaac ttcctccaac gacttgtgag ggttgccgat gtgttgtacc    540
```

-continued

```
gtgacggttg cctggctcct cgacaccttc gtgaactcca agtttacgaa cgcggctgca    600
actggtaccc aatcacgggg cccgtgcctg ggatgggttt gttcgcaaac tccatgcacg    660
tatccgacca gccgttccct ggtgccaccc atgtgttgac gaactcgccg ttgcctcaac    720
aagcctgtcg gcagctgttt tgtccatttg aggaagctca ttctagcatg tacaggtgga    780
aaagatttgt ggttttcgcg gattcctctc ctaacggtcg acctcgtatg atgtggatgc    840
cggagtccga tggttcagcc gtcttggagg tattaccgcc tgaattagaa catcaggtcg    900
aaatcctcat tcggaatttt cctgctcatc accctgtcaa cctggccgac tgggagctca    960
ctgagtcccc tgagaacggt tttttccttca acacgtccta ttcttgcggt cacctcgtcc   1020
agaaccccga cgtgtttgat ggtaagtgct ggctttcctg ctttttgggc cagccggccg   1080
aggtgcgacg ccatgaggaa catttagctg acgcattcgg ttaccagacc aagtggggcg   1140
tgcctggcaa gtacctccag cgcaggcttc aggttcgcgg cattcgtgct gtaattgatc   1200
ctgacggccc cattcatgtc gaagcgctgt cttgccccgg gtcttggatc aggcacctga   1260
cctttgatga taatgtcacc ccgggatttg ttcgccttac gtcccttcgc attgtgccaa   1320
acaccgagtc tactggtctc cgaatcttcc ggtttggagc gcataagtgg tatggcgctg   1380
caggcagacg tgctcgtgct aagcgtgccg ctagaagtga gggaatttcg gcccctatcc   1440
ccgaggttgt tcagccggtc tccacctgcg aaattaccac ctattctccg ccgacagacg   1500
ggtcttgtgg ttggcatgtt cttgccgcca taataaaccg gatgatgaat ggtgacttca   1560
cgtctcctct gactcagtac aacaggccag aggatgactg ggcttctgat tatgaccttg   1620
ctcaggcaat ccaatgtttg caactgcccg ctaccgtagt tcggaatcgt gcctgcccta   1680
acgccaagta cctcataaaa cttaatggag ttcattggga ggtagaggtg aggtctggaa   1740
tggccccccg ctccctttcc cgcgagtgtg tggttggcgt ttgttctgaa gactgtatcg   1800
caccgcctta cccacaagac gggctgcctg aacgtgcact tgaggccttg gcgtctgctt   1860
acagactacc ctccgattgt gtttgttctg gtattactga ttttcttgcc aacccgcccc   1920
ctaaggagtt ttggaccctt gacaaaatgt tgacctcccc gtcaccggaa cggtccggyt   1980
tctctagctt gtataaatta ctattggagr ttgtcccgca gaaatgcggt gccacggagg   2040
gggccttcgt ctatgctgtt gagaggatgt tgaaggattg tccgagctcc aaacaagcca   2100
tggccctcct ggcaaaaatc aaagttccat cctccaaggc cccgtctgtg tctctggatg   2160
agtgtttccc cacggatgtt ccggcggact ccgagtcagc gtttcaggaa aggccccgag   2220
cttctggtgc tgctgttgtc ctgtgttcgc caggcatgaa agagttcgag gaagcagtcc   2280
cagaagaagt tcaagagggt ggccgtaagg ccgtccactc tgcactcctc gccgagggtc   2340
ttaacaatga gcgggcgcag gtggttgcca gtgcgcaacc aaagcccgga agttgcggtt   2400
tggcatctgg gaatactcat ggaggtgttc cggttctagc tagcccaatc aacctagcag   2460
acgggaattt gccctcctcg gaatccatga aaggaaacat gcccaatggt cgggaggacg   2520
aaccactgga tttgtcccaa tcagcaccgg caatcacaac gacccttatg agagagcaag   2580
caccggacag tctgagtttt ggcgccggtg ctccccctgt cacgattcga gaatttgccc   2640
cgacaaggcc cgtaccccgt cttgttgagc tctgcggcac agagtcagac gacagcagtt   2700
cgcctctgga tctgtccaat gcacaaaccc cggaccagcc tttggatcta tctttggctg   2760
cttggccagt gagggccacc gcgtctgacc ccggctgggt ccacggtagg cgtgagcctg   2820
tttttgtaaa gcctcggggt gctttctctg atggcgattc agtccttcag ttcggggagt   2880
tttccgaatc cggttctatc accgagatcg accggacaaa acatgctcca gtggttaatg   2940
```

cccccgtcga cttgacggtt tcaaatgaag ctctctctgg ggtcgatcct tttgaatttg 3000
ccgaacccaa gcgcccgcgt ttctccgctc aagccctaat tgaccgaggc ggcccactag 3060
ccgatgtcca tgcaaaaata aagaatcggg tatacgaaca gtgcctccag gcttgtgagc 3120
ctggcagtcg tgcaacccca gccactaagg agtggcttga caaaatgtgg gacagggtgg 3180
acatgaagac ctggcgctgc acctcgcagt tccaagctgg tcgcattctt gcgtccctca 3240
aatttctccc cgacatgatt caagacacac cgcctcctgt tcccaggaag agccgagcta 3300
gtgataatgc cggcctgaag cgactggtgg cgcagcggga cagaaaattg ggtgcaaccc 3360
ccccccctaaa atcggttggg tcggcacttg accaaaccgc ccctccgcct gcggatattc 3420
agcaagaaga tgtcaccccc tccgataggc cacctcatat gccggatctt cctagtcaag 3480
tgagcacggg tgggagttgg aaaggccttg tgctttccgg cactcgtctc gcggggtcta 3540
ctagtcaaca cctcatgaca tgggtttttg aagttttctc ccatctcccg gctttcatgc 3600
tcacactttt ctcgccacgg ggctctatgg ctccaggtga ttggctgttt gcaggtgttg 3660
ttttacttgc tctcctgctc tgtcgttctt acccggtatt cgggtgcctt cccttattgg 3720
gtgtcttttc tggttctttg cggcgtgttc gtctgggtgt tttggttct tggatggctt 3780
ttgctgtatt tttattctcg actccatccg acccagtcgg ttcttcttgt gaccacgatt 3840
cgccggagtg tcatgctgag cttttggctc ttgagcagcg ccaactttgg gaacctgtgc 3900
ggggccttgt ggtcggtccc tcgggtctct tatgcgtcat tcttggtaag ttactcggtg 3960
ggtcacgtta tctctggcat attctcttac gtttatgcat gcttgcggat ttggcccttt 4020
ctcttgttta tgtggtgtcc caggggcgtt gtcacaagtg ttggggaaag tgtataagaa 4080
cagctcctac ggaggtggca ctcaacgtgt tccctttctt gcgcgctacc cgcacctcgc 4140
ttgtgtcctt atgtgatcga ttccaagcgc cgaaaggggt tgatcctgtg cacttggcaa 4200
caggttggcg cgggtgctgg cgcggtgaga gtcccattca tcaaccgcac caaaagccca 4260
tagcttatgc caacttggat gaaaagaaaa tatctgccca aacggtggtt gctgtcccgt 4320
atgatcccag tcaggccatc aaatgcctga aagttctgca ggcgggaggg gctattgtgg 4380
accaacccac acctgaggtc gtccgtgtgt ccgaaatccc tttctcagcc ccatttttc 4440
caaaggttcc agttaaccca gattgcaggg ttgtggtaga ttcggacact tttgtggctg 4500
cagttcgctg tggttactcg acggctcaac tggtcttagg ccgtggcaac tttgccaagt 4560
taaatcagac tccccccagg aactctgtct ccaccaagac gactggtggg gcttcttaca 4620
cccttgctgt ggctcaggtg tctgtgtgga cccttgttca tttcatcctc ggtctttggt 4680
ttacatcacc tcaagtgtgt ggtcgaggaa cctctgaccc atggtgttca aatcctttt 4740
cataccctac ctatggcccc ggaatagtgt gctcctcccg actttgcgtg tctgccgacg 4800
gagtcactct gccattgttt tcagcagtag cacaactctc cggtagagag gtggggattt 4860
ttattttggt gctcgtctcc ttgactgctc tggcccaccg tatggctctt aaggcagaca 4920
tgttagtggt cttttcggct tttgtgctt acgcctggcc aatgagctcc tggttaatmt 4980
gtttctttcc tgtatccctg aagtgggtca cccttcaccc tcttaccatg ctttgggtgc 5040
actcattctt ggtgttttgt ctgccagcag ccggcgtcct ctcactaggg ataaccggcc 5100
ttctctgggc agttggccgc tttacccagg tcgccgggat tattacacct tatgacatcc 5160
accagtacac ctctggacca cgtggtgcag ccgctgtggc cacggccccg gaaggcactt 5220
acatggccgc cgtccggaga gctgccttaa ccggacgaac cctcattttc acaccatctg 5280

-continued

```
cagttggatc ccttcttgaa ggtgctttca ggacccacaa accctgcctt aacactgtga   5340
acgttgtggg ctcttccctt ggttccgggg gggttttcac cattgatggc aggagaactg   5400
ttgttactgc tgcccatgtg ttgaacggcg acacagctag agtcaccggc gactcctaca   5460
accgcatgca cactttcaag accaatggtg attatgcctg gtcccatgct gatgactggc   5520
ggggcgtygc ccctgtggtc aaggtcgcga aggggtaccg cggtcgtgcc tactggcaaa   5580
catcaactgg tgtcgaaccc ggtattgttg ggaagggtt cgccttttgt tttaccaact   5640
gtggcgattc gggatcacct gtcatctcgg aatccggtga tcttgtcggg atccacaccg   5700
gttcaaacaa actcggttct ggtcttgtga caacccctga aggggagacc tgctccatca   5760
aagaaaccaa gctctctgac ctttccaggt attttgcagg cccaagcgtc cctctcgggg   5820
atattaaatt gagtccggcc attatccctg atgtaacaac cattccgagt gacttggcat   5880
cgcttctagc ctctgtccct gtaatggaag gcggyctctc gactgttcaa cttttgtgtg   5940
tctttttcct tctctggcgt atgatgggcc atgcctggac acccattgtt gccgtgggct   6000
tctttttgct gaatgaaatc cttccagcag tcttggtcag agccgtgttt tcttttgcac   6060
tctttgtgct cgcatgggcc accccttggt ctgcacaggt gttgatgatc agactcctca   6120
cagcagctct caaccgcaac aggctttctc tggcgttcta cgcactcggg ggtgtcgtcg   6180
gtttggctgc tgaaattggg acctttgctg gtagattttc cgaattatct caagctcttt   6240
cgacatactg cttcttacct agggttctcg ctgtgactag ttatgttccc accattatta   6300
ttggcggact ccatgccctt ggtgtgatct tgtggctatt caaataccgg tgcctccaca   6360
acatgttagt tggtgatggg agtttttcaa gtgctttttt cttacggtac tttgcagaag   6420
gcaatctcag aaaaggtgta tcgcaatcct gcggcatgaa taacgagtcc ctgacagctg   6480
ctttggcttr taagttgtca caggccgacc ttgacttttt gtccagcttg acgaacttta   6540
agtgctttgt gtctgcttca aacatgaagg atgccgctgg acagtacatt gaggcagcgt   6600
atgccaaggc cctgcgccga gagttggcct ccctagtcca ggttgacaaa atgaaaggag   6660
ttttgtccaa gctcgaggcc tttgctgaaa cagccacccc gtcccttgac acaggtgacg   6720
tgattgtcct gcttgggcaa catcctcatg gatccatcct cgatatcaat gtggggactg   6780
aaaggaaaac tgtgtccgtt caagagactc ggagcctagg cggctccaaa ttcagtgtct   6840
gcactgtcgt gtccaacaca cccgtggacg ccttgaccgg cattccactc cagacaccaa   6900
ccccgctttt tgagaatggc ccgcgccatc gcggtgagga agatgatctt aaagttgaga   6960
ggatgaagaa acattgtgtg tctctcggct tccacaayat caatggcaaa gtttactgta   7020
aagtttggga caagtccacc ggtgacacct tttacacgga tgattcycgg tacacccaag   7080
actatgcttt tcaggacagg tcagctgact atagagacag ggactatgag ggcgtgcaaa   7140
tcgcccccca acagggattt gacccaaaat ctgaaacccc tgttggcact gttgtaattg   7200
gcggtatcac gtataataag tatttggtca aaggcaagga ggttctggtt cccaaacccg   7260
acaactgcct tgaagccgcc aggctgtccc ttgagcaagc acttgctggg atgggccaaa   7320
cctgtgacct tacagctgca gaggtggaaa agctaaagcg catcatcagt caacttcaag   7380
gtttgaccac tgaacaggct ttaaactgct agccgccagc ggcttgaccc gctgtggccg   7440
cggcggwttg gttgtaactg aaacggcggt aaaaattrta aaataccaca gcagaacttt   7500
cactttgggc cctttagacc taaaagtcac ttctgaggta gaggtgaaga agtcaactga   7560
gcagggccac gccgttgtgg caaatctatg ttctggtgtt gtkttgatga gacctcaccc   7620
accgtccctt gttgacgtcc ttctgaaacc cggacttgac acaacacccg gtattcaacc   7680
```

cgggcatggg gccgggaata tgggcgtgga cggttccatt tgggattttg aaaccacacc 7740
cacaaaagca gaacttgagt tgtccaagca aataattcaa gcatgtgaag tcaggcgcgg 7800
ggatgccccg aacctccaac tcccctacaa gctctatcct gtcagagggg atcctgagcg 7860
gcataaaggc cgccttatca acaccaggtt tggagattta ccttacaaaa ctcctcaaga 7920
caccaagtcc gctatccatg cggcttgttg cctgcatccc aacggtgccc ctgtgtctga 7980
tggtaaatcc acactaggca ccactcttca acatggtttc gagctttacg tycccacagt 8040
gccttatagt gtcatggaat accttgattc acgcccygac acccctccca tgttcactaa 8100
acatggcact tccaaggccg ctgcagaaga cctccaaaaa tatgacctat ccacccaagg 8160
rtttgtcctg cctggggtcc tgcgcctagt gcgcagattc atctttggcc atrttggcaa 8220
ggcaccrcca ttgttcctyc crtcaacyta ccccgcyaag aactccatgg cagggattaa 8280
tggccagaga ttcccaacaa aggacgtcca gagcatacct gaaattgatg aaatgtgtgc 8340
cskcgcygtc aargmgaatt ggcaaaccgt gacaccttgt actctcaaga aacagtactg 8400
ttccaagccc aaaaccagga ctatcctagg taccaataac tttattgcct tggctcacag 8460
atcggcgctc agtggcgtca ctcaggcatt catgaagaaa gcttggaagt ccccaattgc 8520
cttggggaaa aacaagttca aggaactgca ttgtaccgtc gccggcagat gtcttgaggc 8580
tgacctggcc tcctgtgatc gcagcacccc cgccattgta aggtggtttg ttgccaacct 8640
cctgtatgaa cttgcagggt gtgaagagta cttgcctagc tatgtgctta actgctgcca 8700
tgaccttgtg gcaacacagg atggtgcctt cacaaaacgc ggtggcctgt cgtccgggga 8760
ccccgttacc agtgtgtcca ataccgtgta ttcactggta atatatgccc agcacatggt 8820
attgtcagcc ttgaagatgg gtcatgaaat tggtcttaag ttcctcgagg agcagctcaa 8880
attcgaggat ctccttgaaa ttcagcctat gttagtatac tctgacgacc ttgtcttgta 8940
cgctgaaaga cccgcttttc ccaattacca ctggtgggtc gagcaccttg acctgatgct 9000
gggtttcaaa acggacccaa agaagactgt cataactgat aaacccagct tcctcggctg 9060
taggattgag gcagggcgac agctagtccc caatcgcgac cgcatcctag cagcccttgc 9120
atatcacatg aaggcgcaga acgcctcaga atattatgcg tctgccgccg caatcctaat 9180
ggattcgtgc gcttgcattg accatgatcc tgagtggtat gaggacctca tctgtggtat 9240
cgcccggtgt gctcgccaag atggctatag tttcccgggc ccggcatttt tcatgtccat 9300
gtgggagaaa ctgaaaagtc ataacgaagg aaaaaaattc cgccactgcg gcatctgcga 9360
cgccaaggcc gaccatgcgt ccgcctgtgg gctcgatttg tgcttgttcc actcgcattt 9420
tcatcaacac tgccctgtca ctctgggctg tggccatcat gccggttcta aggaatgtcc 9480
gcagtgtcag tcaccggttg ggggctggtag aactcctctt gacgccgtgc taaaacaaat 9540
tccatacaaa ccccctcgca ctgtcattat gaaggtggat aataaaacaa cggccctcga 9600
tccggggagg tatcagtccc gtcgaggtct cgttgcagtc aagaggggta ttgcaggcaa 9660
tgaggttgat cttgcagatg gagactacca ggtggtgcct cttttgccga cctgcaaaga 9720
tataaacatg gtgaaggtag cttgtaatgt gctactcagc aagttcatag tagggccacc 9780
aggttccgga aagaccacct ggttgctgag tcaagtccag gacgatgatg tcatctacac 9840
acccacccat cagactatgt ttgatatagt cagtgctctc aaagtttgca ggtattccat 9900
tccgggggcc tcaggactcc ctttcccacc acctgccaga tccgggccgt gggtcaggct 9960
tgttgccagc gggcacgccc ctggccgagt gtcatacctt gatgaggctg gatattgtaa 10020

-continued

```
tcatctggac attcttagac tgctttccaa aacacccctt gtgtgtttag gcgaccttca  10080
gcaactccac cctgtcggct ttgattccta ctgttatgtg tttgaccaaa tgcctcagaa  10140
gcagctgact actatttaca ggtttggccc caacatctgc gcagccattc agccttgtta  10200
caaggagaaa cttgaatcca aggctaggaa caccaggata gttttcacca tccgacctgt  10260
ggcattcggg caggtgctga caccatacca caaagatcgc accggctcag cgataaccat  10320
agattcgtct caggggggcca ccttcgacat tgtgacattg catctaccat cgccaaagtc  10380
cctaaataaa tcccgagcac tagtagccat cactcgggca agacacgggt tgttcatcta  10440
tgatcctcat aatcagcttc aggagttttt caacctgact cctgaacgca ctgattgtaa  10500
ccttgtgttt aaccgtgggg atgagctgat agttctggac gcagctaatg cagtcacaac  10560
tgttgcgaag gccctagaaa cgggtccatc tcggtttcga gtatcagacc caaggtgcaa  10620
gtctcttttg gccgcttgtt cggtcagcct ggagggaagc tgcatgccac taccacaagt  10680
ggcacataac ctagggtttt acttttcccc agatagttca gcattcgcgc ccttgccaaa  10740
agaattggcg ccacactggc cggtggtcac tcatcaggac aaccgggcgt ggcctgaccg  10800
acttgtcgct agtatgcgcc caattgatgc ccgttacagc aagccaatgg ttggtgcagg  10860
gtatgtggtc ggtccgtcca cttttcttgg cactcctggt gtggtatcat attacttgac  10920
actgtacatc aggggtgagc cccaggcctt accagaaaca cttgtgtcaa cagggcgcat  10980
agccacagat tgtcgggagt atctcgacgc cgctgaggaa gaggcggcaa aagaactccc  11040
ccacgcattc attggcgatg tcaaaggcac cacggttggg gggtgtcatc acatcacatc  11100
aaaataccta cctaggtccc tgcctaagga ctctgttgcc gtagttggag taagttcgcc  11160
cggccgggcc gccaaagccg tgtgcactct caccgatgtt taccttcccg agctccggcc  11220
gtatctgcat cctgagacgg catcaaaatg ctggaaactc aaattagact tcagagatgt  11280
tcgactaatg gtctggaaag gagccaccgc ctacttccag ctggaagggc ttacatggtc  11340
ggcgctgcct gactacgcca ggtttattca gctgcctaag gatgccgtcg tgtacattga  11400
tccgtgcata ggaccggcaa cagccaaccg taaggtcgtg cggaccacgg actggcgggc  11460
tgacctggca gtaacaccgt atgattacgg tgcccagaac attttgacaa cagcctggtt  11520
cgaggacctc gggccgcagt ggaagattct ggggttgcag ccctttagac gatcatttgg  11580
ccttgaaaac actgaggatt gggcaatcct tgcacgccgt atgaatgacg gcaaggacta  11640
cactgactac aactggaact gtgttcgagt acgcccacac gccatttacg ggcgtgctcg  11700
tgaccatacg tatcattttg ccctcggcac ggaattgcag gtagagctgg gtaaaccccg  11760
gctgacgcct gagcaagtgc cgtgaatccg gagtgatgca atggggtcac tgtggagtaa  11820
aattagccag ctgttcgtgg acgcyttcac tgagttcctt gtcagtgtgg ttgatattgt  11880
cattttcctt gccatactgt ttgggttcac cgtcgcagga tggttactgg tctttcttct  11940
cagggtggtt tgctccgcgc ttctccgttc gcgctctgcc attcaccctc ccgaactatc  12000
gaaggtccta tgaaagctta ctacccaatt gcagaccgga cgtcccacaa tttgcattta  12060
agcacccatt gggcatgtta tggcacatgc gagtctccca cctaatcgat gaaatggtct  12120
ctcgtcgcat ttaccggact atggaacact cgggtcaagc ggcctggaag caggtggtta  12180
gtgaagccac cctcacaaag ttgtcagggc ttgatatagt tactcatttc caacacctgg  12240
ccgcagtgga ggcagattct tgccgtttcc tcagctcacg acttgcgatg ctaaagaatc  12300
ttgccgttgg caatgtgagc ctgcagtata ataccacgtt ggatcatgtt gagctcatct  12360
ttcctacgcc aggtacgagg cccaagttga ccgatttcag acaatggctc atcagtgtgc  12420
```

```
acgcctccat cttttcctct gtggcttcat ctgttacctt gttcatagtg ttttggcttc  12480
gaattccagc cgtacgctat gtttttggtt tccattggcc cacggcaata catcattcga  12540
gctaaccatc aattacacca tatgtatgcc ctgctctacc agccaagcgg ctagtcaaag  12600
actcgagccc ggtcgtaaca tgtggtgcag aatagggcat gacaggtgtg aggaacgcga  12660
ccatgatgag ttgtcaatgt ccatcccgtc agggtacgag aacctcaaac ttgagggtta  12720
ttatgcttgg ctggcttttt tgtccttttc ctatgcggca caatttcacc cggagttgtt  12780
cggaatagga aatgtgtcgc gcgtcttcgt ggacaagcga caccagttca tttgtgccga  12840
gcatgatgga caaaattcaa ccgtatctgc cggacacgac atctccgcat tatacgcggt  12900
gtattaccat caccaaatag acgggggcaa ttggttccat ttggaatggc tgcggccatt  12960
cttttcctcc tggctggtgc tcaacatctc atggtttctg aggcgttcgc ctgtaagccc  13020
tgtttctcga cgcatttatc agatattaag accaacacga ccgcggctgc cggtttcatg  13080
gtccttcagg acatcarttg tctccaaccc cacggggtct cgacagcgca agagggacct  13140
cccttcagaa agtcgtccca atgtcgcgag gccatcggta ctccccagta cattacgata  13200
acggctaatg tgaccgatga atcgtatttg tacaacgcgg acctgctgat gctctctgcg  13260
tgcctttttt acgcctcgga aatgagtgaa aagggcttca aagtcatctt tgggaacgtt  13320
tctggcgttg tttctgcttg tgtcaatttt acagattatg tggctcatgt aacccaacat  13380
actcagcagc atcatctggt gattgatcat gttcggttgc tgcatttcct gacaccatca  13440
acaatgaggt gggctacaac cattgcttgt ttgttcgcca ttctcttggc gatatgaaat  13500
gttctcacag attggagcgt ttcttgactc ctcacttttg cttctggtgg tttttttgc  13560
tttgtaccgg cttgtcttgg tcctttgtcg atggcaacga caacagctcg acataccaat  13620
acatatataa tttgacgata tgygagctga atgggaccgc atggttgtcc agccattttg  13680
actgggcagt cgagaccttt gtgctttacc cggttgccac tcatatcctt tcactgggtt  13740
ttctcacaac aagccatttt yttgatgcgc tcggtctcgg cgctgtgtcc actacaggat  13800
ttgttggcgg gcggtatgta ctcagcagcg tgtatggcgc ttgtgctttc gcagcgctcg  13860
tatgttttgt catccgcgct gcaaaaaatt gcatggcttg ccgttatgcc cgtacccggt  13920
ttaccaactt cattgtggac gaccggggga ggatccatcg atggaagtca ccaatagtgg  13980
tagagaagtt gggcaaagcc gaagtcggtg gcaacctcgt caccatcaaa catgtcgtcc  14040
tcgaaggggt taaagctcaa cccttgacga ggacttcggc tgagcaatgg gaagcctaga  14100
cggtttttgc aatgattcta ccgccgcaca aaagcttgtg ttagctttca gcatcacata  14160
cacacctata atgatatacg ccctcaaggt gtcacgcggt cgcctcctag ggctattgca  14220
catcctgata ttcctgaact gttcctttac gttcggatac atgacgtatg tgcattttca  14280
atccaccaac cgtgtcgcac ttactctggg ggccgttgtc gcccttctat ggggtgttta  14340
cagcttcaca gagtcatgga agtttattac ttccagatgc agattgtgtt gcctaggccg  14400
gcgatacatt ctggcccctg cccatcacgt agaaagtgct gcaggtctcc attcaatccc  14460
agcgtctggt aaccgagcat acgctgtgag aaagcccgga ctaacatcag tgaacggcac  14520
tctagtacca ggacttcgga gcctcgtgct gggcggcaaa cgagctgtta aacgaggagt  14580
ggttaacctc gtcaagtatg gccggtaaaa atcagagcca gaagaaaaag aagaatacag  14640
ctccgatggg gaatggccag ccagtcaatc aactgtgcca gctgctgggt gcaatgataa  14700
agtcccagcg ccagcaatct aggagaggac aggcaaaaaa aggaaagcct gagaagccac  14760
```

-continued atttcccct agctgctgaa gatgacattc ggcaccacct cacccaaact gaacgttccc 14820
tctgcttgca atcgatccag acggctttta atcaaggcgc aggaactgcg tcgctttcat 14880
ccagcgggaa ggtcggtttt caggttgagt tcatgctgcc ggttgctcat acagtgcgcc 14940
tgattcgcgt gacttccaca tccgccagtc agggtgcaaa ttaatttgat agtcaggtga 15000
atggccacga ttgacgtgtg gcctytaagt cacctattca attagggcga tcacatgggg 15060
gtcagactta atcaggcagg aaccatgtga ccgaaattaa aaaaaaaaaa aaaaaaaaaa 15120
aaaaaaaaaa aaaaaaaaaa aaaaaa 15146

<210> SEQ ID NO 164
<211> LENGTH: 27
<212> TYPE: DNA
<213> ORGANISM: Artificial Sequence
<220> FEATURE:
<223> OTHER INFORMATION: primer

<400> SEQUENCE: 164
gctaggttga ttgggctagc tagaacc 27

<210> SEQ ID NO 165
<211> LENGTH: 24
<212> TYPE: DNA
<213> ORGANISM: Artificial Sequence
<220> FEATURE:
<223> OTHER INFORMATION: primer

<400> SEQUENCE: 165
acttctagag tgccacctcc gtag 24

<210> SEQ ID NO 166
<211> LENGTH: 28
<212> TYPE: DNA
<213> ORGANISM: Artificial Sequence
<220> FEATURE:
<223> OTHER INFORMATION: primer

<400> SEQUENCE: 166
acttctagag tctcttgaac ggacacag 28

<210> SEQ ID NO 167
<211> LENGTH: 28
<212> TYPE: DNA
<213> ORGANISM: Artificial Sequence
<220> FEATURE:
<223> OTHER INFORMATION: primer

<400> SEQUENCE: 167
acttctagat gaggtcctca taccactc 28

<210> SEQ ID NO 168
<211> LENGTH: 25
<212> TYPE: DNA
<213> ORGANISM: Artificial Sequence
<220> FEATURE:
<223> OTHER INFORMATION: primer

<400> SEQUENCE: 168
cccgagtgat ggctactagt gctcg 25

<210> SEQ ID NO 169
<211> LENGTH: 24
<212> TYPE: DNA
<213> ORGANISM: Artificial Sequence
<220> FEATURE:
<223> OTHER INFORMATION: primer

<400> SEQUENCE: 169
actctagagc agggcataca tatg 24

<210> SEQ ID NO 170
<211> LENGTH: 33
<212> TYPE: DNA
<213> ORGANISM: Artificial Sequence
<220> FEATURE:
<223> OTHER INFORMATION: primer

<400> SEQUENCE: 170
acttctagag gttaaccact cctcgtttaa cag 33

<210> SEQ ID NO 171
<211> LENGTH: 68
<212> TYPE: DNA
<213> ORGANISM: Artificial Sequence
<220> FEATURE:
<223> OTHER INFORMATION: primer

<400> SEQUENCE: 171
ggcgatcggg cgtctaggaa ttctagattt tttttttttt tttttttttt tttttttttt 60
tttttttt 68

<210> SEQ ID NO 172
<211> LENGTH: 29
<212> TYPE: DNA
<213> ORGANISM: Artificial Sequence
<220> FEATURE:
<223> OTHER INFORMATION: primer

<400> SEQUENCE: 172
aaatatgatg tgtggggtat tccccctac 29

<210> SEQ ID NO 173
<211> LENGTH: 27
<212> TYPE: DNA
<213> ORGANISM: Artificial Sequence
<220> FEATURE:
<223> OTHER INFORMATION: primer

<400> SEQUENCE: 173
gctaggttga ttgggctagc tagaacc 27

<210> SEQ ID NO 174
<211> LENGTH: 28
<212> TYPE: DNA
<213> ORGANISM: Artificial Sequence
<220> FEATURE:
<223> OTHER INFORMATION: primer

<400> SEQUENCE: 174
aaattctagc tagcccaatc aacctagc 28

<210> SEQ ID NO 175
<211> LENGTH: 24
<212> TYPE: DNA
<213> ORGANISM: Artificial Sequence
<220> FEATURE:
<223> OTHER INFORMATION: primer -continued

<400> SEQUENCE: 175
acttctagag tgccacctcc gtag 24

<210> SEQ ID NO 176
<211> LENGTH: 27
<212> TYPE: DNA
<213> ORGANISM: Artificial Sequence
<220> FEATURE:
<223> OTHER INFORMATION: primer

<400> SEQUENCE: 176
cgtcattctt ggtaagttac tcggtgg 27

<210> SEQ ID NO 177
<211> LENGTH: 28
<212> TYPE: DNA
<213> ORGANISM: Artificial Sequence
<220> FEATURE:
<223> OTHER INFORMATION: primer

<400> SEQUENCE: 177
acttctagag tctcttgaac ggacacag 28

<210> SEQ ID NO 178
<211> LENGTH: 24
<212> TYPE: DNA
<213> ORGANISM: Artificial Sequence
<220> FEATURE:
<223> OTHER INFORMATION: primer

<400> SEQUENCE: 178
ttgacacagg tgacgtgatt gtcc 24

<210> SEQ ID NO 179
<211> LENGTH: 28
<212> TYPE: DNA
<213> ORGANISM: Artificial Sequence
<220> FEATURE:
<223> OTHER INFORMATION: primer

<400> SEQUENCE: 179
acttctagat gaggtcctca taccactc 28

<210> SEQ ID NO 180
<211> LENGTH: 28
<212> TYPE: DNA
<213> ORGANISM: Artificial Sequence
<220> FEATURE:
<223> OTHER INFORMATION: primer

<400> SEQUENCE: 180
cctctagact taagttcctc gaggagca 28

<210> SEQ ID NO 181
<211> LENGTH: 25
<212> TYPE: DNA
<213> ORGANISM: Artificial Sequence
<220> FEATURE:
<223> OTHER INFORMATION: primer

<400> SEQUENCE: 181
cccgagtgat ggctactagt gctcg 25

<210> SEQ ID NO 182

<211> LENGTH: 19
<212> TYPE: DNA
<213> ORGANISM: Artificial Sequence
<220> FEATURE:
<223> OTHER INFORMATION: primer

<400> SEQUENCE: 182
tagcagccct tgcatatca 19

<210> SEQ ID NO 183
<211> LENGTH: 24
<212> TYPE: DNA
<213> ORGANISM: Artificial Sequence
<220> FEATURE:
<223> OTHER INFORMATION: primer

<400> SEQUENCE: 183
actctagagc agggcataca tatg 24

<210> SEQ ID NO 184
<211> LENGTH: 26
<212> TYPE: DNA
<213> ORGANISM: Artificial Sequence
<220> FEATURE:
<223> OTHER INFORMATION: primer

<400> SEQUENCE: 184
gcttcgaatt ccagccgtac gctatg 26

<210> SEQ ID NO 185
<211> LENGTH: 33
<212> TYPE: DNA
<213> ORGANISM: Artificial Sequence
<220> FEATURE:
<223> OTHER INFORMATION: primer

<400> SEQUENCE: 185
acttctagag gttaaccact cctcgtttaa cag 33

<210> SEQ ID NO 186
<211> LENGTH: 25
<212> TYPE: DNA
<213> ORGANISM: Artificial Sequence
<220> FEATURE:
<223> OTHER INFORMATION: primer

<400> SEQUENCE: 186
ggcaacctcg tcaccatcaa acatg 25

<210> SEQ ID NO 187
<211> LENGTH: 23
<212> TYPE: DNA
<213> ORGANISM: Artificial Sequence
<220> FEATURE:
<223> OTHER INFORMATION: primer

<400> SEQUENCE: 187
ggcgatcggg cgtctaggaa ttc 23

<210> SEQ ID NO 188
<211> LENGTH: 21
<212> TYPE: DNA
<213> ORGANISM: Artificial Sequence
<220> FEATURE:
<223> OTHER INFORMATION: primer

<400> SEQUENCE: 188
taggcttgta aaacaagcca a 21

<210> SEQ ID NO 189
<211> LENGTH: 22
<212> TYPE: DNA
<213> ORGANISM: Artificial Sequence
<220> FEATURE:
<223> OTHER INFORMATION: primer

<400> SEQUENCE: 189
gcaaggtcag tttcctgaag ct 22

<210> SEQ ID NO 190
<211> LENGTH: 22
<212> TYPE: DNA
<213> ORGANISM: Artificial Sequence
<220> FEATURE:
<223> OTHER INFORMATION: primer

<400> SEQUENCE: 190
gcaaggtcag tttcctgaag ct 22

<210> SEQ ID NO 191
<211> LENGTH: 20
<212> TYPE: DNA
<213> ORGANISM: Artificial Sequence
<220> FEATURE:
<223> OTHER INFORMATION: primer

<400> SEQUENCE: 191
aagtcgttgg aggaagttgt 20

<210> SEQ ID NO 192
<211> LENGTH: 22
<212> TYPE: DNA
<213> ORGANISM: Artificial Sequence
<220> FEATURE:
<223> OTHER INFORMATION: primer

<400> SEQUENCE: 192
acactcatcc agagacacag ac 22

<210> SEQ ID NO 193
<211> LENGTH: 17
<212> TYPE: DNA
<213> ORGANISM: Artificial Sequence
<220> FEATURE:
<223> OTHER INFORMATION: primer

<400> SEQUENCE: 193
gtaaaacgac ggccagt 17

<210> SEQ ID NO 194
<211> LENGTH: 17
<212> TYPE: DNA
<213> ORGANISM: Artificial Sequence
<220> FEATURE:
<223> OTHER INFORMATION: primer

<400> SEQUENCE: 194
caggaaacag ctatgac 17

<210> SEQ ID NO 195

<211> LENGTH: 23
<212> TYPE: DNA
<213> ORGANISM: Artificial Sequence
<220> FEATURE:
<223> OTHER INFORMATION: primer

<400> SEQUENCE: 195
cactgcgcca ccagtcgctt cag 23

<210> SEQ ID NO 196
<211> LENGTH: 23
<212> TYPE: DNA
<213> ORGANISM: Artificial Sequence
<220> FEATURE:
<223> OTHER INFORMATION: primer

<400> SEQUENCE: 196
accctrggya rgaagcagta tgt 23

<210> SEQ ID NO 197
<211> LENGTH: 21
<212> TYPE: DNA
<213> ORGANISM: Artificial Sequence
<220> FEATURE:
<223> OTHER INFORMATION: primer

<400> SEQUENCE: 197
aggaactctg tctccaccaa g 21

<210> SEQ ID NO 198
<211> LENGTH: 22
<212> TYPE: DNA
<213> ORGANISM: Artificial Sequence
<220> FEATURE:
<223> OTHER INFORMATION: primer

<400> SEQUENCE: 198
catacgctgc ctcaatgtac tg 22

<210> SEQ ID NO 199
<211> LENGTH: 22
<212> TYPE: DNA
<213> ORGANISM: Artificial Sequence
<220> FEATURE:
<223> OTHER INFORMATION: primer

<400> SEQUENCE: 199
raccacygar cargctttaa ac 22

<210> SEQ ID NO 200
<211> LENGTH: 22
<212> TYPE: DNA
<213> ORGANISM: Artificial Sequence
<220> FEATURE:
<223> OTHER INFORMATION: primer

<400> SEQUENCE: 200
ggacttccar gccttyttca tg 22

<210> SEQ ID NO 201
<211> LENGTH: 23
<212> TYPE: DNA
<213> ORGANISM: Artificial Sequence
<220> FEATURE:
<223> OTHER INFORMATION: primer

<400> SEQUENCE: 201
gacggtggrt gaggyctcat caa 23

<210> SEQ ID NO 202
<211> LENGTH: 17
<212> TYPE: DNA
<213> ORGANISM: Artificial Sequence
<220> FEATURE:
<223> OTHER INFORMATION: primer

<400> SEQUENCE: 202
gtaaaacgac ggccagt 17

<210> SEQ ID NO 203
<211> LENGTH: 17
<212> TYPE: DNA
<213> ORGANISM: Artificial Sequence
<220> FEATURE:
<223> OTHER INFORMATION: primer

<400> SEQUENCE: 203
caggaaacag ctatgac 17

<210> SEQ ID NO 204
<211> LENGTH: 25
<212> TYPE: DNA
<213> ORGANISM: Artificial Sequence
<220> FEATURE:
<223> OTHER INFORMATION: primer

<400> SEQUENCE: 204
atgatccaac gtggtattat actgc 25

<210> SEQ ID NO 205
<211> LENGTH: 19
<212> TYPE: DNA
<213> ORGANISM: Artificial Sequence
<220> FEATURE:
<223> OTHER INFORMATION: primer

<400> SEQUENCE: 205
tagacggggg yaaytggtt 19

<210> SEQ ID NO 206
<211> LENGTH: 22
<212> TYPE: DNA
<213> ORGANISM: Artificial Sequence
<220> FEATURE:
<223> OTHER INFORMATION: primer

<400> SEQUENCE: 206
tgttaaacga ggagtggtta ac 22

<210> SEQ ID NO 207
<211> LENGTH: 29
<212> TYPE: DNA
<213> ORGANISM: Artificial Sequence
<220> FEATURE:
<223> OTHER INFORMATION: primer

<400> SEQUENCE: 207
aaatatgatg tgtggggtat tccccctac 29

<210> SEQ ID NO 208

<211> LENGTH: 27
<212> TYPE: DNA
<213> ORGANISM: Artificial Sequence
<220> FEATURE:
<223> OTHER INFORMATION: primer

<400> SEQUENCE: 208
gctaggttga ttgggctagc tagaacc 27

<210> SEQ ID NO 209
<211> LENGTH: 25
<212> TYPE: DNA
<213> ORGANISM: Artificial Sequence
<220> FEATURE:
<223> OTHER INFORMATION: primer

<400> SEQUENCE: 209
ttctagctag cccaatcaac ctagc 25

<210> SEQ ID NO 210
<211> LENGTH: 24
<212> TYPE: DNA
<213> ORGANISM: Artificial Sequence
<220> FEATURE:
<223> OTHER INFORMATION: primer

<400> SEQUENCE: 210
acttctagag tgccacctcc gtag 24

<210> SEQ ID NO 211
<211> LENGTH: 18
<212> TYPE: DNA
<213> ORGANISM: Artificial Sequence
<220> FEATURE:
<223> OTHER INFORMATION: primer

<400> SEQUENCE: 211
cagtaccgac ggtgatat 18

<210> SEQ ID NO 212
<211> LENGTH: 20
<212> TYPE: DNA
<213> ORGANISM: Artificial Sequence
<220> FEATURE:
<223> OTHER INFORMATION: primer

<400> SEQUENCE: 212
ccgtcgtgta gataactacg 20

<210> SEQ ID NO 213
<211> LENGTH: 24
<212> TYPE: DNA
<213> ORGANISM: Artificial Sequence
<220> FEATURE:
<223> OTHER INFORMATION: primer

<400> SEQUENCE: 213
ttgacacagg tgacgtgatt gtcc 24

<210> SEQ ID NO 214
<211> LENGTH: 28
<212> TYPE: DNA
<213> ORGANISM: Artificial Sequence
<220> FEATURE:
<223> OTHER INFORMATION: primer

<400> SEQUENCE: 214
acttctagat gaggtcctca taccactc 28

<210> SEQ ID NO 215
<211> LENGTH: 28
<212> TYPE: DNA
<213> ORGANISM: Artificial Sequence
<220> FEATURE:
<223> OTHER INFORMATION: primer

<400> SEQUENCE: 215
cctctagact taagttcctc gaggagca 28

<210> SEQ ID NO 216
<211> LENGTH: 25
<212> TYPE: DNA
<213> ORGANISM: Artificial Sequence
<220> FEATURE:
<223> OTHER INFORMATION: primer

<400> SEQUENCE: 216
cccgagtgat ggctactagt gctcg 25

<210> SEQ ID NO 217
<211> LENGTH: 19
<212> TYPE: DNA
<213> ORGANISM: Artificial Sequence
<220> FEATURE:
<223> OTHER INFORMATION: primer

<400> SEQUENCE: 217
tagcagccct tgcatatca 19

<210> SEQ ID NO 218
<211> LENGTH: 20
<212> TYPE: DNA
<213> ORGANISM: Artificial Sequence
<220> FEATURE:
<223> OTHER INFORMATION: primer

<400> SEQUENCE: 218
agactgcttt ccaaaacacc 20

<210> SEQ ID NO 219
<211> LENGTH: 26
<212> TYPE: DNA
<213> ORGANISM: Artificial Sequence
<220> FEATURE:
<223> OTHER INFORMATION: primer

<400> SEQUENCE: 219
gcttcgaatt ccagccgtac gctatg 26

<210> SEQ ID NO 220
<211> LENGTH: 33
<212> TYPE: DNA
<213> ORGANISM: Artificial Sequence
<220> FEATURE:
<223> OTHER INFORMATION: primer

<400> SEQUENCE: 220
acttctagag gttaaccact cctcgtttaa cag 33

<210> SEQ ID NO 221

<211> LENGTH: 40
<212> TYPE: DNA
<213> ORGANISM: Artificial Sequence
<220> FEATURE:
<223> OTHER INFORMATION: primer

<400> SEQUENCE: 221
cgagagttgg cctccctagt ccaggttgac aaaatgaaag 40

<210> SEQ ID NO 222
<211> LENGTH: 40
<212> TYPE: DNA
<213> ORGANISM: Artificial Sequence
<220> FEATURE:
<223> OTHER INFORMATION: primer

<400> SEQUENCE: 222
ctttcatttt gtcaacctgg actagggagg ccaactctcg 40

<210> SEQ ID NO 223
<211> LENGTH: 18745
<212> TYPE: DNA
<213> ORGANISM: Artificial Sequence
<220> FEATURE:
<223> OTHER INFORMATION: Clone pVAC 5.0 (full)

<400> SEQUENCE: 223
atgatgtgta gggtactccc cctacataca cgacacttct agtgtttgtg tgccttggag 60
gcgtgggtat agccccgccc cacccccttgg cccctgttct agcccaacag gtatccttct 120
ctctcggggc gagcgcgccg cctgctgctc ccttgcagcg ggaaggacct cccgagtatt 180
tccggagagc acctgcttta cggggatctcc accctttaac catgtctggg acgttctccc 240
ggtgcatgtg caccccggct gcccgggtat tttggaacgc cggccaagtc ttttgcacac 300
ggtgtctcag tgcgcggtct cttctccctc cggagcttca ggaaactgac ctcgctgcaa 360
ttggcttgtt ttacaagcct aaagacaagc ttcactggaa agtccctatc ggcatccctc 420
aggtggagtg cactccatcc gggtgctgtt ggctctcagc catcttccca ttggcgcgca 480
tgacctccgg caatcacaac ttcctccaac gacttgtgag ggttgccgat gtgttgtacc 540
gtgatggttg cttggctcct cgacaccttc gtgaactcca agtttacgag cgcggctgca 600
actggtaccc gatcacgggg cccgtgcccg ggatgggttt gttcgcaaac tccatgcacg 660
tatccgacca gccgttccct ggtgccaccc atgtgttgac gaactcgccg ttgcctcaac 720
aggcttgtcg gcagccgttc tgtccatttg aggaggctca ttctagtgtg tacaggtgga 780
aaagatttgt ggttttcacg gattcctctc ccaacggtcg atctcgcatg atgtggacgc 840
cggaatccga tgattcagcc gccttggagg tattaccgcc tgaattagaa cgtcaggtcg 900
aaatcctcat tcggagtttt cctgctcatc accctgtcaa cctggccgac tgggagctca 960
ctgagtcccc tgagaacggt tttttccttca acacgtctta ttcttgcggt caccttgtcc 1020
aaaaccccga cgtgtttgat ggcaagtgct ggctttcctg ctttttgggc cagtcggccg 1080
aagtgcgccg ccatgaggaa catttagctg acgccctcgg ttaccagacc aagtggggcg 1140
tgcctggcaa gtacctccag cgcaggcttc aggttcgcgg cattcgtgct gtagttgatc 1200
ctgatggccc cattcacgtc gaagcgctgt cttgcccccg gtcttggatc aggcacctga 1260
cttttgatga taatgtcacc ccaggatttg ttcgccttac gtcccttcgc attgtgccaa 1320
acaccgagcc tactgcttcc cggatcttcc ggtttggagc gcataagtgg tatggcgctg 1380
ccggcaaacg agctcgtgct aagcgtgccg ctaaaagtga gaaaatttcg gcccctaccc 1440

-continued

```
ccaaggttgc tcagccggtc cccacctgcg aaattaccac ctattctcca ccgacagacg   1500
ggtcttgtgg ttggcatgtt cttgccgcca taatgaaccg gatgatgaat ggtgacttca   1560
cgtcccctct gactcagtac aacagaccag aggatgactg ggcttctgat tatgaccttg   1620
ctcaggcgat ccaatgtctg caactgcccg ctaccgtagt tcggaatcgc gcctgtccta   1680
acgccaagta ccttataaaa cttaatggag ttcattggga ggtagaggtg aggcctggaa   1740
tggcccctcg ttccctttcc cgtgagtgtg tggttggcgt ctgttctgaa ggctgtatcg   1800
caccgcctta cccacaagac gggctgccta aacgtgcact tgaggccttg gcgtctgctt   1860
acagactacc ctccgactgt gttggttctg gtattgctga ctttcttgct aacccgcccc   1920
ctcaggagtt ttggaccctt gacaaaatgt tgacctcccc gtcaccagaa cggtccggct   1980
tctctagctt gtataaatta ctattggagg ttgttccgca gaaatgcggt gccacggaag   2040
gggctttcgt ctatgctgtt gagaggatgt tgaaggattg tccgagctcc aaacaggcca   2100
tggcccttct ggcaaaaatt aaagtcccat cctcaaaggc ccgtctgtg tctctggacg   2160
agtgcttccc tacggatgtt ccagcggact ccgagccagc gtttcaggaa aggccccaaa   2220
gttctggtgc tgctgttgtc ctgtgttcac cggacataaa agagttcgag gaagcagccc   2280
cagaagaagt tcaagagggt ggccacaagg ccgtccactc tgcactcctt gccgagggtc   2340
ttaacaatga gcaggtacag gtggttgccg gtgcgcaact aaagctcggc agttgtggct   2400
tggcagtcgg gaatactcat ggaggtgttc cggtttcagc tagtccaatt aacctggcag   2460
acgggaattt gcccccctcg gactccatga aaggaaacat gcccaatggc tgggaggacg   2520
aaccactgga tttgtcccaa tcagcactag caaccacaac gacccttgtg agagagcaaa   2580
cacccgacaa tctaggttct ggcgccggtg ccctccctgt caccattcga gaatttgtcc   2640
cgacaaggcc tataccccgt catgttgagc actgcggcac ggagtcgggc gacagcagtt   2700
cgcctctgga tctgtccgat gcgcaaaccc cggaccagcc tttaaatcta tccctggccg   2760
cttggccagt gagggccacc gcgtctgacc ccggctgggt ccacggtagg cgtgagcctg   2820
tttttgtaaa gcctcggggt gctttctctg atggcgattc agtccttcag ttcggggagc   2880
tttccgaatc cagctctatc atcgagattg accggacaaa agatgctcca gtggttgatg   2940
cccccgtcga cttgacggtt tcgaacgaag ctctctctgg gatcgatcct tttgaatttg   3000
ccgaactcaa gcgcccgcgt ttctccgctc aagccttaat tgaccgaggc ggcccactag   3060
ccgatgtcca tgcaaaaata aagaaccggg tatatgaaca gtgcctccag gcttgtgagc   3120
ctggcagtcg tgcaacccca gccaccaggg agtggctcga caaaatgtgg gatagggtgg   3180
acatgaagac ttggcgctgc acctcgcagt tccaagctgg tcacattctt gcgtccctca   3240
aattcctccc cgacatgatt caagacacac cgcctcctgt tcccaggaag agccgggcta   3300
gtgataatgc cggcctgaag caactggtgg cgcagtggga cagaaaattg agtgtaaccc   3360
ccccccctaaa accggttggg ccggcgcttg gccaaaccgt ccctccgcct acggatattc   3420
agcaagaaga tgtcaccccc tccgataggc cacctcatgt gccggatctt cctagtcgag   3480
tgagcacggg tgggagttgg aaaggcctta tgctttccgg cacccgtctc gcggggtcta   3540
ttagtcagca cctcatgaca tgggtttttg aagttttctc ccatctccca gcttttatgc   3600
tcacactttt ctcgccacgg ggctctatgg ctccaggtga ttggctattt gcaggtgttg   3660
ttttacttgc tctcctgctc tgtcgttctt acccagtact cgggtgcctt cccttattgg   3720
gtgtcttttc tggttctttg cggcgtgttc gtctgggtgt ttttggttct tggatggctt   3780
```

-continued ttgctgtatt tttattctcg actccatccg acccagtcgg ttcttcttgt gaccacgatt 3840
cgccggagtg tcatgctgag cttttggctc ttgagcagcg ccaactttgg gaacctgtgc 3900
gcggccttgt ggtcggcccc tcgggtctct tatgtgtcat tcttggcaag ttactcggtg 3960
ggtcacgtta tctctggcat gttttcttac gtttatgcat gcttgcggat ttggcccttt 4020
ctcttgttta tgtggtgtcc caggggcgtt gtcacaagtg ttggggaaag tgtataagga 4080
cagctcctgc ggaggtggct ctcaatgtgt tccctttctt gcgcgctacc cgtgcctctc 4140
ttgtgtcctt gtgcgatcga ttccaagcgc caaaaggggt tgatcctgtg cacttggcaa 4200
caggttggcg cgggtgctgg cgcggtgaga gccccattca tcaaccgcac caaaagccca 4260
tagcttatgc caatttggat gaaaagaaaa tatctgccca aacggtggtt gctgtcccgt 4320
atgatcccag tcaggccatc aaatgcctga aagttctgca ggcgggaggg gctatcgtgg 4380
accagcccac acctgaggtc gtccgtgtgt ccgagatccc tttctcagcc ccatttttc 4440
caaaggttcc agtcaaccca gattgcaggg ttgtggtaga ttcggacact tttgtggctg 4500
cagttcgctg cggttactcg acggctcaac tggtcttagg ccggggcaac tttgccaagt 4560
taaatcagat cccctccagg aactctgtct ccaccaaaac gactggtggg gcctcttaca 4620
cccttgctgt ggctcaagtg tctgtgtgga ctcttgttca tttcatcctc ggtctttggt 4680
tcacgtcacc tcaagtgtgt ggccgaggaa cctctgaccc atggtgttca aatccttttt 4740
catatcctac ctatggcccc ggaatagtgt gctcctctcg actttgtgtg tctgccgacg 4800
gagtcactct gccattgttc tcagcagtgg cacaactctc cggtagagag gtggggattt 4860
tcattttggt gctcgtctcc ttgactgctc tggcccaccg tatggctctt aaggcagaca 4920
tgttagtggt cttttcggct tttgtgctt acgcctggcc catgagctcc tggttaatct 4980
gcttctttcc tatattcttg aagtgggtca cccttcaccc tctcactatg ctttgggtgc 5040
actcattctt ggtgttttgt ctgccagcag ccggcgtcct ctcactaggg ataaccggcc 5100
ttctctgggc agttggccgc tttacccagg tcgccggaat tattacacct tatgacatcc 5160
accagtacac ctctgggcca cgtggtgcag ccgctgtggc cacggcccca gaaggcactt 5220
acatggccgc cgtccggaga gctgccttaa ctggacgaac cctcatcttc acaccatctg 5280
cggttggatc ccttcttgaa ggtgctttca ggacccataa accctgcctt aacaccgtga 5340
atgttgtagg ctcttccctt ggttccgggg gggttttcac cattgatggc agaagaactg 5400
ttgtcactgc tgcccatgtg ttgaacggcg acacagctag agtcaccggc gactcctaca 5460
accgcatgca cactttcaag accaatggtg attatgcctg gtcccatgct gatgactggc 5520
ggggcgttgc ccctgtggtc aaggtcgcga aggggtaccg cggtcgtgcc tactggcaaa 5580
catcaactgg tgtcgaaccc ggtattgttg gggaagggtt cgccttctgt tttaccaact 5640
gtggcgattc ggggtcacct gtcatctcag aatctggtga tcttgttgga atccacaccg 5700
gttcaaacaa actcggttct ggtcttgtga caacccctga aggggagacc tgctccatca 5760
aagaaaccaa gctctctgac ctttccaggt attttgcagg cccaagcgtc cctcttgggg 5820
atattaaatt gagtccggcc atcatccctg atgtaacatc cattccgagt gacttggcat 5880
cgctcctagc ctccgtccct gtaatggaag gcggcctctc gactgtccaa cttttgtgtg 5940
tctttttcct tctctggcgt atgatgggcc atgcctggac acccattgtt gccgtgggct 6000
tctttttgct gaatgaaatt cttccagcag ttttggtccg agccgtgttt tcttttgcgc 6060
tctttgtgct tgcatgggcc accccctggt ctgcacaggt gttgatgatc agactcctca 6120
cggcagctct caaccgcaac aggctttctc tggcgttcta cgcactcggg ggtgtcgtcg 6180
gtttggctgc tgaaattggg acctttgctg gtagattgtc tgaattgtct caagctcttt 6240
cgacatactg cttcttacct agggttcttg ctgtgactag ttatgttccc accatcatca 6300
ttggtggact ccataccctt ggtgtgatct tgtggctatt caaataccgg tgcctccaca 6360
acatgttagt tggtgatggg agtttttcaa gtgccttttt cctacggtat tttgcagagg 6420
gtaatctcag aaaaggtgtt tcacagtcct gtggcatgaa taacgagtcc ctgacagctg 6480
ctttagcttg caagttgtca caggctgacc ttgatttttt gtccagcttg acgaacttca 6540
agtgctttgt atctgcttca aacatgaaag atgctgctgg ccagtacatt gaggcagcgt 6600
atgccaaggc cctgcgccga gagttggcct ccctagtcca ggttgacaaa atgaaaggag 6660
ttttgtccaa gctcgaggcc tttgctgaaa cagccacccc gtcccttgac acaggtgacg 6720
tgattgtcct gcttgggcaa catcctcacg gatccatcct cgatattaat gtggggactg 6780
aaaggaaaac tgtgtctgtt caagagactc ggagcctagg cggctccaaa ttcagtgtct 6840
gcactgtcgt gtccaacaca cccgtggacg ccttggccgg cattccactt cagacaccaa 6900
ccccgctttt tgagaatggc ccgcgtcatc gcggtgagga agatgatctc aaagttgaga 6960
ggatgaagaa acattgtgtg tccctcggct tccacaacat caatggcaaa gtttactgta 7020
aagtttggga caagtccacc ggtgacacct tttacacgga tgattcccgg tacacccaag 7080
accatgcttt tcaggacagg tcagctgact atagagacag ggactatgag ggtgtgcaaa 7140 ccgccccccca acagggattt gatccaaaat ctgaaacccc tgttggcact gttgtaatcg 7200
gcggtattac gtataataag tatctggtca aaggcaagga ggttctggtt cccaaacctg 7260
acaactgcct tgaagccgcc aagctgtccc tcgagcaagc acttgctggg atgggccaaa 7320
cttgcgacct tacagttgcc gaggtggaaa agctaaagcg catcatcagt caactccaag 7380
gtttgaccac tgaacaggct ttaaactgct agccgccagc ggcttgaccc gctgtggccg 7440
cggcggcttg gttgtaactg aaacggcggt aaaaattata aaataccaca gcagaacttt 7500
cactttaggc cctttagacc taaaagtcac ttctgaggta gaggtgaaga aatcaactga 7560
gcagggccac gccgttgtgg caaacctatg ttctggtgtc gtattgatga gacctcaccc 7620
accgtccctt gttgacgtcc ttctgaaacc cggacttgac acaacacccg acattcaacc 7680
ggggcatggg gccgggaata tgggcgtgga cggttctatt tgggattttg aaaccgcacc 7740
cacaaaggca gaactcgagt tgtccaagca aataattcaa gcatgtgaag ttaggcgcgg 7800
agacgccccg aacctccaac tcccctacaa gctctatcct gtcagagggg atcctgagcg 7860
gcataaaggc cgccttatca acaccaggtt tggagacttg ccttacaaaa ctcctcaaga 7920
caccaagtcc gctatccatg cggcttgttg cctgcacccc aacggggccc ctgtgtctga 7980
tggtaaatcc acactaggca ccactcttca acatggtttc gagctttatg ttcccacagt 8040
gccctatagt gtcatggagt accttgattc acgccctgac acccctccca tgttcactaa 8100
acatggcact tccaaggctg ctgcagaaga cctccaaaaa tatgacctat ccacccaagg 8160
atttgtcctg cctggggtcc tacgcctagt gcgcagattc atctttggcc atgttggtaa 8220
ggcaccgcca ttgttcctcc catcaaccta tcccgccaag aactccatgg cagggattaa 8280
tggccagaga ttcccaacaa aggacgtcca gagcatacct gaaattgatg aaatgtgtgc 8340
ccgcgccgtc aaggagaatt ggcaaaccgt gacaccttgt actctcaaga aacagtactg 8400
ttccaagccc aaaaccagga ccatcctggg caccaacaac tttattgcct tggctcacag 8460
atcggcgctc agtggcgtca cccaggcatt catgaagaag gcttggaagt ccccaattgc 8520

-continued

```
cttggggaaa aacaagttca aggagctgca ttgtactgtc gccggcaggt gtcttgaggc   8580
tgacttggcc tcctgtgatc gcagcacccc cgccattgta agatggtttg ttgccaacct   8640
cctgtatgaa cttgcaggat gtgaagagta cttgcctagc tatgtgctta actgctgcca   8700
tgaccttgtg gcaacacagg atggtgcctt cacaaaacgc ggtggcctgt cgtccgggga   8760
ccccgtcacc agtgtgtcca ataccgtata ttcactggta atctatgccc agcacatggt   8820
attgtcagcc ttgaaaatgg gtcatgaaat tggtcttaag ttcctcgagg agcagctcaa   8880
attcgaggac ctccttgaaa ttcagcctat gttagtatac tctgacgacc ttgtcttgta   8940
cgctgaaaga cccacttttc ccaattacca ttggtgggtc gagcaccttg acctgatgct   9000
gggtttcaaa acggacccaa agaaaactgt cataactgat aaacccagct tcctcggctg   9060
caggattgag gcagggcgac agttagtccc caatcgcgac cgcatcctgg ctgcccttgc   9120
atatcacatg aaggcgcaga acgcctcaga atattatgcg tctgctgccg caatcctgat   9180
ggattcgtgt gcttgcattg accatgaccc tgagtggtat gaggacctca tctgtggtat   9240
tgcccggtgt gctcgccaag atggctatag tttcccgggc ccggcatttt tcatgtccat   9300
gtgggagaaa ctgaaaagtc ataatgaagg gaaaaaattc cgccactgcg gcatctgcga   9360
cgccaaggcc gaccatgcgt ccgcctgtgg actcgatttg tgcttgttcc actcgcattt   9420
tcatcagcac tgccctgtca ctctgagctg cggccatcat gccggttcta aggaatgtcc   9480
gcagtgtcag tcaccggttg gggctggtag atctcctctc gatgccgtgc taaaacaaat   9540
tccgtacaaa cctcctcgta ctgtcatcat gaaggtggat aataaaacaa cggcccttga   9600
tccggggagg tatcagtccc gtcgaggtct cgttgcagtc aagaggggta ttgcaggcaa   9660
tgaagttgac cttgctaatg gagactacca ggtggtgcct cttttgccga cttgcaaaga   9720
cataaacatg gtgaaggtgg cttgtaatgt gctactcagc aagttcatag tagggccacc   9780
aggttccgga aagaccacct ggttgctgag tcaagtccag gacgatgatg tcatttatac   9840
acccacccat cagactatgt ttgatatagt cagtgctctc aaagtttgca ggtattccat   9900
tccaggggct tcaggactcc ctttcccacc acctgccagg tccgggccgt gggtcaggct   9960
tgttgccagc gggcacgtcc ctggccgagt atcatacctc gatgaggctg gatattgtaa  10020
tcatctggac attctcagac tgctttccaa aacacccctt gtgtgtttag gtgaccttca  10080
gcaactccac cctgtcggct ttgattccta ctgttatgtg tttgatcaga tgcctcagaa  10140
gcagctgacc actatttaca gatttggctc caacatctgc gcagctatcc agccttgtta  10200
cagggagaaa cttgaatcca aggccaggaa caccaggata gtttttacca cccgacctgt  10260
agctttcggg caggtgctga caccatacca caaagatcgc atcggctcag cgataaccat  10320
agattcatct caggggggcca cctttgacat tgtgacattg catctaccat cgccaaagtc  10380
cctaaataaa tcccgagcac ttgtagccat cactcgggca agacacgggt tgttcatcta  10440
tgaccctcat aatcagctcc aggagttttt caacctaact cctgagcgca ctgattgtaa  10500
ccttgtgttt aaccgtgggg atgagctggt agttctggac gcggataatg cagtcacaac  10560
tgtggcgaag gccctagaga cgggtccatc tcgatttcga gtatcagacc caaggtgcga  10620
gtctctcttg gccgcttgct cggccagcct ggagggaagc tgcatgccac taccgcaagt  10680
ggcacataac ctggggtttt acttttcccc agatagtcca gcattcgcgc ctctgccaaa  10740
agaattggca ccacattggc cggtggttac ccatcagaat aaccgggcgt ggcctgaccg  10800
acttgttgct agtatgcgcc caattgatgc ccgttatagc aagccaatgg ttggtgcagg  10860
gtacgcggtc gggccgtcca cttttcttgg cactcctggt gtggtatcat actatctgac  10920
```

actgtacatc aggggtgagc cccaggcctt accagaaaca ctcgtgtcaa cagggcgcat 10980
agccacagat tgtcgggaat atctcgacgc cgctgaggaa gaggcagcaa aagaactccc 11040
tcacgcattc attggcgatg tcaaaggtac cacggttggg gggtgtcatc acatcacatc 11100
aaaataccta cctaggtccc tgcctaagga ctctgttgcc gtagttggag taagttcgcc 11160
cggcagggcc gctaaagccg tgtgcactct caccgatgtt tacctccccg agctccggcc 11220
atatctgcaa cctgagacgg catcaaaatg ctggaaactc aaattagact ttagagatgt 11280
ccgactaatg gtctggaaag gagccaccgc ctacttccag ctggaagggc ttacatggtc 11340
ggcgctgccc gactatgcca ggtttattca gctgcctaag gatgccgttg tgtacattga 11400
tccgtgcata ggaccggcaa cagccaaccg taaggtcgtg cggaccacag actggcgggc 11460
tgacctggca gtgacaccgt atgattacgg tgcccagaac attttgacaa cagcctggtt 11520
cgaggacctc gggccgcagt ggaagatttt ggggttgcag ccctttaggc gatcatttgg 11580
ctttgaaaac actgaggatt gggcaatcct tgcacgccgt atgaatgacg gcaaggacta 11640
cactgactat aactggaact gtgttcgaga acgcccacac gccatctacg ggcgcgctcg 11700
tgaccatacg tatcattttg cccccggcac agaattgcag gtagagctag gtaaaccccg 11760
gctgccgcct gagcaagtgc cgtgaatccg gagtgatgca atggggttac tgtggagtaa 11820
aattagccag ctgttcgtgg acgccttcac tgagttcctt gttagtgtgg ttgatattgt 11880
cattttcctt gccatactgt ttgggttcac cgtcgcagga tggttactgg tctttcttct 11940
cagagtggtt tgctccgcgc ttctccgttc gcgctctgcc attcactctc ccgaactatc 12000
gaaggtccta tgaaagcttg ctacccaatt gcagaccgga tgtcccacaa tttgcattca 12060
agcacccatt gggcatactt tggcacatgc gagtctccca cctaattgat gaaatggtct 12120
ctcgtcgcat ttaccggacc atggaacact caagtcaagc ggcctggaag caggtagtta 12180
gtgaggccac cctcacaaag ctgtcagggc ttgatatagt tactcatttc caacacctgg 12240
ccgcagtgga ggcggattct tgccgtttcc tcagctcacg acttgtgatg ctaaagaatc 12300
ttgccgttgg caatgtgagc ctacagtata acaccacgtt ggaccatgtt gagctcatct 12360
tccctacgcc aggtacgagg cccaagttga ccgatttcag acaatggctc atcagtgtgc 12420
acgcttccat tttttcctct gtggcttcat ctgttacctt gttcatagtg ttttggcttc 12480
gaattccagc cgtacgctat gtttttggtt tccattggcc cacggcaaca catcattcga 12540
gctaaccatc aactacacca tatgtatgcc ctgctctacc agccaagcgg ctagccaaag 12600
actcgagccc ggtcgtaaca tgtggtgcag aatagggcac gacaggtgtg aggaacgtga 12660
ccatgatgag ttgtcaatgt ccattccgtc agggtacgag aacctcaaac ttgagggtta 12720
ttatgcttgg ctggcctttt tgtccttttc ctacgcggcc caatttcatc cggagttgtt 12780
cggaatagga aacgtgtcgc gcgtctttgt ggacaagcga caccagttca tttgcgccga 12840
gcatgatgga caaaattcaa ccatatctac cggacacaac atctccgcat tatatgcggt 12900
gtattaccat caccaaatag acgggggcaa ttggttccat ttggaatggc tgcggccatt 12960
cttttcctcc tggctggtgc tcaatatctc atggtttctg aggcgttcgc ctgtaagccc 13020
tgtttctcga cgcatctatc agatattaag accaacacga ccgcggctgc cggtttcatg 13080
gtccttcagg acatcaattg tctccgacct cacggggtct caacagcgca agagaacatt 13140
cccttcggaa agccgtccca atgtcgcgag gctgtcggta ttccccagta cattacgata 13200
acggctaatg tgaccgatga atcgtatttg tacaacgcgg acttgctgat gctttctgcg 13260

-continued

```
tgccttttct acgcttcaga aatgagcgaa aagggcttca aagttatctt tgggaacgtc  13320
tctggcgttg tttctgcttg tgtcaatttt acagattatg tggctcatgt aatccaacat  13380
acccagcagc atcatctggt gattgatcac attcggttgc tgcatttcct gacaccatca  13440
acaatgaggt gggctacaac cattgcttgt ttgttcgcca ttctcttggc gatatgagat  13500
gttctcacaa attggagtgt ttcttgactc ctcactcttg cttctggtgg cttttttgc  13560
tgtgtaccgg cttgtcttgg tcctttgtcg atggcaacga cagcagctcg acataccaat  13620
acatatataa tttgacgata tgcgagctga atgggaccga atcgttgtcc agccattttg  13680
actgggcagt cgagaccttt gtgctttacc cggttgccac tcatatcctt tcactgggtt  13740
ttctcacaac aagccatttt tttgatgcgc tcggtctcgg cgctgtgtcc actacaggat  13800
ttgttggcgg gcggtatgta ctcagcagcg tgtacggcgc ttgtgctttc gcagcgctcg  13860
tatgttttgt catccgcgct gctaaaaatt gcatggcttg ccgttatgcc cgtacccggt  13920
tcaccaactt cattgtggac gaccggggga ggatccatcg atggaagtct ccaatagtgg  13980
tagagaaatt gggcaaagct gaagtcggtg gcgacctcgt caccatcaaa catgtcgtcc  14040
tcgaaggggt taaagctcaa cccttgacga ggacttcggc tgagcaatgg gaagcctaga  14100
cgatttttgc aacgatccta ccgccgcaca aaagcttgtg ctagccttta gcatcacata  14160
tacacctata atgatatacg cccttaaggt gtcacgcggc cgcctcctgg ggctattgca  14220
catcttgata ttcctgaact gttcctttac attcggatac atgacatatg tgcattttca  14280
atccaccaac cgtgtcgcat ttactctggg ggccgttgtc gcccttctgt ggggtgttta  14340
cagcttcaca gagtcatgga agttcattac ttccagatgc agattgtgtt gcctaggccg  14400
gcaatacatt ctggcccctg cccatcacgt agaaagtgct gcaggtctcc attcaatccc  14460
agcgtctggt aaccgagcat acgctgtgag aaagcccgga ctaacatcag tgaacggcac  14520
tctagtacca ggacttcgga gcctcgtgct gggcggcaaa cgagctgtta aacgaggagt  14580
ggttaacctc gtcaagtatg gccggtaaaa atcagagcca gaagaaaaag aagaatacag  14640
ctccgatggg gaatggccag ccagtcaatc aactgtgcca gttgctgggt gcaatgataa  14700
agtcccagcg ccagcaacct aggggaggac aggcaaaaaa aagaaagcct gagaagccac  14760
attttcccct agctgctgaa gatgacattc ggcaccacct cacccagacc gaacgttccc  14820
tctgcttgca atcgatccag acggctttta accaaggcgc aggaactgcg tcgctttcat  14880
ccagcgggaa ggtcagtttt caggttgagt tcatgctgcc ggttgctcat acagtgcgcc  14940
tgattcgcgt gacttctaca tccgccagtc agggtgcaaa ttaatttgac agtcaggtga  15000
atggccgcga ttgacgtgtg gcctctaagt cacctattca attagggcga tcacatgggg  15060
gtcaaactta atcaggcagg aaccatgtga ccgaaattaa aaaaaaaaaa aaaaaaaaaa  15120
aaaggccggc atggtcccag cctcctcgct ggcgccggct gggcaacatt ccgaggggac  15180
cgtcccctcg gtaatggcga atgggactct agagcccttc cggctggctg gtttattgct  15240
gataaatctg gagccggtga gcgtgggtct cgcggtatca ttgcagcact ggggccagat  15300
ggtaagccct cccgtatcgt agttatctac acgacgggga gtcaggcaac tatggatgaa  15360
cgaaatagac agatcgctga gataggtgcc tcactgatta agcattggta actgtcagac  15420
caagtttact catatatact ttagattgat ttaaaacttc atttttaatt taaaaggatc  15480
taggtgaaga tcctttttga taatctcatg accaaaatcc cttaacgtga gttttcgttc  15540
cactgagcgt cagacccctt aataagatga tcttcttgag atcgttttgg tctgcgcgta  15600
atctcttgct ctgaaaacga aaaaaccgcc ttgcagggcg gtttttcgaa ggttctctga  15660
```

gctaccaact ctttgaaccg aggtaactgg cttggaggag cgcagtcacc aaaacttgtc 15720
ctttcagttt agccttaacc ggcgcatgac ttcaagacta actcctctaa atcaattacc 15780
agtggctgct gccagtggtg cttttgcatg tctttccggg ttggactcaa gacgatagtt 15840
accggataag gcgcagcggt cggactgaac ggggggttcg tgcatacagt ccagcttgga 15900
gcgaactgcc tacccggaac tgagtgtcag gcgtggaatg agacaaacgc ggccataaca 15960
gcggaatgac accggtaaac cgaaaggcag gaacaggaga gcgcacgagg gagccgccag 16020
gggaaacgc ctggtatctt tatagtcctg tcgggtttcg ccaccactga tttgagcgtc 16080
agatttcgtg atgcttgtca gggggcgga gcctatggaa aaacggcttt gccgcggccc 16140
tctcacttcc ctgttaagta tcttcctggc atcttccagg aaatctccgc cccgttcgta 16200
agccatttcc gctcgccgca gtcgaacgac cgagcgtagc gagtcagtga gcgaggaagc 16260
ggaatatatc ctgtatcaca tattctgctg acgcaccggt gcagcctttt ttctcctgcc 16320
acatgaagca cttcactgac accctcatca gtgccaacat agtaagccag tatacactcc 16380
gctagcgctg aggtctgcct cgtgaagaag gtgttgctga ctcataccag gcctgaatcg 16440
ccccatcatc cagccagaaa gtgagggagc cacggttgat gagagctttg ttgtaggtgg 16500
accagttggt gattttgaac ttttgctttg ccacggaacg gtctgcgttg tcgggaagat 16560
gcgtgatctg atccttcaac tcagcaaaag ttcgatttat tcaacaaagc cacgttgtgt 16620
ctcaaaatct ctgatgttac attgcacaag ataaaaatat atcatcatga acaataaaac 16680
tgtctgctta cataaacagt aatacaaggg gtgttatgag ccatattcaa cgggaaacgt 16740
cttgctcgag gccgcgatta aattccaaca tggatgctga tttatatggg tataaatggg 16800
ctcgcgataa tgtcgggcaa tcaggtgcga caatctatcg attgtatggg aagcccgatg 16860
cgccagagtt gtttctgaaa catggcaaag gtagcgttgc caatgatgtt acagatgaga 16920
tggtcagact aaactggctg acggaattta tgcctcttcc gaccatcaag cattttatcc 16980
gtactcctga tgatgcatgg ttactcacca ctgcgatccc cgggaaaaca gcattccagg 17040
tattagaaga atatcctgat tcaggtgaaa atattgttga tgcgctggca gtgttcctgc 17100
gccggttgca ttcgattcct gtttgtaatt gtccttttaa cagcgatcgc gtatttcgtc 17160
tcgctcaggc gcaatcacga atgaataacg gtttggttga tgcgagtgat tttgatgacg 17220
agcgtaatgg ctggcctgtt gaacaagtct ggaaagaaat gcataagctt ttgccattct 17280
caccggattc agtcgtcact catggtgatt tctcacttga taaccttatt tttgacgagg 17340
ggaaattaat aggttgtatt gatgttggac gagtcggaat cgcagaccga taccaggatc 17400
ttgccatcct atggaactgc ctcggtgagt tttctccttc attacagaaa cggctttttc 17460
aaaaatatgg tattgataat cctgatatga ataaattgca gtttcatttg atgctcgatg 17520
agtttttcta atcagaattg gttaattggt tgtaacactg gcagagcatt acgctgactt 17580
gacgggacgg cggctttgtt gaataaatcg aacttttgct gagttgaagg atcagatcac 17640
gcatcttccc gacaacgcag accgttccgt ggcaaagcaa aagttcaaaa tcaccaactg 17700
gtccacctac aacaaagctc tcatcaaccg tggctccctc actttctggc tggatgatgg 17760
ggcgattcag gcctggtatg agtcagcaac accttcttca cgaggcagac ctcagcgctc 17820
aaagatgcag gggtaaaagc taaccgcatc tttaccgaca aggcatccgg cagttcaaca 17880
gatcgggaag ggctggattt gctgaggatg aaggtggagg aaggtgatgt cattctggtg 17940
aagaagctcg accgtcttgg ccgcgacacc gccgacatga tccaactgat aaaagagttt 18000

-continued gatgctcagg gtgtagcggt tcggtttatt gacgacggga tcagtaccga cggtgatatg 18060
gggcaaatgg tggtcaccat cctgtcggct gtggcacagg ctgaacgccg gagtcggctg 18120
tggcacaggc tgaacgccgg aggatccggc gcgccatgca ttagttatta atagtaatca 18180
attacggggt cattagttca tagcccatat atggagttcc gcgttacata acttacggta 18240
aatggcccgc ctggctgacc gcccaacgac ccccgcccat tgacgtcaat aatgacgtat 18300
gttcccatag taacgccaat agggactttc cattgacgtc aatgggtgga gtatttacgg 18360
taaactgccc acttggcagt acatcaagtg tatcatatgc caagtacgcc ccctattgac 18420
gtcaatgacg gtaaatggcc cgcctggcat tatgcccagt acatgacctt atgggacttt 18480
cctacttggc agtacatcta cgtattagtc atcgctatta ccatggtgat gcggttttgg 18540
cagtacatca atgggcgtgg atagcggttt gactcacggg gatttccaag tctccacccc 18600
attgacgtca atgggagttt gttttggcac caaaatcaac gggactttcc aaaatgtcgt 18660
aacaactccg ccccattgac gcaaatgggc ggtaggcgtg tacggtggga ggtctatata 18720
agcagagctg gtttagtatt taaat 18745

<210> SEQ ID NO 224
<211> LENGTH: 18745
<212> TYPE: DNA
<213> ORGANISM: Artificial Sequence
<220> FEATURE:
<223> OTHER INFORMATION: Clone pVAC 5.1 (full)

<400> SEQUENCE: 224
atgatgtgta gggtactccc cctacataca cgacacttct agtgtttgtg tgccttggag 60
gcgtgggtat agccccgccc cacccccttgg ccccctgttct agcccaacag gtatccttct 120
ctctcggggc gagcgcgccg cctgctgctc ccttgcagcg ggaaggacct cccgagtatt 180
tccggagagc acctgcttta cgggatctcc accctttaac catgtctggg acgttctccc 240
ggtgcatgtg caccccggct gcccgggtat tttggaacgc cggccaagtc ttttgcacac 300
ggtgtctcag tgcgcggtct cttctccctc cggagcttca ggaaactgac ctcgctgcaa 360
ttggcttgtt ttacaagcct aaagacaagc ttcactggaa agtccctatc ggcatccctc 420
aggtggagtg cactccatcc gggtgctgtt ggctctcagc catcttccca ttggcgcgca 480
tgacctccgg caatcacaac ttcctccaac gacttgtgag ggttgccgat gtgttgtacc 540
gtgatggttg cttggctcct cgacaccttc gtgaactcca agtttacgag cgcggctgca 600
actggtaccc gatcacgggg cccgtgcccg ggatgggttt gttcgcaaac tccatgcacg 660
tatccgacca gccgttccct ggtgccaccc atgtgttgac gaactcgccg ttgcctcaac 720
aggcttgtcg gcagccgttc tgtccatttg aggaggctca ttctagtgtg tacaggtgga 780
aaagatttgt ggttttcacg gattcctctc ccaacggtcg atctcgcatg atgtggacgc 840
cggaatccga tgattcagcc gccttggagg tattaccgcc tgaattagaa cgtcaggtcg 900
aaatcctcat tcggagtttt cctgctcatc accctgtcaa cctggccgac tgggagctca 960
ctgagtcccc tgagaacggt tttccttca acacgtctta ttcttgcggt caccttgtcc 1020
aaaaccccga cgtgtttgat ggcaagtgct ggctttcctg ctttttgggc cagtcggccg 1080
aagtgcgccg ccatgaggaa catttagctg acgccctcgg ttaccagacc aagtggggcg 1140
tgcctggcaa gtacctccag cgcaggcttc aggttcgcgg cattcgtgct gtagttgatc 1200
ctgatggccc cattcacgtc gaagcgctgt cttgcccccg gtcttggatc aggcacctga 1260
cttttgatga taatgtcacc ccaggatttg ttcgccttac gtcccttcgc attgtgccaa 1320

-continued

```
acaccgagcc tactgcttcc cggatcttcc ggtttggagc gcataagtgg tatggcgctg   1380
ccggcaaacg agctcgtgct aagcgtgccg ctaaaagtga gaaaatttcg gcccctaccc   1440
ccaaggttgc tcagccggtc cccacctgcg aaattaccac ctattctcca ccgacagacg   1500
ggtcttgtgg ttggcatgtt cttgccgcca taatgaaccg gatgatgaat ggtgacttca   1560
cgtcccctct gactcagtac aacagaccag aggatgactg ggcttctgat tatgaccttg   1620
ctcaggcgat ccaatgtctg caactgcccg ctaccgtagt tcggaatcgc gcctgtccta   1680
acgccaagta ccttataaaa cttaatggag ttcattggga ggtagaggtg aggcctggaa   1740
tggcccctcg ttccctttcc cgtgagtgtg tggttggcgt ctgttctgaa ggctgtatcg   1800
caccgcctta cccacaagac gggctgccta aacgtgcact tgaggccttg gcgtctgctt   1860
acagactacc ctccgactgt gttggttctg gtattgctga ctttcttgct aacccgcccc   1920
ctcaggagtt ttggaccctt gacaaaatgt tgacctcccc gtcaccagaa cggtccggct   1980
tctctagctt gtataaatta ctattggagg ttgttccgca gaaatgcggt gccacggaag   2040
gggctttcgt ctatgctgtt gagaggatgt tgaaggattg tccgagctcc aaacaggcca   2100
tggcccttct ggcaaaaatt aaagtcccat cctcaaaggc cccgtctgtg tctctggacg   2160
agtgcttccc tacggatgtt ccagcggact ccgagccagc gtttcaggaa aggccccaaa   2220
gttctggtgc tgctgttgtc ctgtgttcac cggacataaa agagttcgag gaagcagccc   2280
cagaagaagt tcaagagggt ggccacaagg ccgtccactc tgcactcctt gccgagggtc   2340
ttaacaatga gcaggtacag gtggttgccg gtgcgcaact aaagctcggc agttgtggct   2400
tggcagtcgg gaatactcat ggaggtgttc cggtttcagc tagtccaatt aacctggcag   2460
acgggaattt gccccccctcg gactccatga aaggaaacat gcccaatggc tgggaggacg   2520
aaccactgga tttgtcccaa tcagcactag caaccacaac gacccttgtg agagagcaaa   2580
cacccgacaa tctaggttct ggcgccggtg ccctccctgt caccattcga gaatttgtcc   2640
cgacaaggcc tataccccgt catgttgagc actgcggcac ggagtcgggc gacagcagtt   2700
cgcctctgga tctgtccgat gcgcaaaccc cggaccagcc tttaaatcta tccctggccg   2760
cttggccagt gagggccacc gcgtctgacc ccggctgggt ccacggtagg cgtgagcctg   2820
tttttgtaaa gcctcggggt gctttctctg atggcgattc agtccttcag ttcggggagc   2880
tttccgaatc cagctctatc atcgagattg accggacaaa agatgctcca gtggttgatg   2940
cccccgtcga cttgacggtt tcgaacgaag ctctctctgg gatcgatcct tttgaattta   3000
ccgaactcaa gcgcccgcgt ttctccgctc aagccttaat tgaccgaggc ggcccactag   3060
ccgatgtcca tgcaaaaata aagaaccggg tatatgaaca gtgcctccag gcttgtgagc   3120
ctggcagtcg tgcaacccca gccaccaggg agtggctcga caaaatgtgg gatagggtgg   3180
acatgaagac ttggcgctgc acctcgcagt tccaagctgg tcacattctt gcgtccctca   3240
aattcctccc cgacatgatt caagacacac cgcctcctgt tcccaggaag agccgggcta   3300
gtgataatgc cggcctgaag caactggtgg cgcagtggga cagaaaattg agtgtaaccc   3360
ccccccctaaa accggttggg ccggcgcttg gccaaaccgt ccctccgcct acggatattc   3420
agcaagaaga tgtcaccccc tccgataggc cacctcatgt gccggatctt cctagtcgag   3480
tgagcacggg tgggagttgg aaaggcctta tgctttccgg cacccgtctc gcggggtcta   3540
ttagtcagca cctcatgaca tgggtttttg aagttttctc ccatctccca gcttttatgc   3600
tcacactttt ctcgccacgg ggctctatgg ctccaggtga ttggctattt gcaggtgttg   3660
```

-continued

```
ttttacttgc tctcctgctc tgtcgttctt acccagtact cgggtgcctt cccttattgg   3720
gtgtcttttc tggttctttg cggcgtgttc gtctgggtgt tttggttct tggatggctt   3780
ttgctgtatt tttattctcg actccatccg acccagtcgg ttcttcttgt gaccacgatt   3840
cgccggagtg tcatgctgag cttttggctc ttgagcagcg ccaactttgg gaacctgtgc   3900
ggggccttgt ggtcggcccc tcgggcctct tatgtgtcat tcttggcaag ttactcggtg   3960
ggtcacgtta tctctggcat gtttttcttac gtttatgcat gcttgcggat ttggcccttt  4020
ctcttgttta tgtggtgtcc caggggcgtt gtcacaagtg ttggggaaag tgtataagga   4080
cagctcctgc ggaggtggct ctcaatgtgt tccctttctt gcgcgctacc cgtgcctctc   4140
ttgtgtcctt gtgcgatcga ttccaagcgc caaaaggggt tgatcctgtg cacttggcaa   4200
caggttggcg cgggtgctgg cgcggtgaga gccccattca tcaaccgcac caaaagccca   4260
tagcttatgc caatttggat gaaaagaaaa tatctgccca aacggtggtt gctgtcccgt   4320
atgatcccag tcaggccatc aaatgcctga aagttctgca ggcgggaggg gctatcgtgg   4380
accagcccac acctgaggtc gtccgtgtgt ccgagatccc tttctcagcc ccattttttc   4440
caaaggttcc agtcaaccca gattgcaggg ttgtggtaga ttcggacact tttgtggctg   4500
cagttcgctg cggttactcg acggctcaac tggtcttagg ccggggcaac tttgccaagt   4560
taaatcagat cccctccagg aactctgtct ccaccaaaac gactggtggg gcctcttaca   4620
cccttgctgt ggctcaagtg tctgtgtgga ctcttgttca tttcatcctc ggtctttggt   4680
tcacgtcacc tcaagtgtgt ggccgaggaa cctctgaccc atggtgttca aatccttttt   4740
catatcctac ctatggcccc ggaatagtgt gctcctctcg actttgtgtg tctgccgacg   4800
gagtcactct gccattgttc tcagcagtgg cacaactctc cggtagagag gtggggattt   4860
tcattttggt gctcgtctcc ttgactgctc tggcccaccg tatggctctt aaggcagaca   4920
tgttagtggt cttttcggct tttgtgcct acgcctggcc catgagctcc tggttaatct    4980
gcttctttcc tatattcttg aagtgggtca cccttcaccc tctcactatg ctttgggtgc   5040
actcattctt ggtgttttgt ctgccagcag ccggcgtcct ctcactaggg ataaccggcc   5100
ttctctgggc agttggccgc tttacccagg tcgccggaat tattacacct tatgacatcc   5160
accagtacac ctctgggcca cgtggtgcag ccgctgtggc cacggcccca gaaggcactt   5220
acatggccgc cgtccggaga gctgccttaa ctggacgaac cctcatcttc acaccatctg   5280
cggttggatc ccttcttgaa ggtgctttca ggacccataa accctgcctt aacaccgtga   5340
atgttgtagg ctcttccctt ggttccgggg gggttttcac cattgatggc agaagaactg   5400
ttgtcactgc tgcccatgtg ttgaacggcg acacagctag agtcaccggc gactcctaca   5460
accgcatgca cactttcaag accaatggtg attatgcctg gtcccatgct gatgactggc   5520
ggggcgttgc ccctgtggtc aaggtcgcga aggggtaccg cggtcgtgcc tactggcaaa   5580
catcaactgg tgtcgaaccc ggtattgttg gggaagggtt cgccttctgt tttaccaact   5640
gtggcgattc ggggtcacct gtcatctcag aatctggtga tcttgttgga atccacaccg   5700
gttcaaacaa actcggttct ggtcttgtga caacccctga aggggagacc tgctccatca   5760
aagaaaccaa gctctctgac ctttccaggt attttgcagg cccaagcgtc cctcttgggg   5820
atattaaatt gagtccggcc atcatccctg atgtaacatc cattccgagt gacttggcat   5880
cgctcctagc ctccgtccct gtaatggaag gcggcctctc gactgtccaa cttttgtgtg   5940
tctttttcct tctctggcgt atgatgggcc atgcctggac acccattgtt gccgtgggct   6000
tctttttgct gaatgaaatt cttccagcag ttttggtccg agccgtgttt tcttttgcgc   6060
```

```
tctttgtgct tgcatgggcc accccctggt ctgcacaggt gttgatgatc agactcctca   6120
cggcagctct caaccgcaac aggctttctc tggcgttcta cgcactcggg ggtgtcgtcg   6180
gtttggctgc tgaaattggg acctttgctg gtagattgtc tgaattgtct caagctcttt   6240
cgacatactg cttcttacct agggttcttg ctgtgactag ttatgttccc accatcatca   6300
ttggtggact ccataccctt ggtgtgatct tgtggctatt caaataccgg tgcctccaca   6360
acatgttagt tggtgatggg agtttttcaa gtgccttttt cctacggtat tttgcagagg   6420
gtaatctcag aaaaggtgtt tcacagtcct gtggcatgaa taacgagtcc ctgacagctg   6480
ctttagcttg caagttgtca caggctgacc ttgatttttt gtccagcttg acgaacttca   6540
agtgctttgt atctgcttca aacatgaaag atgctgctgg ccagtacatt gaggcagcgt   6600
atgccaaggc cctgcgccga gagttggcct ccctagtcca ggttgacaaa atgaaaggag   6660
ttttgtccaa gctcgaggcc tttgctgaaa cagccacccc gtcccttgac acaggtgacg   6720
tgattgtcct gcttgggcaa catcctcacg gatccatcct cgatattaat gtggggactg   6780
aaaggaaaac tgtgtctgtt caagagactc ggagcctagg cggctccaaa ttcagtgtct   6840
gcactgtcgt gtccaacaca cccgtggacg ccttggccgg cattccactt cagacaccaa   6900
ccccgctttt tgagaatggc ccgcgtcatc gcggtgagga agatgatctc aaagttgaga   6960
ggatgaagaa acattgtgtg tccctcggct tccacaacat caatggcaaa gtttactgta   7020
aagtttggga caagtccacc ggtgacacct tttacacgga tgattcccgg tacacccaag   7080
accatgcttt tcaggacagg tcagctgact atagagacag ggactatgag ggtgtgcaaa   7140
ccgcccccca acagggattt gatccaaaat ctgaaacccc tgttggcact gttgtaatcg   7200
gcggtattac gtataatagg tatctggtca aaggcaagga ggttctggtt cccaaacctg   7260
acaactgcct tgaagccgcc aagctgtccc ttgagcaagc acttgctggg atgggccaaa   7320
cttgcgacct tacagttgca gaggtggaaa agctaaagcg catcatcagt caactccaag   7380
gtttgaccac tgaacaggct ttaaactgct agccgccagc ggcttgaccc gctgtggccg   7440
cggcggcttg gttgtaactg aaacggcggt aaaaattata aaataccaca gcagaacttt   7500
cactttaggc cctttagacc taaaagtcac ttctgaggta gaggtgaaga aatcaactga   7560
gcagggccac gccgttgtgg caaacctatg ttctggtgtc gtattgatga gacctcaccc   7620
accgtccctt gttgacgtcc ttctgaaacc cggacttgac acaacacccg acattcaacc   7680
ggggcatggg gccgggaata tgggcgtgga cggttctatt tgggattttg aaaccgcacc   7740
cacaaaggca gaactcgagt tgtccaagca aataattcaa gcatgtgaag ttaggcgcgg   7800
agacgccccg aacctccaac tcccctacaa gctctatcct gtcagagggg atcctgagcg   7860
gcataaaggc cgccttatca acaccaggtt tggagacttg ccttacaaaa ctcctcaaga   7920
caccaagtcc gctatccatg cggcttgttg cctgcacccc aacggggccc ctgtgtctga   7980
tggtaaatcc acactaggca ccactcttca acatggtttc gagctttatg ttcccacagt   8040
gccctatagt gtcatggagt accttgattc acgccctgac acccctccca tgttcactaa   8100
acatggcact tccaaggctg ctgcagaaga cctccaaaaa tatgacctat ccacccaagg   8160
atttgtcctg cctggggtcc tacgcctagt gcgcagattc atctttggcc atgttggtaa   8220
ggcaccgcca ttgttcctcc catcaaccta tcccgccaag aactccatgg cagggattaa   8280
tggccagaga ttcccaacaa aggacgtcca gagcatacct gaaattgatg aaatgtgtgc   8340
ccgcgccgtc aaggagaatt ggcaaaccgt gacaccttgt actctcaaga aacagtactg   8400
```

-continued

```
ttccaagccc aaaaccagga ccatcctggg caccaacaac tttattgcct tggctcacag   8460
atcggcgctc agtggcgtca cccaggcatt catgaagaag gcttggaagt ccccaattgc   8520
cttggggaaa aacaagttca aggagctgca ttgtactgtc gccggcaggt gtcttgaggc   8580
tgacttggcc tcctgtgatc gcagcacccc cgccattgta agatggtttg ttgccaacct   8640
cctgtatgaa cttgcaggat gtgaagagta cttgcctagc tatgtgctta actgctgcca   8700
tgaccttgtg gcaacacagg atggtgcctt cacaaaacgc ggtggcctgt cgtccgggga   8760
ccccgtcacc agtgtgtcca ataccgtata ttcactggta atctatgccc agcacatggt   8820
attgtcagcc ttgaaaatgg gtcatgaaat tggtcttaag ttcctcgagg agcagctcaa   8880
attcgaggac ctccttgaaa ttcagcctat gttagtatac tctgacgacc ttgtcttgta   8940
cgctgaaaga cccacttttc ccaattacca ttggtgggtc gagcaccttg acctgatgct   9000
gggtttcaaa acggacccaa agaaaactgt cataactgat aaacccagct tcctcggctg   9060
caggattgag gcagggcgac agttagtccc caatcgcgac cgcatcctgg ctgcccttgc   9120
atatcacatg aaggcgcaga acgcctcaga atattatgcg tctgctgccg caatcctgat   9180
ggattcgtgt gcttgcattg accatgaccc tgagtggtat gaggacctca tctgtggtat   9240
tgcccggtgt gctcgccaag atggctatag tttcccgggc ccggcatttt tcatgtccat   9300
gtgggagaaa ctgaaaagtc ataatgaagg gaaaaaattc cgccactgcg gcatctgcga   9360
cgccaaggcc gaccatgcgt ccgcctgtgg actcgatttg tgcttgttcc actcgcattt   9420
tcatcagcac tgccctgtca ctctgagctg cggccatcat gccggttcta aggaatgtcc   9480
gcagtgtcag tcaccggttg gggctggtag atctcctctc gatgccgtgc taaaacaaat   9540
tccgtacaaa cctcctcgta ctgtcatcat gaaggtggat aataaaacaa cggcccttga   9600
tccggggagg tatcagtccc gtcgaggtct cgttgcagtc aagaggggta ttgcaggcaa   9660
tgaagttgac cttgctaatg gagactacca ggtggtgcct cttttgccga cttgcaaaga   9720
cataaacatg gtgaaggtgg cttgtaatgt gctactcagc aagttcatag tagggccacc   9780
aggttccgga aagaccacct ggttgctgag tcaagtccag gacgatgatg tcatttatac   9840
acccacccat cagactatgt ttgatatagt cagtgctctc aaagtttgca ggtattccat   9900
tccaggggct tcaggactcc ctttcccacc acctgccagg tccgggccgt gggtcaggct   9960
tgttgccagc gggcacgtcc ctggccgagt atcatacctc gatgaggctg gatattgtaa  10020
tcatctggac attctcagac tgctttccaa aacacccctt gtgtgtttag gtgaccttca  10080
gcaactccac cctgtcggct ttgattccta ctgttatgtg tttgatcaga tgcctcagaa  10140
gcagctgacc actatttaca gatttggctc caacatctgc gcagctatcc agccttgtta  10200
cagggagaaa cttgaatcca aggccaggaa caccaggata gtttttacca cccgacctgt  10260
agctttcggg caggtgctga caccatacca caaagatcgc atcggctcag cgataaccat  10320
agattcatct caggggggcca cctttgacat tgtgacattg catctaccat cgccaaagtc  10380
cctaaataaa tcccgagcac ttgtagccat cactcgggca agacacgggt tgttcatcta  10440
tgaccctcat aatcagctcc aggagttttt caacctaact cctgagcgca ctgattgtaa  10500
ccttgtgttt aaccgtgggg atgagctggt agttctggac gcggataatg cagtcacaac  10560
tgtggcgaag gccctagaga cgggtccatc tcgatttcga gtatcagacc caaggtgcga  10620
gtctctcttg gccgcttgct cggccagcct ggagggaagc tgcatgccac taccgcaagt  10680
ggcacataac ctggggtttt acttttcccc agatagtcca gcattcgcgc ctctgccaaa  10740
agaattggca ccacattggc cggtggttac ccatcagaat aaccgggcgt ggcctgaccg  10800
```

```
acttgttgct agtatgcgcc caattgatgc ccgttatagc aagccaatgg ttggtgcagg  10860
gtacgcggtc gggccgtcca cttttcttgg cactcctggt gtggtatcat actatctgac  10920
actgtacatc aggggtgagc cccaggcctt accagaaaca ctcgtgtcaa cagggcgcat  10980
agccacagat tgtcgggaat atctcgacgc cgctgaggaa gaggcagcaa aagaactccc  11040
tcacgcattc attggcgatg tcaaaggtac cacggttggg gggtgtcatc acatcacatc  11100
aaaataccta cctaggtccc tgcctaagga ctctgttgcc gtagttggag taagttcgcc  11160
cggcagggcc gctaaagccg tgtgcactct caccgatgtt tacctccccg agctccggcc  11220
atatctgcaa cctgagacgg catcaaaatg ctggaaactc aaattagact ttagagatgt  11280
ccgactaatg gtctggaaag gagccaccgc ctacttccag ctggaagggc ttacatggtc  11340
ggcgctgccc gactatgcca ggtttattca gctgcctaag gatgccgttg tgtacattga  11400
tccgtgcata ggaccggcaa cagccaaccg taaggtcgtg cggaccacag actggcgggc  11460
tgacctggca gtgacaccgt atgattacgg tgcccagaac attttgacaa cagcctggtt  11520
cgaggacctc gggccgcagt ggaagatttt ggggttgcag ccctttaggc gatcatttgg  11580
ctttgaaaac actgaggatt gggcaatcct tgcacgccgt atgaatgacg gcaaggacta  11640
cactgactat aactggaact gtgttcgaga acgcccacac gccatctacg ggcgcgctcg  11700
tgaccatacg tatcattttg cccccggcac agaattgcag gtagagctag gtaaaccccg  11760
gctgccgcct gagcaagtgc cgtgaatccg gagtgatgca atggggttac tgtggagtaa  11820
aattagccag ctgttcgtgg acgccttcac tgagttcctt gttagtgtgg ttgatattgt  11880
cattttcctt gccatactgt ttgggttcac cgtcgcagga tggttactgg tctttcttct  11940
cagagtggtt tgctccgcgc ttctccgttc gcgctctgcc attcactctc ccgaactatc  12000
gaaggtccta tgaaagcttg ctacccaatt gcagaccgga tgtcccacaa tttgcattca  12060
agcacccatt gggcatactt tggcacatgc gagtctccca cctaattgat gaaatggtct  12120
ctcgtcgcat ttaccggacc atggaacact caagtcaagc ggcctggaag caggtagtta  12180
gtgaggccac cctcacaaag ctgtcagggc ttgatatagt tactcatttc caacacctgg  12240
ccgcagtgga ggcggattct tgccgtttcc tcagctcacg acttgtgatg ctaaagaatc  12300
ttgccgttgg caatgtgagc ctacagtata acaccacgtt ggaccatgtt gagctcatct  12360
tccctacgcc aggtacgagg cccaagttga ccgatttcag acaatggctc atcagtgtgc  12420
acgcttccat tttttcctct gtggcttcat ctgttacctt gttcatagtg ttttggcttc  12480
gaattccagc cgtacgctat gtttttggtt tccattggcc cacggcaaca catcattcga  12540
gctaaccatc aactacacca tatgtatgcc ctgctctacc agccaagcgg ctagccaaag  12600
actcgagccc ggtcgtaaca tgtggtgcag aatagggcac gacaggtgtg aggaacgtga  12660
ccatgatgag ttgtcaatgt ccattccgtc agggtacgag aacctcaaac ttgagggtta  12720
ttatgcttgg ctggcctttt tgtccttttc ctacgcggcc caatttcatc cggagttgtt  12780
cggaatagga aacgtgtcgc gcgtctttgt ggacaagcga caccagttca tttgcgccga  12840
gcatgatgga caaaattcaa ccatatctac cggacacaac atctccgcat tatatgcggt  12900
gtattaccat caccaaatag acgggggcaa ttggttccac ttggaatggc tgcggccatt  12960
cttttcctcc tggctggtgc tcaatatctc atggtttctg aggcgttcgc ctgtaagccc  13020
tgtttctcga cgcatctatc agatattaag accaacacga ccgcggctgc cggtttcatg  13080
gtccttcagg acatcaattg tctccgacct cacggggtct caacagcgca agagaccatt  13140
```

-continued

```
tccttcggaa agccgtccca atgtcgcgag gccgtcggta ttccccagta cattacgata  13200
acggctaatg tgaccgatga atcgtatttg tacaacgcgg acttgctgat gctttctgcg  13260
tgccttttct acgcttcaga aatgagcgaa aagggcttca aagttatctt tgggaacgtt  13320
tctggcgttg tttctgcttg tgtcaatttt acagattatg tggctcatgt aatccaacat  13380
acccagcagc atcatctggt gattgatcac attcggttgc tgcatttcct gacaccatca  13440
acaatgaggt gggctacaac cattgcttgt ttgttcgcca ttctcttggc gatatgagat  13500
gttctcacaa attggagcgt ttcttgactc ctcactcttg cttctggtgg ctttttttgc  13560
tttgtaccgg cttgtcttgg tcctttgtcg atggcaacga cagcagctcg acataccaat  13620
acatatataa tttgacgata tgcgagctga atgggaccga atggttgccc agccattttg  13680
actgggcagt cgagaccttt gtgctttacc cggttgccac tcatatcctt tcactgggtt  13740
ttctcacaac aagccatttt tttgatgcgc tcggtctcgg cgctgtgtcc actacaggat  13800
ttgttggcgg gcggtatgta ctcagcagcg tgtacggcgc ttgtgctttc gcagcgctcg  13860
tatgttttgt catccgcgct gctaaaaatt gcatggcttg ccgttatgcc cgcacccggt  13920
ttaccaactt cattgtggac gaccggggga ggatccatcg atggaagtct ccaatagtgg  13980
tagagaaatt gggcaaagct gaagtcggtg gcgacctcgt caccatcaaa catgtcgtcc  14040
tcgaaggggt taaagctcaa ccccttgacga ggacttcggc tgagcaatgg gaagcctaga  14100
cgatttttgc aacgatccta ccgccgcaca aaagcttgtg ctagccttta gcatcacata  14160
tacacctata atgatatacg cccttaaggt gtcacgcggc cgcctcctgg ggctattgca  14220
catcttgata ttcctgaact gttcctttac attcggatac atgacatatg tgcattttca  14280
atccaccaac cgtgtcgcat ttactctggg ggccgttgtc gcccttctgt ggggtgttta  14340
cagcttcaca gagtcatgga agttcattac ttccagatgc agattgtgtt gcctaggccg  14400
gcaatacatt ctggcccctg cccatcacgt agaaagtgct gcaggtctcc attcaatccc  14460
agcgtctggt aaccgagcat acgctgtgag aaagcccgga ctaacatcag tgaacggcac  14520
tctagtacca ggacttcgga gcctcgtgct gggcggcaaa cgagctgtta aacgaggagt  14580
ggttaacctc gtcaagtatg gccggtaaaa atcagagcca gaagaaaaag aagaatacag  14640
ctccgatggg gaatggccag ccagtcaatc aactgtgcca gttgctgggt gcaatgataa  14700
agtcccagcg ccagcaacct aggggaggac aggcaaaaaa aagaaagcct gagaagccac  14760
attttcccct agctgctgaa gatgacattc ggcaccacct cacccagacc gaacgttccc  14820
tctgcttgca atcgatccag acggctttta accaaggcgc aggaactgcg tcgctttcat  14880
ccagcgggaa ggtcagtttt caggttgagt tcatgctgcc ggttgctcat acagtgcgcc  14940
tgattcgcgt gacttctaca tccgccagtc agggtgcaaa ttaatttgac agtcaggtga  15000
atggccgcga ttgacgtgtg gcctctaagt cacctattca attagggcga tcacatgggg  15060
gtcaaactta atcaggcagg aaccatgtga ccgaaattaa aaaaaaaaaa aaaaaaaaaa  15120
aaaggccggc atggtcccag cctcctcgct ggcgccggct gggcaacatt ccgaggggac  15180
cgtcccctcg gtaatggcga atgggactct agagcccttc cggctggctg gtttattgct  15240
gataaatctg gagccggtga gcgtgggtct cgcggtatca ttgcagcact ggggccagat  15300
ggtaagccct cccgtatcgt agttatctac acgacgggga gtcaggcaac tatggatgaa  15360
cgaaatagac agatcgctga gataggtgcc tcactgatta agcattggta actgtcagac  15420
caagtttact catatatact ttagattgat ttaaaacttc atttttaatt taaaaggatc  15480
taggtgaaga tcctttttga taatctcatg accaaaatcc cttaacgtga gttttcgttc  15540
```

cactgagcgt cagacccctt aataagatga tcttcttgag atcgttttgg tctgcgcgta 15600
atctcttgct ctgaaaacga aaaaaccgcc ttgcagggcg gtttttcgaa ggttctctga 15660
gctaccaact ctttgaaccg aggtaactgg cttggaggag cgcagtcacc aaaacttgtc 15720
ctttcagttt agccttaacc ggcgcatgac ttcaagacta actcctctaa atcaattacc 15780
agtggctgct gccagtggtg cttttgcatg tctttccggg ttggactcaa gacgatagtt 15840
accggataag gcgcagcggt cggactgaac ggggggttcg tgcatacagt ccagcttgga 15900
gcgaactgcc tacccggaac tgagtgtcag gcgtggaatg agacaaacgc ggccataaca 15960
gcggaatgac accggtaaac cgaaaggcag gaacaggaga gcgcacgagg gagccgccag 16020
ggggaaacgc ctggtatctt tatagtcctg tcgggtttcg ccaccactga tttgagcgtc 16080
agatttcgtg atgcttgtca ggggggcgga gcctatggaa aaacggcttt gccgcggccc 16140
tctcacttcc ctgttaagta tcttcctggc atcttccagg aaatctccgc cccgttcgta 16200
agccatttcc gctcgccgca gtcgaacgac cgagcgtagc gagtcagtga gcgaggaagc 16260
ggaatatatc ctgtatcaca tattctgctg acgcaccggt gcagcctttt ttctcctgcc 16320
acatgaagca cttcactgac accctcatca gtgccaacat agtaagccag tatacactcc 16380
gctagcgctg aggtctgcct cgtgaagaag gtgttgctga ctcataccag gcctgaatcg 16440
ccccatcatc cagccagaaa gtgagggagc cacggttgat gagagctttg ttgtaggtgg 16500
accagttggt gattttgaac ttttgctttg ccacggaacg gtctgcgttg tcgggaagat 16560
gcgtgatctg atccttcaac tcagcaaaag ttcgatttat tcaacaaagc cacgttgtgt 16620
ctcaaaatct ctgatgttac attgcacaag ataaaaatat atcatcatga acaataaaac 16680
tgtctgctta cataaacagt aatacaaggg gtgttatgag ccatattcaa cgggaaacgt 16740
cttgctcgag gccgcgatta aattccaaca tggatgctga tttatatggg tataaatggg 16800
ctcgcgataa tgtcgggcaa tcaggtgcga caatctatcg attgtatggg aagcccgatg 16860
cgccagagtt gtttctgaaa catggcaaag gtagcgttgc caatgatgtt acagatgaga 16920
tggtcagact aaactggctg acggaattta tgcctcttcc gaccatcaag cattttatcc 16980
gtactcctga tgatgcatgg ttactcacca ctgcgatccc cgggaaaaca gcattccagg 17040
tattagaaga atatcctgat tcaggtgaaa atattgttga tgcgctggca gtgttcctgc 17100
gccggttgca ttcgattcct gtttgtaatt gtccttttaa cagcgatcgc gtatttcgtc 17160
tcgctcaggc gcaatcacga atgaataacg gtttggttga tgcgagtgat tttgatgacg 17220
agcgtaatgg ctggcctgtt gaacaagtct ggaaagaaat gcataagctt ttgccattct 17280
caccggattc agtcgtcact catggtgatt tctcacttga taaccttatt tttgacgagg 17340
ggaaattaat aggttgtatt gatgttggac gagtcggaat cgcagaccga taccaggatc 17400
ttgccatcct atggaactgc ctcggtgagt tttctccttc attacagaaa cggctttttc 17460
aaaaatatgg tattgataat cctgatatga ataaattgca gtttcatttg atgctcgatg 17520
agtttttcta atcagaattg gttaattggt tgtaacactg gcagagcatt acgctgactt 17580
gacgggacgg cggctttgtt gaataaatcg aacttttgct gagttgaagg atcagatcac 17640
gcatcttccc gacaacgcag accgttccgt ggcaaagcaa aagttcaaaa tcaccaactg 17700
gtccacctac aacaaagctc tcatcaaccg tggctccctc actttctggc tggatgatgg 17760
ggcgattcag gcctggtatg agtcagcaac accttcttca cgaggcagac ctcagcgctc 17820
aaagatgcag ggtaaaagc taaccgcatc tttaccgaca aggcatccgg cagttcaaca 17880
gatcgggaag ggctggattt gctgaggatg aaggtggagg aaggtgatgt cattctggtg 17940
aagaagctcg accgtcttgg ccgcgacacc gccgacatga tccaactgat aaaagagttt 18000
gatgctcagg gtgtagcggt tcggtttatt gacgacggga tcagtaccga cggtgatatg 18060
gggcaaatgg tggtcaccat cctgtcggct gtggcacagg ctgaacgccg gagtcggctg 18120
tggcacaggc tgaacgccgg aggatccggc gcgccatgca ttagttatta atagtaatca 18180
attacggggt cattagttca tagcccatat atggagttcc gcgttacata acttacggta 18240
aatggcccgc ctggctgacc gcccaacgac ccccgcccat tgacgtcaat aatgacgtat 18300
gttcccatag taacgccaat agggactttc cattgacgtc aatgggtgga gtatttacgg 18360
taaactgccc acttggcagt acatcaagtg tatcatatgc caagtacgcc ccctattgac 18420
gtcaatgacg gtaaatggcc cgcctggcat tatgcccagt acatgacctt atgggacttt 18480
cctacttggc agtacatcta cgtattagtc atcgctatta ccatggtgat gcggttttgg 18540
cagtacatca atgggcgtgg atagcggttt gactcacggg gatttccaag tctccacccc 18600
attgacgtca atgggagttt gttttggcac caaaatcaac gggactttcc aaaatgtcgt 18660
aacaactccg ccccattgac gcaaatgggc ggtaggcgtg tacggtggga ggtctatata 18720
agcagagctg gtttagtatt taaat 18745

<210> SEQ ID NO 225
<211> LENGTH: 18745
<212> TYPE: DNA
<213> ORGANISM: Artificial Sequence
<220> FEATURE:
<223> OTHER INFORMATION: Clone pVAC 5.2 (full)

<400> SEQUENCE: 225
atgatgtgta gggtactccc cctacataca cgacacttct agtgtttgtg tgccttggag 60
gcgtgggtat agccccgccc cacccccttgg cccctgttct agcccaacag gtatccttct 120
ctctcggggc gagcgcgccg cctgctgctc ccttgcagcg ggaaggacct cccgagtatt 180
tccggagagc acctgcttta cgggatctcc accctttaac catgtctggg acgttctccc 240
ggtgcatgtg caccccggct gcccgggtat tttggaacgc cggccaagtc ttttgcacac 300
ggtgtctcag tgcgcggtct cttctccctc cggagcttca ggaaactgac ctcgctgcaa 360
ttggcttgtt ttacaagcct aaagacaagc ttcactggaa agtccctatc ggcatccctc 420
aggtggagtg cactccatcc gggtgctgtt ggctctcagc catcttccca ttggcgcgca 480
tgacctccgg caatcacaac ttcctccaac gacttgtgag ggttgccgat gtgttgtacc 540
gtgatggttg cttggctcct cgacaccttc gtgaactcca agtttacgag cgcggctgca 600
actggtaccc gatcacgggg cccgtgcccg ggatgggttt gttcgcaaac tccatgcacg 660
tatccgacca gccgttccct ggtgccaccc atgtgttgac gaactcgccg ttgcctcaac 720
aggcttgtcg gcagccgttc tgtccatttg aggaggctca ttctagtgtg tacaggtgga 780
aaagatttgt ggttttcacg gattcctctc ccaacggtcg atctcgcatg atgtggacgc 840
cggaatccga tgattcagcc gccttggagg tattaccgcc tgaattagaa cgtcaggtcg 900
aaatcctcat tcggagtttt cctgctcatc accctgtcaa cctggccgac tgggagctca 960
ctgagtcccc tgagaacggt ttttccttca acacgtctta ttcttgcggt caccttgtcc 1020
aaaaccccga cgtgtttgat ggcaagtgct ggctttcctg ctttttgggc cagtcggccg 1080
aagtgcgccg ccatgaggaa catttagctg acgccctcgg ttaccagacc aagtggggcg 1140
tgcctggcaa gtacctccag cgcaggcttc aggttcgcgg cattcgtgct gtagttgatc 1200

-continued

```
ctgatggccc cattcacgtc gaagcgctgt cttgcccccg gtcttggatc aggcacctga   1260
cttttgatga taatgtcacc ccaggatttg ttcgccttac gtcccttcgc attgtgccaa   1320
acaccgagcc tactgcttcc cggatcttcc ggtttggagc gcataagtgg tatggcgctg   1380
ccggcaaacg agctcgtgct aagcgtgccg ctaaaagtga gaaaatttcg gcccctaccc   1440
ccaaggttgc tcagccggtc cccacctgcg aaattaccac ctattctcca ccgacagacg   1500
ggtcttgtgg ttggcatgtt cttgccgcca taatgaaccg gatgatgaat ggtgacttca   1560
cgtcccctct gactcagtac aacagaccag aggatgactg ggcttctgat tatgaccttg   1620
ctcaggcgat ccaatgtctg caactgcccg ctaccgtagt tcggaatcgc gcctgtccta   1680
acgccaagta ccttataaaa cttaatggag ttcattggga ggtagaggtg aggcctggaa   1740
tggcccctcg ttccctttcc cgtgagtgtg tggttggcgt ctgttctgaa ggctgtatcg   1800
caccgcctta cccacaagac gggctgccta aacgtgcact tgaggccttg gcgtctgctt   1860
acagactacc ctccgactgt gttggttctg gtattgctga ctttcttgct aacccgcccc   1920
ctcaggagtt ttggaccctt gacaaaatgt tgacctcccc gtcaccagaa cggtccggct   1980
tctctagctt gtataaatta ctattggagg ttgttccgca gaaatgcggt gccacggaag   2040
gggctttcgt ctatgctgtt gagaggatgt tgaaggattg tccgagctcc aaacaggcca   2100
tggcccttct ggcaaaaatt aaagtcccat cctcaaaggc cccgtctgtg tctctggacg   2160
agtgcttccc tacggatgtt ccagcggact ccgagccagc gtttcaggaa aggccccaaa   2220
gttctggtgc tgctgttgtc ctgtgttcac cggacataaa agagttcgag gaagcagccc   2280
cagaagaagt tcaagagggt ggccacaagg ccgtccactc tgcactcctt gccgagggtc   2340
ttaacaatga gcaggtacag gtggttgccg gtgcgcaact aaagctcggc agttgtggct   2400
tggcagtcgg gaatactcat ggaggtgttc cggtttcagc tagtccaatt aacctggcag   2460
acgggaattt gcccccctcg gactccatga aaggaaacat gcccaatggc tgggaggacg   2520
aaccactgga tttgtcccaa tcagcactag caaccacaac gacccttgtg agagagcaaa   2580
cacccgacaa tctaggttct ggcgccggtg ccctccctgt caccattcga gaatttgtcc   2640
cgacaaggcc tataccccgt catgttgagc actgcggcac ggagtcgggc gacagcagtt   2700
cgcctctgga tctgtccgat gcgcaaaccc cggaccagcc tttaaatcta tccctggccg   2760
cttggccagt gagggccacc gcgtctgacc ccggctgggt ccacggtagg cgtgagcctg   2820
tttttgtaaa gcctcggggt gctttctctg atggcgattc agtccttcag ttcggggagc   2880
tttccgaatc cagctctatc atcgagattg accggacaaa agatgctcca gtggttgatg   2940
cccccgtcga cttgacggtt tcgaacgaag ctctctctgg gatcgatcct tttgaatttg   3000
ccgaactcaa gcgcccgcgt ttctccgctc aagccttaat tgaccgaggc ggcccactag   3060
ccgatgtcca tgcaaaaata aagaaccggg tatatgaaca gtgcctccag gcttgtgagc   3120
ctggcagtcg tgcaacccca gccaccaggg agtggctcga caaaatgtgg gatagggtgg   3180
acatgaagac ttggcgctgc acctcgcagt tccaagctgg tcacattctt gcgtccctca   3240
aattcctccc cgacatgatt caagacacac cgcctcctgt tcccaggaag agccgggcta   3300
gtgataatgc cggcctgaag caactggtgg cgcagtggga cagaaaattg agtgtaaccc   3360
ccccccctaaa accggttggg ccggcgcttg gccaaaccgt ccctccgcct acggatattc   3420
agcaagaaga tgtcaccccc tccgataggc cacctcatgt gccggatctt cctagtcgag   3480
tgagcacggg tgggagttgg aaaggcctta tgctttccgg cacccgtctc gcggggtcta   3540
```

-continued

```
ttagtcagca cctcatgaca tgggtttttg aagttttctc ccatctccca gcttttatgc   3600
tcacactttt ctcgccacgg ggctctatgg ctccaggtga ttggctattt gcaggtgttg   3660
ttttacttgc tctcctgctc tgtcgttctt acccagtact cgggtgcctt cccttattgg   3720
gtgtcttttc tggttctttg cggcgtgttc gtctgggtgt tttggttctt tggatggctt   3780
ttgctgtatt tttattctcg actccatccg acccagtcgg ttcttcttgt gaccacgatt   3840
cgccggagtg tcatgctgag cttttggctc ttgagcagcg ccaactttgg gaacctgtgc   3900
gcggccttgt ggtcggcccc tcgggtctct tatgtgtcat tcttggcaag ttactcggtg   3960
ggtcacgtta tctctggcat gttttcttac gtttatgcat gcttgcggat ttggcccttt   4020
ctcttgttta tgtggtgtcc caggggcgtt gtcacaagtg ttggggaaag tgtataagga   4080
cagctcctgc ggaggtggct ctcaatgtgt tccctttctt gcgcgctacc cgtgcctctc   4140
ttgtgtcctt gtgcgatcga ttccaagcgc caaaaggggt tgatcctgtg cacttggcaa   4200
caggttggcg cgggtgctgg cgcggtgaga gccccattca tcaaccgcac caaaagccca   4260
tagcttatgc caatttggat gaaaagaaaa tatctgccca aacggtggtt gctgtcccgt   4320
atgatcccag tcaggccatc aaatgcctga aagttctgca ggcgggaggg gctatcgtgg   4380
accagcccac acctgaggtc gtccgtgtgt ccgagatccc tttctcagcc ccatttttc    4440
caaaggttcc agtcaaccca gattgcaggg ttgtggtaga ttcggacact tttgtggctg   4500
cagttcgctg cggttactcg acggctcaac tggtcttagg ccggggcaac tttgccaagt   4560
taaatcagat cccctccagg aactctgtct ccaccaaaac gactggtggg gcctcttaca   4620
cccttgctgt ggctcaagtg tctgtgtgga ctcttgttca tttcatcctc ggtctttggt   4680
tcacgtcacc tcaagtgtgt ggccgaggaa cctctgaccc atggtgttca aatccttttt   4740
catatcctac ctatggcccc ggaatagtgt gctcctctcg actttgtgtg tctgccgacg   4800
gagtcactct gccattgttc tcagcagtgg cacaactctc cggtagagag gtggggattt   4860
tcattttggt gctcgtctcc ttgactgctc tggcccaccg tatggctctt aaggcagaca   4920
tgttagtggt cttttcggct tttgtgctt acgcctggcc catgagctcc tggttaatct    4980
gcttctttcc tatattcttg aagtgggtca cccttcaccc tctcactatg ctttgggtgc   5040
actcattctt ggtgttttgt ctgccagcag ccggcgtcct ctcactaggg ataaccggcc   5100
ttctctgggc agttggccgc tttacccagg tcgccggaat tattacacct tatgacatcc   5160
accagtacac ctctgggcca cgtggtgcag ccgctgtggc cacggcccca gaaggcactt   5220
acatggccgc cgtccggaga gctgccttaa ctggacgaac cctcatcttc acaccatctg   5280
cggttggatc ccttcttgaa ggtgctttca ggacccataa accctgcctt aacaccgtga   5340
atgttgtagg ctcttccctt ggttccgggg gggttttcac cattgatggc agaagaactg   5400
ttgtcactgc tgcccatgtg ttgaacggcg acacagctag agtcaccggc gactcctaca   5460
accgcatgca cactttcaag accaatggtg attatgcctg gtcccatgct gatgactggc   5520
ggggcgttgc ccctgtggtc aaggtcgcga aggggtaccg cggtcgtgcc tactggcaaa   5580
catcaactgg tgtcgaaccc ggtattgttg gggaagggtt cgccttctgt tttaccaact   5640
gtggcgattc ggggtcacct gtcatctcag aatctggtga tcttgttgga atccacaccg   5700
gttcaaacaa actcggttct ggtcttgtga caacccctga aggggagacc tgctccatca   5760
aagaaaccaa gctctctgac ctttccaggt attttgcagg cccaagcgtc cctcttgggg   5820
atattaaatt gagtccggcc atcatccctg atgtaacatc cattccgagt gacttggcat   5880
cgctcctagc ctccgtccct gtaatggaag gcggcctctc gactgtccaa cttttgtgtg   5940
```

-continued

```
tctttttcct tctctggcgt atgatgggcc atgcctggac acccattgtt gccgtgggct   6000
tctttttgct gaatgaaatt cttccagcag ttttggtccg agccgtgttt tcttttgcgc   6060
tctttgtgct tgcatgggcc acccccctggt ctgcacaggt gttgatgatc agactcctca   6120
cggcagctct caaccgcaac aggctttctc tggcgttcta cgcactcggg ggtgtcgtcg   6180
gtttggctgc tgaaattggg acctttgctg gtagattgtc tgaattgtct caagctcttt   6240
cgacatactg cttcttacct agggttcttg ctgtgactag ttatgttccc accatcatca   6300
ttggtggact ccataccctt ggtgtgatct tgtggctatt caaataccgg tgcctccaca   6360
acatgttagt tggtgatggg agtttttcaa gtgccttttt cctacggtat tttgcagagg   6420
gtaatctcag aaaaggtgtt tcacagtcct gtggcatgaa taacgagtcc ctgacagctg   6480
ctttagcttg caagttgtca caggctgacc ttgatttttt gtccagcttg acgaacttca   6540
agtgctttgt atctgcttca aacatgaaag atgctgctgg ccagtacatt gaggcagcgt   6600
atgccaaggc cctgcgccga gagttggcct ccctagtcca ggttgacaaa atgaaaggag   6660
ttttgtccaa gctcgaggcc tttgctgaaa cagccacccc gtcccttgac acaggtgacg   6720
tgattgtcct gcttgggcaa catcctcacg gatccatcct cgatattaat gtggggactg   6780
aaaggaaaac tgtgtctgtt caagagactc ggagcctagg cggctccaaa ttcagtgtct   6840
gcactgtcgt gtccaacaca cccgtggacg ccttggccgg cattccactt cagacaccaa   6900
ccccgctttt tgagaatggc ccgcgtcatc gcggtgagga agatgatctc aaagttgaga   6960
ggatgaagaa acattgtgtg tccctcggct tccacaacat caatggcaaa gtttactgta   7020
aagtttggga caagtccacc ggtgacacct tttacacgga tgattcccgg tacacccaag   7080
accatgcttt tcaggacagg tcagctgact atagagacag ggactatgag ggtgtgcaaa   7140
ccgcccccca acagggattt gatccaaaat ctgaaacccc tgttggcact gttgtaatcg   7200
gcggtattac gtataataag tatctggtca aaggcaagga ggttctggtt cccaaacctg   7260
acaactgcct tgaagccgcc aagctgtccc tcgagcaagc acttgctggg atgggccaaa   7320
cttgcgacct tacagttgcc gaggtggaaa agctaaagcg catcatcagt caactccaag   7380
gtttgaccac tgaacaggct ttaaactgct agccgccagc ggcttgaccc gctgtggccg   7440
cggcggcttg gttgtaactg aaacggcggt aaaaattata aaataccaca gcagaacttt   7500
cactttaggc cctttagacc taaaagtcac ttctgaggta gaggtgaaga aatcaactga   7560
gcagggccac gccgttgtgg caaacctatg ttctggtgtc gtattgatga gacctcaccc   7620
accgtccctt gttgacgtcc ttctgaaacc cggacttgac acaacacccg acattcaacc   7680
ggggcatggg gccgggaata tgggcgtgga cggttctatt tgggattttg aaaccgcacc   7740
cacaaaggca gaactcgagt tgtccaagca aataattcaa gcatgtgaag ttaggcgcgg   7800
agacgccccg aacctccaac tcccctacaa gctctatcct gtcagagggg atcctgagcg   7860
gcataaaggc cgccttatca acaccaggtt tggagacttg ccttacaaaa ctcctcaaga   7920
caccaagtcc gctatccatg cggcttgttg cctgcacccc aacggggccc ctgtgtctga   7980
tggtaaatcc acactaggca ccactcttca acatggtttc gagctttatg ttcccacagt   8040
gccctatagt gtcatggagt accttgattc acgccctgac acccctccca tgttcactaa   8100
acatggcact tccaaggctg ctgcagaaga cctccaaaaa tatgacctat ccacccaagg   8160
atttgtcctg cctggggtcc tacgcctagt gcgcagattc atctttggcc atgttggtaa   8220
ggcaccgcca ttgttcctcc catcaaccta tcccgccaag aactccatgg cagggattaa   8280
```

-continued

```
tggccagaga ttcccaacaa aggacgtcca gagcatacct gaaattgatg aaatgtgtgc   8340
ccgcgccgtc aaggagaatt ggcaaaccgt gacaccttgt actctcaaga aacagtactg   8400
ttccaagccc aaaaccagga ccatcctggg caccaacaac tttattgcct tggctcacag   8460
atcggcgctc agtggcgtca cccaggcatt catgaagaag gcttggaagt ccccaattgc   8520
cttggggaaa aacaagttca aggagctgca ttgtactgtc gccggcaggt gtcttgaggc   8580
tgacttggcc tcctgtgatc gcagcacccc cgccattgta agatggtttg ttgccaacct   8640
cctgtatgaa cttgcaggat gtgaagagta cttgcctagc tatgtgctta actgctgcca   8700
tgaccttgtg gcaacacagg atggtgcctt cacaaaacgc ggtggcctgt cgtccgggga   8760
ccccgtcacc agtgtgtcca ataccgtata ttcactggta atctatgccc agcacatggt   8820
attgtcagcc ttgaaaatgg gtcatgaaat tggtcttaag ttcctcgagg agcagctcaa   8880
attcgaggac ctccttgaaa ttcagcctat gttagtatac tctgacgacc ttgtcttgta   8940
cgctgaaaga cccacttttc ccaattacca ttggtgggtc gagcaccttg acctgatgct   9000
gggtttcaaa acggacccaa agaaaactgt cataactgat aaacccagct tcctcggctg   9060
caggattgag gcagggcgac agttagtccc caatcgcgac cgcatcctgg ctgcccttgc   9120
atatcacatg aaggcgcaga acgcctcaga atattatgcg tctgctgccg caatcctgat   9180
ggattcgtgt gcttgcattg accatgaccc tgagtggtat gaggacctca tctgtggtat   9240
tgcccggtgt gctcgccaag atggctatag tttcccgggc ccggcatttt tcatgtccat   9300
gtgggagaaa ctgaaaagtc ataatgaagg gaaaaaattc cgccactgcg gcatctgcga   9360
cgccaaggcc gaccatgcgt ccgcctgtgg actcgatttg tgcttgttcc actcgcattt   9420
tcatcagcac tgccctgtca ctctgagctg cggccatcat gccggttcta aggaatgtcc   9480
gcagtgtcag tcaccggttg gggctggtag atctcctctc gatgccgtgc taaaacaaat   9540
tccgtacaaa cctcctcgta ctgtcatcat gaaggtggat aataaaacaa cggcccttga   9600
tccggggagg tatcagtccc gtcgaggtct cgttgcagtc aagaggggta ttgcaggcaa   9660
tgaagttgac cttgctaatg gagactacca ggtggtgcct cttttgccga cttgcaaaga   9720
cataaacatg gtgaaggtgg cttgtaatgt gctactcagc aagttcatag tagggccacc   9780
aggttccgga aagaccacct ggttgctgag tcaagtccag gacgatgatg tcatttatac   9840
acccacccat cagactatgt ttgatatagt cagtgctctc aaagtttgca ggtattccat   9900
tccaggggct tcaggactcc ctttcccacc acctgccagg tccgggccgt gggtcaggct   9960
tgttgccagc gggcacgtcc ctggccgagt atcatacctc gatgaggctg gatattgtaa  10020
tcatctggac attctcagac tgctttccaa aacacccctt gtgtgtttag gtgaccttca  10080
gcaactccac cctgtcggct ttgattccta ctgttatgtg tttgatcaga tgcctcagaa  10140
gcagctgacc actatttaca gatttggctc caacatctgc gcagctatcc agccttgtta  10200
cagggagaaa cttgaatcca aggccaggaa caccaggata gtttttacca cccgacctgt  10260
agctttcggg caggtgctga caccatacca caaagatcgc atcggctcag cgataaccat  10320
agattcatct caggggggcca cctttgacat tgtgacattg catctaccat cgccaaagtc  10380
cctaaataaa tcccgagcac ttgtagccat cactcgggca agacacgggt tgttcatcta  10440
tgaccctcat aatcagctcc aggagttttt caacctaact cctgagcgca ctgattgtaa  10500
ccttgtgttt aaccgtgggg atgagctggt agttctggac gcggataatg cagtcacaac  10560
tgtggcgaag gccctagaga cgggtccatc tcgatttcga gtatcagacc caaggtgcga  10620
gtctctcttg gccgcttgct cggccagcct ggagggaagc tgcatgccac taccgcaagt  10680
```

```
ggcacataac ctggggtttt acttttcccc agatagtcca gcattcgcgc ctctgccaaa  10740
agaattggca ccacattggc cggtggttac ccatcagaat aaccgggcgt ggcctgaccg  10800
acttgttgct agtatgcgcc caattgatgc ccgttatagc aagccaatgg ttggtgcagg  10860
gtacgcggtc gggccgtcca cttttcttgg cactcctggt gtggtatcat actatctgac  10920
actgtacatc aggggtgagc cccaggcctt accagaaaca ctcgtgtcaa cagggcgcat  10980
agccacagat tgtcgggaat atctcgacgc cgctgaggaa gaggcagcaa aagaactccc  11040
tcacgcattc attggcgatg tcaaaggtac cacggttggg gggtgtcatc acatcacatc  11100
aaaataccta cctaggtccc tgcctaagga ctctgttgcc gtagttggag taagttcgcc  11160
cggcagggcc gctaaagccg tgtgcactct caccgatgtt tacctccccg agctccggcc  11220
atatctgcaa cctgagacgg catcaaaatg ctggaaactc aaattagact ttagagatgt  11280
ccgactaatg gtctggaaag gagccaccgc ctacttccag ctggaagggc ttacatggtc  11340
ggcgctgccc gactatgcca ggtttattca gctgcctaag gatgccgttg tgtacattga  11400
tccgtgcata ggaccggcaa cagccaaccg taaggtcgtg cggaccacag actggcgggc  11460
tgacctggca gtgacaccgt atgattacgg tgcccagaac attttgacaa cagcctggtt  11520
cgaggacctc gggccgcagt ggaagatttt ggggttgcag ccctttaggc gatcatttgg  11580
ctttgaaaac actgaggatt gggcaatcct tgcacgccgt atgaatgacg gcaaggacta  11640
cactgactat aactggaact gtgttcgaga acgcccacac gccatctacg ggcgcgctcg  11700
tgaccatacg tatcattttg cccccggcac agaattgcag gtagagctag gtaaaccccg  11760
gctgccgcct gagcaagtgc cgtgaatccg gagtgatgca atggggttac tgtggagtaa  11820
aattagccag ctgttcgtgg acgccttcac tgagttcctt gttagtgtgg ttgatattgt  11880
cattttcctt gccatactgt ttgggttcac cgtcgcagga tggttactgg tctttcttct  11940
cagagtggtt tgctccgcgc ttctccgttc gcgctctgcc attcactctc ccgaactatc  12000
gaaggtccta tgaaagcttg ctacccaatt gcagaccgga tgtcccacaa tttgcattca  12060
agcacccatt gggcatactt tggcacatgc gagtctccca cctaattgat gaaatggtct  12120
ctcgtcgcat ttaccggacc atggaacact caagtcaagc ggcctggaag caggtagtta  12180
gtgaggccac cctcacaaag ctgtcagggc ttgatatagt tactcatttc caacacctgg  12240
ccgcagtgga ggcggattct tgccgtttcc tcagctcacg acttgtgatg ctaaagaatc  12300
ttgccgttgg caatgtgagc ctacagtata acaccacgtt ggaccatgtt gagctcatct  12360
tccctacgcc aggtacgagg cccaagttga ccgatttcag acaatggctc atcagtgtgc  12420
acgcttccat tttttcctct gtggcttcat ctgttacctt gttcatagtg ttttggcttc  12480
gaattccagc cgtacgctat gtttttggtt tccattggcc cacggcaaca catcattcga  12540
gctaaccatc aactacacca tatgtatgcc ctgctctacc agccaagcgg ctagccaaag  12600
actcgagccc ggtcgtaaca tgtggtgcag aatagggcac gacaggtgtg aggaacgtga  12660
ccatgatgag ttgtcaatgt ccattccgtc agggtacgag aacctcaaac ttgagggtta  12720
ttatgcttgg ctggcctttt tgtccttttc ctacgcggcc caatttcatc cggagttgtt  12780
cggaatagga aacgtgtcgc gcgtctttgt ggacaagcga caccagttca tttgcgccga  12840
gcatgatgga caaaattcaa ccatatctac cggacacaac atctccgcat tatatgcggt  12900
gtattaccat caccaaatag acgggggcaa ttggttccac ttggaatggc tgcggccatt  12960
cttttcctcc tggctggtgc tcaatatctc atggtttctg aggcgttcgc ctgtaagccc  13020
```

tgtttctcga cgcatctatc agatattaag accaacacga ccgcggctgc cggtttcatg 13080
gtccttcagg acatcaattg tctccgacct cacggggtct caacagcgca agagaccatt 13140
tccttcggaa agccgtccca atgtcgcgag gccgtcggta ttccccagta cattacgata 13200
acggctaatg tgaccgatga atcgtatttg tacaacgcgg acttgctgat gctttctgcg 13260
tgccttttct acgcttcaga aatgagcgaa aagggcttca aagttatctt tgggaacgtt 13320
tctggcgttg tttctgcttg tgtcaatttt acagattatg tggctcatgt aatccaacat 13380
acccagcagc atcatctggt gattgatcac attcggttgc tgcatttcct gacaccatca 13440
acaatgaggt gggctacaac cattgcttgt ttgttcgcca ttctcttggc gatatgagat 13500
gttctcacaa attggagcgt ttcttgactc ctcactcttg cttctggtgg ctttttttgc 13560
tttgtaccgg cttgtcttgg tcctttgtcg atggcaacga cagcagctcg acataccaat 13620
acatatataa tttgacgata tgcgagctga atgggaccga atggttgccc agccattttg 13680
actgggcagt cgagaccttt gtgctttacc cggttgccac tcatatcctt tcactgggtt 13740
ttctcacaac aagccatttt tttgatgcgc tcggtctcgg cgctgtgtcc actacaggat 13800
ttgttggcgg gcggtatgta ctcagcagcg tgtacggcgc ttgtgctttc gcagcgctcg 13860
tatgttttgt catccgcgct gctaaaaatt gcatggcttg ccgttatgcc cgcacccggt 13920
ttaccaactt cattgtggac gaccggggga ggatccatcg atggaagtct ccaatagtgg 13980
tagagaaatt gggcaaagct gaagtcggtg gcgacctcgt caccatcaaa catgtcgtcc 14040
tcgaaggggt taaagctcaa cccttgacga ggacttcggc tgagcaatgg gaagcctaga 14100
cgatttttgc aacgatccta ccgccgcaca aaagcttgtg ctagccttta gcatcacata 14160
tacacctata atgatatacg cccttaaggt gtcacgcggc cgcctcctgg ggctattgca 14220
catcttgata ttcctgaact gttcctttac attcggatac atgacatatg tgcattttca 14280
atccaccaac cgtgtcgcat ttactctggg ggccgttgtc gcccttctgt ggggtgttta 14340
cagcttcaca gagtcatgga agttcattac ttccagatgc agattgtgtt gcctaggccg 14400
gcaatacatt ctggcccctg cccatcacgt agaaagtgct gcaggtctcc attcaatccc 14460
agcgtctggt aaccgagcat acgctgtgag aaagcccgga ctaacatcag tgaacggcac 14520
tctagtacca ggacttcgga gcctcgtgct gggcggcaaa cgagctgtta aacgaggagt 14580
ggttaacctc gtcaagtatg gccggtaaaa atcagagcca gaagaaaaag aagaatacag 14640
ctccgatggg gaatggccag ccagtcaatc aactgtgcca gttgctgggt gcaatgataa 14700
agtcccagcg ccagcaacct aggggaggac aggcaaaaaa aagaaagcct gagaagccac 14760
attttcccct agctgctgaa gatgacattc ggcaccacct cacccagacc gaacgttccc 14820
tctgcttgca atcgatccag acggctttta accaaggcgc aggaactgcg tcgctttcat 14880
ccagcgggaa ggtcagtttt caggttgagt tcatgctgcc ggttgctcat acagtgcgcc 14940
tgattcgcgt gacttctaca tccgccagtc agggtgcaaa ttaatttgac agtcaggtga 15000
atggccgcga ttgacgtgtg gcctctaagt cacctattca attagggcga tcacatgggg 15060
gtcaaactta atcaggcagg aaccatgtga ccgaaattaa aaaaaaaaaa aaaaaaaaaa 15120
aaaggccggc atggtcccag cctcctcgct ggcgccggct gggcaacatt ccgaggggac 15180
cgtcccctcg gtaatggcga atgggactct agagcccttc cggctggctg gtttattgct 15240
gataaatctg gagccggtga gcgtgggtct cgcggtatca ttgcagcact ggggccagat 15300
ggtaagccct cccgtatcgt agttatctac acgacgggga gtcaggcaac tatggatgaa 15360
cgaaatagac agatcgctga gataggtgcc tcactgatta agcattggta actgtcagac 15420

-continued

```
caagtttact catatatact ttagattgat ttaaaacttc atttttaatt taaaaggatc  15480
taggtgaaga tcctttttga taatctcatg accaaaatcc cttaacgtga gttttcgttc  15540
cactgagcgt cagacccctt aataagatga tcttcttgag atcgttttgg tctgcgcgta  15600
atctcttgct ctgaaaacga aaaaaccgcc ttgcagggcg gtttttcgaa ggttctctga  15660
gctaccaact ctttgaaccg aggtaactgg cttggaggag cgcagtcacc aaaacttgtc  15720
ctttcagttt agccttaacc ggcgcatgac ttcaagacta actcctctaa atcaattacc  15780
agtggctgct gccagtggtg cttttgcatg tctttccggg ttggactcaa gacgatagtt  15840
accggataag gcgcagcggt cggactgaac ggggggttcg tgcatacagt ccagcttgga  15900
gcgaactgcc tacccggaac tgagtgtcag gcgtggaatg agacaaacgc ggccataaca  15960
gcggaatgac accggtaaac cgaaaggcag gaacaggaga gcgcacgagg gagccgccag  16020
ggggaaacgc ctggtatctt tatagtcctg tcgggtttcg ccaccactga tttgagcgtc  16080
agatttcgtg atgcttgtca ggggggcgga gcctatggaa aaacggcttt gccgcggccc  16140
tctcacttcc ctgttaagta tcttcctggc atcttccagg aaatctccgc cccgttcgta  16200
agccatttcc gctcgccgca gtcgaacgac cgagcgtagc gagtcagtga gcgaggaagc  16260
ggaatatatc ctgtatcaca tattctgctg acgcaccggt gcagcctttt ttctcctgcc  16320
acatgaagca cttcactgac accctcatca gtgccaacat agtaagccag tatacactcc  16380
gctagcgctg aggtctgcct cgtgaagaag gtgttgctga ctcataccag gcctgaatcg  16440
ccccatcatc cagccagaaa gtgagggagc cacggttgat gagagctttg ttgtaggtgg  16500
accagttggt gattttgaac ttttgctttg ccacggaacg gtctgcgttg tcgggaagat  16560
gcgtgatctg atccttcaac tcagcaaaag ttcgatttat tcaacaaagc cacgttgtgt  16620
ctcaaaatct ctgatgttac attgcacaag ataaaaatat atcatcatga acaataaaac  16680
tgtctgctta cataaacagt aatacaaggg gtgttatgag ccatattcaa cgggaaacgt  16740
cttgctcgag gccgcgatta aattccaaca tggatgctga tttatatggg tataaatggg  16800
ctcgcgataa tgtcgggcaa tcaggtgcga caatctatcg attgtatggg aagcccgatg  16860
cgccagagtt gtttctgaaa catggcaaag gtagcgttgc caatgatgtt acagatgaga  16920
tggtcagact aaactggctg acggaattta tgcctcttcc gaccatcaag cattttatcc  16980
gtactcctga tgatgcatgg ttactcacca ctgcgatccc cgggaaaaca gcattccagg  17040
tattagaaga atatcctgat tcaggtgaaa atattgttga tgcgctggca gtgttcctgc  17100
gccggttgca ttcgattcct gtttgtaatt gtccttttaa cagcgatcgc gtatttcgtc  17160
tcgctcaggc gcaatcacga atgaataacg gtttggttga tgcgagtgat tttgatgacg  17220
agcgtaatgg ctggcctgtt gaacaagtct ggaaagaaat gcataagctt ttgccattct  17280
caccggattc agtcgtcact catggtgatt tctcacttga taaccttatt tttgacgagg  17340
ggaaattaat aggttgtatt gatgttggac gagtcggaat cgcagaccga taccaggatc  17400
ttgccatcct atggaactgc ctcggtgagt tttctccttc attacagaaa cggctttttc  17460
aaaaatatgg tattgataat cctgatatga ataaattgca gtttcatttg atgctcgatg  17520
agtttttcta atcagaattg gttaattggt tgtaacactg gcagagcatt acgctgactt  17580
gacgggacgg cggctttgtt gaataaatcg aacttttgct gagttgaagg atcagatcac  17640
gcatcttccc gacaacgcag accgttccgt ggcaaagcaa aagttcaaaa tcaccaactg  17700
gtccacctac aacaaagctc tcatcaaccg tggctccctc actttctggc tggatgatgg  17760
```

-continued

```
ggcgattcag gcctggtatg agtcagcaac accttcttca cgaggcagac ctcagcgctc  17820

aaagatgcag gggtaaaagc taaccgcatc tttaccgaca aggcatccgg cagttcaaca  17880

gatcgggaag ggctggattt gctgaggatg aaggtggagg aaggtgatgt cattctggtg  17940

aagaagctcg accgtcttgg ccgcgacacc gccgacatga tccaactgat aaaagagttt  18000

gatgctcagg gtgtagcggt tcggtttatt gacgacggga tcagtaccga cggtgatatg  18060

gggcaaatgg tggtcaccat cctgtcggct gtggcacagg ctgaacgccg gagtcggctg  18120

tggcacaggc tgaacgccgg aggatccggc gcgccatgca ttagttatta atagtaatca  18180

attacggggt cattagttca tagcccatat atggagttcc gcgttacata acttacggta  18240

aatggcccgc ctggctgacc gcccaacgac ccccgcccat tgacgtcaat aatgacgtat  18300

gttcccatag taacgccaat agggactttc cattgacgtc aatgggtgga gtatttacgg  18360

taaactgccc acttggcagt acatcaagtg tatcatatgc caagtacgcc ccctattgac  18420

gtcaatgacg gtaaatggcc cgcctggcat tatgcccagt acatgacctt atgggacttt  18480

cctacttggc agtacatcta cgtattagtc atcgctatta ccatggtgat gcggttttgg  18540

cagtacatca atgggcgtgg atagcggttt gactcacggg gatttccaag tctccacccc  18600

attgacgtca atgggagttt gttttggcac caaaatcaac gggactttcc aaaatgtcgt  18660

aacaactccg ccccattgac gcaaatgggc ggtaggcgtg tacggtggga ggtctatata  18720

agcagagctg gtttagtatt taaat                                       18745
```

PORCINE REPRODUCTIVE AND RESPIRATORY SYNDROME VIRUS CDNA CLONE AND USES THEREOF

CROSS REFERENCE TO RELATED APPLICATIONS

The present application is a 35 U.S.C. § 371 national phase application from, and claims priority to, International Application No. PCT/EP2017/069329, filed Jul. 31, 2017, and published under PCT Article 21(2) in English, which claims priority to European Patent Application No. 16382391.7, filed on Aug. 5, 2016, all of which applications are incorporated herein by reference in their entireties.

TECHNICAL FIELD

The present invention relates to cDNA clones and uses thereof for the preparation of efficacious and safety-enhanced vaccines against the Porcine Reproductive and Respiratory Syndrome Virus (PRRSV).

TECHNICAL BACKGROUND

Porcine reproductive and respiratory syndrome (PRRS) is widespread in most swine-producing countries worldwide, causing significant economic losses to swine producers. The disease causes reproductive failure in breeding stock and respiratory distress to growing pigs.

In 1991, the causal agent, the PRRS virus (PRRSV) was first isolated in in the Netherlands, being the Lelystad virus (LV) the prototype of European PRRSV isolates and shortly after in the USA, being the VR-2332 strain the prototype of the North American PRRSV isolates. Later, PRRSV was classified into 2 major genotypes, type 1 or I (European) and type 2 or II (North American), that share 65% genomic sequence identity. In the early 2000s a highly pathogenic strain of the North American genotype emerged in China. This strain, HP-PRRSV, is more virulent than all other strains, and causes great losses in Asian countries. It is also demonstrated the rapid evolution of the virus, reported initially for Chinese variants.

PRRSV is a small, enveloped RNA virus. It contains a single-stranded, positive-sense, RNA genome with a size of approximately 15 kb. The PRRSV is a member of the genus *Arterivirus*, family Arteriviridae, and order Nidovirales. It contains eight open reading frames (ORFs). The ORFs 1a and 1b comprise about 80% of the genome and encode the RNA replicase complex and the rest of the non-structural proteins. The six smaller ORFs 2 to 7 located at the 3' end of the genome encode structural proteins that are associated with the virion assembly. ORFs 2 to 5 encode glycoproteins GP2 to GP5, ORF6 encodes the membrane protein M, and ORF7 encodes the nucleocapsid protein N. Upstream of ORF1a, PRRSV contains also a 5'UTR (5' untranslated region), and downstream of ORF7 a 3'UTR (3' untranslated region). The region 5'UTR is the region of genomic RNA that is directly upstream from the initiation codon. The region 3'UTR is the section of genomic RNA that immediately follows the translation termination codon.

Extensive sequence analysis of field isolates of PRRSV has revealed high sequence variation between North American and European isolates of PRRSV.

The rapid evolution of RNA viruses complicates the management of chronic infections and the control of emerging infectious agents. These viruses replicate with extremely high mutation rates and exhibit significant genetic diversity.

This diversity allows a viral population to rapidly adapt to dynamic environments and evolve resistance to vaccines and antiviral drugs. Like for any other RNA virus, this was long ago confirmed to be the case for PRRSV, as disclosed in the review article X. J. Meng, Heterogeneity of porcine reproductive and respiratory syndrome virus: implications for current vaccine efficacy and future vaccine development, Vet. Microbiol., 2000, 74, 309-329. It is pointed out that the observed heterogeneity will likely pose a major obstacle for effective prevention and control of PRRSV. The author considers that a multivalent vaccine consisting of multiple antigenically distinct strains of PRRSV is the most promising candidate for the next generation of vaccines.

Currently available commercial vaccines against PRRSV are either conventional modified live virus (attenuated, cell culture) or conventional killed virus (inactivated cell culture preparations of virulent virus). The safety of modified live virus vaccines has been largely questioned because of vaccine virus replicates in vaccinated pigs, causing detectable viremia, and persists in the organism and tissues of vaccinates for weeks and is shed by different routes causing the infection of sentinel pigs (Done et al., Porcine reproductive and respiratory syndrome (PRRS): a review, with emphasis on pathological, virological and diagnostic aspects, Br. Vet. J., 1996, 152(2), 153-174). In addition, reversions to virulence have been suspected in the field based on the similarity between the vaccine strain and some strains that have caused clinical problems in areas where the vaccine has been used.

Several approaches based on specific deletions and modifications to the PRRS genome have been studied since the first constructions of full-length cDNA clones of PRRS viruses for manipulation by molecular biology techniques.

A full-length infectious cDNA clone of the European PRRS virus has been reported by Meulenberg, et al., Infectious transcripts from cloned genome-length cDNA of porcine reproductive and respiratory syndrome virus, J. Virol., 1998, 72 (1), 380-387, and Snijder et al., The molecular biology of arteriviruses, J. Gen. Virol., 1998, 79, 961-979.

Database EMBL (online) U87392 discloses the complete genome of PRRS virus strain VR-2332, North American prototype PRRS virus.

Infectious cDNA clones have been used to study the biological features of virulent PRRSV and its attenuated counterparts as shown below.

A first approach based on cDNA clones is the use of an attenuated strain of PRRSV as disclosed, for example, in the article Kwon et al., Infectious clone-derived viruses from virulent and vaccine strains of porcine reproductive and respiratory syndrome virus mimic biological properties of their parental viruses in a pregnant sow model, Vaccine, 2006, 24(49-50), 7071-7080. In this article it is shown that Prime Pac (PP) is an attenuated vaccine strain of PRRSV, which was used to generate chimeric constructs on the basis of a highly virulent PRRSV derived from infectious clone FL12. It is further disclosed that a full-length cDNA clone of the PP vaccine strain was constructed by serially replacing the genomic fragments of the FL12 with the corresponding regions from the PP strain.

A second approach is the construction of infectious cDNA clones derived from PRRSV, which was first disclosed in International patent application WO-A-98/18933. In that document it is disclosed a method for generating an infectious clone of a positive strand RNA virus (e.g. PRRSV). The infectious clone can include mutations in the virulence markers or serological markers in order to prepare vaccines.

This technology has been followed by different groups introducing further modifications in the PRRSV genome, as shown below.

For example, European patent application EP-A-1018557 refers to infectious cDNA clones containing a deletion of the nucleocapsid gene or the membrane glycoprotein gene.

In International patent application WO-A-2006/006813, it is disclosed that virus rescued from infectious cDNA clones of PRRSV, which lack contiguous nucleotides at the 5' end of the viral genome, had specific infectivity reduced (deletion of 1 to 7 nucleotides) or completely abolished deletion of 9 to 15 nucleotides).

In International patent application WO-A-2007/002321, it is disclosed an infectious cDNA clone of PRRSV, containing a deletion in a region of ORF1, which encodes a non-structural protein.

In International patent application WO-A-2011/153351 are disclosed infectious chimeric PRRS viruses and vaccines containing them. The method for producing such chimeric viruses is DNA shuffling. It is taken into consideration the genetic diversity of PRRSV for providing vaccines with broad protection against different PRRSV field isolates. Specifically it is disclosed an infectious chimeric PRRSV which comprises viral protein GP5 that is chimeric of a plurality of genetically distinct strains.

International patent application WO-A-2013/017570 refers to PRRS virus (genotype I, EU, and genotype II, US) comprising mutations in the nsp1 genes, and it refers specifically to the same infectious cDNA clone of EU PRRSV as in WO-A-2013/017568.

International patent application WO-A-2015/092058 refers to a PRRSV variant, to a European PRRSV cDNA clone and uses thereof. In Example 3 it is disclosed the introduction of a deletion within the ORF4 protein of the EU type PRRSV infectious cDNA clone and the introduction of the PRRSV ORF5 protein neutralizing epitope sequence into the ORF4 gene of the infectious cDNA clone.

For the last 30 years, quasispecies theory has provided a population-based framework for understanding RNA viral evolution. Virologists use the term viral quasispecies to mean distributions of non-identical but related genomes subjected to a continuous process of genetic variation, competition, and selection and which act as a unit of selection. Strictly speaking, a viral quasispecies should be considered a single replicative unit in an infected cell. However, heterogeneous viral progeny from a single cell will invade neighbouring cells in culture or from the same tissue or organ in vivo creating a second and successive level of competition among viral particles and viral genomes, as disclosed in Domingo et al., Viral quasispecies evolution, Microbiol. Mol. Biol. Rev., 2012, 76, 159-216. Therefore, a quasispecies is a cloud of diverse genetic variants that interact cooperatively on a functional level, and collectively contribute to the phenotypic characteristics of the viral population. This quasispecies variation could account for the inability of traditional approaches such as vaccination to control PRRS adequately. Some experiments have reported that population diversity is a virulence determinant, as disclosed in Vignuzzi, et al., Quasispecies diversity determines pathogenesis through cooperative interactions in a viral population, Nature, 2006, 439, 344-348. Moreover, to date the cDNA clone technology has been focused on the use of consensus sequence of the virus and therefore missing out relevant data of the quasiespecies virus population.

Several inactivated and attenuated vaccines are commercially available for the prevention of PRRS, e.g. AMERVAC® PRRS, UNISTRAIN® PRRS, SUIPRAVAC® PRRS (Laboratorios HIPRA, S.A., Spain), INGELVAC® PRRS MLV (Boehringer Ingelheim, USA), PORCILIS® PRRS (Merck, Sharp and Dohme Animal Health, USA), PYRSVAC-183 (Laboratorios Syva, S.A., Spain). However, the rapid evolution of PRRSV complicate the management of the disease as the long term efficiency of the vaccines is jeopardized by the constant generation of escape variants within PRRSV quasispecies populations. In addition, the safety of the modified live vaccines in terms of virus replication in vaccinated pigs and the risk of reversions to virulence are not completely resolved by commercially available vaccines.

There is, thus, a need to provide a new generation of vaccines against PRRSV, with a better degree in terms of safety while maintaining the efficacy when compared with current available PRRS vaccines.

OBJECT OF THE INVENTION

The object of the present invention provides a method for generating an infectious cDNA clone based on the genome of an attenuated PRRSV.

The object of the present invention further provides an infectious cDNA clone obtainable by such method.

The object of the present invention further provides a recombinant nucleic acid comprising that infectious cDNA clone.

The object of the present invention further provides a DNA construct comprising a copy of such recombinant nucleic acid.

The object of the present invention further provides a RNA transcript of such DNA construct.

The object of the present invention further provides a host cell transfected with that DNA construct.

The object of the present invention further provides an attenuated PRRSV encoded by that RNA transcript.

The object of the present invention further provides an immunogenic composition comprising that attenuated PRRSV.

The object of the present invention further provides a vaccine comprising that attenuated PRRSV or the infectious cDNA clone and a pharmaceutically acceptable diluent or excipient.

The object of the present invention further provides a vaccine comprising that attenuated PRRSV and a pharmaceutically acceptable diluent or excipient for use in the prophylaxis and/or the treatment of PRRSV infections.

The object of the present invention further provides the attenuated PRRSV for use in the prophylaxis and/or the treatment of PRRSV infections.

The object of the present invention further provides the attenuated PRRSV for use as vaccine or medicament in the prophylaxis and/or the treatment of PRRSV infections.

Step 1: Introduction of AscI and SwaI restriction sites upstream PRRSV genome. Primers are represented by horizontal arrows. Restriction sites included in the primers sequence are indicated. pVAC-T7-5 sites SwaI and RsrII used for replacing the 5' terminal cDNA are indicated.

Step 2: Introduction of the Hepatitis delta virus ribozyme (HDV-Rz) downstream PRRSV genome by PCR. Primers are represented by horizontal arrows. pVAC-T7-5 sites HpaI and XbaI used for replacing of the 3' terminal cDNA and introduction of the ribozyme are shown.

Step 3: Cloning of Human cytomegalovirus promoter in the intermediate clone Asc-Swa-pVAC5-HDV-Rz. Primers used for PCR amplification of the promoter, and their restriction sites are represented. The AscI and SwaI sites of the intermediate clone pVAC-T7-5 Asc-Swa-pVAC5-HDV-Rz used to introduce the promoter are shown.

Figure 4:
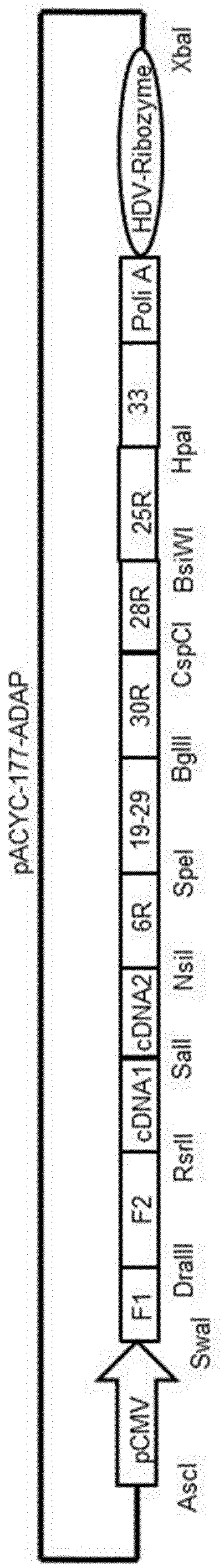

FIG. 4 depicts the structure of clone pVAC 5.0. Viral cDNAs assembled to obtain the full-length clone are represented by boxes. Restriction sites used to assemble cDNAs are indicated. Human cytomegalovirus promoter (pCMV) is represented by an arrow. The Hepatitis delta virus ribozyme (HDV-Rz) is represented by an oval. pACYC-177-ADAP vector is represented by a line. Restriction sites suitable to release full insert (AscI and XbaI) are shown.

Figure 5:
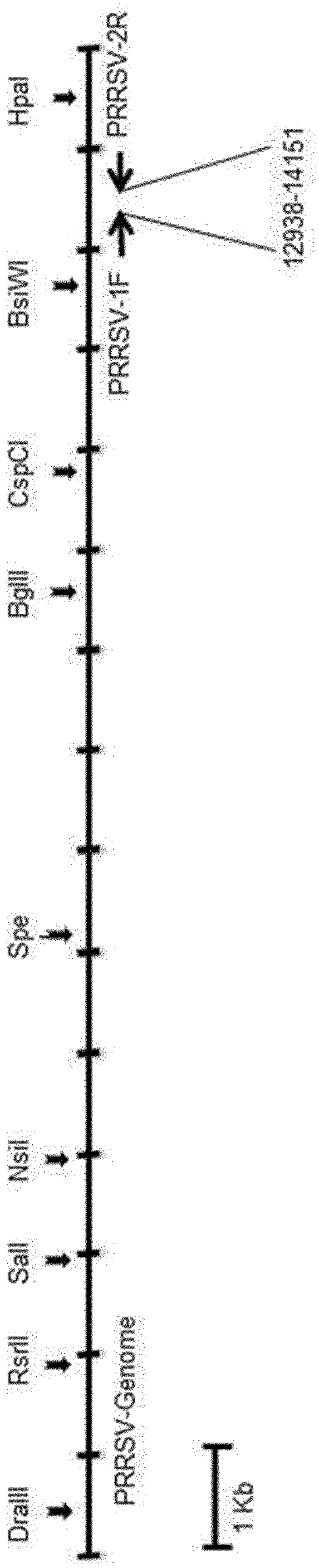

FIG. 5 represents the location of primers used, and the positions sequenced in the variability study of strain VP-046 BIS of PRRSV for construction of clone pVAC 5.2.

Figure 6:
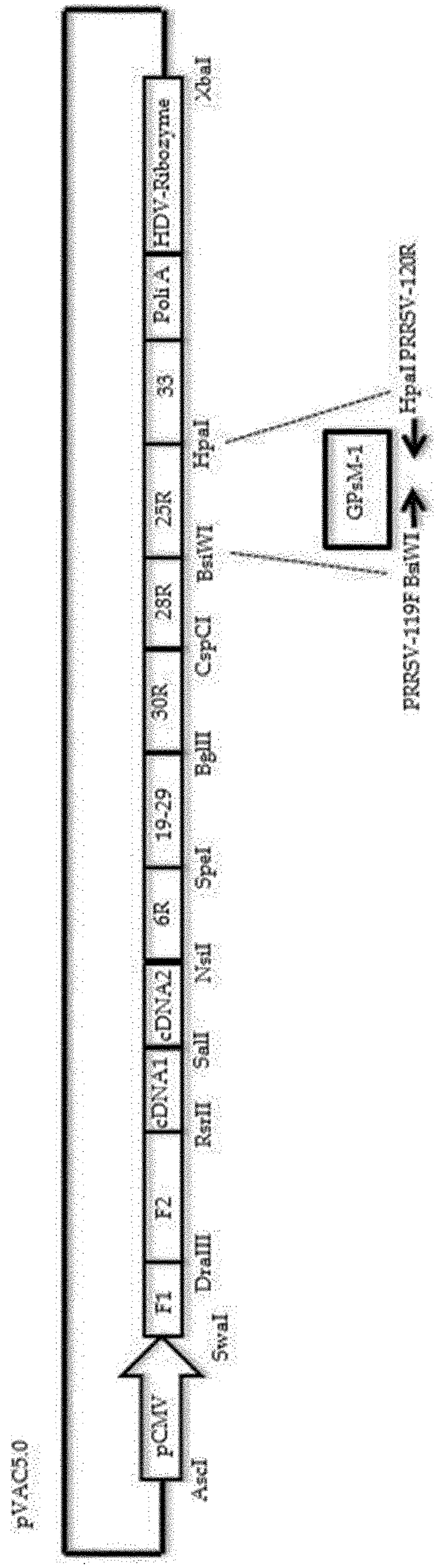

FIG. 6 depicts the cloning event from pVAC 5.0 to pVAC 5.2. Location of the primers used to amplify the most frequent sequence variant and of the cleavage sites used to replace the cDNA region 25R in pVAC 5.0 for the most frequent sequence variant cDNA.

Figure 7:
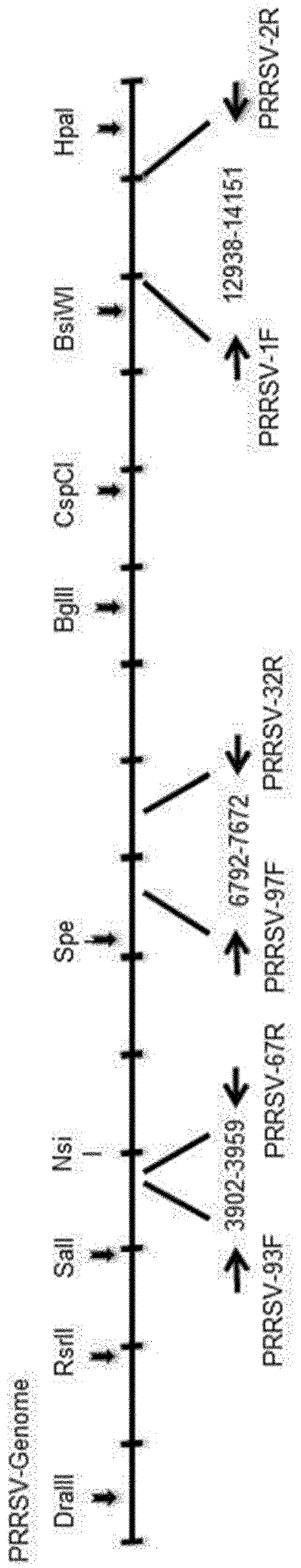

FIG. 7 indicates the location of primers used, and the positions sequenced in the variability study of strain VP-046 BIS of PRRSV for construction of clone pVAC 5.1.

Figure 8:
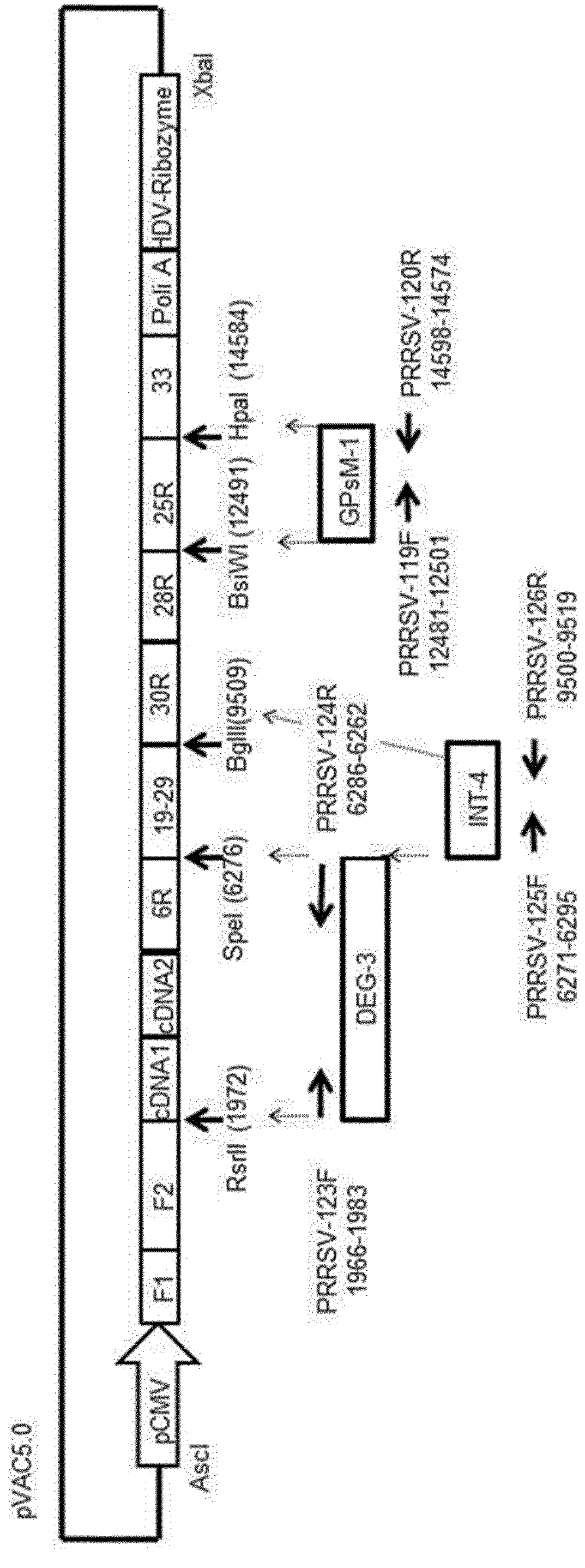

FIG. 8 represents the cloning events from pVAC 5.0 to pVAC 5.1. Location of the primers used to amplify the most frequent sequence variants and of the cleavage sites used to replace cDNA regions in pVAC 5.0 for the most frequent sequence variant cDNA.

Figure 9:
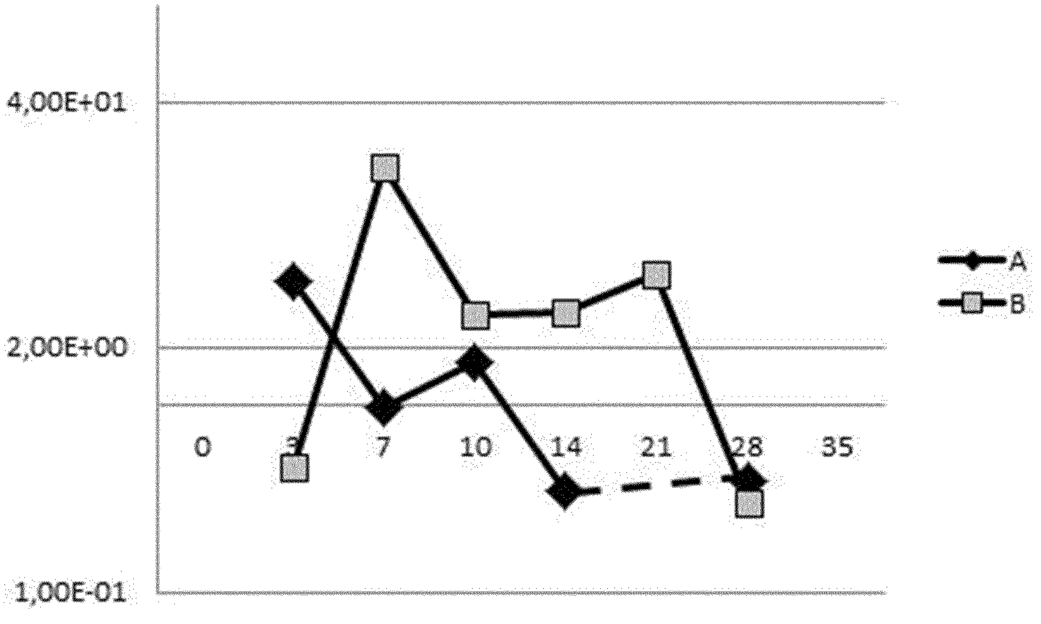

FIG. 9 represents the mean titers ($CCID_{50}$/mL, being $CCID_{50}$, 50% cell culture infective dose) of viremia at day 3 up to day 37 of the study after for group A (pVAC 5.2) and group B (VP-046 BIS), as described in Example 4.

Figure 10:
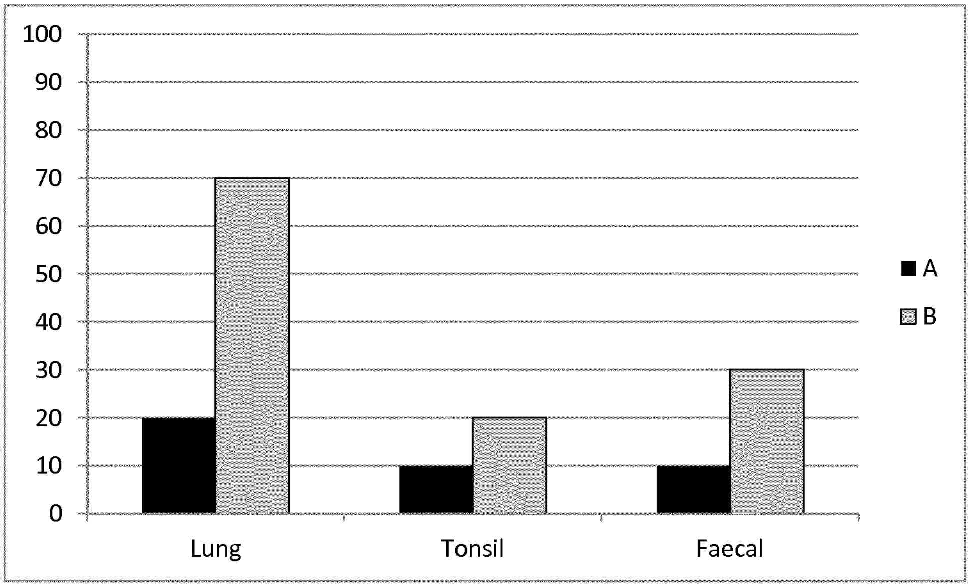

FIG. 10 shows the percentages of animals positive to PRRSV in lung tissues, tonsil and faecal swabs for inoculated animals of group A (pVAC 5.2) and group B (VP-046 BIS), as described in Example 4.

Figure 11:
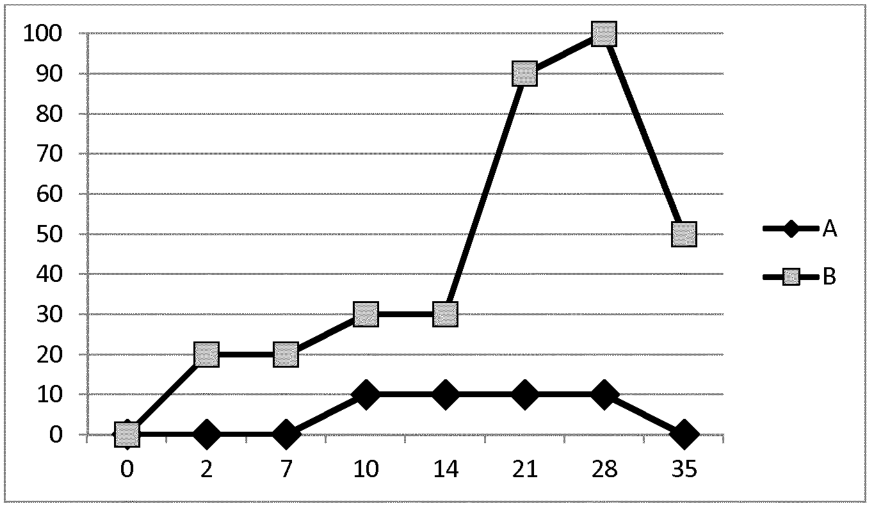

FIG. 11 represents the percentages of viremic animals (Second serial passage) in inoculated pVAC 5.2 group (group A) and VP-046 BIS (group B), as described in Example 4.

Figure 12:
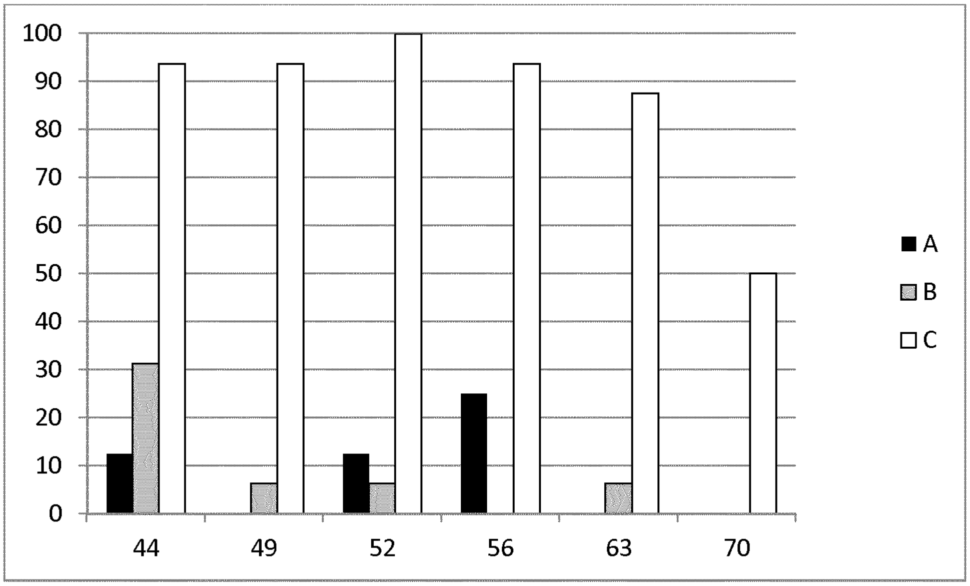

FIG. 12 represents the percentages of viremic animals for each group (Group A=group vaccinated with pVAC 5.2, Group B=group vaccinated with VP-046 BIS, and Group C=Control group, non-vaccinated) after challenge with a homologous virulent strain of PRRSV as a function of the day of study, as described in Example 5.

Figure 13:
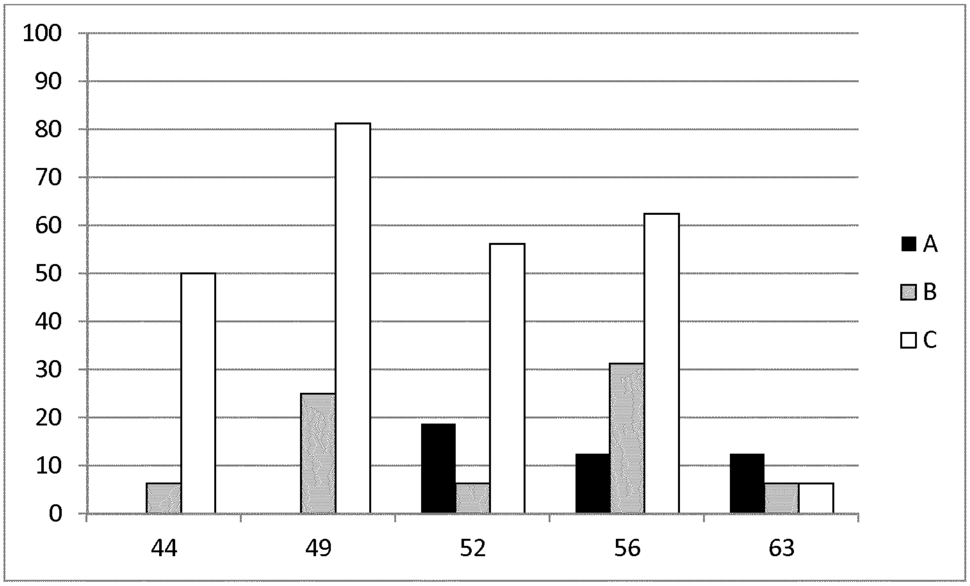

FIG. 13 represents the percentage of positive animals with faecal shedding for each group (Group A=group vaccinated with pVAC 5.2, Group B=group vaccinated with VP-046 BIS, and Group C=Control group, non-vaccinated) after challenge with a homologous virulent strain of PRRSV as a function of the day of study, as disclosed in Example 5.

Figure 14:
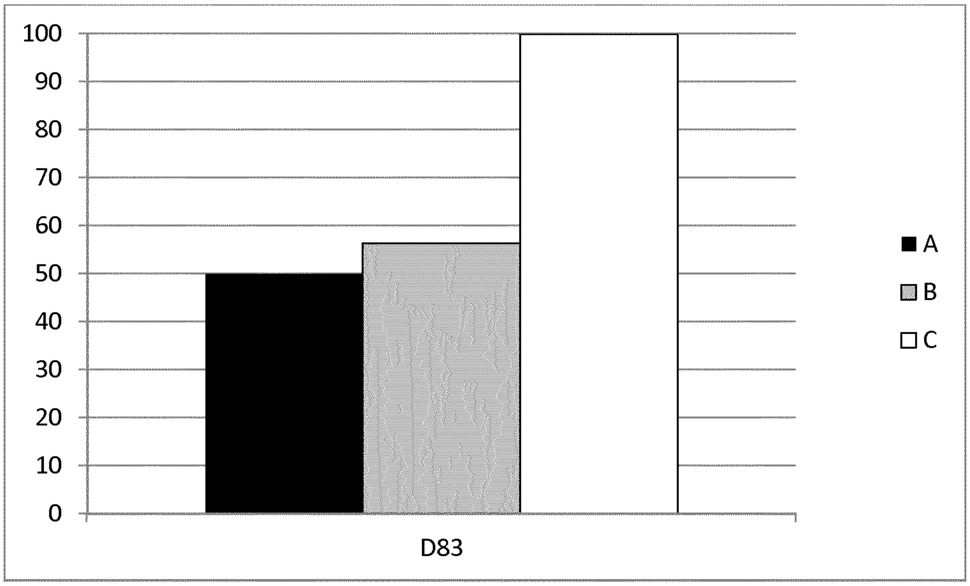

FIG. 14 represents the percentage of positive animals to PRRSV in tonsil swabs at day 83 of the study for each group (Group A=group vaccinated with pVAC 5.2, Group B=group vaccinated with VP-046 BIS, and Group C=Control group, non-vaccinated) after homologous challenge, as shown in Example 5.

Figure 15:
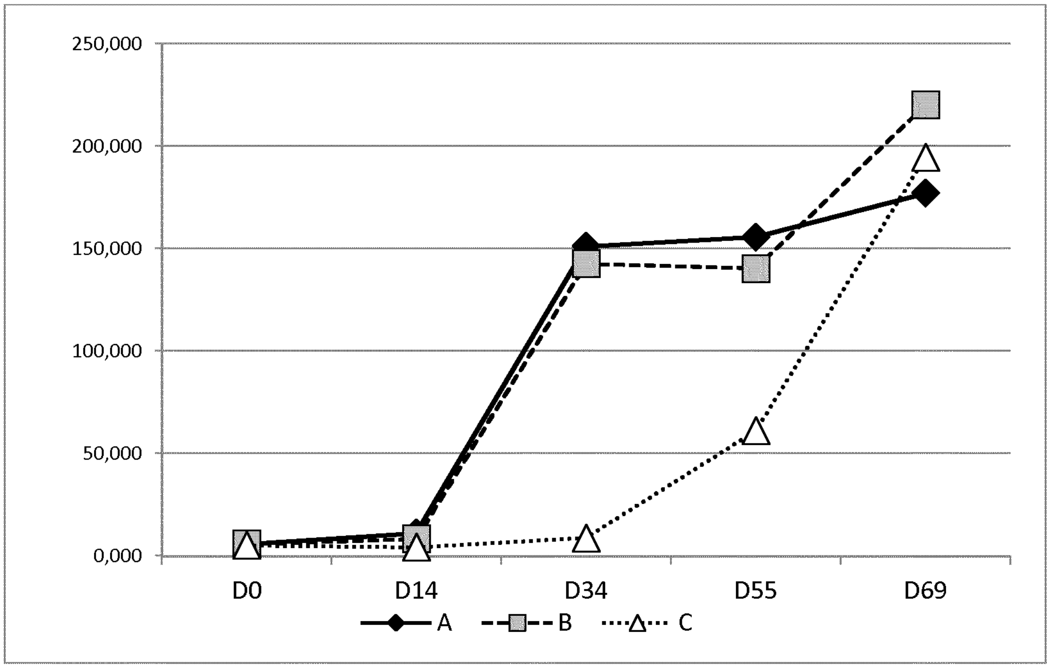

FIG. 15 shows the relative index of antibodies against PRRSV for the vaccinated and non-vaccinated animals (Group A=group vaccinated with pVAC 5.2, Group B=group vaccinated with VP-046 BIS, and Group C=Control group, non-vaccinated) before and after challenge (D34) with a heterologous virulent strain of PRRS virus, as disclosed in Example 6. Antibodies were determined by means of ELISA Civtest suis PRRS-E (Laboratorios Hipra, S.A., Amer, Girona, Spain).

Figure 16:
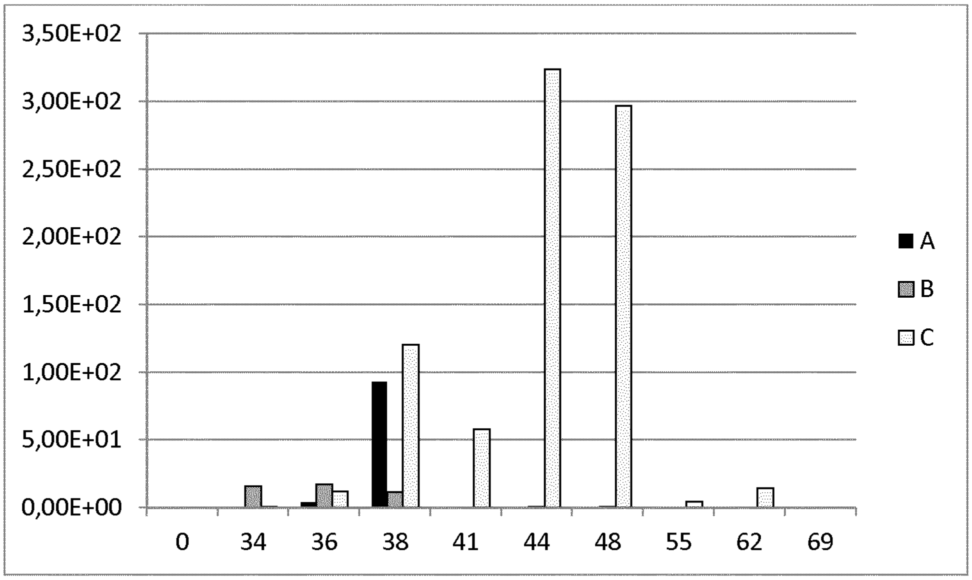

FIG. 16 represents the mean viremia titers after challenge with a heterologous virulent strain of PRRS virus, as $CCID_{50}$/mL, for the vaccinated and non-vaccinated animals (Group A=group vaccinated with pVAC 5.2, Group B=group vaccinated with VP-046 BIS, and Group C=Control group, non-vaccinated) as a function of the day of study, as described in Example 6

Figure 17:
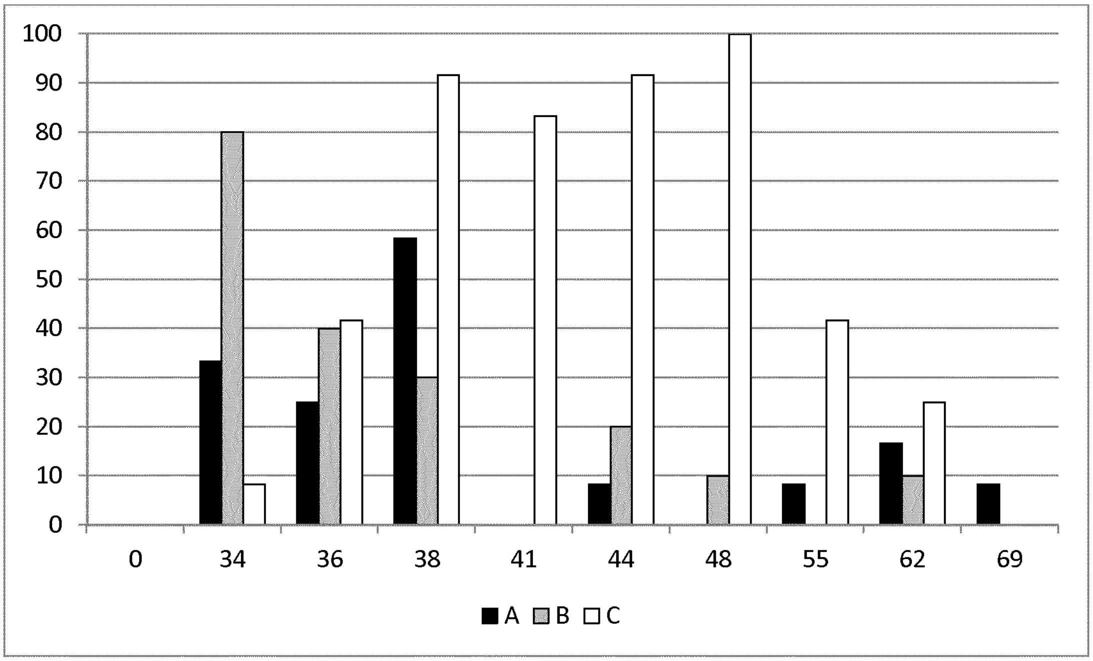

FIG. 17 represents the percentage of viremic animals after challenge with a heterologous virulent strain of PRRS virus, as $CCID_{50}$/mL, for the vaccinated and non-vaccinated animals (Group A=group vaccinated with pVAC 5.2, Group B=group vaccinated with VP-046 BIS, and Group C=Control group, non-vaccinated) as a function of the day of study, as described in Example 6.

Figure 18:
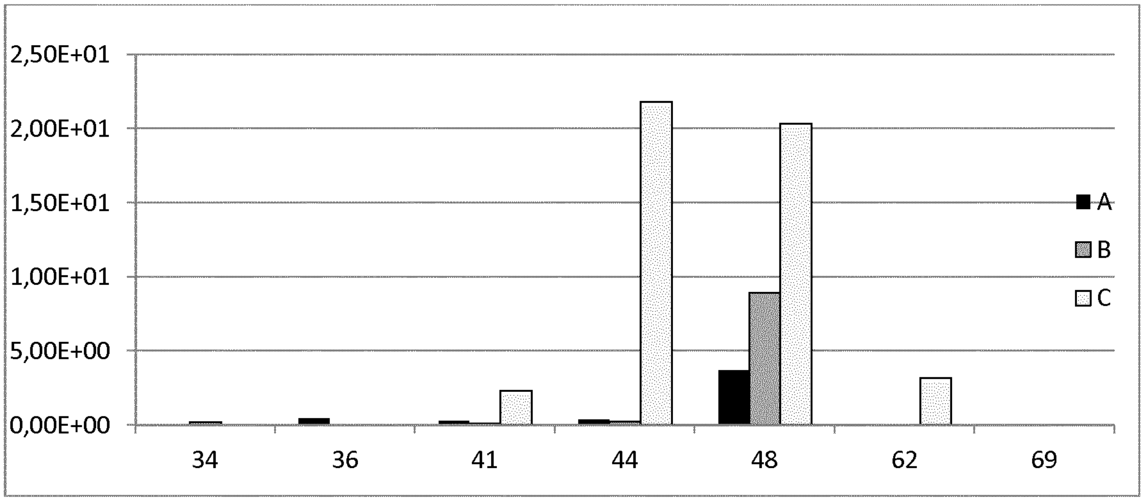

FIG. 18 represents the mean value of PRRSV titer obtained from faecal swabs expressed as $CCID_{50}$/mL for each group of animals (Group A=group vaccinated with pVAC 5.2, Group B=group vaccinated with VP-046 BIS, and Group C=Control group, non-vaccinated) as a function of the day of study, as disclosed in Example 6.

Figure 19:
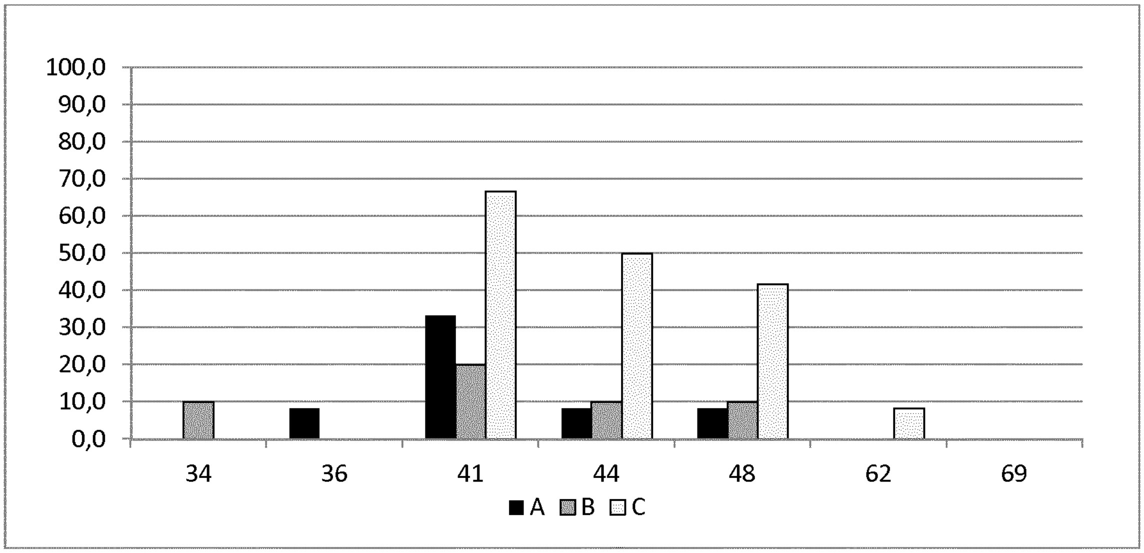

FIG. 19 shows the percentage of positive animals with faecal shedding for each group (Group A=group vaccinated with pVAC 5.2, Group B=group vaccinated with VP-046 BIS, and Group C=Control group, non-vaccinated) as a function of the day of study, as described in Example 6.

Figure 20:
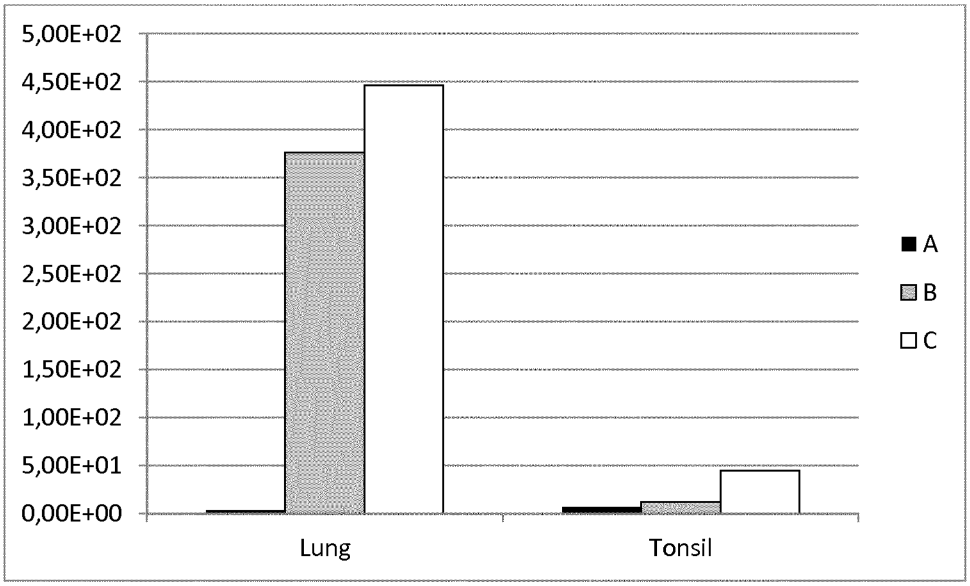

FIG. 20 represents the mean quantity of PRRSV, expressed in $CCID_{50}$/ml, for each group (Group A=group vaccinated with pVAC 5.2, Group B=group vaccinated with VP-046 BIS, and Group C=Control group, non-vaccinated) present in lung tissues and in tonsil swabs, as described in Example 6.

Figure 21:
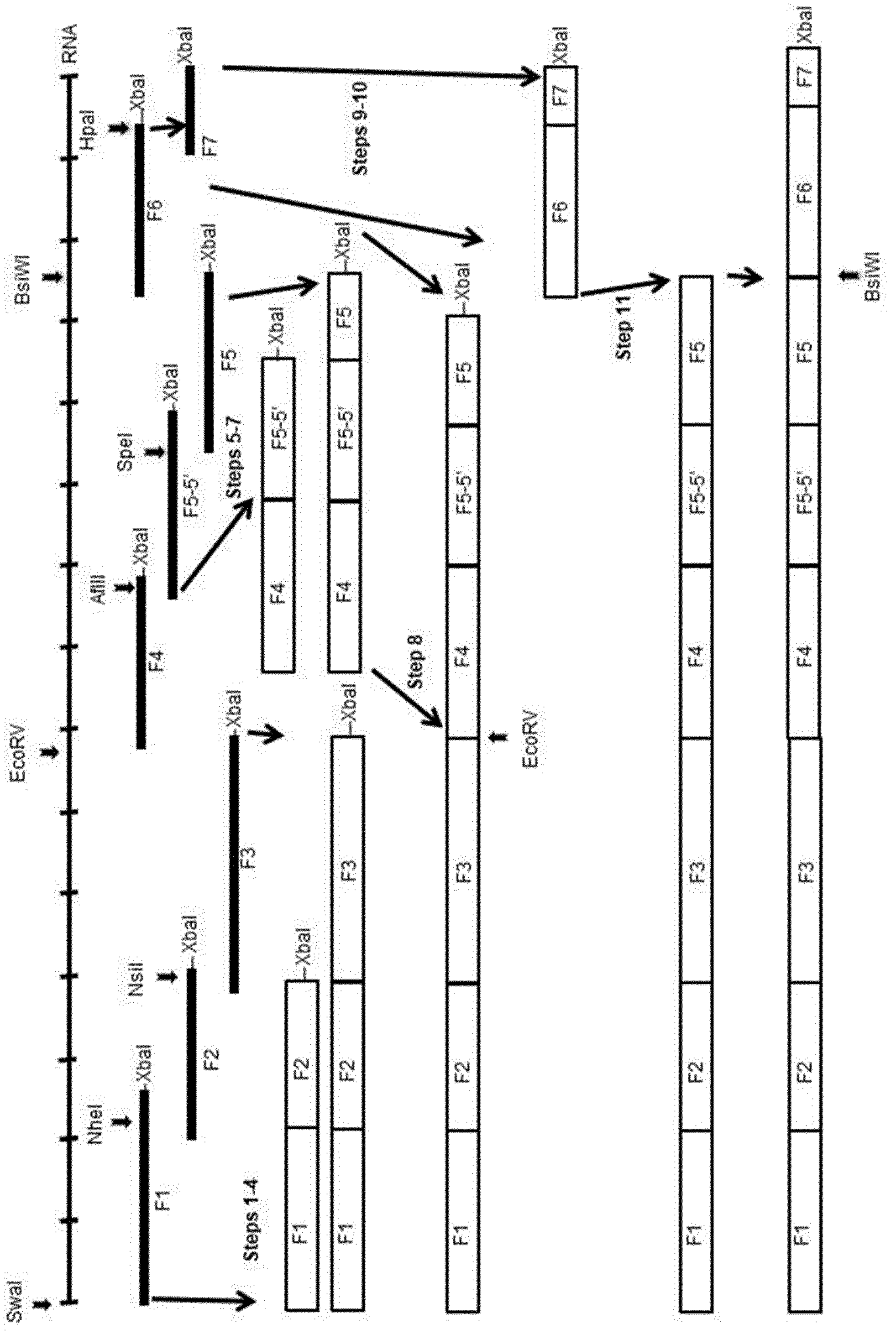

FIG. 21 shows the assembling of restriction fragments for clone pVAC 6.1. The segmented line represents PRRSV genome. Thick arrows above indicate the restriction sites used to assemble the viral cDNAs. Thick lines represent the viral cDNAs produced by RT-PCR. Boxes represent intermediate cDNA clones. The sequence of subcloning of cDNAs is indicated by thin arrows (steps 1 to 11).

Figure 22:
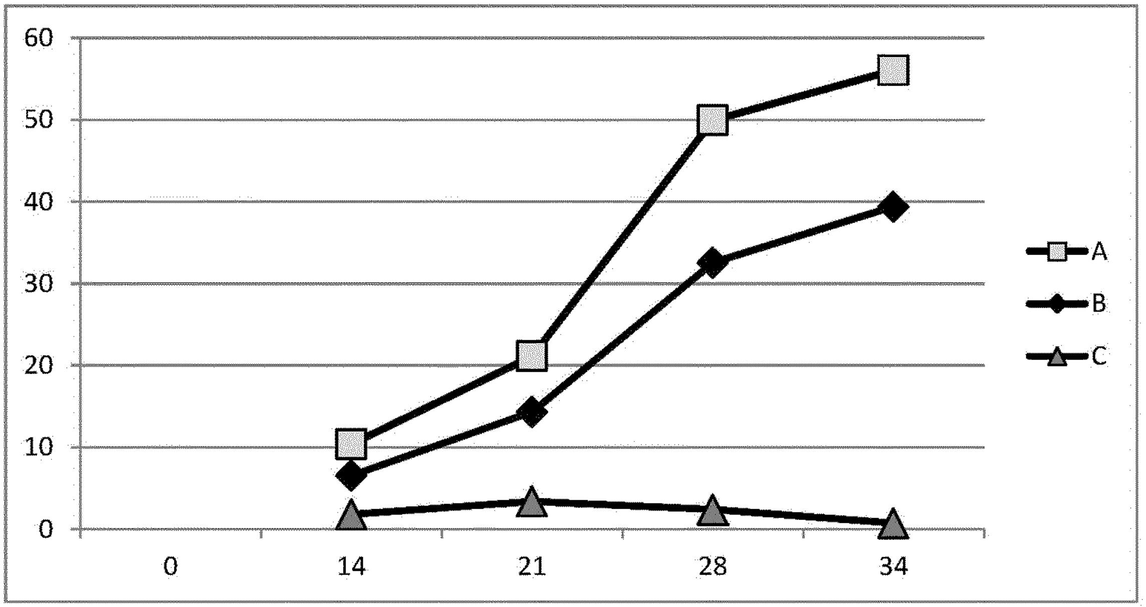

FIG. 22 represents the mean titers of antibodies against PRRSV (IRPC) for the vaccinated and non-vaccinated animals, being Group A=vaccinated with the V1042-P62 PRRSV quasispecies, Group B=vaccinated with the clone pVAC 6.1, and Group C=non-vaccinated, at different days post-vaccination, as disclosed in Example 8.

Figure 23:
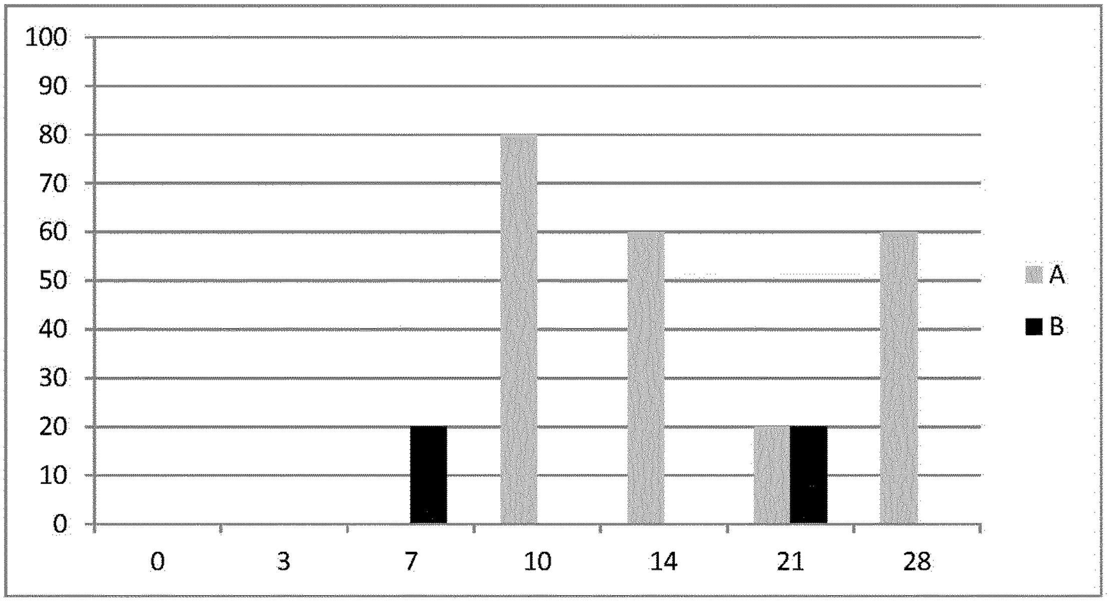

FIG. 23 represents the percentage of cohabitant animals positive to viremia for each group (Group A=vaccinated with the V1042-P62 PRRSV quasispecies, and Group B=vaccinated with the clone pVAC 6.1) at different days post-vaccination, as disclosed in Example 8.

DETAILED DESCRIPTION OF THE INVENTION

The object of the present invention is a method for generating an infectious cDNA clone based on the genome of an attenuated PRRSV strain, which comprises:

a) identifying polymorphic zones of the genome sequence of an attenuated strain of PRRSV,
b) determining the most frequent sequence within the polymorphic zones identified in step a), and
c) constructing an infectious cDNA clone comprising the most frequent sequence in at least one of the polymorphic zones identified in step a).

The authors of the present invention have developed for the first time a method for generating an infectious cDNA clone based on the genome of an attenuated PRRSV, wherein at least a part of the nucleotides of the whole sequence is substituted by the most frequent sequence present in polymorphic population that constitutes an attenuated PRRSV. The vaccine comprising virus rescued from such infectious clone shows higher safety than a commercially available vaccine, as it reduces faecal and salivary shedding in infected animals, and it reduces the number of positive animals with virus load in lung tissues, and surprisingly the efficacy of the vaccine is maintained. Safety and efficacy of vaccines are two distinct features but they are completely interrelated. Usually when trying to improve safety vaccine profile results in a lost on the efficacy and vice versa. Therefore, with this invention, a new generation of efficacious and safer modified live vaccines is provided against PRRSV.

In the present description as well as in the claims, the singular forms "a" and "an" include also the plural reference unless the context clearly indicates otherwise.

Also, when reference to a particular sequence from the "Sequence Listing" section of the subject application is made, it is intended, unless otherwise specified, to refer to both the DNA of the "Sequence Listing", as well as RNA corresponding to the DNA sequence, and includes sequences complementary to the DNA and RNA sequences. In such contexts in this application, "corresponding to" refers to sequences of DNA and RNA that are identical to one another but for the fact that the RNA sequence contains uracil in place of thymine and the backbone of the RNA molecule contains ribose instead of deoxyribose.

Sequencing can be carried out using standard methods well known by the skilled person, which comprise the use of several cDNA clones or Sanger sequencing of RT-PCR reaction products, as disclosed in Sanger et al., A rapid method for determining sequences in DNA by primed synthesis with DNA polymerase, J. Mol. Biol., 1975, 94(3), 441-448, and also massive sequencing, as disclosed, for example, in Buermans et al., Next generation sequencing technology: Advances and applications, Biochim. Biophys. Acta, 2014, 1842, 1932-1941.

Assessment of the variability in a region, i.e. polymorphism, can be done by sequencing a specific number of clones, e.g. about 20 or more. Alternatively, restriction fragment length polymorphism (RFLP), deep-sequencing or single-strand conformation polymorphism (SSCP) can be used. Such methodologies are disclosed, for example, in Beckmann et al., Restriction fragment length polymorphisms in genetic improvement: methodologies, mapping and costs, Theor. Appl. Genet., 1983, 67, 35-43; Goldman et al., Making sense of deep sequencing, Int. J. Neuropsychopharmacol., 2014, 17, 1717-1725, and Sheffield et al., The Sensitivity of Single-Strand Conformation Polymorphism Analysis for the detection of Single Base Substitutions, Genomics, 1993, 16, 325-332.

Construction of the genome sequences can be done by assembling of restriction fragments, as shown in the examples in the present invention, or by chemical synthesis.

Substitution of specific regions in a genome sequence can be done by standard cloning methods or directed mutagenesis, as shown in the examples of the present invention, or chemical synthesis.

An infectious clone is a plasmid vector molecule in which the whole genome of a virus has been cloned under the control of a promotor and, if necessary, other control elements (e.g., the Hepatitis delta virus ribozyme used as terminator) such as direct transcription of the cloned genome results in a RNA molecule that directly is able of initiating an infection.

The infectious cDNA clone can be introduced into cells by transfection (transformation-infection) to produce infectious virus.

Infectious clone and infectious cDNA clone are used as synonyms in the present invention.

The method for generating an infectious clone of the present invention is based on the genome of an attenuated PRRSV.

The term "attenuated PRRSV" means a viable PRRSV strain, which has been attenuated in vitro and/or in vivo, and which shows a reduced virulence in comparison to wild type pathogenic PRRSV, wherein virulence means a degree of pathogenicity, i.e. the ability of the pathogen to produce clinical signs in the host or the offspring of the host, such as elevated body temperature or reproductive failure. In the case of pigs, lung lesion, temperature increases up to 41° C. are also associated with virulence of the PRRSV. The presence of the virus in sera and body secretions are also reduced in attenuated virus compared to the virulent ones.

The attenuation of a strain can be determined by the skilled person, for example, by in vitro unadaptation to the porcine alveolar macrophages, changes of the replication kinetics, or changes of the shape of the cytopathic effect in the cell culture.

Preferably, the attenuated PRRSV strain may be a European PRRSV or a North American PRRSV.

The term "European PRRSV" refers to any strain of PRRSV having the genetic characteristics associated with the PRRSV that was first isolated in Europe around 1991 (see, e.g., Wensvoort et al., Mystery swine disease in the Netherlands: the isolation of Lelystad virus, Vet. Quart., 1991, 13, 121-130). "European PRRS virus" is also sometimes referred to in the art as genotype 1 or I, and being the "Lelystad virus" the prototype of the European PRRSV isolates. Therefore, any Lelystad-like isolate is also comprised as European PRRSV. Lena strain is also representative of genotype 1 (Karniychuck et al., Research article Pathogenesis and antigenic characterization of a new East European subtype 3 porcine reproductive and respiratory syndrome virus isolate, BMC Vet. Res., 2010, 6, 30 (1-10)).

The term "North American PRRSV" means any PRRSV having genetic characteristics associated with a North American PRRSV isolate, such as, but not limited to the PRRSV that was first isolated in the United States around the early 1990's (see, e.g., Collins et al., Isolation of swine infertility and respiratory syndrome virus (isolate ATCC VR-2332) in North America and experimental reproduction of the disease in gnotobiotic pigs J. Vet. Diagn. Invest., 1992, 4, 117-126). "North American PRRSV" is also referred as genotype 2 or II, being the VR-2332 strain the prototype of the North American PRRSV isolates. Other North American PRRSV isolates are: North American PRRS virus isolate MN-1 b (Kwang et al., Cloning, expression, and sequence analysis of the ORF4 gene of the porcine reproductive and respiratory syndrome virus MN-1 b, J. Vet. Diagn. Invest., 1994, 6, 293-296); the Quebec IAF-exp91 strain of PRRSV (Mardassi et al., Molecular analysis of the ORFs 3 to 7 of porcine reproductive and respiratory syndrome virus, Quebec reference strain, Arch. Virol., 1995, 140, 1405-1418); and North American PRRSV isolate VR 2385 (Meng et al., Molecular cloning and nucleotide sequencing of the 3'-terminal genomic RNA of the porcine reproductive and respiratory syndrome virus, J. Gen. Virol., 1994, 75, 1795-1801).

In a preferred embodiment the attenuated PRRSV strain is an attenuated European PRRSV strain, and more preferably is VP-046 BIS strain (Accession number CNCM I-1642, deposited on Nov. 23, 1995, in Collection Nationale de Cultures de Micro-organismes-Pasteur Institute (CNCM), Institut Pasteur, 25-28, Rue du Dr. Roux, 75724 Paris Cédex 15, France). In another preferred embodiment the attenuated European PRRSV strain is VP1042-P62 strain (Accession number CNCM 1-5219, deposited on Jul. 19, 2017 by Hipra Scientific S.L.U. in Collection Nationale de Cultures de Micro-organismes-Pasteur Institute (CNCM)).

Step a): Identification of the Polymorphic Zones of the Genome Sequence of an Attenuated Strain of PRRSV In the method of the invention it is used the genome sequence of an attenuated strain of PRRSV. In a preferred embodiment, the genome sequence corresponds to a sequence having at least 99.90%, 99.91%, 99.92%, 99.93%, 99.94%, 99.95%, 99.96%, 99.97%, 99.98%, 99.99%, 99.999% degree of identity with the consensus sequence. In a more preferred embodiment, the genome sequence is the consensus sequence of an attenuated strain of PRRSV, i.e. the sequence has 100.00% identity with the consensus sequence. A degree of identity of 99.90% represents 10 different nucleotides in a sequence of 10000 nucleotides, and a degree of identity of 99.99% represents 1 different nucleotide in a sequence of 10000 nucleotides.

The term "consensus sequence" is used to describe a number of related, but not identical sequences. It is compiled by inserting the nucleotide or amino acid, in the case of a polypeptide sequence, occurring most often at each position in the real sequences. Usually it is generated by aligning several PRRSV full-genome sequences, followed by selecting the most common nucleotide found at each position of the alignment. Alternatively, consensus sequences can be generated using suitable online tools or software such as, for example, JalView, ClustalW2 or Ugene. The consensus sequence can be also obtained by direct Sanger sequencing method of RT-PCR products. Other techniques such as those disclosed in Buermans et al., op.cit., are also useful to generate a consensus sequence. In that case, polymorphic zones are automatically identified on the genome sequence of the attenuated PRRSV strain.

Preferably, the consensus sequence is the calculated order of nucleotides that are found at a frequency equal or higher than at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% at each position of the sequence. Alternatively, the consensus sequence is obtained by direct Sanger sequencing of RT-PCR reaction products, wherein, a position is named polymorphic if more than one peak is observed in the chromatogram.

In the present invention, in the event of sequencing cDNA clones, the consensus sequence is obtained from at least two, preferably from at least five, more preferably from at least 50, and yet more preferably up to 100 overlapping DNA clones complementary to RNA extracted of attenuated PRRSV strain, and for each position the consensus sequence is obtained as the nucleotide present in at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% at each position of the sequences. Alternatively, the consensus sequence is obtained by direct Sanger sequencing of RT-PCR reaction products, wherein, in this case, a position is named polymorphic if more than one peak is observed in the chromatogram.

In a preferred embodiment the consensus sequence of the attenuated PRRSV is SEQ ID NO:1, which is obtained from attenuated virus VP-046 BIS strain.

In another preferred embodiment the consensus sequence of the attenuated PRRSV is SEQ ID NO:163, which is obtained from attenuated virus V1042-P62 strain.

The infectious clone pVAC 5.0 contains the genome sequence SEQ ID NO:2, which is the PRRSV genome present in clone pVAC-T7-5, and which shows a degree of identify of 99.98% with the consensus sequence SEQ ID NO:1.

A partial pVAC 5.0 infectious clone includes a fragment of pACYC177-ADAP and has the following structure:

1-32: pACYC-ADAP (partial),
33-40: AscI restriction site,
41-622: Promoter pCMV from Human cytomegalovirus,
623-630: SwaI restriction site,
631-15753: PRRSV genome SEQ ID NO:2,
15754-15837: Hepatitis delta virus ribozyme,
15838-15843: XbaI restriction site,
15844-15917: pACYC177-ADAP (partial).

The partial nucleotide sequence of infectious clone pVAC 5.0 is SEQ ID NO:3. The full nucleotide sequence of infectious clone pVAC 5.0 is SEQ ID NO:223, which also includes the full sequence of pACYC-ADAP.

The infectious clone pVAC 5.0 was deposited by Hipra Scientific S.L.U. in the Leibnitz-Institut DSMZ-Deutsche Sammlung von Mikroorganismen and Zellkulturen, Inhoffenstrasse 7B, 38124 Braunschweig, Germany, under accession number DSM 32339 (Jul. 19, 2016). The preparation of clones pVAC-T7-5 and pVAC 5.0 is described in Example 1.

A polymorphic zone is a genomic region with a size lower than 2.5 kb, preferably lower than 2.0 kb, more preferably lower than 1.5 kb, yet more preferably lower than 1.3 kb, which contains one or more polymorphic positions. In the context of the present invention, a polymorphic position is defined as a position at which all nucleotides found were at a frequency lower than 75%.

The identification of the polymorphic zones is usually carried out by assembling nucleotide sequences from different overlapping clones covering the full attenuated PRRSV genome using mapping tools, for example those included in Geneious R.9.0.2 package (Biomatters Ltd). After assembly, tools included in the software allow to construct the consensus sequence as defined above. Alternatively, polymorphic zones can be identified by visual inspection when more than one peak is observed in the chromatograms resulting from direct Sanger sequencing of RT-PCR reaction products. The analysis can be also performed for example with the tools included in Geneious R.9.0.2. package (Biomatters Ltd.). Massive sequencing, as disclosed, for example, in Buermans et al., op. cit., can also be used for identifying polymorphic regions.

Polymorphic zones may be selected from the group consisting of 5' UTR, ORF1a, ORF1b, ORF2, ORF3, ORF4, ORF5, ORF6, ORF7 and 3'UTR, preferably ORF1a, ORF1b, ORF4, ORF5 and ORF7, and more preferably ORF1a, ORF1b, ORF4, and ORF5.

In a preferred embodiment the polymorphic zones are selected from ORF1a, ORF1b, ORF3, ORF4, ORF5, and ORF6, and more preferably from ORF1a, ORF1b, ORF3, ORF4, ORF5, and ORF6 of the attenuated virus VP-046 BIS strain. In another preferred embodiment the polymorphic zones selected from ORF1a, ORF1b, ORF2, ORF3, ORF4, ORF5, ORF7, and 3'UTR, and more preferably from ORF1a, ORF1b, ORF2, ORF3, ORF4, ORF5, ORF7, and 3'UTR of the attenuated virus V1042-P62 strain.

The open reading frames (ORF) identified in the attenuated virus VP-046 BIS strain are located in the following positions of the consensus sequence of the attenuated PRRS virus defined by SEQ ID NO:1:

5'UTR: from 1 to 221
ORF1A: from 222 to 7412
ORF1B: from 7394 to 11785
ORF2A: from 11796 to 12545
ORF2B: from 11801 to 12013
ORF3: from 12404 to 13201
ORF4: from 12946 to 13497
ORF5: from 13494 to 14099
ORF6: from 14087 to 14608
ORF7: from 14598 to 14984
3'UTR: from 14985 to 15098

The position of the open reading frames (ORF) can vary slightly depending on the PRRSV strain. In the case of the attenuated virus V1042-P62 strain, ORFs are located in the same positions of the virus VP-046 BIS strain.

In a preferred embodiment for a European PRRSV, polymorphic zones are located:

i) from position 3902 to 3959,
ii) from 6792 to 7672, and
iii) at the region comprising ORF2 to ORF5, encoding for the corresponding glycoproteins GP2 to GP5; preferably at the region comprising ORF4 to ORF5, and more preferably from position 12938 to 14151, wherein positions are referred to the consensus sequence of the attenuated PRRS virus defined by SEQ ID NO:1.

In another preferred embodiment for a European PRRSV, polymorphic zones are located:

i) from position 3902 to 3959,
ii) from 6792 to 7672, and
iii) at the region comprising ORF3 to ORF6, and more preferably from position 12938 to 14151, wherein positions are referred to the consensus sequence of the attenuated PRRS virus defined by SEQ ID NO:1.

In another preferred embodiment that the polymorphic zones are located at the regions:

i) from position 1164 to 2113,
ii) from 4630 to 6543,
iii) from 6906 to 8402,
iv) from 11618 to 12274, and
v) at the region comprising ORF3 to 3'UTR, and more preferably at the region selected from position 12970 to 13887 and from position 14633 to 15082, wherein positions are referred to the consensus sequence of the attenuated PRRS virus defined by SEQ ID NO:163.

The characterization of proteins encoded by ORFs 2 to 7 of PRRS virus (Lelystad virus) is disclosed in Meulenberg et al., Characterization of Proteins Encoded by ORFs 2 to 7 of Lelystad Virus, Virology, 1995, 206, 155-163. Nucleotide sequences of the whole genome of Lelystad virus and the ORF's are disclosed under GenBank accession M96262.2.

Step b): Determination of the Most Frequent Sequence within the Identified Polymorphic Zones The determination of the most frequent sequence within the polymorphic zones identified in the previous step is carried out by obtaining at least about 20 clones of the region, preferably from at least about 50, more preferably from up to about 100 overlapping DNA clones complementary to RNA extracted of attenuated PRRSV strain, and aligning the sequences using adequate software, for example, Geneious package (Biomatters Ltd). Tools included in the software allow the identification of the sequence shared by the largest number of clones, i.e. the most frequent sequence. Alternatively, deep sequencing can also be used for the determination of the most frequent sequence.

Alternatively, the determination of the most frequent nucleotide sequence within the identified polymorphic zones can be carried out by obtaining at least about 20 clones of the region, preferably from at least about 50, more preferably from up to about 100 overlapping DNA clones complementary to the region of interest in the attenuated PRRSV strain. If no majority nucleotide sequence is found, nucleotide sequences are then translated into protein, aligned using any suitable software package and the most frequent amino acid sequences is subsequently identified. A nucleotide sequence that encodes for the most abundant amino acid sequence is then chosen.

Step c): Construction of an Infectious Clone Comprising the Most Frequent Sequence in at Least One of the Polymorphic Zones Identified in Step a).

In the method of the present invention once the most frequent sequence in at least one polymorphic zone is determined, then an infectious clone comprising such most frequent sequence in at least one polymorphic zone is constructed using standard methods of molecular cloning, as shown in the Examples section.

Infectious cDNA Clone

The object of the present invention further provides an infectious cDNA clone obtainable by such method.

The infectious clone obtainable by the method of the invention comprises the viral genome and control elements, wherein the viral genome comprises the most frequent sequence in at least one of the polymorphic zones identified in the sequence of an attenuated strain of PRRSV, preferably an attenuated European PRRSV, and more preferably selected from VP-046 BIS PRRSV strain and VP1042-P62 PRRSV strain.

In a preferred embodiment, the sequence corresponds to the consensus sequence of an attenuated strain of PRRSV, and in a more preferred embodiment of an attenuated European PRRSV, and more preferably selected from VP-046 BIS PRRSV strain and VP1042-P62 PRRSV strain.

In a preferred embodiment, the infectious clone comprises the most frequent sequence in at least one of the polymorphic zones selected from the group consisting of:

i) from position 3902 to 3959,
ii) from position 6792 to 7672, and
iii) at the region comprising ORF2 to ORF5, encoding for the corresponding glycoproteins GP2 to GP5, preferably ORF4 to ORF5, and more preferably from position 12938 to 14151, wherein positions being referred to the consensus sequence of the attenuated PRRS virus defined by SEQ ID NO:1.

In a particularly preferred embodiment the infectious clone comprises the most frequent sequence corresponding to the region comprising ORF2 to ORF5, encoding for the corresponding glycoproteins GP2 to GP5, preferably to the region comprising ORF4 to ORF5, and more preferably the region from position 12938 to 14151, positions being referred to the consensus sequence of the attenuated PRRS virus defined by SEQ ID NO:1. In a particularly preferred embodiment, the infectious clone comprises only the most frequent sequence in the region from position 12938 and 14151.

In another preferred embodiment the infectious clone comprises the most frequent sequence in at least one polymorphic zone selected from the group consisting of:

i) from position 3902 to 3959, ii) from 6792 to 7672, and iii) at the region comprising ORF3 to ORF6, and more preferably from position 12938 to 14151, wherein positions are referred to the consensus sequence of the attenuated PRRS virus defined by SEQ ID NO:1.

In a particularly preferred embodiment the infectious clone comprises the most frequent sequence corresponding to the region comprising ORF3 to ORF6, and more preferably the region from position 12938 to 14151, positions being referred to the consensus sequence of the attenuated PRRS virus defined by SEQ ID NO:1. In a particularly preferred embodiment, the infectious clone comprises only the most frequent sequence in the region from position 12938 and 14151.

The infectious clone containing the most frequent sequence corresponding to the region from position 12938 to 14151 is named pVAC 5.2.

A partial pVAC 5.2 infectious clone includes a fragment of pACYC177-ADAP and has the following structure:

1-32: pACYC177-ADAP (partial), 33-40: AscI restriction site, 41-622: Promoter pCMV from Human cytomegalovirus, 623-630: SwaI restriction site, 631-15753: attenuated virus VP-046 BIS Genome sequence variant 5.2, 15754-15837: Hepatitis delta virus ribozyme, 15838-15843: XbaI restriction site, 15844-15917: pACYC177-ADAP (partial).

The partial nucleotide sequence of infectious clone pVAC 5.2 is SEQ ID NO:4. The full nucleotide sequence of infectious clone pVAC 5.2 is SEQ ID NO:225, which also includes the full sequence of pACYC-ADAP.

The infectious clone pVAC 5.2 was deposited by Hipra Scientific S.L.U. in the Leibnitz-Institut DSMZ-Deutsche Sammlung von Mikroorganismen and Zellkulturen, Inhoffenstrasse 7B, 38124 Braunschweig, Germany, under accession number DSM 32341 (Jul. 19, 2016). The preparation of infectious clone pVAC 5.2 is described in Example 2.

In another preferred embodiment, the infectious clone comprises the most frequent sequence in the following polymorphic zones:

i) from position 3902 to 3959, ii) from 6792 to 7672, and iii) from position 12938 to 14151, wherein positions being referred to the consensus sequence of the attenuated PRRSV defined by SEQ ID NO:1.

The infectious clone containing the most frequent sequence corresponding to these three regions from position 3902 to 3959, from 6792 to 7672 and from 12938 to 14151, is named pVAC 5.1.

A partial pVAC 5.1 infectious clone includes a fragment of pACYC177-ADAP and has the following structure:

1-32: pACYC177-ADAP (partial), 33-40: AscI restriction site, 41-622: Promoter pCMV from Human cytomegalovirus, 623-630: SwaI restriction site, 631-15753: attenuated virus VP-046 BIS Genome sequence variant 5.1, 15754-15837: Hepatitis delta virus ribozyme, 15838-15843: XbaI restriction site, 15844-15917: pACYC177-ADAP (partial).

The partial nucleotide sequence of infectious clone pVAC 5.1 is SEQ ID NO:5. The full nucleotide sequence of infectious clone pVAC 5.1 is SEQ ID NO:224, which also includes the full sequence of pACYC-ADAP.

The infectious clone pVAC 5.1 was deposited by Hipra Scientific S.L.U. in the Leibnitz-Institut DSMZ-Deutsche Sammlung von Mikroorganismen and Zellkulturen, Inhoffenstrasse 7B, 38124 Braunschweig, Germany, under accession number DSM 32340 (Jul. 19, 2016). The preparation of infectious clone pVAC 5.1 is described in Example 3.

In a preferred embodiment, the infectious clone comprises the most frequent sequence corresponding to at least one of the following polymorphic zones:

i) from position 1164 to 2113, ii) from 4630 to 6543, iii) from 6906 to 8402, iv) from 11618 to 12274, and v) at the region comprising ORF3 to ORF7, and more preferably at the region selected from position 12970 to 13887 and from position 14633 to 15082, wherein positions are referred to the consensus sequence of the attenuated PRRS virus defined by SEQ ID NO:163.

In a more preferred embodiment, the infectious clone comprises the most frequent sequence corresponding to the polymorphic zones:

i) from position 1164 to 2113, ii) from 4630 to 6543, iii) from 6906 to 8402, iv) from 11618 to 12274, v) from 12970 to 13887 and vi) from 14633 to 15082, wherein positions are referred to the consensus sequence of the attenuated PRRS virus defined by SEQ ID NO:163.

The infectious clone that contains the most frequent nucleotide sequence variant in genomic regions ranging from positions 1164 to 2113, 6906 to 8402, 11618 to 12274, and 14633 to 15082; one of the nucleotide sequence variants coding for the most frequent protein in positions 4630 to 6543 and 12970 to 13887; and the consensus nucleotide sequence in the rest of positions, except for position 8806 that contains C instead of U, referred to the consensus sequence of the attenuated PRRS virus defined by SEQ ID NO:163, is named clone pVAC 6.1 The full nucleotide sequence of infectious clone pVAC 6.1 is SEQ ID NO:162.

The infectious clone pVAC 6.1 was deposited by Hipra Scientific S.L.U. in the Leibnitz-Institut DSMZ-Deutsche Sammlung von Mikroorganismen and Zellkulturen, Inhoffenstrasse 7B, 38124 Braunschweig, Germany, under accession number DSM 32542 (Jun. 22, 2017). The preparation of infectious clone pVAC 6.1 is described in Example 7.

The clone pVAC 6.1 has the following structure:

1-15123: PRRSV V1042-P62 genome, 15124-15206: HDV-Rz, 15207-15212: XbaI restriction site, 15213-18737: Vector pACYC177-ADAP-Pcmv, 18738-18745: SwaI restriction site.

In a preferred embodiment the infectious cDNA clone is selected from the group of clone pVAC 5.2, clone pVAC 5.1 and clone pVAC 6.1. In a more preferred embodiment the infectious cDNA clone is pVAC 5.2. In another preferred embodiment the infectious cDNA clone is pVAC 5.1. In another preferred embodiment the infectious cDNA clone is pVAC 6.1.

The configuration of the infectious clone of the invention includes the viral genome, which comprises the most frequent sequence in at least one of the polymorphic zones identified in the consensus sequence of an attenuated PRRSV strain, and also control elements such as direct transcription of the cloned genome results in a RNA molecule that directly is able of initiating an infection. Such control elements comprise a promoter sequence, preferably the Human cytomegalovirus promoter (pCMV), a ribozyme, for example, the one from the Hepatitis delta virus. Viral cDNA and control elements are carried by a bacterial plasmid with suitable restriction sites for cloning.

Nucleic Acids, DNA-Vectors, Host Cells, and Virus

It is an object of the present invention a recombinant nucleic acid comprising the infectious cDNA clone of the invention. The recombinant nucleic acid on the invention comprises the most frequent sequence in at least one polymorphic zone. It is an object of the present invention a DNA construct comprising a copy of the recombinant nucleic acid of the invention. In a preferred embodiment said DNA construct is a DNA vector such as a plasmid. In a preferred embodiment the DNA construct is an isolated DNA construct.

It is an object of the present invention a RNA transcript of such DNA construct. In a preferred embodiment the RNA transcript is an isolated RNA transcript.

Standard cloning procedures and preparation of nucleic acid molecules can be carried out as described in well-known manuals to the skilled person in the art such as, for example, J. Sambrook and D. W. Russell, Molecular Cloning: A laboratory manual, 4$^{th}$ edition, Cold Spring Harbor Laboratory Press, New York, 2012.

It is an object of the present invention a host cell transfected with the DNA construct of the invention.

The transfection can be done either with circular infectious cDNA plasmid or with a previously linearization molecule, according to standard methods in the art. Cells suitable for transfection are for example clone 8 cells (Collection Nationale de Cultures de Microorganismes accession number 1-1643), BHK-21 cells, VERO cells or MARC-145 cells (ATCC CRL-11171). Preferably, clone 8 cells are used.

The results observed in the transfection and amplification experiments confirm the ability of the infectious clone of the invention to generate biologically active PRRSV in in vitro conditions.

It is an object of the present invention an attenuated PRRSV encoded by the RNA transcript of the invention.

Attenuated PRRSV can be obtained from cell culture supernatant after transfection of host cells according to standard methods.

A process for preparing attenuated PRRSV comprises transfection of a host cell with the infectious cDNA clone of the invention and the isolation of the virus particles from the cell culture supernatant.

The transfection process of a host cell produces attenuated PRRSV particles, encoded by the RNA transcript of the invention.

Therefore, the invention also provides an attenuated PRRSV produced by the aforementioned host cell, preferably an attenuated European PRRSV or an attenuated American PRRSV, and more preferably an isolated attenuated European PRRSV.

Vaccines and Immunogenic Compositions

It is an object of the present invention an immunogenic composition comprising the attenuated PRRSV, preferably an attenuated PRRSV selected from the group consisting of an attenuated European PRRSV and attenuated North American PRRSV.

In a preferred aspect, the immunogenic composition comprises a titer per dose of 10 to $10^7$ $CCID_{50}$ of the attenuated PRRSV strain of the invention, preferably $10^2$ to $10^6$, and more preferably $10^3$ to $10^6$.

It is an object of the present invention a vaccine comprising an immunologically effective amount of attenuated PRRSV of the invention and a pharmaceutically acceptable diluent or excipient, preferably an attenuated PRRSV selected from the group of an attenuated European PRRSV and an attenuated North American PRRSV, more preferably an attenuated European PRRSV, and more preferably selected from VP-046 BIS PRRSV strain and VP1042-P62 PRRSV strain.

Alternatively the vaccine comprises an immunologically effective amount of the infectious cDNA clone of the invention and a pharmaceutically acceptable diluent or excipient.

The vaccine of the invention is a composition, which elicits a protective response in an animal, which has been exposed to the composition.

The expression "immunologically effective" means that the amount of virus administered in the vaccination process is sufficient to induce an effective immunological response in the host against an infection by the virulent forms of PRRSV.

It is known that the dose to be used depends on the age, physiological status and weight of the animal to be vaccinated and on the administration route. Suitable doses are generally comprised in the range 10 to $10^7$ $CCID_{50}$ of the attenuated PRRSV strain of the invention per dose, preferably $10^2$ to $10^6$, and more preferably $10^3$ to $10^6 CCID_{50}$ per dose.

The vaccine of the invention is intended for swine including, among others, pigs, boars, sows, and piglets of any age or in any phase of their production cycle; it is preferably intended for pigs in the fattening stage, and more preferably for pigs from 1 week of age onwards, and for breeding females (gilts and sows in gestation and/or in lactation).

The vaccine can be administered intranasally, intradermally, mucosally or submucosally, subcutaneously, by means of aerosol, intramuscularly, or orally.

Said vaccine can be prepared according to the typical methods used by the person skilled in the art for preparing pharmaceutical formulations suitable for the different dosage forms, such as described, for example, in the manual *Remington The Science and Practice of Pharmacy*, 20$^{th}$ edition, Lippincott Williams & Wilkins, Philadelphia, 2000 [ISBN: 0-683-306472].

The vaccines are typically prepared as injection vaccines in the form of emulsions or liquid suspensions. They can also be prepared in a solid form suitable to be dissolved or suspended in a liquid vehicle before injection.

The typical volume of a dose of an injection vaccine is between 0.2 ml and 5 ml, preferably between 1 ml and 3 ml, and more preferably between 1 ml and 2 ml.

The liquid vehicles which can be used for preparing the vaccine include, for example, water, saline solution with a physiological salt concentration, or the culture liquid in which the host cells are cultured.

Additionally, if desired, the vehicle can contain pharmaceutically acceptable excipients or auxiliary substances such as, for example, wetting agents, dispersing agents, emulsifying agents, buffering agents (for example, phosphate buffer), stabilizing agents such as carbohydrates (for example, glucose, sucrose, mannitol, sorbitol, starch, or dextrans), or proteins (for example, albumin, casein, bovine serum, or skimmed milk).

The physicochemical characteristics of the excipients as well as the name of the commercial products under which they are marketed can be found in the book by R. C. Rowe et al., *Handbook of Pharmaceutical Excipients,* $4^{th}$ edition, Pharmaceutical Press, London, 2003 [ISBN: 0-85369-472-9].

Adjuvants can also optionally be incorporated in the vaccine to enhance the effectiveness thereof. Preferably the vaccine of the invention further comprises an adjuvant. Adjuvants are non-specific immune system stimulants which increase immunological response of the host against the vaccine antigen. Examples of adjuvants are: aluminium hydroxide, aluminium phosphate, aluminium oxide, vitamin E, squalene, vegetable oil, saponins, ginseng, zymosan, glucans, dimethylaminoethyldextran, dextrans, non-ionic block polymers, complete Freund's adjuvant, incomplete Freund's adjuvant, muramyl dipeptides, W/O, O/W, W/OW type emulsions, and mixtures thereof.

In a preferred embodiment the vaccine is an injection vaccine and comprises the attenuated PRRSV of the invention suspended in a vehicle, e.g. MEM G (Glasgow Minimum Essential Medium, Thermo Fisher Scientific) supplemented with 10% FBS (Fetal Bovine Serum, Gibco).

In a preferred embodiment the vaccine can comprise the strain of the invention in a lyophilised form. The lyophilisation process is carried out by means of methods well known by the person skilled in the art.

In a preferred embodiment the vaccine includes an antigenic component against another disease or additional pathological conditions affecting pigs. The vaccine is preferably aimed at conferring protection to pigs against diseases or pathological conditions such as, for example, those caused by the *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli* microorganisms, *Swine influenza virus, Contagious gastroenteritis virus, Porcine parvo virus, Encephalomyocarditis virus*, coronavirus, rotavirus, *Porcine circovirus*, porcine periweaning failure to thrive syndrome agent, *Classical swine fever virus, African swine fever virus*, calicivirus and/or *Torque teno virus.*

In a more preferred embodiment, the additional disease is that known as PCVAD (Porcine Circovirus Associated Diseases) caused by *Porcine circovirus* (PCV2), and/or mycoplasmal pneumonia caused by *Mycoplasma hyopneumoniae.*

It is an object of the present invention a vaccine comprising that attenuated PRRSV and a pharmaceutically acceptable diluent or excipient for use in the prophylaxis and/or the treatment of PRRSV infections.

It is an object of the present invention the attenuated PRRSV virus for use in the prophylaxis and/or the treatment of PRRSV virus infections.

It is an object of the present invention the attenuated PRRSV for use as vaccine or medicament in the prophylaxis and/or the treatment of PRRSV infections.

The prophylaxis and/or treatment of PRRSV infections refers to the ability of the attenuated PRRSV of the invention to prevent an animal from clinical signs of a PRRSV infection and/or to reduce such clinical signs such as, for example, respiratory signs, body temperature, viremia, or faecal, nasal or saliva shedding, reproductive disorders, ameliorate the pig performance (i.e., average daily weight gain, weight at weaning), and reduction of weak piglets and mortality.

The prophylaxis is associated to the prevention process, in which an animal, preferably swine, more preferably a breeding female, more preferably a pig, and even more preferably a piglet, is exposed to the immunogenic composition or to the vaccine of the present invention prior to the induction or onset of the disease process by a virulent strain of PRRSV.

The treatment is associated to the reduction of the clinical signs caused by PRRS virus infection in an animal, preferably swine, and more preferably a pig.

Within the scope of this invention, the reduction of clinical signs means the reduction of viremia, i.e. the reduction of the PRRSV load, the reduction of the viral load in faecal shedding, and the reduction of the body temperature in an animal that has received the vaccine or the immunogenic composition of the invention in comparison to animals not receiving it. Preferably these clinical signs are reduced in subjects receiving the attenuated PRRSV of the present invention by at least 10%, preferably by at least 20%, more preferably by at least 30%, more preferably by at least 40%, and yet more preferably by at least 50% in comparison to animals not receiving it.

The viremia in the blood serum of animals was measured as $CCID_{50}$/mL, being $CCID_{50}$ the 50% cell culture infective dose. The viremia in animals receiving the immunogenic composition or the vaccine of the invention is reduced usually by at least 10%, 20%, 30%, 40%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.90%, 99.91%, 99.92%, 99.93%, 99.94%, 99.95%, 99.96%, 99.97%, 99.98%, or 99.99%, in comparison to subjects not receiving the composition.

Attenuation and Reversion to Virulence Trials

Trials to assess attenuation and reversion to virulence of the infectious clones of the invention show the following results in comparison to the attenuated PRRS virus strain VP-046 BIS:

First Serial Passage

Viremia in inoculated animals Lower viremia titer for the group vaccinated with pVAC 5.2 in comparison to the group vaccinated with VP-046 BIS.

Lower percentage of viremic animals in the pVAC 5.2 group.

Viremia in cohabitant animals pVAC 5.2 did not raise viremia, in comparison to VP-046 BIS.

Lower percentage of viremic animals in the pVAC 5.2 group.

Virus tissue load and shedding in inoculated animals Lower percentage of animals positive to PRRSV in lung tissues, tonsil and faecal swabs in the pVAC 5.2 group.

Virus tissue load and shedding in cohabitant animals Significant reduction in lung virus load for the pVAC 5.2 group in comparison to the VP-046 BIS group.

Lower percentage of animals positive to PRRSV in lung tissues and tonsil swabs favourable to pVAC 5.2 group.

Second Serial Passage

Viremia in inoculated animals Lower percentage of viremic animals in the pVAC 5.2 group.

Viremia in cohabitant animals Clearance of the viremia in the cohabitant animals for the pVAC 5.2 group.

Lower percentage of cohabitant animals positive to viremia in the pVAC 5.2 group.

Virus tissue load and shedding in inoculated and cohabitant animals Undetectable PRRSV in lung virus load and in tonsil swabs for the pVAC 5.2 group in comparison to the VP-046131S group.

Clear reduction (to zero) in the percentage of animals with lung virus load and in tonsil swabs for the pVAC 5.2 group.

No faecal shedding was seen in animals inoculated with pVAC 5.2

General conclusions pVAC 5.2 shows lower viremia and replication capacity, which represents lower capacity of accumulation in lungs and tonsils, and consequently less capacity of reversion.

The reduced viremia and shedding seen in the pVAC 5.2 group in comparison to the VP-046 BIS group reduces the trend to infection in cohabitant animals and consequently less opportunities of reversion.

Probability of reversion to virulence due to serial passages in vivo is clearly reduced.

Efficacy in Front of an Homologous Infection

The efficacy of the infectious clone of the invention against of a homologous infection by a virulent PRRSV is comparable to a commercially available vaccine (Laboratorios Hipra, Amer, Girona, Spain) in terms of viremia, faecal and salivary shedding, and the presence of virus in tonsil swabs.

Efficacy in Front of an Heterologous Infection

The efficacy of the infectious clone of the invention is comparable to a commercially available vaccine (Laboratorios Hipra, Amer, Girona, Spain) against of a heterologous infection with a PRRSV, Serological profiles Increase in the antibody level for vaccinated animals either with the vaccine prepared from clone pVAC 5.2 or commercial vaccine, in comparison to the Control group after experimental infection.

Viremia Significant differences in mean viremia between the groups of vaccinated animals and the Control group at days 38, 41, 44, and 48 post-vaccination.

Reduction of two orders of magnitude in viremia for the group of pVAC 5.2 in comparison to the Control group.

Significant differences in the percentages of viremic animals after challenge for each group of vaccinated animals and the Control group at days 38, 41, 44, and 48 post-vaccination (4, 7, 10 days post-infection).

Faecal shedding Significant differences in the mean faecal shedding at day 41 (pVAC 5.2) and 44 post-vaccination (VP-046 BIS) in comparison to Control group.

At day 48 it was observed a clear reduction in the shedding for the vaccinated groups.

Lower percentage of shedding animals and statistically differences between vaccinated and non-vaccinated animals at days 41 and 44 post-vaccination (4, 7 days post-infection).

Lung and tonsil swabs Significant differences in virus loads in lung tissues favourable to the group of vaccinated animals with pVAC 5.2 than the control group at day 70 post-vaccination (day 36 post-infection).

Significant reduction in percentage of animals with PRRSV detected in lung in pVAC 5.2 group in comparison to Control group.

General conclusions Clear reduction in the percentage of viremic animals and titre of the detected viremia after challenge for the vaccinated groups.

Clear reduction of shedding animals for the vaccinated groups.

Vaccination with pVAC 5.2 reduced the presence of virus in lung tissues and in tonsil swabs after a heterologous infection.

Thus, the vaccine comprising the attenuated PRRSV, obtained according to the method of the invention, shows higher safety than a commercially available vaccine, as it reduces faecal and salivary shedding in infected animals, it reduces the number of positive animals with virus load in lung tissues and the transmission of the virus from vaccinated animals to non-vaccinated ones is also clearly reduced. Surprisingly, the efficacy of the vaccine is maintained.

Therefore, the vaccine of the invention has very interesting safety features and represents an improved alternative over the prior art in the control of PRRSV infections.

Assessment of the Seroconversion and Safety of Clone pVAC 6.1

The seroconversion obtained using clone pVAC 6.1 as vaccine is comparable to that obtained by using the V1042-P62 PRRS quasispecies. In Example 8, it is shown that 73% of animals vaccinated in both groups were already seropositive (IRPC>20%) at day 28 after vaccination (D28).

The PRRSV dissemination was assessed by means of viremia values in cohabitant animals. It is shown that cohabitant animals with the group vaccinated using the clone pVAC 6.1 is significantly lower than in the cohabitant animals with the group vaccinated using the V1042-P62 PRRSV quasiespecies.

The lower viremia of pVAC 6.1 group in contrast to V1042-P62 PRRSV quasispecies represents lower capacity of accumulation in lungs and tonsils, and consequently less capacity of reversion to virulence of the vaccine of the invention.

The invention comprises the flowing embodiments:

1.—A method for generating an infectious cDNA clone based on the genome of an attenuated PRRSV strain, characterized in that it comprises:

a) identifying polymorphic zones of the genome sequence of an attenuated strain of PRRSV, b) determining the most frequent sequence within the polymorphic zones identified in step a), and c) constructing an infectious cDNA clone comprising the most frequent sequence in at least one of the polymorphic zones identified in step a).

2.—A method according to embodiment 1, characterized in that the genome sequence corresponds to a sequence having at least 99.90% degree of identity with the consensus sequence of an attenuated strain of PRRSV.

3.—A method according to embodiment 2, characterized in that the genome sequence is the consensus sequence of an attenuated strain of PRRSV.

4.—A method according to any of embodiments 1 to 3, characterized in that the polymorphic zones are selected from the group consisting of 5'UTR, ORF1a, ORF1b, ORF2, ORF3, ORF4, ORF5, ORF6, ORF7, and 3'UTR.

5.—A method according to embodiment 4, characterized in that the polymorphic zones are selected from the group consisting of ORF1a, ORF1b, ORF2, ORF3, ORF4, ORF5, ORF6, ORF7, and 3'UTR.

6.—A method according to any of embodiments 1 to 5, characterized in that the attenuated PRRSV strain is selected from the group consisting of an attenuated European PRRSV strain and an attenuated North American PRRSV strain.

7.—A method according to embodiment 6, characterized in that the attenuated PRRSV strain is VP-046 BIS strain.

8.—A method according to embodiment 7, characterized in that the consensus sequence is SEQ ID NO:1.

9.—A method according to embodiment 8, characterized in that the polymorphic zones are located at the regions:

i) from position 3902 to 3959,
ii) from 6792 to 7672, and
iii) at the region comprising ORF3 to ORF6, and more preferably from position 12938 to 14151, wherein positions are referred to the consensus sequence of the attenuated PRRS virus defined by SEQ ID NO:1.

10.—A method according to embodiment 6, characterized in that the attenuated PRRSV strain is V1042-P62 strain.

11.—A method according to embodiment 10, characterized in that the consensus sequence is SEQ ID NO: 163.

12.—A method according to embodiment 11, characterized in that the polymorphic zones are located at the regions:

i) from position 1164 to 2113,
ii) from 4630 to 6543,
iii) from 6906 to 8402,
iv) from 11618 to 12274, and
v) at the region comprising ORF3 to 3'UTR, encoding for the corresponding glycoproteins GP2 to GP5, the membrane protein and the nucleocapsid protein; and preferably at the region selected from position 12970 to 13887 and from position 14633 to 15082, wherein positions are referred to the consensus sequence of the attenuated PRRS virus defined by SEQ ID NO: 163.

13.—An infectious cDNA clone obtainable by the method of any of embodiments 1 to 12.

14.—An infectious clone according to embodiment 13, characterized in that it comprises the most frequent sequence corresponding to at least one of the following polymorphic zones:

i) from position 3902 to 3959,
ii) from position 6792 to 7672, and
iii) at the region comprising ORF3 to ORF6, and more preferably the region from position 12938 to 14151, wherein positions are referred to the consensus sequence of the attenuated PRRS virus defined by SEQ ID NO:1

15.—An infectious clone according to embodiment 14, characterized in that it comprises the most frequent sequence corresponding to the region comprising ORF3 to ORF6, and more preferably the region from position 12938 to 14151, positions being referred to the consensus sequence of the attenuated PRRSV defined by SEQ ID NO:1.

16.—An infectious clone according to embodiment 15, characterized in that the infectious clone is named pVAC 5.2 and deposited in the Leibnitz-Institut DSMZ-Deutsche Sammlung von Mikroorganismen and Zellkulturen accession number DSM 32341.

17.—An infectious clone according to embodiment 13, characterized in that the infectious clone comprises the most frequent sequence corresponding to the polymorphic zones:

i) from position 3902 to 3959,
ii) from 6792 to 7672, and
iii) from position 12938 to 14151, wherein positions are referred to the consensus sequence of the attenuated PRRS virus defined by SEQ ID NO:1.

18.—An infectious clone according to embodiment 17, characterized in that the infectious clone is named pVAC 5.1 and deposited in the Leibnitz-Institut DSMZ-Deutsche Sammlung von Mikroorganismen und Zellkulturen accession number DSM 32340.

19.—An infectious clone according to embodiment 13, characterized in that it comprises the most frequent sequence corresponding to at least one of the following polymorphic zones:

i) from position 1164 to 2113,
ii) from 4630 to 6543,
iii) from 6906 to 8402,
iv) from 11618 to 12274, and
v) at the region comprising ORF3 to 3'UTR, and preferably at the region selected from position 12970 to 13887 and from position 14633 to 15082, wherein positions are referred to the consensus sequence of the attenuated PRRS virus defined by SEQ ID NO:163.

20.—An infectious clone according to embodiment 19, characterized in that the infectious clone comprises the most frequent sequence corresponding to the polymorphic zones:

i) from position 1164 to 2113,
ii) from 4630 to 6543,
iii) from 6906 to 8402,
iv) from 11618 to 12274,
v) from 12970 to 13887 and
vi) from 14633 to 15082, wherein positions are referred to the consensus sequence of the attenuated PRRS virus defined by SEQ ID NO:163.

21.—An infectious clone according to embodiment 20, characterized in that the infectious clone is named pVAC 6.1 and deposited in the Leibnitz-Institut DSMZ-Deutsche Sammlung von Mikroorganismen und Zellkulturen accession number DSM 32542.

22.—A recombinant nucleic acid comprising the infectious cDNA clone of any of embodiments 13 to 21.

23.—A DNA construct comprising a copy of the recombinant nucleic acid of embodiment 22.

24.—A DNA construct according to embodiment 23, characterized in that the said DNA construct is a plasmid.

25.—A RNA transcript of DNA construct of embodiment 24.

26.—An attenuated PRRSV encoded by the RNA transcript of embodiment 25.

27.—An immunogenic composition comprising the attenuated PRRSV of embodiment 26.

28.—An immunogenic composition according to embodiment 27, characterized in that the attenuated PRRSV is selected from the group consisting of an attenuated European PRRSV and an attenuated North American PRRSV.

29.—A vaccine comprising an immunologically effective amount of attenuated PRRSV of embodiment 26 or infectious cDNA clone of embodiment 13 and a pharmaceutically acceptable diluent or excipient.

30.—A vaccine according to embodiment 29, characterized in that the attenuated PRRSV is selected from the group of an attenuated European PRRSV and an attenuated North American PRRSV, more preferably an attenuated European PRRSV.

31.—A vaccine according to any of embodiments 29 or 30, characterized in that it includes an antigenic component against another disease or additional pathological conditions affecting pigs selected from the group consisting of those caused by the *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli* microorganisms, *Swine influenza virus, Contagious gastroenteritis virus, Porcine parvo virus, Encephalomyocarditis virus*, coronavirus, rotavirus, *Porcine circovirus*, porcine periweaning failure to thrive syndrome agent, *Classical swine fever virus, African swine fever virus*, calicivirus and/or *Torque teno virus.*

32.—A vaccine comprising the attenuated PRRSV of embodiment 26 and a pharmaceutically acceptable diluent or excipient for use in the prophylaxis and/or the treatment of PRRS virus infections.

33.—An attenuated PRRSV of embodiment 26 for use in the prophylaxis and/or the treatment of PRRSV infections.

34.—An attenuated PRRSV of embodiment 26 for use as vaccine or medicament in the prophylaxis and/or the treatment of PRRSV infections.

35.—A host cell transfected with the DNA construct according to embodiment 23.

Next, several examples of the invention are provided for illustrative but not limitative purposes.

EXAMPLES

General Procedures

Standard cloning procedures were carried out as described in J. Sambrook and D. W. Russell, Molecular Cloning: A laboratory manual, 4$^{th}$ edition, Cold Spring Harbor Laboratory Press, New York, 2012. Commercial kits and enzymes were used; otherwise indicated, following the instructions provided by the manufacturer.

Example 1: Construction of Infectious Clone pVAC 5.0 (SEQ ID NO:3)

Clone pVAC 5.0 contains a consensus genomic sequence of the quasispecies found in the attenuated PRRSV strain VP-046 BIS except for positions 13173 and 13922, i.e. it has a degree of identity of 99.98%. Consensus genomic sequence is defined as the sequence composed at each position by the nucleotide present in a frequency of at least 75% among all the molecular clones sequenced. Consensus sequence of PRRSV strain VP-046 BIS was determined by a number of 2 to 5 (median=3.5) overlapping molecular clones. A position is named polymorphic here if the frequency of all the nucleotides is lower than 75%. In positions 13173 and 13922 the consensus sequence (SEQ ID NO:1) contained a C and U, respectively (both at frequency of 75%), whereas at these positions clone pVAC 5.0 contained a U and a C, respectively (both found at a frequency of 2.5%). Clone pVAC 5.0 shares 99.868% nucleotide identity with a previously reported sequence (GenBank accession GU067771).

1.a) Virus

The starting material for this work was PRRSV strain VP-046 BIS (GenBank accession GU067771, CNCM accession 1-1642, 23 Nov. 1995), sampled from a frozen dried material commercially available through Laboratorios Hipra, S.A., Amer, Girona, Spain.

1.b) Isolation of Viral RNA

Frozen dried material was resuspended in 10 mL of sterilized deionized water. RNA extractions were carried out using the kit High Pure Viral RNA (Roche).

1.c) Reverse Transcription cDNAs were obtained using the reverse transcriptase AccuScript High Fidelity Reverse Transcriptase (Agilent Technologies) and primers shown in Table I:

TABLE I

| cDNA name | Primer | Sequence | Position[1] |
|---|---|---|---|
| F1 | PRRSV-56R | AAGTCGTTGGAGGAAGTTGT (SEQ ID NO: 85) | 515-496 |
| F2 | PRRSV-47R | CCTAGATTGTCGGGTGTTTG (SEQ ID NO: 86) | 2596-2577 |
| 4R | PRRSV-4R | CCSAGTAACYTGCCAAGAATG (SEQ ID NO: 87) | 3958-3938 |
| Nsi-cDNA1 | PRRSV-67R | CCAAATCCTCTAGAATGCATAAACG TAAGAAAAC (SEQ ID NO: 88) | 4000-3981 |
| 6R | PRRSV-6R | TTKGAAGCAGAWACAAAGCACTT (SEQ ID NO: 89) | 6562-6540 |
| 19R | PRRSV-19R | GGACTTCCARGCCTTYTTCATG (SEQ ID NO: 90) | 8512-8491 |
| 29R | PRRSV-29R | TCRAAGCCRACAGGGTGAAGTTG (SEQ ID NO: 91) | 10104-10082 |
| 19-29 | PRRSV-29R | TCRAAGCCRACAGGGTGAAGTTG (SEQ ID NO: 92) | 10104-10082 |
| 30R | PRRSV-30R | CAACCACACTAACAAGRAACTC (SEQ ID NO: 93) | 11873-11852 |
| 28R | PRRSV-28R | TAAAAAAGRCACGCRGARAG (SEQ ID NO: 94) | 13271-13252 |

TABLE I-continued

| cDNA name | Primer | Sequence | Position[1] |
|---|---|---|---|
| 25R | PRRSV-25R | CRCGAATYARGCGCACYGTRTG (SEQ ID NO: 95) | 14949-14928 |
| 33 | PRRSV-33R | GGCGATCGGGCGTCTAGGAATTCT AGA(T)41V (SEQ ID NO: 96) | poly(A) tail |
| Nsi (cDNA2) | PRRSV-48R | CCCACATTTTRTCRAGCCAC (SEQ ID NO: 97) | 3171-3152 |

[1]The position corresponds to the genome of the isolated VP-046 BIS strain with the GenBank accession GU067771.

1.d) Amplification of cDNA by PCR

Before the amplification of cDNA, primers were phosphorylated using T4 polynucleotide kinase (Thermo Fisher Scientific) to ligate the resulting PCR products into the vector pUC19 linearized by digestion with SmaI (Thermo Fisher Scientific).

cDNAs were amplified by PCR using Phusion high fidelity DNA polymerase (Finnzymes) and primers shown in Table II:

TABLE II

| cDNA name | Primer | Sequence | Position[1] |
|---|---|---|---|
| F1 | PRRSV-62F | GGCGCGCCTAATACGACTCACTATAGAT GATGTGTAGGGTA (SEQ ID NO: 98) | 1-15 |
| | PRRSV-58R | CAGTGAAGCTTTCTAGAAGGCTTGTAAA ACAAG (SEQ ID NO: 99) | 380-365 |
| F2 | PRRSV-53F | TTYCGGAGMGSACCTGCTTTAC (SEQ ID NO: 100) | 180-201 |
| | PRRSV-47R | CCTAGATTGTCGGGTGTTTG (SEQ ID NO: 101) | 2596-2577 |
| 4R2 | PRRSV-38F | TTYTGGACYCTYGACAAAATG (SEQ ID NO: 102) | 1929-1949 |
| | PRRSV-4R | CCSAGTAACYTGCCAAGAATG (SEQ ID NO: 103) | 3958-3938 |
| Nsi-cDNA1 | PRRSV-66F | ACTGTGTTGGTTCTGGTATTGCTGACTT TC (SEQ ID NO: 104) | 1876-1905 |
| | PRRSV-67R | CCAAATCCTCTAGAATGCATAAACGTAA GAAAAC (SEQ ID NO: 105) | 4000-3981 |
| 6R | PRRSV-26F | TYAARTTCCTCCCYGACATG (SEQ ID NO: 106) | 3238-3257 |
| | PRRSV-6R | TTKGAAGCAGAWACAAAGCACTT (SEQ ID NO: 107) | 6562-6540 |
| 19R2 | PRRSV-7F | ATGATGGRCCATGCCTGGAC (SEQ ID NO: 108) | 5961-5980 |
| | PRRSV-19R | GGACTTCCARGCCTTYTTCATG (SEQ ID NO: 109) | 8512-8491 |
| 29R2 | PRRSV-20F | RACCACYGARCARGCTTTAAAC (SEQ ID NO: 110) | 7385-7406 |
| | PRRSV-29R | TCRAAGCCRACAGGGTGAAGTTG (SEQ ID NO: 111) | 10104-10082 |
| 19-29 | PRRSV-7F | ATGATGGRCCATGCCTGGAC (SEQ ID NO: 112) | 5961-5980 |
| | PRRSV-71R | GACTGCATCTAGACCTCGACG (SEQ ID NO: 113) | 9640-9620 |
| 30R | PRRSV-27F | CTYGCATAYCACATGAARG (SEQ ID NO: 114) | 9116-9134 |
| | PRRSV-30R | CAACCACACTAACAAGRAACTC (SEQ ID NO: 115) | 11873-11852 |
| 28R | PRRSV-31F | AYAACYTRGGGTTYTACTTTTC (SEQ ID NO: 116) | 10686-10707 |

TABLE II-continued

| cDNA name | Primer | Sequence | Position[1] |
|---|---|---|---|
| | PRRSV-28R | TAAAAAAGRCACGCRGARAG (SEQ ID NO: 117) | 13271-13252 |
| 25R | PRRSV-11F | TACGYTMTGTTTTTGGTTTCCAYTGG (SEQ ID NO: 118) | 12493-12518 |
| | PRRSV-25R | CRCGAATYARGCGCACYGTRTG (SEQ ID NO: 119) | 14949-14928 |
| 33 | PRRSV-35F | TTCCAGATGCAGATTGTGTTGCCTAGG (SEQ ID NO: 120) | 14371-14397 |
| | PRRSV-34R | GGCGATCGGGCGTCTAGGAATTCTAGA $(T)_{41}V$ (SEQ ID NO: 121) | PolyAdenine |
| Nsi-cDNA2 | PRRSV-66F | ACTGTGTTGGTTCTGGTATTGCTGACTTTC (SEQ ID NO: 122) | 1876-1905 |
| | PRRSV-67R | CCAAATCCTCTAGAATGCATAAACGTAAGAAAAC (SEQ ID NO: 123) | 4014-3981 |

[1]The position corresponds to the genome of the isolated VP-046 BIS strain with the GenBank accession GU067771.
[2]The obtained cDNA was used to determine consensus sequence but not included in the infectious clones described below.

1.e) Preparation of the Vectors

Linearized vector pUC19-SmaI was used to clone cDNAs F2, 4R, Nsi-cDNA1, 6R, 19R, 29R, 30R, 28R, 25R, 33R and Nsi-cDNA2 (Table II).

Vector pUC19-SmaI was digested with XbaI and purified from 1% agarose gel using GeneJet Gel Purification Kit (Thermo Fisher Scientific) for directional cloning of cDNA F1 (Table II).

Commercial vector pACYC177 (New England Biolabs) was modified to insert a new multiple cloning site. First, the polynucleotide fragment GAACGCCGGAGGATCC GGCGCGCC GATATC TTAATTAA ACGCGT TCTAGA GCCCTTCCGG15 CTGGCTGGTT (SEQ ID NO:124) was synthetized by the company IDT (IntegratedDNA Technologies) and cloned between the BamHI and Asel sites of the plDTSMART-Amp vector. Second, plasmids pACYC177 andp1DTSMART-Amp were prepared from pre-transformed *E. coli* cultures using the MaxiPlasmid kit (Qiagen). Third, both plasmids were digested with the restriction enzymes20 BamHI and Asel. The fragment of pACYC177 that contains the kanamycin resistancemarker and the fragment from plDTSMART-Amp that contained the new multiplecloning sites were purified from an agarose gel using the Zymoclean TMgel DNA recovery kit (Zymo Research), ligated using the T4 DNA ligase (Thermo Fisher Scientific), and transformed in *E. coli* DH5a electro-competent cells. The resulting plasmid DNA was isolated using the Maxi Plasmid kit (Qiagen) and named pACYC177-ADAP. For ligation of cDNA 19-29 (table II) the plasmid was digested with EcoRV.

Digested vectors were dephosphorylated using shrimp alkaline phosphatase (Sigma).

1.f) Preparation of the Inserts

RT-PCR products F2, 4R, Nsi-cDNA1, 6R, 19R, 29R, 19-29, 30R, 28R, 25R, 33R and Nsi-cDNA2 (Table II) were purified from a 1% agarose gels using the Zymoclean™ gel DNA recovery kit (Zymo Research).

For directional cloning in SmaI-XbaI-digested pUC19 vector RT-PCR product F1 (Table II) was purified using the purification columns GeneJet (Thermo Fisher Scientific), digested with XbaI and purified from an agarose gel.

1.g) Production and Amplification of cDNA for the 5' Terminus of Viral Genomic RNA The sequence corresponding to the 5' terminus of the viral genomic RNA was determined using the 5' RACE technique and using the 5' RACE system kit (Invitrogen), according to the instructions provided by the manufacturer. Primers used for this experiment are shown in Table III:

TABLE III

| cDNA name | Primer | Position[1] | Sequence 5'-3' |
|---|---|---|---|
| 5' RACE | RACE-56R | 515-496 | AAGTCGTTGGAGGAAGTTGT (SEQ ID NO: 125) |
| | RACE-57R | 472-453 | AATGGGAAGATGGCTGAGAG (SEQ ID NO: 126) |
| | RACE-58R | 380-365 | CAGTGAAGCTTTCTAGAAGGCTTGTAAAACAAG (SEQ ID NO: 127) |

[1]The position corresponds to the genome of the isolated VP-046 BIS strain with the GenBank accession GU067771.

1.h) Cloning and Sequencing of the Fragments

Inserts F2, 4R, Nsi-cDNA1, 6R, 19R, 29R, 30R, 28R, 33R, Nsi-cDNA2 and 5'RACE (Tables II and III) were ligated in SmaI-digested pUC19 plasmid. Insert F1 was ligated into and SmaI-XbaI-digested pUC19 vector.

Insert 19-29 was ligated in EcoRV-digested pACYC177-ADAP vector.

Ligations were carried out using the enzyme T4 DNA ligase (Thermo Fisher Scientific). Ligation products were electroporated into *E. coli* DH5a.

Plasmids were isolated from 1 to 5 transformant colonies. Viral cDNAs cloned in pUC19 were first sequenced using primers M13F and M13R, shown in Table IV:

TABLE IV

| Name | Sequence 5'-3' | Position[1] | cDNA sequenced |
|---|---|---|---|
| M13F | GTAAAACGACGGCCAGT (SEQ ID NO: 128) | pUC19 | All except 19-29 |

TABLE IV-continued

| Name | Sequence 5'-3' | Position[1] | cDNA sequenced |
|---|---|---|---|
| M13R | CAGGAAACAGCTATGAC (SEQ ID NO: 129) | | pUC19 |

[1]The position corresponds to the genome of the isolated VP-046 BIS strain with the GenBank accession GU067771.

To obtain full insert sequences adequate primers in tables I and II were used. Gaps were covered by sequencing with primers designed from the obtained sequences. Viral cDNA 19-29, cloned in pACYC-177-ADAP, was sequenced using the same strategy, but using exclusively PRRSV specific primers.

1.i) Construction of the Consensus Sequence.

Sequences obtained from 2 to 5 clones of cDNAs F1, F2, 4R, Nsi-cDNA1, 6R, 19R, 29R, 30R, 28R, 25R, and 33 were edited and assembled using the software Geneious R.9.0.2 (Biomatters Ltd). For each position the consensus sequence was obtained as the nucleotide present in at least 75% of the clones (SEQ ID NO:1).

The consensus nucleotide sequence obtained by steps a) to f), shares 99.897% identity with the genome of the isolated VP-046 strain (GenBank accession GU067771).

1.j) Preparation of the Restriction Fragments

Figure 1:
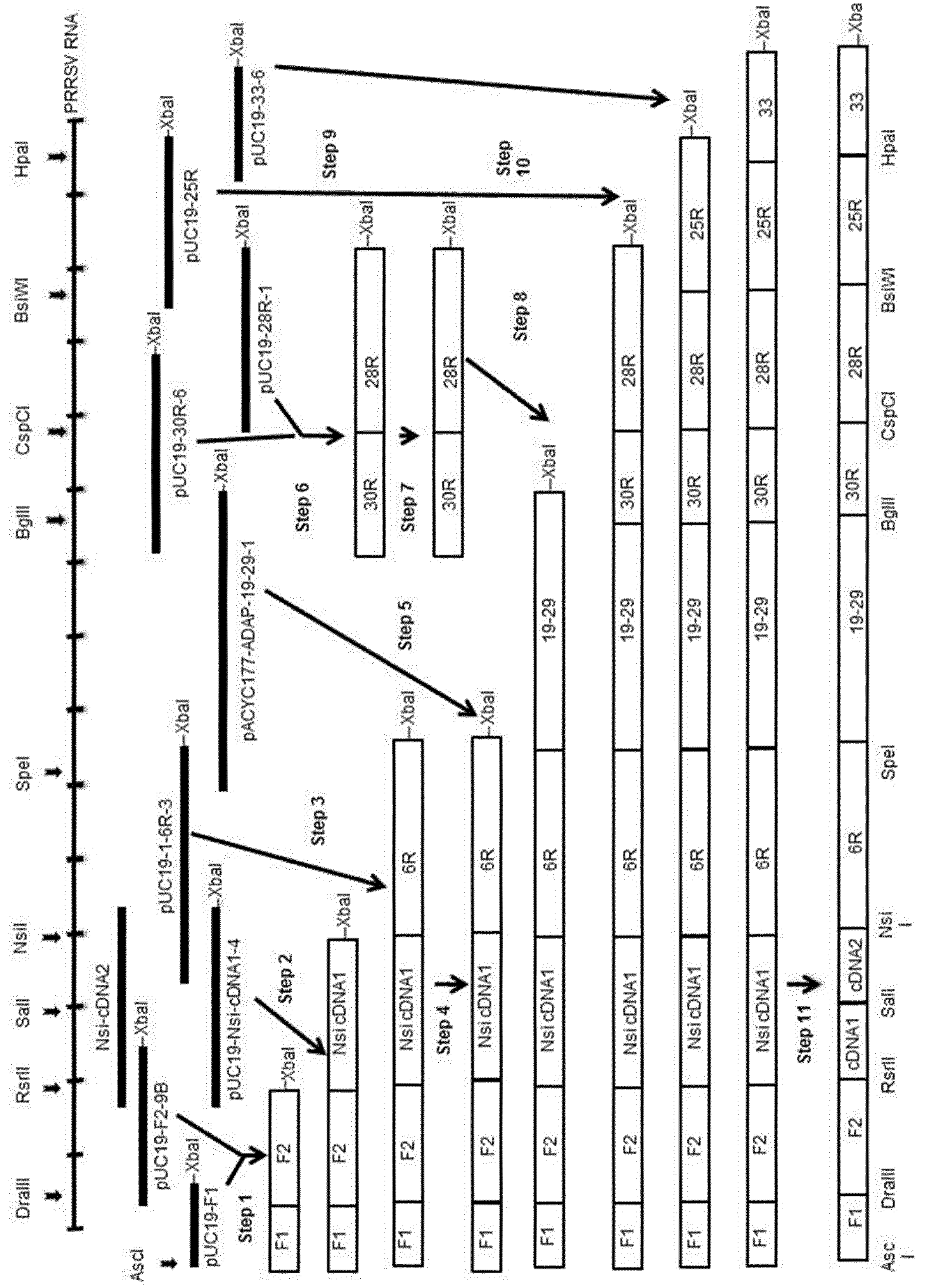
FIG. 1 shows the assembling of restriction fragments. The segmented line represents PRRSV genome. Thick arrows above indicate the restriction sites used to assemble the viral cDNAs. Thick lines represent the viral cDNAs produced by RT-PCR and cloned into pUC19 or pACYC-177-ADAP. The sequence of subcloning of cDNAs is indicated by thin arrows (steps 1 to 11).

Restriction fragments were assembled from 5' to 3' using the sites shown in FIG. 1.

For each region one clone containing the consensus sequence was chosen to be included in the infectious clone. Since all clones corresponding to the region 25R had sequences different from the consensus, the clone used to assemble the infectious clone was randomly chosen.

Whenever necessary, the pUC19 clones obtained in the previous steps, were amplified in *E. coli* and plasmid DNA isolated using the Wizard® Plus SV Minipreps DNA Purification System kit (Promega). In the case of pACYC177-ADAP clones, DNA was purified using the Maxi Plasmid kit (Qiagen).

Whenever necessary, restriction fragments were amplified by PCR using the enzyme Phusion high fidelity DNA polymerase (Finnzymes), plasmids obtained in previous steps as template and primers shown in Table V:

TABLE V

| Name | Position | Sequence 5'-3' |
|---|---|---|
| PRRSV-64F | 218-237[1] | AACCATGTCTGGGACGTTCT (SEQ ID NO: 130) |
| PRRSV-65R | 2007-1989[1] | CCAATAGTAATTTATACAATCTAGAGAAGCC (SEQ ID NO: 131) |
| PRRSV-66F | 1876-1905[1] | ACTGTGTTGGTTCTGGTATTGCTGACTTTC (SEQ ID NO: 132) |
| PRRSV-67R | 4000-3981[1] | CCAAATCCTCTAGAATGCATAAACGTAAGAAAAC (SEQ ID NO: 133) |
| PRRSV-72F | 12485-12512[1] | TCCAGCCGTACGCTATGTTTTTGGTTTC (SEQ ID NO: 134) |
| PRRSV-73R | 14611-14600[1] | TTCTTCTGGCTCTAGATTTTTACCGGCC (SEQ ID NO: 135) |
| pACYC-87F | 3248-3266[2] | CAGTACCGACGGTGATAT (SEQ ID NO: 136) |
| pACYC-88R | 544-525[2] | CCGTCGTGTAGATAACTACG (SEQ ID NO: 137) |
| M13F | 380-395[3] | GTAAAACGACGGCCAGT (SEQ ID NO: 138) |
| M3R | 481-461[3] | CAGGAAACAGCTATGAC (SEQ ID NO: 139) |

[1]The position corresponds to the genome of the isolated VP-046 BIS strain with the GenBank accession GU067771.
[2]Cloning vector pACY177 (GenBank accession X06402.1).
[3]Cloning vector pUC19 (GenBank accession L09137).

1.k) Digestion and Ligation of the Fragments

Plasmids were digested using the suitable restriction enzymes as shown in FIG. 1. Size of the fragments was confirmed by electrophoresis on 1% agarose gel and the fragments showing the expected sizes were purified using the Zymoclean™ gel DNA recovery kit (Zymo Research).

PCR products were purified using the purification columns GeneJet (Thermo Fisher Scientific), digested with the suitable enzymes as shown in FIG. 1 and purified from 1% agarose gels as described above.

Restriction fragments of expected size were purified from agarose gels and ligated using T4 DNA ligase (Thermo Fisher Scientific). Ligation products were used to transform electro-competent *E. coli* cells.

1.l) Assembling of the Restriction Fragments

Restriction fragments were assembled in the sense 5' to 3' according to the following procedure, which is represented in FIG. 1:

Step 1.—Clone pUC19-F1 was digested with DraIII and XbaI. Viral cDNA F2 was PCR-amplified from clone pUC19-F2-9B with primers PRRSV-64F and PRRSV-65R and digested with DraIII and XbaI. Digestion products were ligated.

Step 2.—Clone pUC19-Nsi-cDNA1-4 and the clone generated in Step 1 were digested with RsrII and XbaI and ligated.

Step 3.—Viral cDNA 6R was PCR-amplified from clone pUC19-1-6R-3 (cloned in direction 5' SmaI-3' XbaI) with primers M13F and M13R. The construct obtained in Step 2 and the product of this PCR were both digested with NsiI and XbaI and ligated.

Step 4.—To substitute the pUC19 vector by the pACYC-ADAP one, the clone obtained in Step 3 and the pACYC177-ADAP plasmid were both digested with AscI and XbaI and ligated.

Step 5.—The clone obtained in Step 4 and clone pACYC177-ADAP-19-29-1 were both digested with SpeI and XbaI and ligated.

Step 6.—Clones pUC19-30R-6 and pUC19-28R-1 were both digested with CspCI and XbaI and ligated.

Step 7.—The DNA fragment obtained in Step 6 was excised from vector by digestion with SmaI and XbaI and subcloned into a pACYC177-ADAP previously opened with EcoRV and XbaI digested.

Step 8.—A PCR reaction was done using the construct generated in Step 7 as template and the primers pACYC-87F and pACYC-88R. The result from this PCR and the clone generated in Step 5 were both digested with BglII and XbaI and ligated.

Step 9.—A PCR reaction of clone pUC19-25R was done using primers PRRSV-72F and PRRSV-73R. The resulting product and the clone generated in Step 8 were both digested with Bs/WI and XbaI and ligated.

Step 10.—Clone pUC19-33-6 and the construct generated in Step 9 were digested with HpaI and XbaI and ligated.

Step 11.—Sequencing of the clone generated in Step 10 showed a deletion in the region Nsi-cDNA1. To correct this problem and to introduce the right sequence an additional RT-PCR was done using viral RNA and primers PRRSV-66F and PRRSV-67R. The resulting product and the construct generated in Step 10 were both digested with RsrII and SalI and ligated. The construct resulting in this step was named pVAC-T7-5.

Figure 2:
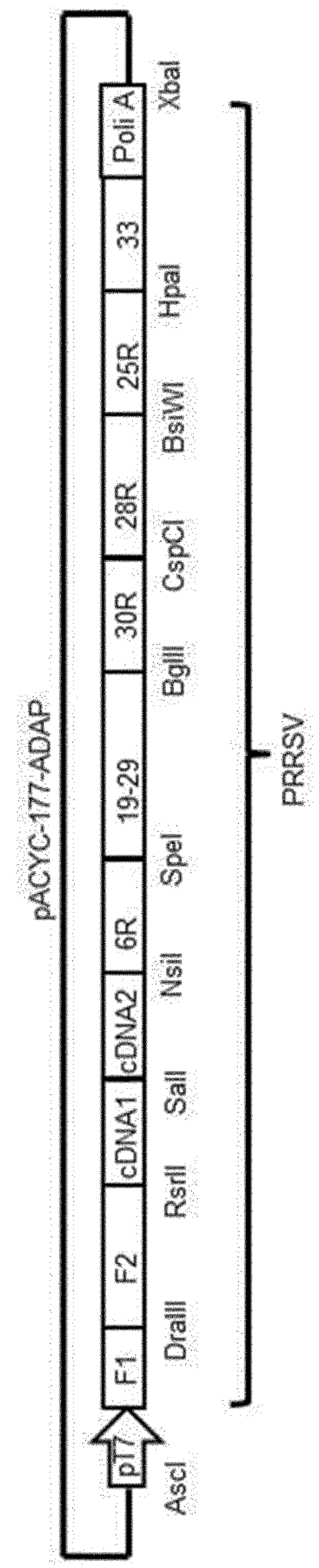
FIG. 2 depicts schematically the structure of full-length clone pVAC-T7-5. Viral cDNAs assembled to obtain the full-length clone are represented by boxes. Restriction sites used to assemble cDNAs are indicated. T7 promoter is represented by an arrow. Vector pACYC-177-ADAP is represented by a line. Restriction sites suitable to release full insert (AscI and XbaI) are shown.

Clone pVAC-T7-5 was sequenced using primers suitable to cover the whole genome (SEQ ID NO:2). FIG. 2 shows a scheme of the clone pVAC-T7-5.

1.m) Preparation of the Human Cytomegalovirus Promoter (pCMV) and of the Hepatitis Delta Virus Ribozyme (HDV-Rz) to be Introduced in pVAC-T7-5

DNA was amplified by PCR with Phusion high fidelity DNA polymerase (Finnzymes) according to the instructions provided by the manufacturer. Before the digestion with the suitable restriction enzyme, PCR products were purified with the GeneJet PCR purification kit (Thermo Fisher Scientific). Digested products were purified from 1% agarose gel using the GeneJet gel extraction kit (Thermo Fisher Scientific). The primers used in this cloning step are shown in Table VI:

TABLE VI

| Name | Position[1] | Sequence 5'-3' |
|---|---|---|
| RRSV-110F | 1-12 | GGCGCGCCATTTAAATATGATGTGTAGG (SEQ ID NO: 140) |
| PRRSV-103R | 1967-1995 | TTATACAAGCTAGAGAAGCCGGACCGTTC (SEQ ID NO: 141) |
| PRRSV-112F | 14566-14587 | TGTTAAACGAGGAGTGGTTAAC (SEQ ID NO: 142) |
| HDV-114R[2] | | ATGTTGCCCAGCCGGCGCCAGCGAGGAGG CTGGGACCATGCCGGCC$(T)_{25}$AATTTCGG (SEQ ID NO: 143) |
| HDV-115R[3] | | GGTCTAGAGTCCCATTCGCCATTACCGAGG GGACGGTCCCCTCGGAATGTTGCCCAGC (SEQ ID NO: 144) |
| pCMV-102F | | GGCGCGCCATGCATTAGTTATTAATAGT (SEQ ID NO: 145) |
| pCMV-116R | | CATATTTAAATACTAAACCAGCTCTGCTTATA TAG (SEQ ID NO: 146) |

[1]The position corresponds to the genome of the isolated VP-046 BIS strain with the GenBank accession GU067771.
[2]Y.W. Huang etal., Virus Res. 2009, 145,1-8, with modifications in 3'.
[3c]Y.W. Huang etal. Virus Res. 2009, 145,1-8.

1.n) Preparation of the Vectors

Plasmids to be used as vectors in steps o) and p) below (pVAC-T7-5, Asc-Swa-pVAC5 and Asc-Swa-pVAC5-HDV) were digested with the suitable restriction enzymes (FIG. 3) and purified from 1% agarose gels using the GeneJet gel purification kit (Thermo Fisher Scientific). Purified vectors were treated with shrimp alkaline phosphatase (Sigma) for dephosphorylation.

1.o) Ligations

Ligations were carried out with the enzyme T4 DNA Ligase (Thermo Fisher Scientific). Ligation products were electroporated in electro-competent *E. coli* DH5a. Plasmid DNA was purified with the QIAGEN® Plasmid Maxi kit (Qiagen).

1.p) Assembly of Fragments

Figure 3:
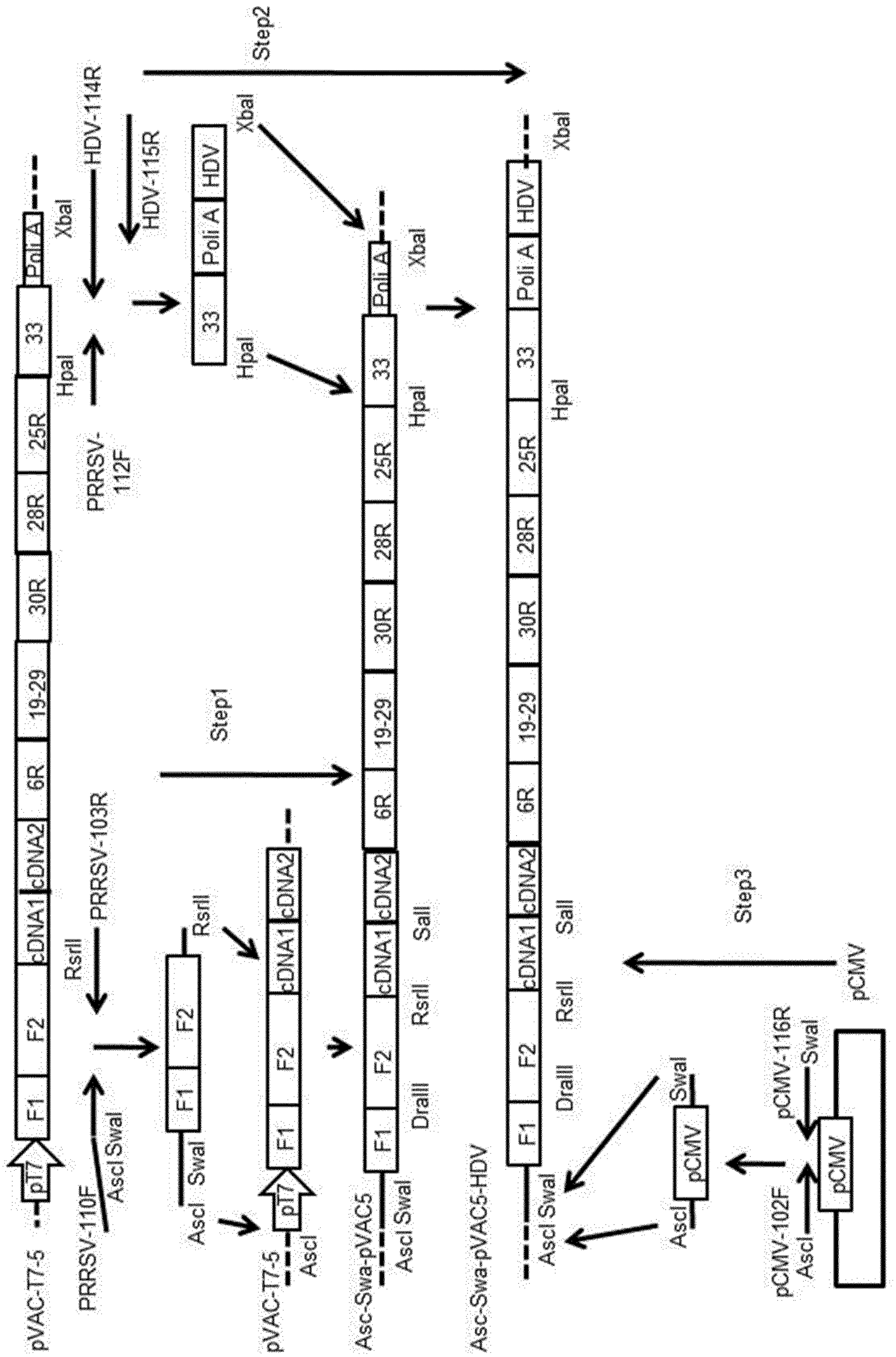
FIG. 3 represents the strategy for modification of pVAC-T7-5 to obtain pVAC 5.0. Template clone pVAC-T7-5 is represented above. Dotted lines indicate uncompleted draw of a full-length clone. The following steps are shown in FIG. 3.

Clone pVAC-T7-5 was modified according to a process comprising the following steps represented in FIG. 3.

Step 1: The 5' terminus of viral genome was PCR amplified using the clone pVAC-T7-5 as template and primers PRRSV-110F and PRRSV-103R (Table VI). The resulting PCR product was digested with AscI and RsrII, and cloned into the vector generated by the digestion of pVAC-T7-5 with the same enzymes. This clone was named Asc-Swa-pVAC5.

Step 2: Two consecutive PCRs were done to introduce the HDV-Rz. In the first PCR, clone pVAC-T7-5 was used as template with primers PRRSV-112F and HDV-114R (Table VI). The resulting PCR product was purified and used as template for a second PCR reaction with primers PRRSV-112F and HDV-115R (Table VI). The resulting PCR product was digested with HpaI and XpaI and cloned into the vector generated by digestion with the same pair of enzymes of the clone obtained in Step 1. This clone was named Asc-Swa-pVAC5-HDV-Rz.

Step 3: The pCMV promoter was obtained by PCR, using the vector pCMV-Script XR (Agilent Technologies) as template and primers pCMV-102F and pCMV-116R (Table VI). The resulting PCR product was digested with AscI and SwaI and cloned into the vector resulting of digesting the clone obtained in Step 2 with the same two restriction enzymes. The clone obtained was named pVAC 5.0 and is shown in FIG. 4.

1.q) Verification of the Sequence

To confirm the PRRSV sequence inserted in pVAC 5.0, DNA was sequenced using primers suitable to obtain the sequence of the genome, the pCMV promoter, the HDV-Rz ribozyme and the joins with the cloning vector. Sequence of clone pVAC 5.0 is provided (SEQ ID NO:3).

In SEQ ID NO:3:

Fragment 1 (positions 1-962) was obtained by sequencing of plasmid pVAC 5.0 with primer pACYC-87F (Table VII). This fragment contains from 5' to 3': partial sequence of vector pACYC177-ADAP (positions 1-32), the sequence of AscI restriction site (positions 33-40), the sequence of pCMV promoter (positions 41-622), the sequence of SwaI restriction site (positions 623-630), the 5' terminal of PRRSV virus (positions 631-962). The sequence of this fragment was confirmed by sequencing with the reverse primer PRRSV-63R.

Fragment 2: Since the genome of PRRSV can be assumed not to change during the introduction of the promoter into the 5' terminus, positions 333-14612 of SEQ ID NO:2 (pVAC-T7-5) were copy and pasted to positions 963-15242 of SEQ ID NO:3 (pVAC5.0).

Fragment 3: Positions 15243-15917 were obtained by sequencing of plasmid pVAC 5.0 with primer pACYC-88R, as shown in Table VII:

TABLE VII

| Name | Sequence 5'-3' | Position |
|---|---|---|
| pACYC-87F | TCAGTACCGACGGTGATAT (SEQ ID NO: 147) | 18041-18059[2] |
| pACYC-88R | CCGTCGTGTAGATAACTACG (SEQ ID NO: 148) | 15318-15337[2] |
| PRRSV-63R | CGATAGGGACTTTCCAGTGAAGTCTAGATTTAGGC TTGTAAAAC (SEQ ID NO: 149) | 368-411[1] |

[1]The position corresponds to the genome of the isolated VP-046 BIS strain with the GenBank accession GU067771.
[2]Cloning vector pACY177 (GenBank accession X06402.1).

This sequence contains 3' terminal part of PRRSV including the poly(A) tail (positions 15243-15753), the HDV-Rz positions (15754-15837), the restriction site of XbaI (15838-15843) and partial sequence of vector pACYC177-ADAP (15844-15917). In Fragment 3 there are two differences between the genome of PRRSV in clones pVAC-T7-5 and pVAC 5.0 (both introduced by primer HDV-114R) cytosine 15098 in SEQ ID NO:2 (pVAC-T7-5) is mutated to thymidine (position 15728 in SEQ ID NO:3, pVAC 5.0). Poly(A) tail (positions 15099-15139) in SEQ ID NO:2 (pVAC-T7-5) is 16 nucleotides shorter in pVAC 5.0 (positions 15729 to 15753).

1.r) Alignment of Consensus Sequence of VP-046 BIS and Clone pVAC 5.0.

As for all RNA viruses, the attenuated virus VP-046 BIS has a quasispecies population structure, meaning that it contains multiple sequence variants. When pVAC 5.0 was generated, the genomic sequence of PRRSV cloned represents a chimeric genome that not necessarily contains the most abundant alleles at all possible polymorphic positions. To explore the existence of polymorphisms at different nucleotide positions, a number of 2 to 5 (median=3.5) overlapping molecular clones were sequenced and assembled as described in i). Median coverage was of 4 reads for each position, ranging between 2 and 13.

Table VIII shows the differences between the consensus sequence and pVAC 5.0 sequences detected with the sample size used, the nucleotides found at each polymorphic position and the nucleotide incorporated in pVAC 5.0:

TABLE VIII

| Position[1] | Consensus[2] | Nucleotide (Number of clones)[3] | Nucleotide in pVAC 5.0[4] |
|---|---|---|---|
| 3902 | S | G (5) C (7) | C |
| 3962 | Y | C (5) T (7) | T |
| 7219 | R | G (2) A (2) | A |
| 7292 | Y | T (2) C (2) | C |
| 7340 | M | A (2) C (2) | C |
| 7540 | R | G (2) A (4) | A |
| 13136 | M | C (2) A (5) | A |
| 13141 | Y | T (2) C (4) | C |
| 13173 | C | C (3) T (1) | T |
| 13922 | T | T (3) C (1) | C |
| 14403 | R | G (4) A (4) | A |
| 14852 | Y | T (2) C (2) | C |
| 15098 | Y | T (2) C (2) | C |

[1]The position corresponds to the consensus sequence of the attenuated virus VP-046 BIS (SEQ ID NO: 1).
[2]SEQ ID NO: 1.
[3]Example 1.h), 1.i).
[4]SEQ ID NO: 3.

It is observed that in most cases, the most frequent allele was already present in pVAC 5.0, but in a few positions the allele presented in the clone does not reflect the most abundant one in the VP-046 BIS attenuated virus.

The full nucleotide sequence of infectious clone pVAC 5.0 is SEQ ID NO:223. The partial nucleotide sequence of infectious clone pVAC 5.0 is SEQ ID NO:3

The infectious clone pVAC 5.0 was deposited in the Leibnitz-Institut DSMZ-Deutsche Sammlung von Mikroorganismen and Zellkulturen under accession number DSM 32339 (Jul. 19, 2016).

Example 2: Construction of Infectious Clone pVAC 5.2

Clone pVAC 5.2 contains the same full PRRSV genomic sequence than clone pVAC 5.0 with the exception of the fragment between positions 12492-14584, which encodes the glycoproteins GP3 (partial), GP4, GP5, and GP6 (partial). This fragment has been replaced by the most frequent sequence variant found in the attenuated virus VP-046 BIS quasispecies. The variability study for the region positions 12938 to 14151, encoding for GP4 and GP5, and the cloning of the most frequent sequence variant in the infectious clone pVAC 5.0 to obtain clone pVAC 5.2, are described below
2.A) Virus.

The starting material for this work was PRRSV strain VP-046 BIS (GenBank accession 00067771, CNCM accession 1-1642, 23 Nov. 1995), sampled from a frozen dried material commercially available through Laboratorios Hipra, S.A., Amer, Girona, Spain.
2.b) Isolation of Viral RNA.

Frozen dried material was resuspended in 10 mL of sterilized deionized water. RNA extractions were carried out using the High Pure Viral RNA kit (Roche).
2.c) Reverse Transcription.

cDNAs were obtained using the AccuScript high fidelity reverse transcriptase (Agilent Technologies) and primer PRRSV-2R shown in Table X.
2.d) Amplification of cDNA by PCR.

Before the amplification of cDNA, primers PRRSV-1F and PRRSV-2R, shown in Table IX, were phosphorylated using the enzyme T4 polynucleotide kinase (Thermo Fisher Scientific).

TABLE IX

| Primer | Sequence | Position |
|---|---|---|
| PRRSV-1F | TAGACGGGGGYAAYTGGTT (SEQ ID NO: 150) | 12918-12936[1] |
| PRRSV-2R | GACACCTTAAGRGCRTATATCAT (SEQ ID NO: 151) | 14193-14171[1] |

[1]The position corresponds to the consensus sequence of the attenuated virus VP-046 BIS (SEQ ID NO: 1).

cDNAs were then amplified by PCR using Phusion high fidelity DNA polymerase (Finnzymes) and primers PRRSV-1F and PRRSV-2R (Table X). RT-PCR products were purified from 1% agarose gels, using the Zymoclean™ gel DNA recovery kit (Zymo Research).
2.e) Cloning and Sequencing of cDNAs.

Purified cDNAs and vector pUC19 previously digested with SmaI (Thermo Fisher Scientific) were ligated with the T4 DNA ligase (Thermo Fisher Scientific). Ligation products were transformed into E. coli DH5a electro-competent cells. Ligation was confirmed by colony PCR with primers M13F and M13R (Table IV). Plasmid DNA was purified with the Wizard® Plus SV Minipreps DNA purification system kit (Promega).

Plasmid DNA was isolated from 21 colonies and inserts were sequenced with primers M13F and M13R (Table IV). Sequences were edited and aligned using the software Geneious R.9.0.2 (Biomatters Ltd), and are provided as SEQ ID NO: 6-26.

Positions 12938-14151 of viral genome were determined for 21 cDNA clones (FIG. 5). Most frequent variant had a frequency of 0.238, while the frequency of the rest was 0.048. The most frequent sequence corresponded to variant defined by SEQ ID NO:6.
2.f) Virus and Isolation of Viral RNA were the Same as in a) and b)
2.g) Reverse Transcription.

Viral cDNA was obtained using AccuScript high fidelity reverse transcriptase (Agilent Technologies) and primer PRRSV-120R (Table X).
2.h) Amplification of cDNA by PCR.

Before the amplification of cDNA, primers PRRSV-119F and PRRSV-120R (Table XI) were phosphorylated using the T4 polynucleotide kinase (Thermo Fisher Scientific). cDNAs were amplified by PCR using Phusion high fidelity DNA polymerase (Finnzymes) and primers PRRSV-119F and PRRSV-120R (Table II). RT-PCR products were purified from agarose gels, using the Zymoclean™ gel DNA recovery kit (Zymo Research).
2.i) Cloning and Sequencing of cDNAs.

Viral cDNA and vector pUC19 digested with SmaI (Thermo Fisher Scientific) were ligated with the enzyme T4 DNA Ligase (Thermo Fisher Scientific). Ligation products were electroporated in E. coli DH5a. Ligation was confirmed by colony PCR with primers M13F and M13R (Table IV). Plasmid DNA was purified from 10 colonies with the Wizard® Plus SV Minipreps DNA Purification System kit (Promega). Inserts were sequenced with primers suitable to obtain the whole insert sequence. Sequences were edited and aligned with the most frequent sequence found in e) (SEQ ID NO:6) using the software Geneious R.9.0.2 (Biomatters Ltd). One clone was chosen for the following steps. This clone was named GPsM-clon 1, the sequence of viral cDNA in this clone is provided (SEQ ID NO: 27).
2.j) Subcloning of Viral cDNA in Clone GPsM-Clon 1 in pVAC 5.0 (FIG. 6).

Viral cDNA in clone GPsM-clon1 was amplified by PCR using Phusion High Fidelity DNA polymerase (Finnzymes) and primers PRRSV-119F and PRRSV-120R, as shown in Table X:

TABLE X

| Primer | Sequence | Position |
|---|---|---|
| PRRSV-119F | GAATTCCAGCCGTACGCTATG (SEQ ID NO: 152) | 12481-12501[1] |
| PRRSV-120R | TACTTGACGAGGTTAACCACTCCTC (SEQ ID NO: 153) | 14598-14574[1] |

[1]The position corresponds to the consensus sequence of the attenuated virus VP-046 BIS (SEQ ID NO: 1).

DNA was purified using GeneJet PCR purification kit (Thermo Fisher Scientific) and digested with Bs/WI and HpaI.

Plasmid pVAC 5.0 was digested with the Bs/WI and HpaI, purified from agarose gel using the Zymoclean™ gel DNA recovery kit (Zymo Research), and dephosphorylated using the shrimp alkaline phosphatase (Sigma).

Restriction products were ligated with the enzyme T4 DNA Ligase (Thermo Fisher Scientific). Ligation products were electroporated in *E. coli* DH5α.

Plasmid DNA was isolated from a transformant colony using the NucleoBond® Xtra Maxi kit (Macherey-Nagel). This new clone was named as pVAC 5.2.

2.k) Alignment of Consensus Sequence of VP-046 BIS and Clones pVAC 5.0 and pVAC 5.2.

Polymorphic positions in consensus sequence of attenuated virus VP-046 BIS, and differences between consensus sequence and clones pVAC 5.0 and pVAC 5.2 are shown in Table XI:

TABLE XI

| Position[1] | Consensus nucleotide and number of clones containing each variant[2] | Nucleotide in clone pVAC 5.0[3] | Nucleotide (Number of clones)[4] | Nucleotide in clone pVAC 5.2[4] |
|---|---|---|---|---|
| 3902 | S: G (5) C (7) | C | | C[3] |
| 3962 | Y: C (5) T (7) | T | | T[3] |
| 7219 | R: G (2) A (2) | A | | A[3] |
| 7292 | Y: T (2) C (2) | C | | C[3] |
| 7340 | M: A (2) C (2) | C | | C[3] |
| 7540 | R: G (2)A (4) | A | | A[3] |
| 12940 | T: >75% | T | T (5) C (16) | C[5] |
| 13136 | M: C (2) A (5) | A | A (6) C (15) | C[5] |
| 13141 | Y: T (2) C (4) | C | C (6) T (15) | T[5] |
| 13173 | C: >75% | T | T (0) C (21) | C[5] |
| 13320 | C: >75% | C | C (4) T (17) | T[5] |
| 13518 | T: >75% | T | T (4) C (17) | C[5] |
| 13562 | G: >75% | G | G (5) T (16) | T[5] |
| 13663 | C: >75% | C | T (1) C (4) G (16) | G[5] |
| 13668 | T: >75% | T | T (5) C (16) | C[5] |
| 13913 | T: >75% | T | C (8) T (13) | C[5] |
| 13922 | T: T (3) C (1) | C | C (0) T (21) | T[5] |
| 14403 | R: G (4) A (4) | A | | A[5] |
| 14852 | Y: T (2) C (2) | C | | C[3] |
| 15098 | Y: T (2) C (2) | C | | C3 |

[1]The position corresponds to the consensus sequence of the attenuated virus VP-046 BIS (SEQ ID NO: 1).
[2]From Example 1.h), 1.i).
[3]SEQ ID NO: 3.
[4]From Example 2.e).
[5]SEQ ID NO: 27.

The infectious clone containing the most frequent sequence corresponding to the region from position 12938 to 14151 is named pVAC 5.2.

The full nucleotide sequence of infectious clone pVAC 5.2 is SEQ ID NO:225. The partial nucleotide sequence of infectious clone pVAC 5.2 is SEQ ID NO:4.

The infectious clone pVAC 5.2 was deposited in the Leibniz-Institut DSMZ-Deutsche Sammlung von Mikroorganismen and Zellkulturen under accession number DSM 32341 (Jul. 19, 2016).

Example 3: Construction of Infectious Clone pVAC 5.1

Clone pVAC 5.1 contains the most frequent sequence variant in the quasispecies of the attenuated virus VP-046 BIS in the regions i) from position 3902 to 3959 ii) from 6792 to 7672 and iii) 12938 to 14151 encoding for GP4 and GP5

The nucleotide variation of the attenuated virus VP-046 BIS in the region from position 6792 to 7672 was assessed according to the following procedure:

3.a) Virus and RNA Isolation were Done as Described in Example 2 a) and b).

3.b) Reverse Transcription was Performed with Primer PRRSV-126R (Table XII) as Described in Example 2 c).

3.c) Amplification of Viral cDNAs by PCR was Performed with Primers PRRSV-125F and PRRSV-126R as Described in Example 2 d).

3.d) Ligation of Viral cDNAs in the Cloning Vector pUC19 and Transformation of *E. coli* Cells was Done as Described in Example 2 e).

3.e) Sequencing of cDNAs and Selection of the Most Frequent Variant.

Colony PCR was conducted with primers PRRSV-97F and PRRSV-32R (Table I). PCR products from 30 colonies were sequenced with primers PRRSV-97F and PRRSV-32R (Table I). Sequences were edited and aligned using the software Geneious R.9.0.2 (Biomatters Ltd) and provided as SEQ ID NO: 28-57.

Positions 6792 to 7672 of viral genome were determined for 30 cDNA clones (FIG. 5). Most frequent variant has a frequency of 0.533 followed by others with frequencies less than 0.167.

Plasmid DNA was isolated from one colony containing the most frequent variant. This clone was named pUC19-INT-4, and sequenced using primers suitable to obtain the complete insert sequence. Sequence of insert in pUC19-INT-4 is provided as SEQ ID NO:58.

The subcloning of viral cDNA insert in clone pUC19-INT-4 in pVAC 5.2 was performed according to the following procedure:

3.f) Viral cDNA was Amplified from Clone pUC19-INT-4 Using the Primers PRRSV-125F and 126R, Shown in Table XII, and Directionally Cloned Between SpeI and BglII Sites of Plasmid pVAC 5.2 Using the Methodology Described in Example 2 j) (FIG. 6):

TABLE XII

| Primer | Sequence | Position |
|---|---|---|
| PRRSV-125F | GTGACTAGTTATGTTCCCACCAT (SEQ ID NO: 154) | 6271-6295[1] |
| PRRSV-126R | AGAGGAGATCTACCAGCCCC (SEQ ID NO: 155) | 9500-9519[1] |
| PRRSV-97F | CGGATCCATCCTCGATATTAATGTG (SEQ ID NO: 156) | 6749-6773[1] |
| PRRSV-32R | TGCAGTTTCAAAATCCCAAA (SEQ ID NO: 157) | 7719-7738[1] |

[1]The position corresponds to the consensus sequence of the attenuated virus VP-046 BIS (SEQ ID NO: 1).

Positive clones were identified by colony PCR with primers PRRSV-97F and PRRSV-32R and sequencing of PCR products with the same primers. Plasmid DNA was purified from one positive colony as in Example 2 j). This construct was named pVAC 5.2-INTm.

The nucleotide variation of the attenuated virus VP-046 BIS in the region from position 3902 to 3959 was assessed according to the following procedure:

3.g) Virus, and isolation of PRRSV genomic RNA were as described in Example 1 a) and b).

3.h) Reverse transcription was performed with primer PRRSV-124R (Table XIV) as described in Example 2 c).

3.i) Amplification of viral cDNAs by PCR was performed with primers PRRSV-123F and PRRSV-124R (Table II) as described in example 2 d).

3.j) Ligation of viral cDNAs in the cloning vector pUC19 and transformation of electro-competent *E. coli* cells was done as described in Example 2 e).

3.k) Sequencing of cDNAs and selection of the most frequent variant.

Colony PCR was conducted with primers PRRSV-93F and PRRSV-67R (Table II). PCR products of 25 colonies were sequenced with primers PRRSV-93F and PRRSV-67R (Table XIII). Sequences were edited and aligned using the software Geneious R.9.0.2 (Biomatters Ltd). Sequences are provided as SEQ ID NO:59-83.

Positions 3902 to 3959 of viral genome were determined for 25 cDNA clones (FIG. 5). The most frequent variant has a frequency of 0.440, closely followed by the variant already present in pVAC 5.0 (0.400), the other two variants have a frequency as low as 0.040.

Plasmid DNA was isolated from one colony containing the most frequent variant. This clone was named pUC19-DEG-3, and sequenced using primers suitable to obtain the complete insert sequence. Sequence is provided as SEQ ID NO: 84.

The subcloning of viral cDNA insert in clone pUC19-DEG-3 in pVAC 5.2-INTm was performed according to the following procedure:

3.l) Viral cDNA was amplified from clone pUC19-DEG-3 using the primers PRRSV-123F and 124R (Table XIII), and directionally cloned between the RsrII and SpeI sites of plasmid pVAC 5.2-INTm using the methodology described in Example 2 j) (FIG. 6). Positive clones were identified by colony PCR with primers PRRSV-93F and PRRSV-67R, shown in Table XIII, and sequencing of PCR products with the same primers. Plasmid DNA was purified from one positive colony as in Example 2 j):

TABLE XIII

| Primer | Sequence | Position |
|---|---|---|
| PRRSV-93F | CATGCTGAGCTTTTGGCTCTTG (SEQ ID NO: 158) | 3852-3873[1] |
| PRRSV-67R | CCAAATCCTCTAGAATGCATAAACGTAAGAAAAC (SEQ ID NO: 159) | 3981-4000[1] |
| PRRSV-123F | CAGAACGGTCCGGCTTCT (SEQ ID NO: 160) | 1966-1983[1] |
| PRRSV-124R | ACATAACTAGTCACAGCAAGAACCC (SEQ ID NO: 161) | 6286-6262[1] |

[1]The position corresponds to the consensus sequence of the attenuated virus VP-046 BIS (SEQ ID NO: 1).
[2]Cloning vector pUC19 (GenBank accession L09137).
This construct was named as pVAC 5.1.

3.m) Alignment of consensus sequence of VP-046 BIS and clones pVAC 5.0 and pVAC 5.2 and pVAC 5.1.

Polymorphic positions in consensus sequence of attenuated virus VP-046 BIS, and differences between consensus sequence and clones pVAC 5.0, pVAC 5.2 and pVAC 5.1 are shown in Table XIV:

TABLE XIV

| Position[1] | Consensus: number of clones containing each variant[2] | Nucleotide in clone pVAC 5.0 [3] | Nucleotide (Number of clones) | Nucleotide in clone pVAC 5.2 | Nucleotide in clone pVAC 5.1 |
|---|---|---|---|---|---|
| 3000 | G | G | | G [3] | A [9] |
| 3902 | S: G (5) C (7) | C | C (12) G (13) [8] | C [3] | G [9] |
| 3962 | Y: C (5) T (7) | T | C (13) T (12) [8] | T [3] | C [9] |
| 7219 | R: G (2) A (2) | A | A (6) G (24) [6] | A [3] | G [7] |
| 7292 | Y: T (2) C (2) | C | C (9) T (21) [6] | C [3] | T [7] |
| 7340 | M: A (2) C (2) | C | C (9) A (21) [6] | C [3] | A [7] |
| 7540 | R: G (2) A (4) | A | A (30) [6] | A [3] | A [7] |
| 12940 | T: >75% | T | T (5) C (16) [4] | C [5] | C [5] |
| 13136 | M: C (2) A (5) | A | A (6) C (15) [4] | C [5] | C [5] |
| 13141 | Y: T (2) C (4) | C | C (6) T (15) [4] | T [5] | T [5] |
| 13173 | C: >75% | T | T (0) C (21) [4] | C [5] | C [5] |
| 13320 | C: >75% | C | C (4) T (17) [4] | T [5] | T [5] |
| 13518 | T: >75% | T | T (4) C (17) [4] | C [5] | C [5] |
| 13562 | G: >75% | G | G (5) T (16) [4] | T [5] | T [5] |
| 13663 | C: >75% | C | T (1) C (4) G (16) [4] | G [5] | G [5] |
| 13668 | T: >75% | T | T (5) C (16) [4] | C [5] | C [5] |
| 13913 | T: >75% | T | C (8) T (13) [4] | C [5] | C [5] |
| 13922 | T: T (3) C (1) | C | C (0) T (21) [4] | T [5] | T [5] |
| 14403 | R: G (4) A (4) | A | | A [3] | A [3] |
| 14852 | Y: T (2) C (2) | C | | C [3] | C [3] |
| 15098 | Y: T (2) C (2) | C | | C [3] | C [3] |

[1]The position corresponds to the consensus sequence of the attenuated virus VP-046 BIS (SEQ ID NO: 1).
[2]Example 1.h), 1.i).
[3] SEQ ID NO: 3.
[4] Example 2.e).
[5] SEQ ID NO: 27.
[6] Example 3.e).
[7] SEQ ID NO: 58.
[8] Example 3.k).
[9] SEQ ID NO: 84.

The infectious clone containing the most frequent sequence corresponding to these three regions from position 3902 to 3959, from 6792 to 7672 and from 12938 to 14151, is named pVAC 5.1.

The full nucleotide sequence of infectious clone pVAC 5.1 is SEQ ID NO:224. The partial nucleotide sequence of infectious clone pVAC 5.1 is SEQ ID NO:5.

The infectious clone pVAC 5.1 was deposited in the Leibnitz-Institut DSMZ-Deutsche Sammlung von Mikroorganismen and Zellkulturen under accession number DSM 32340 (Jul. 19, 2016).

Example 4: Assessment of the Attenuation and Reversion to Virulence of Infectious Clone pVAC 5.2 in Piglets In this example the attenuation of infectious clone pVAC 5.2 in piglets was assessed in view of the infection kinetics compared with the attenuated original virus strain VP-046 BIS of PRRSV (GenBank accession GU067771), and the reversion to virulence of infectious clone pVAC 5.2 was assessed with serial passages in piglets.

The animals were porcine males and females of 5 weeks of age at the beginning of the study, free of PRRSV and antibody free against PRRSV. 35 animals were used in the first serial passage and 35 animals for the second serial passage.

The infection kinetics was measured by real time quantitative PCR (RT-qPCR). Reversion to virulence was assessed by viremia values and the presence of clinical signs in animals.

For the first serial passage in piglets were used the clone pVAC 5.2 and VP-046 BIS strain.

The clone pVAC 5.2 was digested with XbaI and purified with GeneJet PCR purification kit to obtain a linearized DNA. Afterwards it was transfected in Clone 8 cells (Collection Nationale de Cultures de Microorganismes accession 1-1643) at a confluence of 90% using Lipofectamine® 3000 kit (Thermofisher), in 24-veil plates, adjusting at 2 μg of linearized DNA in 100 μl/well. The DNA-lipofectamine complex was incubated 30 minutes at room temperature before adding it to the wells. After the addition, the DNA-lipofectamine complex was incubated 3 h at 37° C. under 5% carbon dioxide atmosphere. After 3 h, MEMg medium supplemented with 10% FBS (fetal bovine serum) was added.

PRRSV were amplified also in Clone 8 cells and after 4 virus passages the titre reached was $9.02\times10^4$ $CCID_{50}$/mL. Virus was diluted in PBS in order to uniform all the virus dose/animals among groups. It was administered a dose of 2 m L/animal.

The result of the transfection and amplification confirms the ability of the infectious clone of the infection to generate PRRS virus.

Vaccine VP-046 BIS was reconstituted with PBS to achieve $1.44\times10^4$ $CCID_{50}$/mL.

In the first serial passage both products were administered intranasally, one single dose of 1 mL in each nostril, corresponding to $1.8\times10^5$ $CCID_{50}$/animal for pVAC 5.2, and $2.88\times10^4$ $CCID_{50}$/animal for vaccine VP-046 BIS.

In the study the following designations were used:

Group A=group inoculated with pVAC 5.2,

Group B=group inoculated with vaccine VP-046 BIS, and

Group C=Control group, inoculated with PBS

Homogenized lung tissues from piglets from the first serial passage, which were positive for PRRS virus by RT-qPCR, were used for the second serial passage in piglets. Viability of such inocula was confirmed by isolation.

In the second serial passage both products were administered intranasally, one single dose of 0.5 mL in each nostril, corresponding to 7.27×10 $CCID_{50}$/animal for pVAC 5.2, and 3.78×10 $CCID_{50}$/animal for vaccine VP-046 BIS In both serial passages 10 animals of each group were inoculated either with pVAC 5.2 o VP-046 BIS, and 5 animals were not inoculated but shared the room with the inoculated ones. These animals were considered cohabitants in order to assess the transmission level of the PRRS virus.

The variables evaluated in this study and the statistical tests applied are listed below:

viral isolates: descriptive statistics and parametric test for comparing groups.

clinical signs: descriptive statistics and non-parametric test for comparing groups, temperature and weight nonparametric ANOVA.

4.1.—Results for the First Serial Passage 4.1.1.—Viremia in Inoculated and Cohabitant Animals Sera at day 3 and up to day 37 of the study were analysed by RT-qPCR.

In FIG. 9 are represented the mean titers ($CCID_{50}$/mL) of viremia at day 3 up to day 37 of the study after for each group. At days 3, 7 and 21 there were significant differences between group A (pVAC 5.2) and group B (VP-046 BIS), and a trend to lower titer for group A is observed.

When comparing the percentages of viremic animals for each group, it was observed a clear trend for group A (pVAC 5.2) to show a reduction in the number of positive animals during the study in comparison to group B (VP-046 BIS). There were statistical differences also at 3, 7 and 21 days post-vaccination.

From sera analysis by RT-qPCR from cohabitant animals it was observed that pVAC 5.2 did not raise viremia in those animals, in comparison to VP-046 BIS, showing a mean value of 2.38×10 $CCID_{50}$/mL.

When comparing the percentages of cohabitant animals positive to viremia for each group, it was observed again a clear trend for group A (pVAC 5.2) to show a reduction in the number of positive animals during the study in comparison to group B (VP-046 BIS).

The lower viremia of pVAC 5.2 group in front of VP-046 BIS represents lower capacity of accumulation in lungs and tonsils, and consequently less capacity of reversion to virulence of the vaccine of the invention.

4.1.2.—Virus Tissue Load and Shedding in Inoculated and Cohabitant Animals

At day 35 after inoculation animals were euthanized and the presence of virus in lung tissue, tonsil and faecal swabs was analysed.

In FIG. 10 are represented the percentages of inoculated animals positive to PRRSV detection in lung tissues, tonsil and faecal swabs for each group, showing a clear reduction in the number of positive animals of group A (pVAC 5.2) in comparison to group B (VP-046 BIS).

At day 35 cohabitant animals were euthanized and the presence of virus in lung tissue, tonsil and faecal swabs was analysed.

It was observed a significant reduction in lung virus load for the pVAC 5.2 group in comparison to the VP-046 BIS group in cohabitant animals. An analogous reduction was observed in the percentages of animals positive to PRRSV in lung tissues and tonsil swabs favourable to group A (pVAC 5.2).

The lower tissue load of pVAC 5.2 in front of VP-046 BIS represents less capacity of reversion to virulence. Therefore, it confirms increased safety of the vaccine of the invention.

4.1.3.—Seroconversion in Inoculated and Cohabitant Animals

It was observed that 70% of animals inoculated with pVAC 5.2 were already seropositive (IRPC>20) at day 14, being 80% for those animals inoculated with VP-046 BIS. 100% of animals of both groups were seropositive at day 35.

In cohabitant animals, it was observed that seroconversion was lower in the group pVAC 5.2. In fact only one animal of this group showed an effective seroconversion. At day 35 the percentages of seroconversion were 20% of the pVAC 5.2 cohabitant animals and 80% of the cohabitants with the VP-046 BIS inoculated animals. The reduced viremia and shedding seen in the group A (pVAC 5.2) in comparison to the group B (VP-046 BIS) reduces the trend to infection in cohabitant animals. In this way, probability of reversion to virulence due to serial passages in vivo is reduced.

4.1.4.—Clinical Signs and Temperature in Inoculated and Cohabitant Animals

Clinical signs are assessed according to the method disclosed in Martelli et al., Vaccine, 2009, 27, 3788-3799.

It was observed that the vaccination with pVAC 5.2 produced better results in terms of reduction of clinical signs in comparison to VP-046 BIS.

Differences between groups of cohabitant animals were not significant.

4.2.—Results for the Second Serial Passage 4.2.1.—Viremia in Inoculated and Cohabitant Animals Sera at day 0 and up to day 35 of the study were analysed by RT-qPCR.

In FIG. 11 are represented the percentages of inoculated animals (Second serial passage) positive to viremia for each group. It was observed a clear trend for group A (pVAC 5.2) to show a reduction in the number of positive inoculated animals and the virus titre during the study in comparison to group B (VP-046 BIS). It was observed also a clear trend for group A (pVAC 5.2) to show the clearance of the viremia in the cohabitant animals (0 $CCID_{50}$/mL for the pVAC 5.2 group during all the study) and a reduction in the number of positive cohabitant animals during the study in comparison to group B (VP-046 BIS).

4.2.2.—Virus Tissue Load and Shedding in Inoculated and Cohabitant Animals

At day 35 after inoculation animals were euthanized and the presence of virus in lung tissue, tonsil and faecal swabs was analysed by RT-qPCR.

It was observed a significant reduction in lung virus load and in tonsil swabs for the pVAC 5.2 group in comparison to the VP-046 BIS group.

It was also observed a clear reduction in the percentage of animals with presence of the virus in lung tissue and/or in tonsil swabs for the pVAC 5.2 group in comparison to the VP-046 BIS group: 0% of animals were positive in the pVAC 5.2 group, whereas 90% and 100% were positive in lung tissues and in tonsil swab respectively in the VP-046 BIS group.

No faecal shedding was practically seen in animals inoculated with pVAC 5.2 (Second serial passage).

Regarding cohabitant animals, analogous results were observed in viremia (lung tissues and tonsil swabs), percentages of animals positive to viremia in lung tissues and tonsil swabs with a clear significant reduction in lung virus load and tonsil swabs for the pVAC 5.2 group in comparison to the VP-046 BIS group, and no faecal shedding was practically seen when pVAC 5.2 (Second serial passage) was inoculated.

4.2.3.—Seroconversion in Inoculated and Cohabitant Animals

It was observed that none of the animals inoculated with pVAC 5.2 (Second serial passage) was seropositive (IRPC>20), because none animal was infected with the virus. In the opposite, animals inoculated with VP-046 BIS (Second serial passage) showed 100% seroconversion, in spite the small amount of virus that was inoculated.

This result confirmed the lower viremia and replication capacity of pVAC 5.2.

Analogously, none of the cohabitant animals of the group pVAC 5.2 was seropositive and the IRPC ELISA showed values below 20 (i.e. negative). This is the consequence of the lower viremia and replication capacity of pVAC 5.2 shown in the inoculated animals (Second serial passage).

4.2.4.—Clinical Signs and Temperature in Inoculated and Cohabitant Animals

Clinical signs are assessed according to the method disclosed in Martelli et al.

No severe clinical signs were observed in inoculated animals with pVAC 5.2 or VP-046 BIS from the second serial passage, or in cohabitant animals.

Example 5: Homologous Efficacy Assessment of Infectious Clone pVAC 5.2 in Piglets In this example of efficacy trial, the PRRSV-infection consequences were compared between a vaccinated group with a vaccine prepared from clone pVAC 5.2 and a non-vaccinated group after a homologous challenge. In the trial it was included also a positive control (commercially available VP-046 BIS strain, Laboratorios Hipra, S.A., Amer, Girona, Spain) that was also challenged.

The clone pVAC 5.2 was transfected and amplified, as disclosed in Example 4, to achieve the desired volume and titer ($10^{3.88}$ $CCID_{50}$/ML). It was administered a dose of 1 mL/animal.

Freeze dried vials of VP-046 BIS strain, were reconstituted with PBS to achieve $10^{3.88}$ $CCID_{50}$/animal in a dose of 1 mL.

The animals were porcine males and females of 4 weeks of age at the vaccination day, free of PRRSV and antibody free against PRRSV. They were randomly distributed into 3 groups of 15 piglets each one. One group was vaccinated with the vaccine prepared from clone pVAC 5.2 by intramuscular route using $10^{3.88}$ $CCID_{50}$/animal. Another group was vaccinated with the same virus titer but with VP-046 BIS vaccine. The last group was vaccinated with sterile PBS and was maintained in the same housing conditions (as a challenge control).

In the study the following designations were used:

Group A=group vaccinated with pVAC 5.2,

Group B=group vaccinated with VP-046 BIS, and

Group C=Control group, non-vaccinated

The efficacy of pVAC 5.2 vaccine and the VP-046 BIS against PRRSV was confirmed by means of a challenge with the homologous virulent strain of PRRSV (5711) in piglets 42 days after the vaccination. The challenge was performed by intranasal route, which is one of the virus' natural infection routes.

After the challenge, the incidence and duration of viremia and the virus excretion in nasal secretion/faeces (RT-qPCR) was followed up to support the efficacy claims of pVAC 5.2 vaccine and VP-046 BIS. The clinical signs of all the piglets (including general and respiratory signs, mortality and temperature increases) and the average daily weight gain were also monitored. The observation period of all animals was prolonged up to 42 days after challenge. Lung and tonsil swabs presence of the PRRS virus in piglets was also determined after euthanasia (RT-qPCR). In addition, each piglet was observed to detect any local or systemic clinical sign after vaccination.

Finally, serology (PRRSV antibody level; total IgG by ELISA) of all the animals was performed after vaccination (in order to assess the correct immunization) and after challenge (antibody kinetics description). Furthermore, the induction of neutralizing antibodies (NA) was also evaluated with the sera from all the animals to support the protective properties of the pVAC 5.2 vaccine with quantification of effective antibodies.

This study was blind, thus the person who vaccinated the animals was not the same that the one who performed the rest of the samplings and observations.

The variables evaluated in this study and the statistical tests applied are listed below:

- Viremia and serological profiles: descriptive statistics and a non-parametric Kruskal Wallis test or ANOVA test were applied for group comparison on viremia. Results were plotted in graphics including the serological profiles of the mean titres for PRRSV antibodies from all groups.
- Body weight of piglet: tabulation of body weights, descriptive statistics, and ANOVA test for comparisons between groups were done.
- Rectal temperature data: taking into account that temperature is normal distributed, body temperature was evaluated using descriptive statistics, an ANOVA model analysis of variance was used to analyse the body temperature evolution over time, taking in account treatment.
- Clinical signs and lesions: relevant clinical signs for vaccinated and control groups were compared. Clinical observations are discrete variables and they were analysed using a non-parametric Kruskal Wallis test of association between treatment and clinical signs.
- Mortality data: descriptive statistics and a non-parametric Kruskal Wallis test were applied for group comparison.

A significance level $p<0.05$ was used for all the variables evaluated in this trial. SPSS® 20.0 (SPSS Inc.), StatCalc (EpiInfo 6) and Microsoft® Excel 2000 (Microsoft Corp.) were used for data analysis.

In view of the results on viremic animals (FIG. 12), mean faecal shedding of the virus (FIG. 13), percentage of animals excreting the virus by faecal and salivary routes, and the presence of virus in tonsil swabs (FIG. 14) obtained from the groups vaccinated with pVAC 5.2 or with VP-046 BIS after a homologous infection, it can be concluded that the pVAC 5.2 vaccine according to the present invention shows an analogous efficacy as VP-046 BIS vaccine. The favourable results of the vaccinated groups were significantly different from the control. The number of permanently infected animals having virus in tonsil swabs was reduced by both vaccines in the same extend. The pVAC 5.2 vaccine has shown a good seroconversion at the date of challenge and onwards, which confirms a persistent immune response and its suitability as immunoprotective agent.

Example 6: Heterologous Efficacy Assessment of Infectious Clone pVAC 5.2 in Piglets In this example of efficacy trial, the PRRSV-infection consequences were compared between a vaccinated group with a vaccine prepared from clone pVAC 5.2 and a non-vaccinated group after a heterologous challenge. In the trial it was included also a positive control (vaccinated with VP-046 BIS strain, Laboratorios Hipra, S.A., Amer, Girona, Spain) that was also challenged.

The clone pVAC 5.2 was transfected and amplified, as disclosed in Example 4, to achieve the desired volume and titer ($10^{3.88}$ $CCID_{50}$/mL). Virus was suspended in MEM G supplemented with 10% FBS. It was administered a dose of 1 mL/animal, i.e. $10^{3.88}$ $CCID_{50}$/animal.

Freeze dried vials of VP-046 BIS strain with a titer of $10^{59}$ $CCID_{50}$/mL were used. They were reconstituted with PBS to achieve $10^{3.88}$ $CCID_{50}$/animal.

The animals were porcine males and females of 5 weeks of age at the vaccination day, free of PRRSV and antibody free against PRRSV. They were randomly distributed into 3 groups of 12 piglets each one. One group was vaccinated with the vaccine prepared from clone pVAC 5.2 by the intramuscular route using $10^{3.88}$ $CCID_{50}$/animal. Another group was vaccinated with the same virus titer but with VP-046 BIS vaccine. The last group was vaccinated with sterile PBS and was maintained in the same housing conditions (as a challenge control).

In the study the following designations were used:

Group A=group vaccinated with pVAC 5.2,

Group B=group vaccinated with VP-046 BIS, and

Group C=Control group, non-vaccinated

The efficacy against PRRSV was confirmed by means of a challenge with a heterologous virulent strain of PRRSV 35 days after the vaccination. The challenge was performed by intranasal route, which is one of the virus' natural infection routes. The challenge strain showed a virus titer of $10^{4.99}$ $CCID_{50}$/mL. At the end of the experimental infection the titre of the inocula was confirmed.

After the challenge, the incidence and duration of viremia and the virus excretion in saliva and faeces (RT-qPCR) was followed up to support the efficacy claims of both clone pVAC 5.2 and VP-046 BIS vaccine. The clinical signs of all the piglets (including general and respiratory signs, mortality and temperature increases) and the average daily weight gain were also monitored. The observation period of all animals was prolonged up to 42 days after challenge. Lung and tonsil swabs presence of the PRRS virus in piglets was also determined after euthanasia (RT-qPCR). In addition, each piglet was observed to detect any local or systemic clinical sign after vaccination.

Finally, serology (PRRSV antibody level; total IgG by ELISA) of all the animals was performed after vaccination (in order to assess the correct immunization) and after challenge (antibody kinetics description).

This study was blind, thus the person who vaccinated the animals was not the same that the one who performed the rest of the samplings and observations.

The variables evaluated in this study and the statistical tests applied are listed below:

Viremia and serological profiles: descriptive statistics and a non-parametric Kruskal Wallis test or ANOVA test were applied for group comparison on viremia. Results were plotted in graphics including the serological profiles of the mean titres for PRRSV antibodies from all groups.

Body weight of piglet: tabulation of body weights, descriptive statistics, and ANOVA test for comparisons between groups was done.

Rectal temperature data: taking into account that temperature is normal distributed, body temperature was evaluated using descriptive statistics, an ANOVA model analysis of variance was used to analyse the body temperature evolution over time, taking in account treatment.

Clinical signs and lesions: relevant clinical signs for vaccinated and control groups were compared. Clinical observations are discrete variables and they were analysed using a non-parametric Kruskal Wallis test of association between treatment and clinical signs.

Mortality data: descriptive statistics and a non-parametric Kruskal Wallis test were applied for group comparison.

A significance level $p<0.05$ was used for all the variables evaluated in this trial. SPSS® 20.0 (SPSS Inc.), StatCalc (EpiInfo 6) and Microsoft® Excel 2000 (Microsoft Corp.) were used for data analysis.

6.1.—Serological Profiles

In FIG. 15 it is observed an increase in the antibody level for vaccinated animals either with the vaccine prepared from clone pVAC 5.2 or VP-046 BIS vaccine, in comparison to the Control group. It is also observed that after challenge with a virulent strain of PRRS, antibody level of the Control group increase up to similar levels shown in the vaccinated animals at day 69 of the study.

6.2.—Viremia

Sera at day 0 and after challenge up to day 69 of the study were analysed by RT-qPCR in order to detect and quantify PRRSV.

In FIG. 16 are represented the mean titers ($CCID_{50}$/mL) viremia after challenge for each group. Significant differences in viremia were observed between the groups of vaccinated animals and the Control group at days 38, 41, 44, and 48. It was observed also a reduction of two orders of magnitude in viremia for the group of pVAC 5.2 in comparison to the Control group.

In FIG. 17 are represented the percentages of viremic animals after challenge for each group. Significant differences these percentages were observed between the groups of vaccinated animals and the Control group at days 38, 41, 44, and 48

6.3.—Shedding

Faecal swabs were obtained from vaccinated and non-vaccinated animals after challenge with a heterologous virulent strain of PRRSV. Titers of PRRSV were analysed by RT-qPCR. In FIG. 18 is represented the mean value of PRRSV titer expressed as $CCID_{50}$/mL for each group of animals. Differences between vaccinated and non-vaccinated animals were clearly observed at days 41 and 44. At day 48 it was observed a clear reduction in the shedding for the vaccinated groups. Vaccine obtained from pVAC 5.2 and VP-046 BIS vaccine provided good heterologous protection in front of PRRSV infection.

In FIG. 19 is represented the percentage of positive animals with faecal shedding for each group. It was observed a clear reduction in the percentage of positive shedding animals for the vaccinated groups. At day 44 these differences were significant. These positive shedding animals are responsible for the spreading of the infection in the farms. It can be observed that the control of viremia influences positively the reduction in the shedding.

6.4.—Lung and Tonsil Swabs

At day 70, it was observed significant differences in the titre of the virus in lung tissue and the percentage of positive lungs to PRRSV between animals of the group A (pVAC 5.2 group) and the Control group. Also, there were differences in the mean virus titre found in tonsil swabs. Control group had significantly more virus than vaccinated animals in group A (pVAC 5.2). In FIG. 20 are represented the mean quantity of PRRS virus expressed in $CCID_{50}$/ml for each group present in lung tissues and in tonsil swabs.

Vaccination with pVAC 5.2 (group A) or VP-046 BIS reduced the presence of virus in lung tissues and in tonsil swabs.

6.5.—Clinical Signs

No significant differences were observed regarding the presence of clinical signs between the different treatment groups.

Example 7: Construction of Infectious Clone pVAC 6.1 (SEQ ID NO:162)

Consensus sequence of the attenuated PRRSV strain V1042-P62 was determined by sequencing of RT-PCR reaction products by the Sanger method (SEQ ID NO:163), wherein a position is considered polymorphic if more than one peak is observed in the chromatogram. Consensus sequence contains thirty polymorphic positions (1979, 2010, 4979, 5528, 5915, 6490, 6998, 7067, 7447, 7478, 7603, 8032, 8077, 8161, 8213, 8227, 8239, 8242, 8248, 8257, 8342, 8343, 8347, 8353, 8355, 11845, 13097, 13643, 13761, and 15025). Clone pVAC 6.1 contains the most frequent nucleotide sequence variant in genomic regions ranging from positions 1164 to 2113, 6906 to 8402, 11618 to 12274, and 14633 to 15082; one of the nucleotide sequence variants coding for the most frequent protein in positions 4630 to 6543 and 12970 to 13887; and the consensus nucleotide sequence in the rest of positions, except for position 8806 that contains C instead of U.

7.a) Virus

The starting material was PRRSV strain V1042-P62 (HIPRA SCIENTIFIC, S.L.U., Amer, Girona, Spain) (Accession number CNCM 1-5219).

7.b) Isolation of Viral RNA

PRRSV RNA extractions were carried out using the High Pure Viral RNA kit (Roche) from cell cultures in Clon 8 cell type (Laboratorios Hipra, S.A., Amer, Girona, Spain).

7.c) Reverse Transcription.

Reverse transcription reactions were performed as in Example 1 c), using the primers shown in Table XV:

TABLE XV

| cDNA name | Primer | Sequence | Position[1] |
|---|---|---|---|
| F1 | PRRSV-455R | GCTAGGTTGATTGGGCTAGCTAG AACC (SEQ ID NO: 164) | 2458-2432 |
| F2 | PRRSV-439R | ACTTCTAGAGTGCCACCTCCGTA G (SEQ ID NO: 165) | 4103-4087 |
| F3 | PRRSV-441R | ACTTCTAGAGTCTCTTGAACGGA CACAG (SEQ ID NO: 166) | 6810-6790 |
| F4 | PRRSV-444R | ACTTCTAGATGAGGTCCTCATAC CACTC (SEQ ID NO: 167) | 9233-9212 |
| F5-5' | PRRSV-462R | CCCGAGTGATGGCTACTAGTGCT CG (SEQ ID NO: 168) | 10394-10418 |
| F5 | PRRSV-445R | ACTCTAGAGCAGGGCATACATAT G (SEQ ID NO: 169) | 12578-12559 |
| F6 | PRRSV-453R | ACTTCTAGAGGTTAACCACTCCTC GTTTAACAG (SEQ ID NO: 170) | 14590-14565 |
| F7 | PRRSV-274R | GGCGATCGGGCGTCTAGGAATTC TAGA(T)41 (SEQ ID NO: 171) | poly(A) tail |

[1]The position corresponds to the consensus sequence of the attenuated virus PRRSV V1042-P62 (SEQ ID NO: 163).

7.d) Amplification of cDNA by PCR

Primer phosphorylation and PCR reactions were performed as in Example 1 d). Primers used here are shown in Table XVI:

TABLE XVI

| cDNA name | Primer | Sequence | Position[1] |
|---|---|---|---|
| F1 | PRRSV-457F | AAATATGATGTGTGGGGTATTCCC CCTAC (SEQ ID NO: 172) | 1-25 |

TABLE XVI-continued

| cDNA name | Primer | Sequence | Position[1] |
|---|---|---|---|
| | PRRSV-455R | GCTAGGTTGATTGGGCTAGCTAGA ACC (SEQ ID NO: 173) | 2458-2432 |
| F2 | PRRSV-448F | AAATTCTAGCTAGCCCAATCAACC TAGC (SEQ ID NO: 174) | 2434-2458 |
| | PRRSV-439R | ACTTCTAGAGTGCCACCTCCGTAG (SEQ ID NO: 175) | 4103-4087 |
| F3 | PRRVS-440F | CGTCATTCTTGGTAAGTTACTCGG TGG (SEQ ID NO: 176) | 3935-3961 |
| | PRRSV-441R | ACTTCTAGAGTCTCTTGAACGGAC ACAG (SEQ ID NO: 177) | 6810-6790 |
| F4 | PRRSV-443F | TTGACACAGGTGACGTGATTGTCC (SEQ ID NO: 178) | 6706-6729 |
| | PRRSV-444R | ACTTCTAGATGAGGTCCTCATACC ACTC (SEQ ID NO: 179) | 9233-9212 |
| F5-5' | PRRSV-461F | CCTCTAGACTTAAGTTCCTCGAGG AGCA (SEQ ID NO: 180) | 8855-8874 |
| | PRRSV-462R | CCCGAGTGATGGCTACTAGTGCT CG (SEQ ID NO: 181) | 10394-10418 |
| F5 | PRRSV-244F | TAGCAGCCCTTGCATATCA (SEQ ID NO: 182) | 9108-9126 |
| | PRRSV-445R | ACTCTAGAGCAGGGCATACATATG (SEQ ID NO: 183) | 12578-12559 |
| F6 | PRRSV-452F | GCTTCGAATTCCAGCCGTACGCTA TG (SEQ ID NO: 184) | 12476-12501 |
| | PRRSV-453R | ACTTCTAGAGGTTAACCACTCCTC GTTTAACAG (SEQ ID NO: 185) | 14590-14565 |
| F7 | PRRSV-446F | GGCAACCTCGTCACCATCAAACAT G (SEQ ID NO: 186) | 14010-14034 |
| | PRRSV-34R | GGCGATCGGGCGTCTAGGAATTC (SEQ ID NO: 187) | PRRSV-274R[2] |

[1]The position corresponds to the consensus sequence of the attenuated virus PRRSV V1042-P62 (SEQ ID NO: 163).
[2]Primer PRRSV-34R anneals with primer PRRSV-274R of Table XV.

7.e) Preparation of the Vectors

Preparation of vectors pUC19-SmaI, pUC19 double digested with SmaI and XbaI, pACYC177-ADAP and pACYC177-ADAP-EcoRV is described in Example 1 e).

7.f) Preparation of the Inserts

RT-PCR products were purified for blunt end or directional cloning as explained in Example 1 f).

7.g) Production and Amplification of cDNA for the 5' Terminus of Viral Genomic RNA The sequence corresponding to the 5' terminus of the viral genomic RNA was determined by 5'RACE system as in Example 1 g). Primers used for this experiment are shown in Table XVII:

TABLE XVII

| cDNA name | Primer | Position[1] | Sequence 5'-3' |
|---|---|---|---|
| 5' RACE | RRSV-286R | 81-361 | TAGGCTTGTAAAACAAGCCAA (SEQ ID NO: 188) |
| | RRSV-288R | 55-334 | GCAAGGTCAGTTTCCTGAAGCT (SEQ ID NO: 189) |

[1]The position corresponds to the consensus sequence of the attenuated virus PRRSV V1042-P62 (SEQ ID NO: 163).

7.h) Cloning and Sequencing of the Fragments

Inserts F2, F3, F4, F5-5' and F5 (Table XVI) were ligated into an SmaI-digested pUC19 plasmid.

Insert F7 was ligated into an SmaI-XbaI-digested pUC19 vector.

Inserts F1, F3, F5 and F6 (Table XVI) were ligated into an EcoRV-digested pACYC177-ADAP vector.

Insert 5' RACE (Table XVII) was ligated in commercial vector pTZ57R/T (Thermo Fisher Scientific).

Ligations were carried out as in Example 1 h). Ligation products were electroporated into *E. coli* Top 10 cells (Invitrogene).

Plasmids carrying cDNAs of genomic regions containing polymorphic positions in the consensus sequence were isolated from 18 to 24 transformant colonies. Plasmids carrying cDNAs of genomic regions not containing polymorphic positions were isolated from 2 to 9 colonies. The number of molecular clones obtained for each genomic region, and the primers used for sequencing are shown in Table XVIII:

TABLE XVIII

| cDNA name | Number of molecular clones obtained | Sequencing primer | Primer sequence | Positions analyzed[1] |
|---|---|---|---|---|
| 5' RACE | 9 | PRRSV-288R | GCAAGGTCAGTTTCCTG AAGCT (SEQ ID NO: 190) | 1-289 |
| F1 | 24 | PRRSV-56R | AAGTCGTTGGAGGAAG TTGT (SEQ ID NO: 191) | 26-461 |
| | | PRRSV-430R | ACACTCATCCAGAGACA CAGAC (SEQ ID NO: 192) | 1164-2113 |
| F2 | 2 | M13F | GTAAAACGACGGCCAG T (SEQ ID NO: 193) | 2434-4103 |
| | | M13R | CAGGAAACAGCTATGAC (SEQ ID NO: 194) | |
| | | PRRSV-410 | CACTGCGCCACCAGTC GCTTCAG (SEQ ID NO: 195) | |
| F3 | 24 | PRRSV-207R | ACCCTRGGYARGAAGC AGTATGT (SEQ ID NO: 196) | 4630-6543 |
| | | PRRSV-413F | AGGAACTCTGTCTCCAC CAAG (SEQ ID NO: 197) | |
| | | PRRSV-442R | CATACGCTGCCTCAATG TACTG (SEQ ID NO: 198) | |
| F4 | 24 | PRRSV-20F | RACCACYGARCARGCTT TAAAC (SEQ ID NO: 199) | 6906-8402 |
| | | PRRSV-19R | GGACTTCCARGCCTTYT TCATG (SEQ ID NO: 200) | |
| | | PRRSV-209R | GACGGTGGRTGAGGYC TCATCAA (SEQ ID NO: 201) | |
| F5-5' | 5 | M13F | GTAAAACGACGGCCAG T (SEQ ID NO: 202) | 8855-10418 |
| | | M13R | CAGGAAACAGCTATGAC (SEQ ID NO: 203) | |
| F5 | 18 | PRRSV-420R | ATGATCCAACGTGGTAT TATACTGC (SEQ ID NO: 204) | 111618-12274 |
| F6 | 24 | PRRSV-1F | TAGACGGGGGYAAYTG GTT (SEQ ID NO: 205) | 12970-13887 |
| F7 | 24 | PRRSV-112F | TGTTAAACGAGGAGTG GTTAAC (SEQ ID NO: 206) | 14633-15082 |

[1]The position corresponds to the consensus sequence of the attenuated virus PRRSV V1042-P62 (SEQ ID NO: 163).

7.i) Sequence Analysis and Selection of cDNA Clones to be Inserted in the Infectious Clone.

Sequences obtained from clones of cDNAs in Table XVIII were edited, assembled, translated (if necessary) and aligned using the software Geneious R.9.0.2 (Biomatters Ltd).

Prior to assembly of the infectious clone, cDNAs of genomic regions not containing polymorphic positions (cDNAs F2 and F5-5') were sequenced as indicated in Table XVIII. Clones containing the consensus sequence (SEQ ID NO:163) were selected for assembly of the infectious clone. Selected clones were named F2-1 and pUC19-F5-5'-5.

For each of the genomic regions F1, F4, F5, and F7 containing polymorphic positions, the most frequent sequence variant was selected. Selected clones were named pUC19-F1-4, pUC19-F4-2A, F5-6B, and F7-1.

Genomic regions F3 and F6 contained polymorphic positions, but there was not most frequent nucleotide sequence variant amongst the sequenced clones (all clones of F3 region contained a different sequence variants, and F6 clones had three sequence variants at equal frequency). Nucleotide sequences were then translated to proteins according to the standard genetic code, and one clone of each region coding for the most frequent protein variant was selected. To select between clones coding for the same protein sequence, 50%, 75% and 100% nucleotide consensus sequences were calculated for each genomic region. The largest percentage consensus sequence not containing polymorphic sites was selected as reference sequence. For region F3 one of the cDNA clones coding for the most frequent protein sequence corresponded to the reference sequence and was selected. For region F6 the reference sequence corresponded to a variant present al low frequency and was discarded; a clone containing one of the three most frequent sequence variants and the most frequent protein variant was randomly selected. Selected clones were named F3-14B and F6-12-1.

7.j) Preparation of the Cloning and Expression Vector pACYC-ADAP-pCMV pACYC-ADAP-pCMV vector was prepared by digestion of clone pVAC 5.0 (Example 1) with SwaI and XbaI.

7.k) Insertion of Hepatitis Delta Virus Ribozyme (HDV-Rz) in 3' End of F7 Region Insertion of HDV-Rz in 3' end of viral genome was performed as in Example 1 p) Step 2, using as template the plasmid F7-1 obtained in i). PCR product was digested with HpaI and XbaI and cloned in vector pUC19-SmaI-XbaI e). This clone was named F7-1-Rz.

7.l) Digestion, Ligation, Transformation and Plasmids Purification

Inserts were prepared by PCR as described in Example 1 j) using as templates the cDNA clones selected in step i) and the primers in Table XIX. Alternatively were prepared by digestion of plasmid DNA with enzymes suitable for V1042-P62 strain (FIG. 21).

Plasmids used as vectors were prepared as in Example 1 k). Ligation reactions, transformation of Top 10 electro competent cells and plasmid purification were performed as described in Example 1 k).

TABLE XIX

| Template cDNA | Primer | Sequence | Position |
|---|---|---|---|
| pUC19-F1-4 | PRRSV-457F | AAATATGATGTGTGGGGTATTC CCCCTAC (SEQ ID NO: 207) | 1-25[1] |
| | PRRSV-455R | GCTAGGTTGATTGGGCTAGCTA GAACC (SEQ ID NO: 208) | 2458-2432[1] |
| F2-1 | PRRSV-438F | TTCTAGCTAGCCCAATCAACCTA GC (SEQ ID NO: 209) | 2434-2458[1] |
| | PRRSV-439R | ACTTCTAGAGTGCCACCTCCGT AG (SEQ ID NO: 210) | 4103-4087[1] |
| F3-14B | pACYC-87F | CAGTACCGACGGTGATAT (SEQ ID NO: 211) | 3248-3266[2] |
| | pACYC-88R | CCGTCGTGTAGATAACTACG (SEQ ID NO: 212) | 544-525[2] |
| pUC19-F4-2A | PRRSV-443F | TTGACACAGGTGACGTGATTGT CC (SEQ ID NO: 213) | 6706-6729[1] |
| | PRRSV-444R | ACTTCTAGATGAGGTCCTCATAC CACTC (SEQ ID NO: 214) | 9233-9212[1] |
| pUC19-F5-5'-5 | PRRSV-461F | CCTCTAGACTTAAGTTCCTCGA GGAGCA (SEQ ID NO: 215) | 8855-8874[1] |
| | PRRSV-462R | CCCGAGTGATGGCTACTAGTGC TCG (SEQ ID NO: 216) | 10394-10418[1] |
| F5-6B | PRRSV-244F | TAGCAGCCCTTGCATATCA (SEQ ID NO: 217) | 9108-9126[1] |
| | PRRSV-42F | AGACTGCTTTCCAAAACACC (SEQ ID NO: 218) | 10037-10056[1] |

TABLE XIX-continued

| Template cDNA | Primer | Sequence | Position |
|---|---|---|---|
| F6-12-1 | PRRSV-452F | GCTTCGAATTCCAGCCGTACGC TATG (SEQ ID NO: 219) | 12476-12501[1] |
|  | PRRSV-453R | ACTTCTAGAGGTTAACCACTCCT CGTTTAACAG (SEQ ID NO: 220) | 14590-14565[1] |

[1]The position corresponds to the consensus sequence of the attenuated virus PRRSV V1042-P62 (SEQ ID NO: 163).
[2]Cloning vector pACY177 (GenBank accession X06402.1).

7.m) Assembling of the Restriction Fragments

Restriction fragments were assembled in the sense 5' to 3' according to the following scheme, which is summarized in FIG. 21:

Step 1.—Correct insert orientation in clone pUC19-F1-4 was verified by colony PCR with primers M13F and PRRSV-56R (Table XVIII).

Step 2.—Insert F2-1 obtained in I) was digested with NheI and XbaI, and ligated into vector pUC19-F1-4 digested with the same enzymes.

Step 3.—Insert F3-14B obtained in I) was digested with NsiI and XbaI, and ligated in the vector obtained in step 2 digested with the same enzymes.

Step 4.—Viral cDNA in the clone obtained in step 3 was amplified by PCR with primers PRRSV-457F and PRRSV-441R (Table XVI), and digested with SwaI and XbaI. This insert was ligated into SwaI and XbaI sites of vector pACYC-ADAP-pCMV, obtained as indicated in j).

Step 5.—Correct insert orientation in clone pUC19-F4-2A was verified by colony PCR with primers M13R (Table XVIII) and a suitable PRRSV specific forward primer. This clone was digested with AflII and XbaI.

Step 6.—Correct insert orientation in clone pUC19-F5-5'-5 was verified by sequencing with primer M13F (Table XVIII). This plasmid was digested with AflII and XbaI, and ligated in the vector obtained in step 5.

Step 7.—Insert F5-6B obtained in I) was digested with SpeI and XbaI, and ligated in the vector obtained in step 6 digested with the same enzymes.

Step 8.—Viral cDNA in clone obtained in step 7 was excised from vector by double digestion with EcoRV and XbaI. This insert was ligated into vector obtained in step 4 digested with the same enzymes.

Step 9.—Insert F6-12-1 obtained in I) was digested with XbaI and subcloned in vector pUC19-SmaI-XbaI e).

Step 10.—Viral cDNA in clone F7-1-Rz obtained in k) was excised from the vector by double digestion with HpaI and XbaI, and cloned between the HpaI and XbaI sites of the vector obtained in step 9.

Step 11.—Viral cDNA in the clone obtained is step 10 was excised from the vector by double digestion with Bs/WI and XbaI and cloned between the Bs/WI and XbaI sites of the vector obtained in step 8. This clone was named CI-1042p62-V1.

7.n) Sequence of the Clone p1042

To confirm the PRRSV sequence inserted in CI-1042p62-V1, DNA was sequenced using suitable primers to obtain the sequence of the whole genome, the pCMV promoter, the HDV-Rz and the joins with the cloning vector. The sequence of the clone showed three mutations compared with the consensus sequence of V1042-P62: C6633T and T8806C.

Mutation C6633T was reversed by PCR performed with the overlapping mutagenic primers PRRSV-465F and PRRSV-466R and Phusion high fidelity DNA polymerase (Finnzymes). The product of PCR reaction was used to transform Top 10 cells. Plasmids were isolated and sequenced with a primer suitable to verify the reversion of the mutation. Viral insert was excised by double digestion with SwaI and EcoRV, and subcloned between the SwaI and EcoRV sites of CI-1042p62-V1. The obtained clone was named pVAC 6.1.

TABLE XX

| Primer | Sequence | Position[1] |
|---|---|---|
| PRRSV-465F | CGAGAGTTGGCCTCCCTAGTCCAG GTTGACAAAATGAAAG (SEQ ID NO: 221) | 6618 |
| PRRSV-466R | CTTTCATTTTGTCAACCTGGACTAG GGAGGCCAACTCTCG (SEQ ID NO: 222) | 6657 |

[1]The position corresponds to the consensus sequence of the attenuated virus PRRSV V1042-P62 (SEQ ID NO: 163).

7.o) Sequence of the Clone pVAC 6.1

Clone pVAC 6.1 was sequenced with suitable primers, sequence is provided (SEQ ID NO: 162).

7.p) Alignment of Consensus Sequence of V1042-P62 and Clone pVAC 6.1 is Shown in Table XXI:

TABLE XXI

| Position[1] | Consensus nucleotide sequence of V1042-P62[2] | Nucleotide (Number of clones)[3] | Nucleotide in clone pVAC 6.1[4] |
|---|---|---|---|
| 1979 | Y | C (20) T (4) | C |
| 2010 | R | G (19) A (5) | G |
| 4979 | M | C (15) A (9) | C |
| 5528 | Y | T (19) C (5) | T |
| 5915 | Y | C (12) T (12) | C |
| 6490 | R | A (18) G (6) | A |
| 6998 | Y | C (14) T (10) | C |
| 7067 | Y | C (15) T (9) | T |
| 7447 | W | T (22) C (2) | T |
| 7478 | R | G (16) A (8) | G |
| 7603 | K | T (17) G (7) | T |
| 8032 | Y | T (14) C (10) | T |
| 8077 | Y | C (14) T (10) | C |
| 8161 | R | A (13) G (11) | A |
| 8191 | G | G (22) A (2) | A |
| 8213 | R | A (13) G (11) | A |
| 8227 | R | A (14) G (10) | A |
| 8239 | Y | C (13) T (11) | T |
| 8242 | R | G (13) A (11) | G |
| 8248 | Y | T (13) C (11) | T |
| 8257 | Y | C (14) T (10) | C |

TABLE XXI-continued

| Position[1] | Consensus nucleotide sequence of V1042-P62[2] | Nucleotide (Number of clones) [3] | Nucleotide in clone pVAC 6.1[4] |
|---|---|---|---|
| 8259 | A | A (22) G (2) | G |
| 8342 | S | C (14) G (10) | C |
| 8343 | K | G (14) T (10) | G |
| 8347 | Y | T (14) C (10) | T |
| 8353 | R | G (14) A (10) | G |
| 8355 | M | C (14) A (10) | C |
| 8806 | T | | C |
| 11845 | Y | C (14) T (4) | C |
| 13097 | R | G (13) A (11) | A |
| 13353 | A | A (19) G (5) | G |
| 13643 | Y | C (13) T (11) | T |
| 13761 | Y | T (16) C (8) | T |
| 15025 | Y | T (13) C (11) | T |

[1]The position corresponds to the consensus sequence of the attenuated virus PRRSV V1042-P62 (SEQ ID NO: 163).
[2](SEQ ID NO: 163).
[3] Section 7.h).
[4](SEQ ID NO: 162).

Example 8: Assessment of the Immunization and Safety of V1042-P62 PRRSV Quasispecies Vs Clone pVAC 6.1

In this example, the immunogenicity and safety characteristics of V1042-P62 PRRS quasispecies and clone pVAC 6.1 were compared. Three groups were used: one group received a vaccine containing clone pVAC 6.1, another group received a vaccine containing V1042-P62 PRRSV quasispecies and the third group was a non-vaccinated group.

Clone pVAC 6.1 was transfected and amplified as disclosed in Example 4 in order to achieve a desired volume and titter of $10^{55}$ $CCID_{50}$/dose. A stock of attenuated V1042-P62 PRRSV strain was also adjusted to the desired titre. Viruses were diluted in PBS in order to uniform all the virus dose/animal among groups. A dose of 2 ml/animal was administered by intramuscular route.

Piglets between 4-5 weeks of age at the beginning of the study were used. All animals were PRRSV-free and antibody free against PRRSV.

A total of 55 animals were used in the study. The animals were distributed randomly into three groups. The two vaccinated groups contained 20 piglets. Fifteen piglets were vaccinated and five piglets were cohabitants (non-vaccinated). One group was vaccinated with the clone pVAC 6.1. Other group was vaccinated with attenuated V1042-P612 PRRSV quasispecies. One extra group of 15 animals was included as a non-vaccinated group. This group were used as a control group and received a 2 ml of sterile PBS solution. The control group was maintained in the same housing conditions.

In the study the following designations were used:

Group A=group vaccinated with the attenuated V1042-P62 PRRSV quasispecies

Group B=group vaccinated with the clone pVAC 6.1

Group C=control group, non-vaccinated

The efficacy and safety of the vaccines was assessed by serology and viremia in both, inoculated and cohabitant animals.

Results

Seroconversion in Inoculated and Cohabitant Animals.

Serology of inoculated and cohabitant animals was performed after vaccination in order to assess the correct immunization.

It was observed that 73% of animals vaccinated in both groups were already seropositive (IRPC>20) at day 28 after vaccination (D28). Animals in groups A and B, demonstrated the same immunization (seroconversion) profile.

In FIG. 22 mean titers of antibodies against PRRSV (IRPC) for the vaccinated and for the non-vaccinated animals are represented at different days post-vaccination. These results demonstrate that the mean of the IRPC in all vaccinated groups was above the cut-off level (>20% IRPC) from D28, which means that the mean IRPC is positive to seroconversion.

In cohabitant animals, seroconversion was not observed in animals of groups A and B.

Viremia in Cohabitant Animals

The PRRSV dissemination was assessed by viremia values in cohabitant animals.

Sera from day 3 to day 28 of the study were analyzed by RT-qPCR. In FIG. 23 it is represented the percentage of cohabitant animals positive to viremia. When comparing the percentages of animals positive to viremia, it was observed a clear trend of the group B (clone pVAC 6.1) to show a reduction in the number of positive animals during the study in comparison to the other vaccinated group A.

The lower viremia of pVAC 6.1 group in contrast to V1042-P62 PRRSV quasiespecies represents lower capacity of accumulation in lungs and tonsils, and consequently less capacity of reversion to virulence of the vaccine of the invention.

The invention claimed is:

1. A method for generating an infectious cDNA clone based on the genome of an attenuated PRRSV strain, the method comprising:

a) identifying polymorphic zones of the genome sequence of a population of quasispecies of an attenuated strain of PRRSV, b) determining the most frequent sequence within the polymorphic zones of the quasispecies population identified in step a), and c) constructing an infectious cDNA clone comprising the most frequent sequence in at least one of the polymorphic zones identified in step a).

2. The method according to claim 1, characterized in that the polymorphic zones are selected from the group consisting of 5'UTR, ORF1a, ORF1b, ORF2, ORF3, ORF4, ORF5, ORF6, ORF7, and 3'UTR.

3. The method according to claim 1, characterized in that the attenuated PRRSV strain is selected from the group consisting of an attenuated European PRRSV strain and an attenuated North American PRRSV strain.

4. An infectious cDNA clone made by the method of claim 1.

5. An infectious cDNA clone according to claim 4, characterized in that it comprises the most frequent sequence corresponding to at least one of the following polymorphic zones:

i) from position 3902 to 3959, ii) from position 6792 to 7672, and iii) at the region comprising ORF3 to ORF6, wherein positions are referred to the consensus sequence of the attenuated PRRS virus defined by SEQ ID NO:1.

6. An infectious cDNA clone according to claim 5, characterized in that the infectious clone is named pVAC 5.2, deposited in the Leibnitz-Institut DSMZ-Deutsche Sammlung von Mikroorganismen und Zellkulturen accession number DSM 32341.

7. An infectious cDNA clone according to claim 4, characterized in that the infectious clone comprises the most frequent sequence corresponding to the polymorphic zones:

i) from position 3902 to 3959, ii) from 6792 to 7672, and iii) from position 12938 to 14151, wherein positions are referred to the consensus sequence of the attenuated PRRS virus defined by SEQ ID NO:1.

8. An infectious cDNA clone according to claim 7, characterized in that the infectious clone is named pVAC 5.1, deposited in the Leibnitz-Institut DSMZ-Deutsche Sammlung von Mikroorganismen und Zellkulturen accession number DSM 32340.

9. An infectious cDNA clone according to claim 4, characterized in that it comprises the most frequent sequence corresponding to at least one of the following polymorphic zones:

i) from position 1164 to 2113, ii) from 4630 to 6543, iii) from 6906 to 8402, iv) from 11618 to 12274, and v) at the region comprising ORF3 to 3'UTR, wherein positions are referred to the consensus sequence of the attenuated PRRS virus defined by SEQ ID NO:163.

10. An infectious cDNA clone according to claim 9, characterized in that the infectious clone is named pVAC 6.1, deposited in the Leibnitz-Institut DSMZ-Deutsche Sammlung von Mikroorganismen and Zellkulturen accession number DSM 32542.

11. A recombinant nucleic acid comprising the infectious cDNA clone of claim 4.

12. A DNA construct comprising a copy of the recombinant nucleic acid of claim 11.

13. An RNA transcript of the DNA construct of claim 12.

14. An attenuated PRRSV encoded by the RNA transcript of claim 13.

15. An immunogenic composition comprising the attenuated PRRSV of claim 14.

16. A vaccine comprising an immunologically effective amount of the attenuated PRRSV of claim 14 and a pharmaceutically acceptable diluent or excipient.

17. A method for the prophylaxis and/or treatment of PRRSV virus infections comprising the step of administering the attenuated PRRSV of claim 14 to a subject.

18. A vaccine comprising an immunologically effective amount of the infectious cDNA clone of claim 4 and a pharmaceutically acceptable diluent or excipient.

* * * * *